US010385128B2

(12) United States Patent
Sutkowski et al.

(10) Patent No.: US 10,385,128 B2
(45) Date of Patent: Aug. 20, 2019

(54) NUCLEOLIN ANTIBODIES

(71) Applicant: MUSC Foundation for Research Development, Charleston, SC (US)

(72) Inventors: Natalie Sutkowski, Charleston, SC (US); Daniel Fernandes, Charleston, SC (US); Brian Hoel, Charleston, SC (US); Semyon Rubinchik, Buffalo Grove, IL (US)

(73) Assignee: MUSC Foundation for Research Development, Charleston, SC (US)

( * ) Notice: Subject to any disclaimer, the term of this patent is extended or adjusted under 35 U.S.C. 154(b) by 0 days.

(21) Appl. No.: 14/972,698

(22) Filed: Dec. 17, 2015

(65) Prior Publication Data

US 2016/0215050 A1 Jul. 28, 2016

Related U.S. Application Data

(62) Division of application No. 13/510,270, filed as application No. PCT/US2010/057046 on Nov. 17, 2010, now Pat. No. 9,260,517.

(60) Provisional application No. 61/261,909, filed on Nov. 17, 2009.

(51) Int. Cl.

| | |
|---|---|
| ***A61K 39/395*** | (2006.01) |
| ***C07K 16/28*** | (2006.01) |
| ***C07K 16/18*** | (2006.01) |
| ***C07K 16/30*** | (2006.01) |
| ***A61K 47/68*** | (2017.01) |

(52) U.S. Cl.

CPC .......... *C07K 16/28* (2013.01); *A61K 47/6843* (2017.08); *C07K 16/18* (2013.01); *C07K 16/30* (2013.01); *C07K 16/303* (2013.01); *C07K 16/3015* (2013.01); *C07K 16/3038* (2013.01); *C07K 16/3069* (2013.01); *C07K 2317/21* (2013.01); *C07K 2317/73* (2013.01); *C07K 2317/734* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,179,337 | A | 12/1979 | Davis et al. |
| 4,275,149 | A | 6/1981 | Litman et al. |
| 4,277,437 | A | 7/1981 | Maggio |
| 4,301,144 | A | 11/1981 | Iwashita et al. |
| 4,366,241 | A | 12/1982 | Tom et al. |
| 4,472,509 | A | 9/1984 | Gansow et al. |
| 4,474,892 | A | 10/1984 | Murad et al. |
| 4,485,045 | A | 11/1984 | Regen |
| 4,496,689 | A | 1/1985 | Mitra |
| 4,522,811 | A | 6/1985 | Eppstein et al. |
| 4,544,545 | A | 10/1985 | Ryan et al. |
| 4,640,835 | A | 2/1987 | Shimizu et al. |
| 4,657,760 | A | 4/1987 | Kung et al. |
| 4,665,897 | A | 5/1987 | Lemelson |
| 4,670,417 | A | 6/1987 | Iwasaki et al. |
| 4,791,192 | A | 12/1988 | Nakagawa et al. |
| 4,816,567 | A | 3/1989 | Cabilly et al. |
| 4,938,948 | A | 7/1990 | Ring et al. |
| 4,975,278 | A | 12/1990 | Senter et al. |
| 5,013,556 | A | 5/1991 | Woodle et al. |
| 5,021,236 | A | 6/1991 | Gries et al. |
| 5,047,335 | A | 9/1991 | Paulson et al. |
| 5,055,459 | A | 10/1991 | Andersson et al. |
| 5,093,246 | A | 3/1992 | Cech et al. |
| 5,192,660 | A | 3/1993 | Reed-Gitomer |
| 5,196,066 | A | 3/1993 | Kusuda et al. |
| 5,206,344 | A | 4/1993 | Katre et al. |
| 5,225,212 | A | 7/1993 | Martin et al. |
| 5,278,299 | A | 1/1994 | Wong et al. |
| 5,510,261 | A | 4/1996 | Goochee et al. |
| 5,530,101 | A | 6/1996 | Queen et al. |
| 5,534,615 | A | 7/1996 | Baker et al. |
| 5,545,806 | A | 8/1996 | Lonberg et al. |
| 5,545,807 | A | 8/1996 | Surani et al. |
| 5,567,595 | A | 10/1996 | Kok |

(Continued)

FOREIGN PATENT DOCUMENTS

| | | | |
|---|---|---|---|
| AU | 762572 | B2 | 6/2003 |
| CA | 2546730 | A1 | 4/2005 |

(Continued)

OTHER PUBLICATIONS

Abaza, M.S.I., et al, "Effects of amino acid substitutions outside an antigenic site on protein binding to monoclonal antibodies of predetermined specificity obtained by peptide immunization: Demonstration with region 94-100 (antigenic site 3) of myoglobin", Journal of Protein Chemistry, vol. 11, No. 5, pp. 433-444, (1992).

(Continued)

*Primary Examiner* — Shulamith H Shafer

(74) *Attorney, Agent, or Firm* — Wilson Sonsini Goodrich & Rosati, P.C.

(57) ABSTRACT

The present invention provides for methods of producing human monoclonal antibodies to human nucleolin, cells producing such antibodies, and the antibodies themselves. Also provided are methods of using the antibodies in diagnosing and treating malignant and non-malignant diseases wherein cells that express nucleolin on the cell surface contribute to the pathophysiology of the disease.

12 Claims, 18 Drawing Sheets

Specification includes a Sequence Listing.

(56) References Cited

U.S. PATENT DOCUMENTS

| | | | |
|---|---|---|---|
| 5,569,825 | A | 10/1996 | Lonberg et al. |
| 5,625,126 | A | 4/1997 | Lonberg et al. |
| 5,629,197 | A | 5/1997 | Ring et al. |
| 5,633,425 | A | 5/1997 | Lonberg et al. |
| 5,658,570 | A | 8/1997 | Newman et al. |
| 5,661,016 | A | 8/1997 | Lonberg et al. |
| 5,681,722 | A | 10/1997 | Newman et al. |
| 5,693,780 | A | 12/1997 | Newman et al. |
| 5,736,348 | A | 4/1998 | Goldenberg et al. |
| 5,739,306 | A | 4/1998 | Fung et al. |
| 5,750,105 | A | 5/1998 | Newman et al. |
| 5,756,096 | A | 5/1998 | Newman et al. |
| 5,770,429 | A | 6/1998 | Lonberg et al. |
| 5,869,045 | A | 2/1999 | Hellstrom et al. |
| 5,925,334 | A | 7/1999 | Rubin et al. |
| 5,932,475 | A | 8/1999 | Bandman et al. |
| 5,981,214 | A | 11/1999 | Skoultchi |
| 6,048,703 | A | 4/2000 | Siman et al. |
| 6,075,181 | A | 6/2000 | Kucherlapati et al. |
| 6,096,532 | A | 8/2000 | Armstrong et al. |
| 6,136,310 | A | 10/2000 | Hanna et al. |
| 6,150,584 | A | 11/2000 | Kucherlapati et al. |
| 6,165,786 | A | 12/2000 | Bennett et al. |
| 6,291,643 | B1 | 9/2001 | Zou et al. |
| 6,306,404 | B1 | 10/2001 | Laposta et al. |
| 6,325,785 | B1 | 12/2001 | Babkes et al. |
| 6,339,075 | B1 | 1/2002 | King et al. |
| 6,350,452 | B1 | 2/2002 | Riss |
| 6,406,705 | B1 | 6/2002 | Davis et al. |
| 6,462,189 | B1 | 10/2002 | Koide |
| 6,506,559 | B1 | 1/2003 | Fire et al. |
| 6,657,103 | B1 | 12/2003 | Kucherlapati et al. |
| 7,338,658 | B2 | 3/2008 | Hanna et al. |
| 7,357,928 | B2 | 4/2008 | Bates et al. |
| 7,452,534 | B1 | 11/2008 | Hanna et al. |
| 7,488,490 | B2 | 2/2009 | Davis et al. |
| 7,494,779 | B2 | 2/2009 | Chin et al. |
| 7,541,150 | B2 | 6/2009 | Miller et al. |
| 7,544,767 | B2 | 6/2009 | Ruoslahti et al. |
| 7,708,994 | B2 | 5/2010 | Benyunes |
| 8,029,784 | B2 | 10/2011 | Bates et al. |
| 8,048,983 | B2 | 11/2011 | Ruoslahti et al. |
| 8,586,717 | B2 | 11/2013 | Bates et al. |
| 9,260,517 | B2 | 2/2016 | Sutkowski et al. |
| 2002/0028488 | A1 | 3/2002 | Singh et al. |
| 2002/0076693 | A1 | 6/2002 | Hovanessian et al. |
| 2003/0091599 | A1 | 5/2003 | Davis et al. |
| 2003/0194754 | A1 | 10/2003 | Miller et al. |
| 2003/0224010 | A1 | 12/2003 | Davis et al. |
| 2004/0132049 | A1 | 7/2004 | Bates et al. |
| 2005/0026860 | A1 | 2/2005 | Lin et al. |
| 2005/0043529 | A1 | 2/2005 | Davis et al. |
| 2005/0053607 | A1 | 3/2005 | Bates et al. |
| 2005/0187176 | A1 | 8/2005 | Bates et al. |
| 2006/0024231 | A1 | 2/2006 | Schnitzer et al. |
| 2006/0024232 | A1 | 2/2006 | Schnitzer et al. |
| 2006/0258605 | A1 | 11/2006 | Luo et al. |
| 2006/0263355 | A1 | 11/2006 | Quan et al. |
| 2007/0065919 | A1 | 3/2007 | Groen et al. |
| 2007/0066554 | A1 | 3/2007 | Krieg et al. |
| 2007/0098711 | A1 | 5/2007 | Groen et al. |
| 2007/0178090 | A1 | 8/2007 | Sukumar et al. |
| 2007/0224201 | A1 | 9/2007 | Wu et al. |
| 2008/0038755 | A1 | 2/2008 | Kauvar et al. |
| 2008/0206254 | A1 | 8/2008 | Jacquemin et al. |
| 2008/0213280 | A1 | 9/2008 | Benyunes |
| 2008/0260650 | A1 | 10/2008 | Tawakol et al. |
| 2009/0017009 | A1 | 1/2009 | Bates et al. |
| 2009/0098633 | A1 | 4/2009 | Ruoslahti et al. |
| 2009/0117038 | A1 | 5/2009 | Sukumar et al. |
| 2009/0117128 | A1 | 5/2009 | Rigal et al. |
| 2009/0149377 | A1 | 6/2009 | Takagi et al. |
| 2009/0191224 | A1 | 7/2009 | Luo et al. |
| 2009/0221036 | A1 | 9/2009 | Hanna et al. |
| 2009/0226914 | A1 | 9/2009 | Bates et al. |
| 2009/0270268 | A1 | 10/2009 | Funaro et al. |
| 2009/0286224 | A1 | 11/2009 | Chin et al. |
| 2009/0291049 | A1 | 11/2009 | Nuno et al. |
| 2010/0021470 | A1 | 1/2010 | Lanzavecchia |
| 2011/0065121 | A1 | 3/2011 | Bates et al. |
| 2011/0091373 | A1 | 4/2011 | Pandey et al. |
| 2011/0111002 | A1 | 5/2011 | Pop |
| 2011/0318758 | A1 | 12/2011 | Sutkowski et al. |
| 2012/0014942 | A1 | 1/2012 | Bates et al. |
| 2012/0121501 | A1 | 5/2012 | Ruoslahti et al. |
| 2014/0170076 | A1 | 6/2014 | Bates et al. |
| 2014/0220013 | A1 | 8/2014 | Bates et al. |

FOREIGN PATENT DOCUMENTS

| | | | |
|---|---|---|---|
| DE | 10037861 | A1 | 2/2002 |
| EP | 0404097 | A2 | 12/1990 |
| EP | 1974017 | A1 | 10/2008 |
| EP | 1928999 | B1 | 4/2011 |
| JP | H01503438 | A | 11/1989 |
| JP | H05244988 | A | 9/1993 |
| JP | H06105910 | A | 4/1994 |
| JP | H07242566 | A | 9/1995 |
| JP | 2001213804 | A | 8/2001 |
| JP | 2007319153 | A | 12/2007 |
| WO | WO-8101145 | A1 | 4/1981 |
| WO | WO-8807378 | A1 | 10/1988 |
| WO | WO-8807543 | A1 | 10/1988 |
| WO | WO-9110741 | A1 | 7/1991 |
| WO | WO-9301161 | A1 | 1/1993 |
| WO | WO-9323572 | A1 | 11/1993 |
| WO | WO-9411026 | A2 | 5/1994 |
| WO | WO-9520401 | A1 | 8/1995 |
| WO | WO-9632478 | A1 | 10/1996 |
| WO | WO-9633735 | A1 | 10/1996 |
| WO | WO-9634096 | A1 | 10/1996 |
| WO | WO-9722250 | A1 | 6/1997 |
| WO | WO-9824893 | A2 | 6/1998 |
| WO | WO-9840480 | A1 | 9/1998 |
| WO | WO-9906588 | A1 | 2/1999 |
| WO | WO-9953057 | A1 | 10/1999 |
| WO | WO-0061597 | A1 | 10/2000 |
| WO | WO-0063250 | A1 | 10/2000 |
| WO | WO-0132832 | A2 | 5/2001 |
| WO | WO-0135093 | A1 | 5/2001 |
| WO | WO-0168836 | A2 | 9/2001 |
| WO | WO-0175164 | A2 | 10/2001 |
| WO | WO-0191787 | A1 | 12/2001 |
| WO | WO-0212437 | A2 | 2/2002 |
| WO | WO-0244231 | A1 | 6/2002 |
| WO | WO-0244321 | A2 | 6/2002 |
| WO | WO-0246233 | A1 | 6/2002 |
| WO | WO-02059377 | A2 | 8/2002 |
| WO | WO-03005617 | A1 | 1/2003 |
| WO | WO-03008617 | A1 | 1/2003 |
| WO | WO-03029277 | A2 | 4/2003 |
| WO | WO-03086174 | A2 | 10/2003 |
| WO | WO-03087124 | A2 | 10/2003 |
| WO | WO-2004003554 | A1 | 1/2004 |
| WO | WO-2004076677 | A2 | 9/2004 |
| WO | WO-2005035579 | A1 | 4/2005 |
| WO | WO-2007016466 | A2 | 2/2007 |
| WO | WO-2008122007 | A1 | 10/2008 |
| WO | WO-2008138017 | A2 | 11/2008 |
| WO | WO-2009020923 | A1 | 2/2009 |
| WO | WO-2009088837 | A2 | 7/2009 |
| WO | WO-2010010549 | A2 | 1/2010 |
| WO | WO-2010075249 | A2 | 7/2010 |
| WO | WO-2011062997 | A2 | 5/2011 |
| WO | WO-2011062997 | A3 | 7/2011 |
| WO | WO-2011119058 | A2 | 9/2011 |
| WO | WO-2012167173 | A1 | 12/2012 |

OTHER PUBLICATIONS

Acevedo, V.D. et al., "Inducible FGFR-1 activation leads to irreversible prostate adenocarcinoma and an epithelial-to-mesenchymal transition", Cancer Cell, vol. 12, No. 6, pp. 559-571, (2007).

(56) References Cited

OTHER PUBLICATIONS

Agrawal, S, et al, "Antisense therapeutics: is it as simple as complementary base recognition?", Mol Med Today, vol. 6, No. 2, pp. 72-81, (2000).
Ai, J. et al., "DNA G-quadruplex-templated formation of the fluorescent silver nanocluster and its application to bioimaging", Talanta, vol. 88, pp. 450-455, (2012).
Aihara, M, et al, "Frequency of apoptotic bodies positively correlates With Gleason grade in prostate cancer", Hum Pathol, vol. 25, No. 8, pp. 797-801, (1994).
Aihara, M, et al, "The frequency of apoptosis correlates with the prognosis of Gleason Grade 3 adenocarcinoma of the prostate", Cancer, vol. 75, No. 2, pp. 522-529, (1995).
Akerman, M.E. et al., "Nanocrystal targeting in vivo", Proceedings of the National Academy of Sciences, vol. 99, No. 20, pp. 12617-12621, (2002).
Ali, S, et al, "Absorption, distribution, metabolism, and excretion of a respirable antisense oligonucleotide for asthma", Am J Respir Crit Care Med, vol. 163, No. 4, pp. 989-993, (2001).
Altman, S, "Nobel lecture. Enzymatic cleavage of RNA by RNA", Biosci Rep, vol. 10, No. 4, pp. 317-337, (1990).
Alvarex-Gonzalez, R, et al, "Selective loss of poly(ADP-ribose) and the 85-kDa fragment of ply(ADP-ribose) polymerase in nucleoli during alkylation-induced apoptosis of HeLa Cells", J Biol Chem., vol. 274, No. 45, pp. 32122-32126, (1999).
American Cancer Society, "Cancer Facts and Figures 2010" found at www.cancer.org/research/cancerfactsfigures/cancerfactsfigures/cancer-facts-and-figures-2010, pp. 1-62, (2010).
Anderson, H.J, et al, "Flow cytometry of mitotic cells", Exp Cell Research, vol. 238, No. 2, pp. 498-502, (1998).
Andrade, F, et al, "Apoptosis in systemic lupus erythematosus", Rheumatic Diseases Clinics of North America, vol. 2, (2000), vol. 26, No. 2, May 200. pp. 215-227.
Andrianasolo, E.H. et al., "DNA methyl transferase inhibiting halogenated monoterpenes from the Madagascar red marine alga *Portieria hornemannii*", Journal of Natural Products, vol. 69, No. 4, pp. 576-579, (2006).
Annunziata, C.M. et al., "PARP inhibitors in BRCA1 /BRCA2 germline mutation carriers with ovarian and breast cancer", F1000 Biology Reports, vol. 2, No. 10, pp. 1-4, (2010).
Aravind, A. et al., "AS1411 aptamer tagged PLGA-lecithin-PEG nanoparticles for tumor cell targeting and drug delivery", Biotechnology and Bioengineering, vol. 109, No. 11, pp. 2920-2931, (2012).
Atherton, et al. A study of rat epididymal sperm adenosine 3',5'-monophosphate-dependent protein kinases: maturation differences and cellular location. Biol Reprod. Feb. 1985;32(1):155-71.
Awang, G, et al, "Mode of dimerization of HIV-1 genomic RNA", Biochemistry, vol. 32, No. 42, pp. 11453-11457, (1993).
Bakhshi, et al. Cloning the chromosomal breakpoint of t(14;18) human lymphomas: clustering around JH on chromosome 14 and near a transcriptional unit. Cell. Jul. 1985;41(3):899-906.
Ballou, B, et al, Abstract of "Cyanine Fluorocrome-Labeled Antibodies In Vivo: Assessment of Tumor Imaging Using Cy3, Cy5, Cy5.5, and Cy7", Cancer Detect Prev, vol. 22, No. 3, pp. 251-257, (1998).
Ballou, B, et al, "Three-Dimensional Imaging of Nucleolin Traffocking in Normal Cells, Transfectants, and Heterokaryons", SPIE, vol. 2680, pp. 124-131, (1996).
Ballou, B, et al, "Tumor Detection and Visualization Using Cyanine Fluorochrome-Labeled Antibodies", Biotechnol Prog, vol. 13, pp. 649-658, (1997).
Ballou, B, et al, "Tumor Labeling in Vivo Using Cyanine-Conjugated Monoclonal Antibodies", Cancer Immunol Immunother, vol. 41, pp. 257-263, (1995).
Baniwal, S.K. et al., "Runx2 transcriptome of prostate cancer cells: insights into invasiveness and bone metastasis", Molecular Cancer, vol. 9, pp. 1-18, (2010).
Baran, N, et al, "The SV40 large T-antigen helicase can unwind four stranded DNA structures linked by G-quartets", Nucleic Acids Research, vol. 25, No. 2, pp. 297-303, (1997).
Barboric et al., "Interplay between 7SK snRNA and oppositely charged regions in HEXIM1 direct the inhibition of P-TEFb" The EMBO Journal., 24(24):4291-4303, 2005.
Barton, C.M, et al, "Antisense oligonucleotides directed against p53 have antiproliferative effects unrelated to effects on p53 expression", Br J Cancer, vol. 71, No. 3, pp. 429-437, (1995).
Bates, P.J, et al, "Antiproliferative activity of G-rich oligonucleotides correlates with protein binding", The Journal of Biological Chemistry, vol. 274, No. 37, pp. 26369-26377, (1999).
Bates, P.J. et al., "Discovery and development of the G-rich oligonucleotide AS1411 as a novel treatment for cancer", Experimental and molecular pathology, vol. 86, No. 3, pp. 151-164, (2009).
Bates, P.J. et al., "G-rich oligonucleotides for cancer treatment", Methods in Molecular Biology, vol. 542, pp. 379-392, (2009).
Beckman, R.A. et al., "Antibody constructs in cancer therapy", Cancer, vol. 109, No. 2, pp. 170-179, (2007).
Beedassy, A, et al, "Chemotherapy in advanced prostate cancer", Semin Oncol, vol. 26, No. 4, pp. 428-438, (1999).
Beltinger, C, et al, "Binding, uptake, and intracellular trafficking of phosphorothioate-modified oligodeoxynucleotides", J Clin Invest, vol. 95, No. 4, pp. 1814-1823, (1995).
Benimetskaya, L, et al, "Formation of a G-tetrad and higher order structures correlates with biological activity of the Re1A (NF-kappaB p65) 'antisense' oligodeoxynucleotide", Nucleic Acids Research, vol. 25, No. 13, pp. 2648-2656, (1997).
Benton, B.M, et al, "A novel FK506- and rapamycin-binding protein (FPR3 gene product) in the yeast *Saccharomyces cerevisiae* is a praline rotamase localized to the nucleolus", J Cell Biol, vol. 127, No. 3, pp. 623-639, (1994).
Bergsmedh, A, et al, "Horizontal transfer of oncogenes by uptake of apoptotic bodies", Proc Natl Acad Science USA, vol. 98, No. 11, pp. 6407-6411, (2001).
Bergsmedh, A, et al, "Loss of the p21(Cip1/Waf1) cyclin kinase inhibitor results in propagation of horizontally transferred DNA", Cancer Research, vol. 62, No. 2, pp. 575-579, (2002).
Bernardi, F.D, et al, "A prognostic model of survival in surgically resected squamous cell carcinoma of the lung using clinical, pathologic, and biologic markers", Mod Pathol, vol. 10, No. 10, pp. 992-1000, (1997).
Bernstein, E, et al, "Role for a bidentate ribonuclease in the initiation step of RNA interference", Nature, vol. 409, No. 6818, pp. 363-366, (2001).
Bharti, A.K, et al, "Identification of a nucleolin binding site in human topoisomerase I", J Biol Chem, vol. 271, No. 4, pp. 1993-1997, (1996).
Biggiogera, M, et al, "Heterogeneous ectopic RNP-derived structures (HERDS) are markers of transcriptional arrest", FASEB J, vol. 14, No. 5, pp. 828-834, (2000).
Biscotti, C.V, et al, "Apoptotic bodies: a consistent morphologic feature of endocervical adenocarcinoma in situ", American Journal of Surgical Pathology, vol. 22, No. 4, pp. 434-439, (1998).
Bishop, J.S, et al, "Intramolecular G-quartet motifs confer nuclease resistance to a potent anti-HIV oligonucleotide", J Biol Chem, vol. 271, No. 10, pp. 5698-5703, (1996).
Blau, H.M, et al, "Tet B or not tet B: Advances in tetracycline-inducible gene expression", Proc Natl Acad Science USA, vol. 96, pp. 797-799, (1999).
Bock, L.C, et al, "Selection of single-stranded DNA molecules that bind and inhibit human thrombin", Nature, vol. 355, No. 6360, pp. 564-566, (1992).
Boerner, et al. Production of antigen-specific human monoclonal antibodies from in vitro-primed human splenocytes. J Immunol. Jul. 1, 1991;147(1):86-95.
Bonkhoff, H. et al., "From pathogenesis to prevention of castration resistant prostate cancer", The Prostate, vol. 70, No. 1, pp. 100-112, (2010).
Borer, R.A, et al, "Major nucleolar proteins shuttle between nucleus and cytoplasm", Cell, vol. 56, No. 3, pp. 379-390, (1989).
Borggrefe, T, et al, "A B-cell-specific DNA recombination complex", J Biol Chem, vol. 273, No. 27, pp. 17025-17035, (1998).

(56) References Cited

OTHER PUBLICATIONS

Borst, P, et al, "Does resistance to apoptosis affect clinical response to antitumor drugs?", Drug Resist Update, vol. 4, No. 2, pp. 129-131, (2001).
Bortul, R, et al, "Nuclear changes in necrotic HL-60 cells", J Cell Biochem, vol. 81, No. S36, pp. 19-31, (2001).
Bose, et al. Role of nucleolin in human parainfluenza virus type 3 infection of human lung epithelial cells. J Virol. Aug. 2004;78(15):8146-58.
Boulares, A.H, et al, "Role of poly (ADP-ribose) polymerase (PARP) cleavage in apoptosis. Caspase 3-resistant PARP mutant increases rates of apoptosis in transfected cells", Journal of Biochemical Chemistry, vol. 274, No. 33, pp. 22932-22940, (1999).
Boulares, A.H, et al, "Roles of DNA fragmentation factor and poly(ADP-ribose) polymerase in an amplification phase of tumor necrosis factor-induced apoptosis", Journal of Biological Chemistry, vol. 276, No. 41, pp. 38185-38192, (2001).
Boyd, et al. The effect of the removal of sialic acid, galactose and total carbohydrate on the functional activity of Campath-1H. Mol Immunol. Dec. 1995;32(17-18):1311-8.
Brockstedt, E, et al, "Identification of apoptosis-associated proteins in a human Burkitt lymphoma cell line. Cleavage of heterogeneous nuclear ribonucleoprotein A1 by caspase 3", J Biol Chem, vol. 273, No. 43, pp. 28057-28064, (1998).
Brown, J.M, et al, "Apoptosis:mediator or mode of cell killing by anticancer agents?", Drug Resist Update, vol. 4, No. 2, pp. 135-136, (2001).
Bruckner, R.C. et al., "The histone-like H protein of *Escherichia coli* is ribosomal protein S3", Nucleic Acids Research, vol. 17, No. 8, pp. 3145-3161, (1989).
Bruggemann, et al. Designer mice: the production of human antibody repertoires in transgenic animals. Year Immunol. 1993;7:33-40.
Brustmann, H, "Apoptotic bodies as a morphological feature in serous ovarian carcinoma: correlation with nuclear grade, Ki-67 and mitotic indices", Pathol Res Pract, vol. 198, No. 2, pp. 85-90, (2002).
Budman, D.R. et al., "Identification of potentially useful combinations of epidermal growth factor receptor tyrosine kinase antagonists with conventional cytotoxic agents using median effect analysis", Anti-cancer Drugs, vol. 17, No. 8, pp. 921-928, (2006).
Burgess, T.L, et al, "The antiproliferative activity of c-myb and c-myc antisense oligonucleotides in smooth muscle cells is caused by a nonantisense mechanism", Proc Natl Acad Science USA, vol. 92, No. 9, pp. 4051-4055, (1995).
Buys, C.H, "Telomeres, telomerase, and cancer", N Engl J Med, vol. 342, No. 17, pp. 1282-1283, (2000).
Cajaiba, M.M. et al., "Sox9 expression is not limited to chondroid neoplasms: variable occurrence in other soft tissue and bone tumors with frequent expression by synovial sarcomas", International Journal of Surgical Pathology, vol. 18, No. 5, pp. 319-323, (2010).
Callebaut, C, et al, "Identification of V3 loop-binding proteins as potential receptors implicated in the binding of HIV particles to CD4(+) cells", J Biol Chem, vol. 273, No. 34, pp. 21988-21997, (1998).
Cannavo, G, et al, "Abnormal intracellular kinetics of cell-cycle-dependent proteins in lymphocytes from patients infected with human immunodeficiency virus: a novel biologic link between immune activation, accelerated t-cell turnover, and high levels of apoptosis", Blood, vol. 97, No. 6, pp. 1756-1764, (2001).
Cao, Z. et al., "Reversible cell-specific drug delivery with aptamer-functionalized liposomes", Angewandte Chemie International Edition, vol. 48, issue 35, pp. 6494-6498, (2009).
Carney, D.N, et al, "Establishment and identification of small cell lung cancer cell lines having classic and variant features", Cancer Research, vol. 45, pp. 2913-2923, (1985).
Carvalho, P.E, et al, "Useful prognostic panel markers to express the biological tumor status in resected lung adenocarcinomas", Jpn J Clin Oncol, vol. 30, No. 11, pp. 478-486, (2000).
Cech, T.R, "Biologic catalysis by RNA", Harvey Lect, vol. 82, pp. 123-144, (1988).
Chames, P. et al., "Therapeutic antibodies: successes, limitations and hopes for the future", British Journal of Pharmacology, vol. 157, pp. 220-233, (2009).
Chen, et al. AU binding proteins recruit the exosome to degrade ARE-containing mRNAs. Cell. Nov. 16, 2001;107(4):451-64.
Chen, et al. Cell surface nucleolin serves as receptor for DNA nanoparticles composed of pegylated polylysine and DNA. Mol. Ther. 2008; 16(2):333-45.
Chen, et al. Nucleolin and YB-1 are required for JNK-mediated interleukin-2 mRNA stabilization during T-cell activation. Genes Dev. May 15, 2000;14(10):1236-48.
Chern, J.H, et al, "Usefulness of AgNOR score in differentiating benign from malignant pulmonary aspiration cytology", Acta Cytol, vol. 41, No. 2, pp. 393-398, (1997).
Choi, J.H. et al., "DNA aptamer-passivated nanocrystals synthesis: A facile approach for nanoparticles-based cancer cell growth inhibition", Small, vol. 5, No. 6, pp. 672-675, (2009).
Choi, N.G, et al, "Apoptosis and nuclear shapes in benign prostate hyperplasia and prostate adenocarcinoma: comparison with and relation to Gleason score", Int J Urol, vol. 6, No. 1, pp. 13-18, (1999).
Christian, S. et al., "Nucleolin expressed at the cell surface is a marker of endothelial cells in angiogenic blood vessels", The Journal of Cell Biology, vol. 163, No. 4, pp. 871-878, (2003).
Clackson, et al. Making antibody fragments using phage display libraries. Nature. Aug. 15, 1991;352(6336):624-8.
Clarke. M.F. et al., "Stem Cells: The Real Culprits in Cancer?", Scientific American, 295, 1, pp. 52-59, (2006).
Cole et al., "The EBV-hybridoma technique and its application to human lung cancer," In: Monoclonal Antibodies and Cancer Therapy, vol. 27, UCLA Symposia on Molecular and Cellular Biology, New Series, Eds. R.A. Reisfeld and S.Sell, pp. 77-96, Alan R. Liss, Inc. N.Y., 1985.
Cole, S.P, et al, "Antibody production by human X human hybridomas in serum-free medium", J Immunol Methods, vol. 78, No. 2, pp. 271-278, (1985).
Coligan, J.E. et al, "Production of Monoclonal Antibodies", Current Protocols in Immunology, vol. 1, pp. 2.5.1-2.6.7, Wiley, New York, (1991).
Coqueret, O, et al, "Functional interaction of STAT3 transcription factor with the cell cycle inhibitor p21.sup.WAF1/CIP1/SDI1", J Biol Chem, vol. 275, No. 25, pp. 18794-18800, (2000).
Cowan, K.H, et al, "Dihydrofolate reductase gene amplification and possible rearrangement in estrogen-responsive methotrexate-resistant human breast cancer cells", J Biol Chem, vol. 257, No. 24, pp. 15079-15086, (1982).
Crooke, S, "Oligonucleotide therapeutics: a prospectus" Antisense Research and Development, vol. 3, No. 1, pp. 1-2, (1993).
Crooke, S, "Progress in antisense technology: the end of the beginning", Methods Enzymol, vol. 313, pp. 3-45, (1999).
Cunningham, et al. High-resolution epitope mapping of hGH-receptor interactions by alanine-scanning mutagenesis. Science. Jun. 2, 1989;244(4908):1081-5.
Cylene Pharmaceuticals, Quarfloxin Nucleolus Targeting Agent (CX-3543), Quarfloxin QPLX/Nucleolin Inhibitor (CX-3543), 1 page, printed on Jan. 21, 2010.
Dagle, J.M, et al, "Selective degradation of targeted mRNAs using partially modified oligonucleotides", Methods Enzymol, vol. 313, pp. 420-436, (1999).
Dam, D.H.M. et al., "Direct observation of nanoparticle-cancer cell nucleus interactions", ACS Nano, vol. 6, No. 4, pp. 3318-3326, (2012).
D'Amours, D, et al, "Poly(ADP-ribosyl)ation reactions in the regulation of nuclear functions", Biochem J, vol. 342, pt. 2, pp. 249-268, (1999).
Daniely, Y, et al, "Formation of a complex between nucleolin and replication protein A after cell stress prevents initiation of DNA replication", J Cell Biology, vol. 149, No. 4, pp. 799-810, (2000).
Dapic, V, et al, "Antiproliferative activity of G-Quartet-forming oligonucleotides with backbone and sugar modifications", Biochemistry, vol. 41, No. 11, pp. 3676-3685, (2002).

(56) References Cited

OTHER PUBLICATIONS

Datasheet [Online], Santa Cruz Biotechnology, http://datasheets.scbt.com/sc-17826. pdf, retrieved on Dec. 19, 2014.
Datasheet [Online], Santa Cruz Biotechnology, http://datasheets.scbt.com/sc-55486. pdf, retrieved on Dec. 19, 2014.
David, K, et al, "Initial characterization of the apoptosis-inducing receptor for natural human anti-neuroblastoma IgM", Med Pediatr Oncol, vol. 36, No. 1, pp. 251-257, (2001).
David-Pfeuty, T, "Potent inhibitors of cyclin-dependent kinase 2 induce nuclear accumulation of wild-type p53 and nucleolar fragmentation in human untransformed and tumor-derived cells", Oncogene, vol. 18, No. 52, pp. 7409-7422, (1999).
Davis, K.A, et al, "Staining of cell surface human CD4 with 2'-F-pyrimidine-containing RNA aptamers for flow cytometry", Nucleic Acids Research, vol. 26, pp. 3915-3924, (1998).
De Bont, J.M. et al., "Differential expression and prognostic significance of SOX genes in pediatric medulloblastoma and ependymoma identified by microarray analysis", Neuro-Oncology, vol. 10, No. 5, pp. 648-660, (2008).
De Jong, J.S, et al, "Number of apoptotic cells as a prognostic marker in invasive breast cancer", Br J Cancer, vol. 82, No. 2, pp. 368-373, (2000).
Dempsey, L.A, et al, "A specific isoform of hnRNP D interacts with DNA in the LR1 heterodimer: canonical RNA binding motifs in a sequence-specific duplex DNA binding protein", J Biol Chem, vol. 273, No. 44, pp. 29224-29229, (1998).
Dempsey, L.A, et al, "G4 DNA binding by LR1 and its subunits, nucleolin and hnRNP D, A role for G-G pairing in immunoglobulin switch recombination", J Biol Chem, vol. 274, No. 2, pp. 1066-1071, (1999).
Deng, J.S, et al, "Internalization of anti-nucleolin antibody into viable HEp-2 cells", Mol Biol Rep, vol. 23, No. 3-4, pp. 191-195, (1996).
Derenzini, M. "The AgNORs", Micron, vol. 31, No. 2, pp. 117-120, (2000).
Derezini, M, et al, "The quantity of nucleolar proteins nucleolin and protein B23 is related to cell doubling time in human cancer cells", Lab Invest, vol. 73, No. 4, pp. 497-502, (1995).
Desnoyers, S, et al, "Alteration of the nucleolar localization of poly(ADP-ribose) polymerase upon treatment with transcription inhibitors", Exp Cell Research, vol. 227, No. 1, pp. 146-153, (1996).
Destouches, D. et al., "Suppression of tumor growth and angiogenesis by a specific antagonist of the cell-surface expressed nucleolin", Plos One, vol. 3, issue 6, e2518, pp. 1-12, (2008).
Dholakia, et al. Photoaffinity labeling of the rabbit reticulocyte guanine nucleotide exchange factor and eukaryotic initiation factor 2 with 8-azidopurine nucleotides. Identification of GTP- and ATP-binding domains. J Biol Chem. Dec. 5, 1989;264(34):20638-42.
Dickinson, L.A, et al, "Nucleolin is a matrix attachment region DNA-binding protein that specifically recognizes a region with base-unpairing potential", Mol Cell Biology, vol. 15, No. 1, pp. 456-465, (1995).
Dranovsky, A, et al, "Cdc2 phosphorylation of nucleolin demarcates mitotic stages and alzheimer's disease pathology", Neurobiol Aging, vol. 22, No. 4, pp. 517-528, (2001).
Drews, J, "Drug discovery: a historical perspective", Science, vol. 287, No. 5460, pp. 1960-1964, (2000).
Drews J, et al, "Classic drug targets (special pull-out)", Nature Biotechnology, vol. 15, (1997).
Dryden, S, et al, "The lack of specificity of neuropeptide Y (NPY) antisense oligodeoxynucleotides administered intracerebroventricularly in inhibiting food intake and NPY gene expression in the rat hypothalamus", J Endocrinol, vol. 157, No. 1, pp. 169-175, (1998).
Dudley, A.G. et al., "Calcification of multi-potent, prostate tumor endothelium", Cancer Cell, vol. 14, No. 3, pp. 201-211, (2008).
Duhagon, M.A. et al., "Genomic profiling of tumor initiating prostatospheres", BMC Genomics, vol. 11, No. 324, pp. 1-16, (2010).
Dumler, I, et al, "Urokinase-induced mitogenesis is mediated by casein kinase 2 and nucleolin", Curr Biol, vol. 9, No. 24, pp. 1468-1476, (1999).
Dundr, M, et al, "The dynamics of postmitotic reassembly of the nucleolus", J Cell Biol, vol. 150, No. 3, pp. 433-446, (2000).
Edwards, T.K, et al, "Role for nucleolin/Nsr1 in the cellular localization of topoisomerase I", J Biol Chem, vol. 275, No. 46, pp. 36181-36188, (2000).
Egorin, M.J. et al., "In vitro metabolism by mouse and human liver preparations of halomon, an antitumor halogenated monoterpene", Cancer Chemother Pharmacol, vol. 41, No. 1, pp. 9-14, (1997).
Egorin, M.J. et al., "Plasma pharmacokinetics, bioavailability, and tissue distribution in CD2F1 mice of halomon, an antitumor halogenated monoterpene isolated from the red algae *Portieria hornemannii*", Cancer Chemother Pharmacol, vol. 39, No. 1-2, pp. 51-60, (1996).
Eguchi, K, "Apoptosis in autoimmune diseases", Intern Med, vol. 40, No. 4, pp. 275-284, (2001).
Endo, Y. et al., "Role of Sox-9, ER81 and VE-cadherin in retinoic acid-mediated trans-differentiation of breast cancer cells", PLoS One, vol. 3, issue 7, pp. 1-11, (2008).
English translation of Office Communication issued in Japanese Patent Application No. 2012/539082, dated Dec. 25, 2014.
Eppstein, et al. Biological activity of liposome-encapsulated murine interferon gamma is mediated by a cell membrane receptor. Proc Natl Acad Sci U S A. Jun. 1985;82(11):3688-92.
Erard, M.S, et al, "A major nucleolar protein, nucleolin, induces chromatin decondensation by binding to histone H1", Eur J Biochem, vol. 175, No. 3, pp. 525-530, (1988).
Euhus, D.M. et al., "Tumor measurement in the nude mouse", Journal of Surgical Oncology, vol. 31, issue 4, pp. 229-234, (1986).
European Search Report dated Oct. 25, 2006 for European application No. 03762073.9.
European Search Report for a corresponding Application No. 03728350.4 dated Jul. 12, 2005.
Evan, et al. Isolation of monoclonal antibodies specific for human c-myc proto-oncogene product. Mol Cell Biol. Dec. 1985;5(12):3610-6.
Extended European Search Report issued in European Patent Application No. 10832109.2, dated Apr. 18, 2013.
Facompre, M, et al, "Apoptotic response of HL-60 human leukemia cells to the antitumor drug NB-506, a glycosylated indolocarbazole inhibitor of topoisomerase 1", Biochem Pharmacol, vol. 61, No. 3, pp. 299-310, (2001).
Farin, et al. Structure-function analysis of nucleolin and ErbB receptors interactions. PLoS One. Jul. 3, 2009;4(7):e6128. doi: 10.1371/journal.pone.0006128.
Fellouse, et al. Synthetic antibodies from a four-amino-acid code: a dominant role for tyrosine in antigen recognition. Proc Natl Acad Sci U S A. Aug. 24, 2004;101(34):12467-72. Epub Aug. 11, 2004.
Feltzer, R.E, et al, "Alkaline proteinase inhibitor of Pseudomonas aeruginosa. Interaction of native and N-terminally truncated inhibitor proteins with Pseudomonas metalloproteinases", J Biol Chem, vol. 275, No. 28, pp. 21002-21009, (2000).
Field, et al. Purification of a RAS-responsive adenylyl cyclase complex from *Saccharomyces cerevisiae* by use of an epitope addition method. Mol Cell Biol. May 1988;8(5):2159-65.
Fielding, P, et al, "Heterogeneous nuclear ribonucleoprotein A2/B1 up-regulation in bronchial lavage specimens: a clinical marker of early lung cancer detection", Clinical Cancer Research, vol. 5, No. 12, pp. 4048-4052, (1999).
Fishwild, et al. High-avidity human IgG kappa monoclonal antibodies from a novel strain of minilocus transgenic mice. Nat Biotechnol. Jul. 1996;14(7):845-51. Nat Biotechnol. Jul. 1996;14(7):845-51.
Fogal, V. et al., "Cell surface nucleolin antagonist causes endothelial cell apoptosis and normalization of tumor vasculature", Angiogenesis, vol. 12, No. 1, pp. 91-100, (2009).
Friedmann, T. Overcoming the obstacles to gene therapy. (Scientific American Jun. 1997, p. 96-101.
Fry, M, et al, "Human Werner syndrome DNA helicase unwinds tetrahelical structures of the fragile X syndrome repeat sequence d(CGG)n", J Biol Chem, vol. 274, No. 18, pp. 12797-12802, (1999).

(56) References Cited

OTHER PUBLICATIONS

Fry, M, et al, "The fragile X syndrome d(CGG)n nucleotide repeats form a stable tetrahelical structure", Proc Natl Acad Science USA, vol. 91, No. 11, pp. 4950-4954, (1994).
Fuller, R.W. et al., "A pentahalogenated monoterpene from the red alga *Portieria hornemannii* produces a novel cytotoxicity profile against a diverse panel of human tumor cell lines", Journal of Medicinal Chemistry, vol. 35, No. 16, pp. 3007-3011, (1992).
Fuller, R.W. et al., "Isolation and structure/activity features of halomon-related antitumor monoterpenes from the red alga *Portieria hornemannii*", Journal of Medicinal Chemistry, vol. 37, No. 25, pp. 4407-4411, (1994).
Gabizon, et al. Pharmacokinetics and tissue distribution of doxorubicin encapsulated in stable liposomes with long circulation times. J Natl Cancer Inst. Oct. 4, 1989;81(19):1484-8.
Gascoyne, R.D, et al, "Prognostic significance of Bcl-2 protein expression and Bcl-2 gene rearrangement in diffuse aggressive non-Hodgkin's lymphoma", Blood, vol. 90, No. 1, pp. 244-251, (1997).
Gattoni-Celli, et al. Overexpression of nucleolin in engrafted acute myelogenous leukemia cells. Am J Hematol. Aug. 2009;84(8):535-8. doi: 10.1002/ajh.21461.
Gautier, F, et al, "Identification of an apoptotic cleavage product of BARD1 as an autoantigen: a potential factor in the antitumoral response mediated by apoptotic bodies", Cancer Research, vol. 60, No. 24, pp. 6895-6900, (2000).
Gautier, F, et al, "Production and characterisation of a monoclonal antibody specific for apoptotic bodies derived from several tumour cell lines", Journal of Immunological Methods, vol. 228, pp. 49-58, (1999).
Gavrieli, Y, et al, "Identification of programmed cell death in situ via specific labeling of nuclear DNA fragmentation", The Journal of Cell Biology, vol. 119, No. 3, pp. 493-501, (1992).
Geahlen, et al. Induction of a substrate for casein kinase II during lymphocyte mitogenesis. Biochim Biophys Acta. Jun. 19, 1984;804(2):169-75.
Gey, G, et al, "Tissue culture studies of the proliferative capacity of cervical carcinoma and normal epithelium", Cancer Research, vol. 12, pp. 264-265, (1952).
Ghosh, M, et al, "Apoptosis in squamous cell carcinoma of the lung: correlation with survival and clinicopathological features", J Clin Pathol, vol. 54, No. 2, pp. 111-115, (2001).
Giaccone, G, et al, "Neuromedin B is present in lung cancer cell lines", Cancer Research, vol. 52, pp. 2732s-2736s, (1992).
Gibbs, J.B, "Mechanism-based target identification and drug discovery in cancer research", Science, vol. 287, No. 5460, pp. 1969-1973, (2000).
Gil, D, et al, "Intracellular redistribution of nucleolin upon interaction with the CD3epsilon chain of the T cell receptor complex", J Biol Chem, vol. 276, No. 14, pp. 11174-11179, (2001).
Giles, R.V, et al, "Selecting optimal oligonucleotide composition for maximal antisense effect following streptolysin O-mediated delivery into human leukaemia cells", Nucleic Acids Research, vol. 26, No. 7, pp. 1567-1575, (1998).
Gilloteaux, J. et al., "Cancer cell necrosis by autoschizis: Synergism of antitumor activity of vitamin C: vitamin K3 on human bladder carcinoma T24 cells", Scanning, vol. 20, No. 8, pp. 564-575, (1998).
Ginisty, et al. Two different combinations of RNA-binding domains determine the RNA binding specificity of nucleolin. J Biol Chem. Apr. 27, 2001;276(17):14338-43. Epub Jan. 18, 2001.
Ginisty, H, et al, "Structure and functions of nucleolin", J Cell Science, vol. 112, Pt. 6, pp. 761-772, (1999).
Giovannangeli, C. et al., "Progress in developments of triplex-based strategies", Antisense & Nucleic Acid Drug Development, vol. 7, No. 4, pp. 413-421, (1997).
Giraldo, R, et al, "The yeast telomere-binding protein RAP1 binds to and promotes the formation of DNA quadruplexes in telomeric DNA", EMBO J, vol. 13, No. 10, pp. 2411-2420, (1994).
Girvan, A.C. et al., "AGRO100 inhibits activation of nuclear factor-.kappa.b (NF-.kappa.B) by forming a complex with NF-.kappa.B essential modulator (NEMO) and nucleolin", Molecular Cancer Therapeutics, vol. 5, No. 7, pp. 1790-1799, (2006).
Gougeon, M-L. et al., "Programmed cell death in peripheral lymphocytes from HIV-Infected persons", The Journal of Immunology, vol. 156, pp. 3509-3520, (1996).
Green, C. et al., "Anti-tumor efficacy and pharmacokinetics of the novel aptamer AS1411 in a continuous infusion nude rat xenograft model", Proceedings of the 101st Annual Meeting of the American Association for Cancer Research, Abstract No. 2614, Apr. 17-21, 2010.
Green, D. W, et al, "Beta-catenin antisense treatment decreases beta-catenin expression and tumor growth rate in colon carcinoma xenografts", J Surg Res, vol. 101, No. 1, pp. 16-20, (2001).
Grinstein, E. et al., "Cellular signaling in normal and cancerous stem cells", Cellular Signaling, 19, pp. 2428-2433, (2007).
Grinstein, E, et al, "Nucleolin as Activator of Human Papillomavirus Type 18 Oncogene Transcription in Cervical Cancer", J Exp Med, vol. 196, No. 8, pp. 1067-1078, The Rockefeller University Press, (2002).
Grinstein, E. et al., "Nucleolin Regulates Gene Expression in CD34-positive Hematopoietic Cells", The Journal of Biological Chemistry, vol. 282, No. 17, pp. 12439-12449, (2007).
Gudas, J.M, et al, "Drug-resistant breast cancer cells frequently retain expression of a functional wild-type p53 protein", Carcinogenesis, vol. 17, No. 7, pp. 1417-1427, (1996).
Guo, J. et al., "Aptamer-functionalized PEG-PLGA nanoparticles for enhanced anti-glioma drug delivery", Biomaterials, vol. 32, pp. 8010-8020, (2011).
Guo, K-T. et al., "A new technique for the isolation and surface immobilization of mesenchymal stem cells from whole bone marrow using high-specific DNA aptamers", Stem Cells, vol. 24, pp. 2220-2231, (2006).
Gura, T. "Systems for identifying new drugs are often faulty", Science, vol. 278, pp. 1041-1042, (1997).
Haese, A, "Serum markers for early detection and staging of prostate cancer, status report on current and future markers", Urologe A, vol. 42, No. 9, pp. 1172-1187, (2003.—(Abstract Only).
Halicka, H.D, et al, "Segregation of RNA and separate packaging of DNA and RNA in apoptotic bodies during apoptosis", Exp Cell Research, vol. 260, No. 2, pp. 248-256, (2000).
Hammerling et al., in: Monoclonal Antibodies and T-Cell Hybridomas, pp. 563-681, Elsevier, N.Y., 1981.
Hanada, et al. Antibody and Aptamer. Protein, Nucleic Acid and Enzyme, 2004, vol. 49, No. 17, pp. 2671-2677.
Hanahan, D, et al, "The hallmarks of cancer", Cell, vol. 100, No. 1, pp. 57-70, (2000).
Hanakahi, L.A, et al, "High affinity interactions of nucleolin with G-G-paired rDNA", J Biol Chem, vol. 274, No. 22, pp. 15908-15912, (1999).
Hanakahi, L.A, et al, "Nucleolin is one component of the B cell-specific transcription factor and switch region binding protein, LR1", Proc Natl Acad Science USA, vol. 94, No. 8, pp. 3605-3610, (1997).
Harlow et al., Antibodies: A Laboratory Manual, Cold Spring Harbor Laboratory Press, 2nd ed. 1988.
Harms, G, et al, "Identification of nucleolin as a new L-selectin ligand", Biochem J, vol. 360, pp. 531-538, (2001).
Harris. Production of humanized monoclonal antibodies for in vivo imaging and therapy. Biochem Soc Trans. Nov. 1995;23(4):1035-8.
Herceg, Z, et al, "Failure of poly(ADP-ribose) polymerase cleavage by caspases leads to induction of necrosis and enhanced apoptosis", Mol Cell Biol, vol. 19, No. 7, pp. 5124-5133, (1999).
Hirata, D, et al, "Nucleolin as the earliest target molecule of autoantibodies produced in MRL/Ipr lupus-prone mice", Clin Immunol, vol. 97, No. 1, pp. 50-58, (2000).
Hirsch, F.R, et al, "Early detection of lung cancer: clinical perspectives of recent advances in biology and radiology", Clinical Cancer Research, vol. 7, No. 1, pp. 5-22, (2001).
Holdenrieder, S, et al, "Circulating nucleosomes in serum", Annals New York Academy of Sciences, vol. 945, pp. 93-102, (2001).
Holdenrieder, S, et al, "Nucleosomes in serum as a marker for cell death", Clin Chem Lab Med, vol. 39, No. 7, pp. 596-605, (2001).

(56) References Cited

OTHER PUBLICATIONS

Holdenrieder, S, et al, "Nucleosomes in serum of patients with benign and malignant diseases", Int. J. Cancer, vol. 95, pp. 114-120, (2001).
Holdenrieder, S, et al, "Quantification of nucleosomes in serum by the cell death detection ELISAplus", Biochemica, No. 1, pp. 25-27, (2002), (http://www.roche-applied-science.com/biochemica/no1.sub.--02/PDF/p25.pdf- ).
Holliger, et al. "Diabodies": small bivalent and bispecific antibody fragments. Proc Natl Acad Sci U S A. Jul. 15, 1993;90(14):6444-8.
Holmgren, L, et al, "Horizontal transfer of DNA by the uptake of apoptotic bodies", Blood, vol. 93, No. 11, pp. 3956-3963, (1999).
Hongo, et al. Development and characterization of murine monoclonal antibodies to the latency-associated peptide of transforming growth factor beta 1. Hybridoma. Jun. 1995;14(3):253-60.
Hoogenboom, et al. By-passing immunisation. Human antibodies from synthetic repertoires of germline VH gene segments rearranged in vitro. J Mol Biol. Sep. 20, 1992;227(2):381-8.
Hopp, et al. A short polypeptide marker sequence useful for recombinant protein identification and purification. Bio/Technology. 1988; 6:1204-1210.
Horky, M, et al, "Segregation of nucleolar components coincides with caspase-3 activation in cisplatin-treated HeLa cells", J Cell Science, vol. 114, pt. 4, pp. 663-670, (2001).
Hovanessian, A.G, et al, "The cell-surface-expressed nucleolin is associated with the actin cytoskeleton", Experimental Cell Research, vol. 261, pp. 312-328, (2000).
Hovanessian. Midkine, a cytokine that inhibits HIV infection by binding to the cell surface expressed nucleolin. Cell Res. Feb. 2006;16(2):174-81.
Hsu, et al. Differential N-glycan patterns of secreted and intracellular IgG produced in Trichoplusia ni cells. J Biol Chem. Apr. 4, 1997;272(14):9062-70.
Huang, E.H. et al., "Cancer stem cells: A new paradigm for understanding tumor progression and therapeutic resistance", Surgery, vol. 141, pp. 415-419, (2007).
Huang, Y. et al., "The angiogenic function of nucleolin is mediated by vascular endothelial growth factor and nonmuscle myosin", Blood, vol. 107, No. 9, pp. 3564-3571, (2006).
Huang, Z, "Bcl-2 family proteins as targets for anticancer drug design", Oncogene, vol. 19, No. 56, pp. 6627-6631, (2000).
Huch, M. et al., "Sox9 marks adult organ progenitors", Nature Genetics, vol. 43, No. 1, pp. 9-10, (2011).
Hudson, et al. Engineered antibodies. Nat Med. Jan. 2003;9(1):129-34.
Hurle, et al. Protein engineering techniques for antibody humanization. Curr Opin Biotechnol. Aug. 1994;5(4):428-33.
Hwang, D.W. et al., "A nucleolin-targeted multimodal nanoparticle imaging probe for tracking cancer cells using an aptamer", Journal of Nuclear Medicine, vol. 51, No. 1, pp. 98-105, (2010).
Hwang, et al. Hepatic uptake and degradation of unilamellar sphingomyelin/cholesterol liposomes: a kinetic study. Proc Natl Acad Sci U S A. Jul. 1980;77(7):4030-4.
Iida, A, et al, "Inducible gene expression by retrovirus-mediated transfer of a modified tetracycline-regulated system", J Birol, vol. 70, No. 9, pp. 6054-6059, (1996).
ImmuPharma, Treatment for Cancer (IPP-204106), pp. 1-3, found at http://immupharma.com/cancer.html, printed on Jan. 21, 2010.
International Search Report and Written Opinion of the International Searching Authority for PCT/US2004/033174 dated Mar. 14, 2005.
International Search Report dated Aug. 3, 2004 for PCT application No. PCT/US03/10745.
International Search Report dated Nov. 13, 2003 for PCT application No. PCT/US03/20167.
International Search Report dated Sep. 19, 2012 for PCT application No. PCT/US2012/040577.
Invitation to Pay Additional Fees and International Fees and Partial Search Report dated Jul. 14, 2009 for PCT/US2008/088491.
Irving, R.A, et al, "Ribosome display and affinity maturation: from antibodies to single v-domains and steps towards cancer therapeutics", J Immunol Methods, vol. 248, issues 1-2, pp. 31-45, (2001).
Ishikawa, F, et al, "Nuclear proteins that bind the pre-mRNA 3' splice site sequence r(UUAG/G) and the human telomeric DNA sequence d(TTAGGG)n", Mol Cell Biology, vol. 13, No. 7, pp. 4301-4310, (1993).
Ishimaru, et al. Regulation of Bcl-2 expression by HuR in HL60 leukemia cells and A431 carcinoma cells. Mol Cancer Res. Aug. 2009;7(8):1354-66. doi: 10.1158/1541-7786.MCR-08-0476. Epub Aug. 11, 2009.
Issa, J-P.J. et al., "Targeting DNA methylation", Clinical Cancer Research, vol. 15, No. 12, pp. 3938-3946, (2009).
Izumi, et al. Nucleolin stimulates viral internal ribosome entry site-mediated translation. Virus Res. Jul. 2001;76(1):17-29.
Jain, K.K. "Advances in the field of nanooncology", BMC Medicine, vol. 8, No. 83, pp. 1-11, (2010).
Jakobovits, et al. Analysis of homozygous mutant chimeric mice: deletion of the immunoglobulin heavy-chain joining region blocks B-cell development and antibody production. Proc Natl Acad Sci U S A. Mar. 15, 1993;90(6):2551-5.
Jakobovits, et al. Germ-line transmission and expression of a human-derived yeast artificial chromosome. Nature. Mar. 18, 1993;362(6417):255-8.
Javier, D.J. et al., "Aptamer-targeted gold nanoparticles as molecular-specific contrast agents for reflectance imaging", Bioconjugate Chemistry, vol. 19, No. 6, pp. 1309-1312, (2008).
Jefferis, et al. Glycosylation of antibody molecules: structural and functional significance. Chem Immunol. 1997;65:111-28.
Jiang, S.S. et al., "Upregulation of SOX9 in Lung Adenocarcinoma and Its Involvement in the Regulation of Cell Growth and Tumorigenicity", Clinical Cancer Research, vol. 16, pp. 4363-4373, (2010).
Jones, et al. Replacing the complementarity-determining regions in a human antibody with those from a mouse. Nature. May 29-Jun. 4, 1986;321(6069):522-5.
Jordan, P, et al, "Major cell surface-located protein substrates of an ecto-protein kinase are homologs of known nuclear proteins", Biochemistry, vol. 33, No. 49, pp. 14696-14706, (1994).
Jungblut, P.R, et al, "Proteomics in human disease: cancer, heart and infectious diseases", Electrophoresis, vol. 20, No. 10, pp. 2100-2110, (1999).
Kamma, H, et al, "Interaction of hnRNP A2/B1 isoforms with telomeric ssDNA and the in vitro function", Biochem Biophys Res Commun, vol. 280, No. 3, pp. 625-630, (2001).
Kaneko, S, et al, "Nucleolar organizer regions as a prognostic indicator for stage I non-small cell lung cancer", Cancer Research, vol. 51, No. 15, pp. 4008-4011, (1991).
Kang, W.J. et al., "Multiplex imaging of single tumor cells using quantum-dot-conjugated aptamers", Small, vol. 5, No. 22, pp. 2519-2522, (2009).
Kennedy, T.C, et al, "Screening for lung cancer revisited and the role of sputum cytology and fluorescence bronchoscopy in a high-risk group", Chest, vol. 117, supplemental 4, pp. 72S-79S, (2000).
Keough, T, et al, "A method for high-sensitivity peptide sequencing using postsource decay matrix-assisted laser desorption ionization mass spectrometry", Proc Natl Acad Science USA, vol. 96, No. 13, pp. 7131-7136, (1999).
Kerr, J.F, et al, "Apoptosis: a basic biological phenomenon with wide-ranging implications in tissue kinetics", Br J Cancer, vol. 26, pp. 239-257, (1972).
Ketting, R.F, et al, "Dicer functions in RNA interference and in synthesis of small RNA involved in developmental timing in C elegans", Genes Dev, vol. 15, No. 20, pp. 2654-2659, (2001).
Khatoon, et al. Aberrant guanosine triphosphate-beta-tubulin interaction in Alzheimer's disease. Ann Neurol. Aug. 1989;26(2):210-5.
Khleif, S.N. et al., "AACR-FDA-NCI Cancer Biomarkers Collaborative consensus report: advancing the use of biomarkers in cancer drug development", Clinical Cancer Research, vol. 16, pp. 3299-3318, (2010).
Kibbey, M.C, et al, "A 110-kD nuclear shuttling protein, nucleolin, binds to the neurite-promoting IKVAV site of laminin-1", J Neurosci Research, vol. 42, No. 3, pp. 314-322, (1995).

(56) References Cited

OTHER PUBLICATIONS

Kim, C.S, et al, "A micro double capillary method for rheologic measurements of lower airway secretions", Bull Eur Physiopathol Respir, vol. 18, pp. 915-927, (1982).
Kim, et al. Specific intermediates in the folding reactions of small proteins and the mechanism of protein folding. Annu Rev Biochem. 1982;51:459-89.
Kim, J.K. et al., "Molecular imaging of a cancer-targeting theragnostics probe using a nucleolin aptamer- and microRNA-221 molecular beacon-conjugated nanoparticle", Biomaterials, vol. 33, pp. 207-217, (2012).
King, et al. Structure of the alpha and beta heavy chains of the outer arm dynein from Chlamydomonas flagella. Nucleotide binding sites. J Biol Chem. Jun. 15, 1989;264(17):10210-8.
Kito, S. et al., "Cleavage of nucleolin and AgNOR proteins during apoptosis induced by anticancer drugs in human salivary gland cells", Journal of Oral Pathology & Medicine, vol. 34, pp. 478-485, (2005).
Klein, et al. Chemosensitivity of B cell chronic lymphocytic leukemia and correlated expression of proteins regulating apoptosis, cell cycle and DNA repair. Leukemia. Jan. 2000;14(1):40-6.
Knorre, D.G, et al, "Antisense oligonucleotide derivatives as gene-targeted drugs", Biomed Sci, vol. 1, No. 4, pp. 334-343, (1990).
Ko, M.H. et al., "In vitro derby imaging of cancer biomarkers using quantum dots", Small, vol. 5, No. 10, pp. 1207-1212, (2009).
Kohler, G, et al, "Continuous cultures of fused cells secreting antibody of predefined specificity", Nature, vol. 256, pp. 495-497, (1975).
Kohler, P.O, "Isolation, cloning, and hybridization of endocrine cell lines", Methods Enzymol, vol. 39, pp. 109-128, (1975).
Krantz, S, et al, "Purification and partial amino acid sequencing of a fructosyllysine-specific binding protein from cell membranes of the monocyte-like cell line U937", Biochim Biophys Acta, vol. 1266, No. 1, pp. 109-112, (1995).
Kuby, J, "Antigens", Immunology, Second Edition, chapter 4, pp. 85-96, W.H. Freeman and Company, New York, (1994).
Kumar, R.K, et al, "Improved double immunofluorescence for confocal laser scanning microscopy", J Histochem Cytochem, vol. 47, No. 9, pp. 1213-1218, (1999).
Kusser, W. Chemically modified nucleic acid aptamers for in vitro selections: evolving evolution. Reviews in Molecular Biotechnology Mar. 2000;74(1):27-38.
Kwiatkowski, B.A, et al, "Identification and cloning of a novel chromatin-associated protein partner of Epstein-Barr nuclear protein 2", Experimental Cell Research, vol. 300, pp. 223-233, (2004).
Laber, D.A. et al., "Extended phase I study of AS1411 in renal and non-small cell lung cancers", Journal of Clinical Oncology, ASCO Annual Meeting Proceedings, vol. 24, No. 18S, Abstract No. 13098, (2006).
Lakka, S.S, et al, "Adenovirus-mediated antisense urokinase-type plasminogen activator receptor gene transfer reduces tumor cell invasion and metastasis in non-small cell lung cancer cell lines", Clinical Cancer Research, vol. 7, No. 4, pp. 1087-1093, (2001).
Langer, P.R, et al, "Enzymatic synthesis of biotin-labeled polynucleotides: novel nucleic acid affinity probes", Proc Natl Acad Sci USA, vol. 78, pp. 6633-6637, (1981).
Lapeyre, et al. Nucleolin, the major nucleolar protein of growing eukaryotic cells: an unusual protein structure revealed by the nucleotide sequence. Proc Natl Acad Sci U S A. Mar. 1987;84(6):1472-6.
Larrucea, S, et al, "Cellular adhesion mediated by factor J, a complement inhibitor. Evidence for nucleolin involvement", J Biol Chem, vol. 273, No. 48, pp. 31718-31725, (1998).
Larrucea, S, et. al, "Internalization of factor J and and cellular signalization after factor J-cell interaction", Biochem Biophys Res Commun, vol. 266, No. 1, pp. 51-57, (1999).
Lau, Q.C, et al, "In vivo pro-apoptotic and antitumor efficacy of a c-Raf antisense phosphorothioate oligonucleotide: relationship to tumor size", Antisense Nucleic Acid Drug Development, vol. 12, No. 1, pp. 11-20, (2002).
Lebedeva, I, et al, "Antisense oligonucleotides: promise and reality", Annu Rev Pharmacol Toxicol, vol. 41, pp. 403-419, (2001).
Lee, et al. Bivalent antibody phage display mimics natural immunoglobulin. J Immunol Methods. Jan. 2004;284(1-2):119-32.
Lee, et al. High-affinity human antibodies from phage-displayed synthetic Fab libraries with a single framework scaffold. J Mol Biol. Jul. 23, 2004;340(5):1073-93.
Leitinger, N, et al, "ADP-ribosylation of nucleolar proteins in HeLa tumor cells", J Cell Biochem, vol. 52, No. 2, pp. 153-158, (1993).
Li, et al. Human antibodies for immunotherapy development generated via a human B cell hybridoma technology. Proc Natl Acad Sci U S A. Mar. 7, 2006;103(10):3557-62. Epub Feb. 27, 2006.
Lichtenstein, A.V, et al, "Circulating nucleic acids and apoptosis", Annuals New York Academy of Sciences, vol. 945, pp. 239-249, (2001).
Lin, D.L, et al, "p53 is a mediator for radiation-repressed human TR2 orphan receptor expression in MCF-7 cells, a new pathway from tumor suppressor to member of the steroid receptor superfamily", J Biol Chem, vol. 271, pp. 14649-14652, (1996).
Lin, S, et al, "The biochemical status of the DNA synthesome can distinguish between permanent and temporary cell growth arrest", Cell Growth Differ, vol. 8, No. 12, pp. 1359-1369, (1997).
Linardou, H. et al., "Assessment of somatic k-RAS mutations as a mechanism associated with resistance to EGFR-targeted agents: a systematic review and meta-analysis of studies in advanced non-small-cell lung cancer and metastatic colorectal cancer", Lancet Oncology, vol. 9, No. 10, pp. 962-972, (2008).
Little, C.D, et al, "Amplification and expression of the c-myc oncogene in human lung cancer lines", Nature, vol. 306, pp. 194-196, (1983).
Liu, H, et al, "Construction of a GAL1-regulated yeast cDNA expression library and its application to the identification of genes whose overexpression causes lethality in yeast", Genetics, vol. 132, No. 3, pp. 665-673, (1992).
Lonberg, et al. Antigen-specific human antibodies from mice comprising four distinct genetic modifications. Nature. Apr. 28, 1994;368(6474):856-9.
Lonberg, et al. Human antibodies from transgenic mice. Int Rev Immunol. 1995;13(1):65-93.
Lopes de Menezes, D, et al, "Pharmacokinetics of Bcl-2 antisense oligonucleotide (G3139) combined with doxorubicin in SCID mice bearing human breast cancer solid tumor xenografts", Cancer Chemother Pharmacol, vol. 49, No. 1, pp. 57-68, (2002).
Lovborg, H, et al, "Modulation of pyridyl cyanoguanidine (CHS 828) induced cytotoxicity by 3-aminobenzamide in U-937 GTB cells", Biochem Pharmacol, vol. 63, No. 8, pp. 1491-1498, (2002).
Lu, B. et al., "Analysis of SOX9 expression in colorectal cancer", American Journal of Clinical Pathology, vol. 130, No. 6, pp. 897-904, (2008).
Lutz-Freyermuth, et al. Quantitative determination that one of two potential RNA-binding domains of the A protein component of the U1 small nuclear ribonucleoprotein complex binds with high affinity to stem-loop II of U1 RNA. Proc Natl Acad Sci U S A. Aug. 1990;87(16):6393-7.
Ma J, et al, "Cells designed to deliver anticancer drugs by apoptosis", Cancer Research, vol. 62, No. 5, pp. 1382-1387, (2002).
Malhotra, et al. Glycosylation changes of IgG associated with rheumatoid arthritis can activate complement via the mannose-binding protein. Nat Med. Mar. 1995;1(3):237-43.
Malik, M.T. et al., "Aptamers conjugated to gold nanoparticles and their potential for breast cancer imaging and therapy", Congressionally Directed Medical Research Programs, Era of Hope 2011, Orlando Florida, Aug. 2-5, 2011, Poster #P43-16.
Malik, M.T. et al., "Multifunctional gold nanoparticles linked with aptamers and fluorophores for breast cancer imaging and therapy", American Association of Cancer Research Annual Meeting, Mar. 31-Apr. 4, 2012, Chicago, IL Abstract #5688.
Malki, S. et al., "Expression and biological role of the prostaglandin D synthase/SOX9 pathway in human ovarian cancer cells", Cancer Letters, vol. 255, No. 2, pp. 182-193, (2007).
Mann, M, et al, "Analysis of proteins and proteomes by mass spectrometry", Annu Rev Biochem, vol. 70, pp. 437-473, (2001).

(56) References Cited

OTHER PUBLICATIONS

Marks, et al. By-passing immunization: building high affinity human antibodies by chain shuffling. Biotechnology (N Y). Jul. 1992;10(7):779-83.
Marks, et al. By-passing immunization. Human antibodies from V-gene libraries displayed on phage. J Mol Biol. Dec. 5, 1991;222(3):581-97.
Martelli, A.M, et al, "Behavior of nucleolar proteins during the course of apoptosis in camptothecin-treated HL60 cells", Journal of Cellular Biochemistry, vol. 78, No. 2, pp. 264-277, (2000).
Martelli, A.M, et al, "Biochemical and Morphological characterization of the nuclear matrix from apoptotic HL-60 Cells", Journal of Cellular Biochemistry, vol. 72, No. 1, pp. 35-46, (1999).
Martelli, A.M, et al, "Nuclear apoptotic changes: an overview", J Cell Biochem, vol. 82, No. 4, pp. 634-646, (2001).
Martin, et al. GAP domains responsible for ras p21-dependent inhibition of muscarinic atrial K+ channel currents. Science. Jan. 10, 1992;255(5041):192-4.
Martin, et al. Irreversible coupling of immunoglobulin fragments to preformed vesicles. An improved method for liposome targeting. J Biol Chem. Jan. 10, 1982;257(1):286-8.
Martin, S.J, et al, "Protease activation during apoptosis: death by a thousand cuts?" Cell, vol. 82, pp. 349-352, (1995).
Massey. Catalytic antibodies catching on. Nature. 1987; 328:457-458.
Masters, J.R.W., "Human cancer cell lines: fact and fantasy", Nature Reviews Molecular Cell Biology, vol. 1, pp. 233-236, (2000).
Matthews, D.A, "Adenovirus protein V induces redistribution of nucleolin and B23 from nucleolus to cytoplasm", J Virol, vol. 75, No. 2, pp. 1031-1038, (2001).
Mattson, M.P., "Apoptosis in neurodegenerative disorders", Nature Reviews Mol Cell Biology, vol. 1, No. 2, pp. 120-129, (2000).
Mayer. Immunology. 2009; Ch 9:1-12.
Mayer, T.U, et al, "Small molecule inhibitor of mitotic spindle bipolarity identified in a phenotype-based screen", Science, vol. 286, No. 5441, pp. 971-974, (1999).
McCabe, M.T. et al., "Cancer DNA methylation: molecular mechanisms and clinical implications", Clinical Cancer Research, vol. 15, No. 12, pp. 3927-3937, (2009).
McEwen, C.N, et al, "Negative gold ion gun for liquid secondary ion mass spectrometry", Anal Chem, vol. 57, No. 4, pp. 890-892, (1985).
McManus, M.T, et al, "Gene silencing in mammals by small interfering RNAs." Nat Rev Genet, vol. 3, No. 10, pp. 737-747, (2002).
McManus, M.T, et al, "Gene silencing using micro-RNA designed hairpins", RNA, vol. 8, No. 6, pp. 842-850, (2002).
McNicol, A.M, et al, "Optimizing immunohistochemistry: antigen retrieval and signal amplification", Histopathology, vol. 32, pp. 97-103, (1998).
Mehes, G, et al, "Nucleolin and fibrillarin expression in stimulated lymphocytes and differentiating HL-60 cells. A flow cytometric assay", Cell Prolif, vol. 28, No. 6, pp. 329-336, (1995).
Mi, Y., et al., "Apoptosis in Leukemia cells is accompanied by alterations in the levels and localization of Nucleolin", The Journal of Biological Chemistry, vol. 278, No. 10, pp. 8572-8579, (2003).
Mi, Y. et al., "Regulation of Nucleolin in U937 Cells Treated with UV-Light and Cytotoxic Drugs", Blood, vol. 98, No. 11, Part 2 of 2, Abstract No. 4223, (2001).
Mi, Y, et al, "Validation of Nucleolin as a Novel Target for Cancer Drug Discovery", Proceedings of the American Association for Cancer Research Annual Meeting, vol. 43, Mar. 2002, pp. 959-960, 93.sup.rd Annual Meeting of the American Association for Cancer Research, San Francisco, California, USA, Apr. 6-10, 2002.
Mickey, D.D, et al, "Heterotransplantation of a human prostatic adenocarcinoma cell line in nude mice", Cancer Research, vol. 37, pp. 4049-4058, (1977).
Mikolajczyk, S, et al, "Tumor-associated forms of prostate specific antigen improve the discrimination of prostate cancer from benign disease", Rinsho Byori, vol. 52, No. 3, pp. 223-230, (2004).
Miller, et al. Release of infectious Epstein-Barr virus by transformed marmoset leukocytes. Proc Natl Acad Sci U S A. Jan. 1973;70(1):190-4.
Minota, S, et al, "Autoantibodies to nucleolin in systemic lupus erythematosus and other diseases", J Immunol, vol. 146, No. 7, pp. 2249-2252, (1991).
Miranda, G.A, et al, "The murine nucleolin protein is an inducible DNA and ATP binding protein which is readily detected in nuclear extracts of lipopolysaccharide-treated splenocytes", Exp Cell Research, vol. 217, No. 2, pp. 294-308, (1995).
Morgan, D.M, "Tetrazolium (MTT) assay for cellular viability and activity", Meth Mol Biol, vol. 79, pp. 179-183, (1998).
Mori-Akiyama, Y. et al., "SOX9 is required for the differentiation of paneth cells in the intestinal epithelium", Gastroenterology, vol. 133, No. 2, pp. 539-546, (2007).
Morimoto, Y, et al, "Alteration of argyrophilic nucleolar organizer region associated (Ag-NOR) proteins in apoptosis-induced human salivary gland cells and human oral aquamous carcinoma cells", J Oral Pathol Med, vol. 30, No. 4, pp. 193-199, (2001).
Morimoto, Y, et al, "Upregulation of the expression of Fas antigen and Fas ligand in a juman submandibular gland ductal cell line by okadaic acid", Arch Oral Biol, vol. 45, No. 8, pp. 657-666, (2000).
Morrison. Immunology. Success in specification. Nature. Apr. 28, 1994;368(6474):812-3.
Morrison, S.L. et al., "Chimeric human antibody molecules: mouse antigen-binding domains with human constant region domains", Proceedings of the National Academy of Science USA, vol. 81, No. 21, pp. 6851-6855, (1984).
Mosmann, T. "Rapid colorimetric assay for cellular growth and survival: application to proliferation and cytotoxicity assays", Journal of Immunological Methods, vol. 65, issue 1-2, pp. 55-63, (1983).
Mukherjee, et al. The mammalian exosome mediates the efficient degradation of mRNAs that contain AU-rich elements. EMBO J. Jan. 15, 2002;21(1-2):165-74.
Muller, P. et al., "SOX9 mediates the retinoic acid-induced HES-1 gene expression in human breast cancer cells", Breast Cancer Research Treatment, vol. 120, No. 2, pp. 317-326, (2010).
Murchie, A.I, et al, "Retinoblastoma susceptibility genes contain 5' sequences with a high propensity to form guanine-tetrad structures", Nucleic Acids Research, vol. 20, No. 1, pp. 49-53, (1992).
Naito, M, et al, "ATP/Mg.sup.2+-dependent binding of vincristine to the plasma membrane of multifrug-resistant K562 cells", J Biol Chem, vol. 263, pp. 11887-11891, (1988).
Nakanishi, K, et al, "Argyrophilic nucleolar-organizer region counts and DNA status in bronchioloalveolar epithelial hyperplasia and adenocarcinoma of the lung", Hum Pathol, vol. 29, No. 3, pp. 235-239, (1998).
National Cancer Institute, Fact Sheet, "Targeted Cancer Therapies", U.S. Department of Health and Human Services, pp. 1-8, May 9, 2012.
Navenot, J.M, et al, "Molecular anatomy of CCR5 engagement by physiologic and viral chemokines and HIV-1 envelope glycoproteins: differences in primary structural requirements for RANTES, MIP-1 alpha, and vMIP-II Binding", J Mol Biol, vol. 313, No. 5, pp. 1181-1193, (2001).
Neuberger. Generating high-avidity human Mabs in mice. Nat Biotechnol. Jul. 1996;14(7):826.
Neuberger, M.S, et al, "Recombinant antibodies possessing novel effector functions", Nature, vol. 312, No. 5995, pp. 604-608, (1984).
Nichols, R.C, et al, "The RGG domain in hnRNP A2 affects subcellular localization", Exp Cell Research, vol. 256, No. 2, pp. 522-532, (2000).
Nonomura et al. Demonstration of nucleolar organizer regions in lung carcinoma by silver staining. (Surg Today 1993:23(6):486-490).
Norgaard, J.M, et al, "FAB M4 and high CD14 surface expression is associated with high cellular resistance to Ara-C and daunorubicin: implications for clinical outcome in acute myeloid leukaemia", European Journal of Haematology, vol. 67, pp. 221-229, (2001).
Nosseri, C, et al, "Possible involvement of poly(ADP-ribosyl) polymerase in triggering-stress-induced apoptosis", Exp Cell Research, vol. 212, No. 2, pp. 367-373, (1994).

(56) References Cited

OTHER PUBLICATIONS

Notice of allowance dated Apr. 16, 2008 for U.S. Appl. No. 10/118,854.
Notice of allowance dated Jun. 1, 2007 for U.S. Appl. No. 10/683,480.
Notice of allowance dated Jun. 9, 2011 for U.S. Appl. No. 12/041,969.
Notice of allowance dated Jul. 5, 2013 for U.S. Appl. No. 13/116,319.
Notice of allowance dated Oct. 25, 2007 for U.S. Appl. No. 10/683,480.
Notice of allowance dated Nov. 3, 2015 for U.S. Appl. No. 13/510,270.
Notice of allowance dated Nov. 13, 2015 for U.S. Appl. No. 13/510,270.
Notice of allowance dated Nov. 27, 2006 for U.S. Appl. No. 10/683,480.
Nucleolin Antibody—Antibody product information from all suppliers, Labome the World of Laboratories, pp. 1-4, found at www.labome.com/gene/human/nucleolin-antibody.html, printed on Jun. 1, 2012.
Office action dated Jan. 3, 2007 for U.S. Appl. No. 10/118,854.
Office action dated Feb. 26, 2013 for U.S. Appl. No. 13/116,319.
Office action dated Mar. 31, 2006 for U.S. Appl. No. 10/118,854.
Office action dated May 19, 2015 for U.S. Appl. No. 13/510,270.
Office action dated May 20, 2015 for U.S. Appl. No. 14/059,211.
Office action dated Jun. 5, 2006 for U.S. Appl. No. 10/683,480.
Office action dated Jun. 7, 2010 for U.S. Appl. No. 12/041,969.
Office action dated Jun. 12, 2014 for U.S. Appl. No. 13/510,270.
Office action dated Jul. 10, 2012 for U.S. Appl. No. 13/116,319.
Office action dated Jul. 26, 2005 for U.S. Appl. No. 10/118,854.
Office action dated Sep. 19, 2007 for U.S. Appl. No. 10/118,854.
Office action dated Oct. 15, 2013 for U.S. Appl. No. 13/510,270.
Office action dated Nov. 3, 2009 for U.S. Appl. No. 12/041,969.
Office action dated Nov. 4, 2004 for U.S. Appl. No. 10/118,854.
O'Shannessy, et al. Quantitation of glycoproteins on electroblots using the biotin-streptavidin complex. Anal Biochem. May 15, 1987;163(1):204-9.
Ohkoudo, M, et al, "Morphometrical analysis of nucleolin immunohistochemistry in meningiomas", Acta Neuropathol, vol. 92, pp. 1-7, (1996).
Orfao, A, et al, "General concepts about cell sorting techniques", Clin Biochem, vol. 29, pp. 5-9, (1996).
Orkin, S.H. et al., "Report and recommendations of the panel to assess the NIH investment in research on gene therapy", NIH ad hoc committee, pp. 1-39, found at http://oba.od.nih.gov/oba/racipanelrep.pdf, (1995).
Orringer, D.A. et al., "In vitro characterization of a targeted, dye-loaded nanodevice for intraoperative tumor delineation", Neurosurgery, vol. 64, No. 5, pp. 965-972, (2009).
Otake, et al. Overexpression of nucleolin in chronic lymphocytic leukemia cells induces stabilization of bc12 mRNA. Blood. 2007; 109(7):3069-75.
Owens, et al. Characterization of the guanosine-3'-diphosphate-5'-diphosphate binding site on *E. coli* RNA polymerase using a photoprobe, 8-azidoguanosine-3'-5'-bisphosphate. Biochem Biophys Res Commun. Feb. 13, 1987;142(3):964-71.
Oyama, T, et al, "Nucleolar organizer regions are independently associated with a shortened survival in patients with non-small cell lung cancer", Surg Oncol, vol. 2, No. 6, pp. 341-347, (1993).
Paborsky, et al. Mammalian cell transient expression of tissue factor for the production of antigen. Protein Eng. May 1990;3(6):547-53.
Paddison, P.J, et al, "Short hairpin RNAs (shRNAs) induce sequence-specific silencing in mammalian cells", Genes Dev, vol. 16, No. 8, pp. 948-958, (2002).
Paddison, P.J, et al, "Stable suppression of gene expression by RNAi in mammalian cells", Proc Natl Acad Science USA, vol. 99, No. 3, pp. 1443-1448, (2002).
Palomba, L, et al, "Apoptosis and necrosis following exposure of U937 cells to increasing concentrations of hydrogen peroxide: the effect of the poly(ADP-ribose) polymerase inhibitor 3-aminobenzamide", Biochem Pharmacol, vol. 58, No. 11, pp. 1743-1750, (1999).
Pandey, A, et al, "Proteomics to study genes and genomes", Nature, vol. 405, No. 6788, pp. 837-846, (2000).
Partridge, M. et al., "A simple method for delivering morpholino antisense oligos into the cytoplasm of cells", Antisense & Nucleic Acid Drug Development, vol. 6, No. 3, pp. 169-175, (1996).
Passeron, T. et al., "SOX9 is a key player in ultraviolet B-induced melanocyte differentiation and pigmentation", Proceedings of the National Academy of Sciences, vol. 104, No. 35, pp. 13984-13989, (2007).
Passeron, T. et al., "Upregulation of SOX9 inhibits the growth of human and mouse melanomas and restores their sensitivity to retinoic acid", The Journal of Clinical Investigation, vol. 119, No. 4, pp. 954-963, (2009).
Pasternack, M.S, et al, "Granzyme A binding to target cell proteins Granzyme A binds to and cleaves nucleolin in vitro", J Biol Chem, vol. 266, No. 22, pp. 14703-14708, (1991).
PCT International Search Report and Written Opinion issued in International Patent Application No. PCT/US10/57046, dated May 9, 2011.
PCT Invitation to Pay Additional Fees issued in International Patent Application No. PCT/US10/57046, dated Jan. 11, 2011.
Perry, S.W, et al, "Simultaneous in situ detection of apoptosis and necrosis in monolayer cultures by TUNEL and trypan blue staining", Biotechniques, vol. 22, No. 6, pp. 1102-1106, (1997).
Pfeifle, et al. Isolation and characterization of phosphoprotein pp 105 from simian virus 40-transformed mouse fibroblasts. Biochim Biophys Acta. Feb. 16, 1983;762(1):86-93.
Pich, A, et al, "Prognostic relevance of AgNORs in tumor pathology", Micron, vol. 31, No. 2, pp. 133-141, (2000).
Piekarz, R.L. et al., "Epigenetic modifiers: basic understanding and clinical development", Clinical Cancer Research, vol. 15, No. 12, pp. 3918-3926, (2009).
Pinton, P, et al, "The Ca.sup.2+ concentration of the endoplasmic reticulum is a key determinant of ceramide-induced apoptosis: significance for the molecular mechanism of Bcl-2 action", EMBO J, vol. 20, pp. 2690-2701, (2001).
Platt, N, et al, "Recognizing death: the phagocytosis of apoptotic cells", Trends Cell Biology, vol. 8, No. 9, pp. 365-372, (1998).
Pleschke, J.M, et al, "Poly(ADP-ribose) binds to specific domains in DNA damage checkpoint proteins", J Biol Chem, vol. 275, No. 52, pp. 40974-40980, (2000).
Portney, N.G. et al., "Nano-oncology: drug delivery, imaging, and sensing", Analytical and Bioanalytical Chemistry, vol. 384, No. 3, pp. 620-630, (2006).
Potter, et al. Photoaffinity labeling of nucleotide binding sites with 8-azidopurine analogs: techniques and applications. Methods Enzymol. 1983;91:613-33.
Presta. Antibody Engineering. Curr. Op. Struct. Bioi. 1992; 2:593-596.
Product Data Sheet for ab7898 from http://www.abcam.com/?datasheet=7898, (1998-2006).
Product Data Sheet for Anti-Nucleolin, Clone 3G4B2, Upstate Biotechnology, http://www.upstate.com/browse/productdetail.asp?ProductId=05-565, (2005).
Product Data Sheet for B23 (C-19): sc-6013, Santa Cruz Biotechnology, Inc., located at http://datasheets.scbt.com/sc-6013.pdf, printed on Aug. 10, 2007.
Product Data Sheet for B23 (H-106): sc-5564, Santa Cruz Biotechnology, Inc., located at http://datasheets.scbt.com/sc-5564.pdf, printed on Aug. 10, 2007.
Product Data Sheet for C23 (C-18): sc-9892, Santa Cruz Biotechnology, Inc, (2003).
Product Data Sheet for C23 (F-18): sc-9893, Santa Cruz Biotechnology, Inc, (2003).
Product Data Sheet for C23 (MS-3): sc-8031, Santa Cruz Biotechnology, Inc, (2004).
Product Data Sheet for Monoclonal Antibody, Anti-Nucleolin M019-3, Medical & Biological Laboratories Co, Ltd, www.mblintl.com, (2003).
Product Data Sheet for p7-1A4, from http://dshb.biology.uiowa.edu/objects/catalog//product/extras/4217.sub.--- p7- 1A4.pdf, Antibody Database Information, printed on Aug. 10, 2007.

(56) References Cited

OTHER PUBLICATIONS

Puttaraju, M, et al, "Messenger RNA repair and restoration of protein function by spliceosome-mediated RNA trans-splicing", Mol Ther, vol. 4, No. 2, pp. 105-114, (2001).
Qi, J. et al., "Siah2-dependent concerted activity of HIF and FoxA2 regulates formation of neuroendocrine phenotype and neuroendocrine prostate tumors", Cancer Cell, vol. 18, No. 1, pp. 23-38, (2010).
Raab de Verdugo, U, et al, "Characterization of a 100-kilodalton binding protein for the six serotypes of coxsackie B viruses", Journal of Virology, vol. 69, No. 11, pp. 6751-6757, (1995).
Remington's Pharmaceutical Sci., 18th ed Maack Publishing Co, Easton Pa., 1990.
Reyes-Reyes, E.M. et al., "A new paradigm for aptamer therapeutic AS1411 action: uptake by macropinocytosis and its stimulation by a nucleolin-dependent mechanism", Cancer Research, vol. 70, No. 21, pp. 8617-8629, (2010).
Richardson, D.S, et al, "Effects of PARP inhibition on drug and Fas-induced apoptosis in leukaemic cells", Adv Exp Med Biol, vol. 457, pp. 267-279, (1999).
Riechmann, et al. Reshaping human antibodies for therapy. Nature. Mar. 24, 1988;332(6162):323-7.
Robertson, et al. Bcl-2 expression in chronic lymphocytic leukemia and its correlation with the induction of apoptosis and clinical outcome. Leukemia. Mar. 1996;10(3):456-9.
Robinson, J.M, et al, "Antigen retrieval in cells and tissues: enhancement with sodium dodecyl sulfate", Histochem Cell Biol, vol. 116, pp. 119-130, (2001).
Roninson, I.B, et al, "If not apoptosis, then what? Treatment-induced senescence and mitotic catastrophe in tumor cells", Drug Resist Update, vol. 4, No. 5, pp. 303-313, (2001).
Rosen, A., et al., "Autoantigens as substrates for apoptotic proteases: implications for the pathogenesis of systemic autoimmune disease", Cell Death and Differentiation, vol. 6, No. 1, pp. 6-12, (1999).
Rosenthal, D.S, et al, "Detection of DNA breaks in apoptotic cells utilizing the DNA binding domain of poly(ADP-ribose) Polymerase with fluorescence microscopy", Nucleic Acids Research, vol. 25, No. 7, pp. 1437-1441, (1997).
Rothenburg, S, et al, "A polymorphic dinucleotide repeat in the rat nucleolin gene forms Z-DNA and inhibits promoter activity", PNAS, vol. 98, No. 16, pp. 8985-8990, (2001).
Roussel, P, et al, "Identification of Ag-NOR proteins, markers of proliferation related to ribosomal gene activity", Experimental Cell Research, vol. 214, No. 2, pp. 465-472, (1994).
Roussel, P, et al, "Quantification of Ag-NOR proteins using Ag-NOR staining on western blots", Histochem Cytochem, vol. 42, No. 11, pp. 1513-1517, (1994).
Rubanyi, G.M. The future of human gene therapy. (Molecular Aspects of Medecine 2001; 22:113-142).
Said, et al. The anti-HIV cytokine midkine binds the cell surface-expressed nucleolin as a low affinity receptor. J Biol Chem. Oct. 4, 2002;277(40):37492-502. Epub Jul. 29, 2002.
Saijo, Y, et al, "Contiguous four-guanosine sequence in c-myc antisense phosphorothioate oligonucleotides inhibits cell growth on human lung cancer cells: possible involvement of cell adhesion inhibition", Jpn J Cancer Research, vol. 88, No. 1, pp. 26-33, (1997).
Saikumar, P, et al, "Apoptosis: definition, mechanisms, and relevance to disease", Am J Med, vol. 107, No. 5, pp. 489-506, (1999).
Sandoval, A, et al, "Distal recognition site for classical pathway convertase located in the C345C/netrin module of complement component C5", J Immunol, vol. 165, No. 2, pp. 1066-1073, (2000).
Schade, R, et al, "Egg yolk antibodies, State of the art and future prospects", Altex 13, supplement 96, pp. 5-9, (1996).
Schade, R, et al, "The production of avian (egg yolk) antibodies IgY. The report and recommendations of ECVAM workshop", Alternatives to laboratory animals (ALTA), vol. 24, pp. 925-934, (1996).
Schaeffer, E.M. et al., "Androgen-induced programs for prostate epithelial growth and invasion arise in embryogenesis and are reactivated in cancer", Oncogene, vol. 27, No. 57, pp. 7180-7191, (2008).
Schimmer, A.D, et al, "Receptor- and mitochondrial-mediated apoptosis in acute leukemia: a translational view", Blood, vol. 98, No. 13, pp. 3541-3553, (2001).
Schmidt-Acevedo, S, et al, "'LE cells' result from phagocytosis of apoptotic bodies induced by antinuclear antibodies", Journal of Autoimmunity, vol. 15, pp. 15-20, (2000).
Schmitt, C.A, et al, "Apoptosis is critical for drug response in vivo", Drug Resist Update, vol. 4, No. 2, pp. 132-134, (2001).
Schrama, et al. Antibody targeted drugs as cancer therapeutics. Nat Rev Drug Discov. Feb. 2006;5(2):147-59.
Sciavolino, P.J, et al, "Molecular biology of prostate development and prostate cancer", Ann Med, vol. 30, No. 4, pp. 357-368, (1998).
Scott, C.E. et al., "SOX9 induces and maintains neural stem cells", Nature Neuroscience, vol. 13, No. 10, pp. 1181-1189, (2010).
Scovassi, A.I, et al, "Poly(ADP-ribosylation) and apoptosis", Molecular and Cellular Biochemistry, vol. 199, pp. 125-137, (1999).
Semenkovich, C.F, et al, "A protein partially expressed on the surface of HepG2 cells that binds lipoproteins specifically is nucleolin", Biochemistry, vol. 29, No. 41, pp. 9708-9713, (1990).
Sen, D, et al, "Formation of parallel four-stranded complexes by guanine-rich motifs in DNA and its implications for meiosis", Nature, vol. 334, No. 6180, pp. 364-366, (1988).
Sengupta, et al. Identification of nucleolin as an AU-rich element binding protein involved in bcl-2 mRNA stabilization. J Biol Chem. Mar. 19, 2004;279(12):10855-63. Epub Dec. 16, 2003.
Serin, et al. Two RNA-binding domains determine the RNA-binding specificity of nucleolin. J Biol Chem. May 16, 1997;272(20):13109-16.
Shah, K. et al., "AS1411, a novel DNA aptamer as a potential treatment of acute myelogenous leukaemia (AML)", Meeting Poster, 48th Annual Meeting of the American Society of Hematology, Orlando, FL, USA. Dec. 9-12, 2006.
Shall, S, et al, "Poly(ASP-ribose) polymerase-1: what have we learned from the deficient mouse model?", Mutat Research, vol. 460, No. 1, 1-15, (2000).
Shall, S, "Poly (ADP-ribosylation)—a common control process?", Bioessays, vol. 24, No. 2, pp. 197-201, (2002).
Sharma, S, et al, "Developmental of inhalational agents for oncologic use", J Clin Oncol, vol. 19, No. 6, pp. 1839-1847, (2001).
Sharp, P.A, et al, "Molecular biology. RNA interference", Science, vol. 287, No. 5462, pp. 2431-2433, (2000).
Sharp, P.A, "RNA interference—2001" Genes Dev, vol. 15, No. 5, pp. 485-490, (2001).
Shaw, J.P, et al, "Modified deoxyoligonucleotides stable to exonuclease degradation in serum", Nucleic Acids Res, vol. 19, No. 4, pp. 747-750, (1991).
Sherwood, J.K. et al, "Controlled antibody delivery systems", Biotechnology, vol. 10, No. 11, pp. 1446-1449, (1992).
Shi, S.R, et al, "Antigen retrieval immunohistochemistry: past, present, and future", J Histochem Cytochem, vol. 45, pp. 327-343, (1997).
Shi, S.R, et al, "Antigen retrieval techniques: current perspectives", J Histochem Cytochem, vol. 49, pp. 931-937, (2001).
Shieh, Y-A. et al., "Aptamer-based tumor-targeted drug delivery for photodynamic therapy", ACS Nano, vol. 4, No. 3, pp. 1433-1442, (2010).
Shiokawa, D, et al, "Inhibitors of poly(ADP-ribose) polymerase suppress nuclear fragmentation and apoptotic-body formation during apoptosis in HL-60 cells", FEBS Letters, vol. 413, No. 1, pp. 99-103, (1997).
Shoemaker, R.H. "The NCI60 human tumour cell line anticancer drug screen", Nature Reviews Cancer, vol. 6, No. 10, pp. 813-823, (2006).
Sidhu, et al. Phage-displayed antibody libraries of synthetic heavy chain complementarity determining regions. J Mol Biol. Apr. 23, 2004;338(2):299-310.
Sigalotti, L. et al., "Epigenetic modulation of solid tumors as a novel approach for cancer immunotherapy", Seminars in Oncology, vol. 32, No. 5, pp. 473-478, (2005).
Simbulan-Rosenthal, C.M, et al, "Involvement of PARP and poly(ADP-ribosyl)ation in the early stages of apoptosis and DNA replication", Mol Cell Biochem, vol. 193, No. 1-2, pp. 137-148, (1999).

(56) References Cited

OTHER PUBLICATIONS

Sinclair and O'Brien et al. Cell surface-localized nucleolin is a eukaryotic receptor for the adhesin intimin-gamma of enterohemorrhagic *Escherichia coli* O157:H7. J. Biol Chem. 2002; 277(4):2876-85.
Sirri, V, et al, "Amount variability of total and individual Ag-NOR proteins in cells stimulated to proliferate", Histochem Cytochem, vol. 43, No. 9, pp. 887-893, (1995).
Skinner, et al. Use of the Glu-Glu-Phe C-terminal epitope for rapid purification of the catalytic domain of normal and mutant ras GTPase-activating proteins. J. Biol. Chem. 1991; 266:14163-14166.
Skulstad, S, et al, "Labeling of surface proteins of herpes simplex virus type 1 using a modified biotin-streptavidin system", Virus Research, vol. 37, No. 3, pp. 253-270, (1995).
Smulson, M.E, et al, "Roles of poly(ADP-ribosyl)ation and PARP in apoptosis, DNA repair, genomic stability and functions of p52 and E2F-1", Adv Enzyme Regul, vol. 40, pp. 183-215, (2000).
Sohn, J.H, et al, "Caspase-3/CPP32 immunoreactivity and its correlation with frequency of apoptotic bodies in human prostatic carcinomas and benign nodular hyperplasias", Histopathology, vol. 37, No. 6, pp. 555-560, (2000).
Solakidi et al., "Differential distribution of glucocorticoid and estrogen receptor isoforms: localization of GRbeta and ERalpha in nucleoli and GRalpha and ERbeta in the mitochondria of human osteosarcoma SaOS-2 and hepatocarcinoma HepG2 cell lines," J. Musculoskelet. Neuronal. Interact., 7(3):240-245, 2007.
Soldani, C, et al, "Poly(ADP-ribose) polymerase cleavage during apoptosis: when and where?", Exp Cell Research, vol. 269, No. 2, pp. 193-201, (2001).
Soldani, C. et al., "Two-color fluorescence detection of Poly (ADP-ribose) polymerase-1 (PARP-1) cleavage and DNA strand breaks in etoposide-induced apoptotic cells", Eur J Histochem, vol. 45, No. 4, pp. 389-392, (2001).
Soltysova, A. et al., "Cancer Stem Cells", Neoplasma, 52, 6, pp. 435-440, (2005).
Sorokina, E.A, et al, "Cloning and preliminary characterization of a calcium-binding protein closely related to nucleolin on the apical surface of inner medullary collecting duct cells", J Biol Chem, vol. 274, No. 39, pp. 27491-27496, (1999).
Soundararajan, S. et al., Plasma membrane nucleolin is a receptor for the anticancer aptamer AS1411 in MV4-11 leukemia cells. Mol. Pharmacol. 2009; 76(5):984-91.
Soundararajan, S. et al., "The nucleolin targeting aptamer AS1411 destabilizes Bcl-2 messenger RNA in human breast cancer cells", Cancer Research, vol. 68, No. 7, pp. 2358-2365, (2008).
Speck, et al. Epstein-Barr virus (EBV) infection visualized by EGFP expression demonstrates dependence on known mediators of EBV entry. Arch Virol. 1999;144(6):1123-37.
Speck, et al. Epstein-Barr virus lacking latent membrane protein 2 immortalizes B cells with efficiency indistinguishable from that of wild-type virus. J Gen Virol. Aug. 1999;80 ( Pt 8):2193-203.
Sperandio, S, et al, "An alternative, nonapoptotic form of programmed cell death", Proc Natl Acad Science USA, vol. 97, No. 26, pp. 14376-14381, (2000).
Sprague, J.E. et al., "Noninvasive imaging of osteoclasts in parathyroid hormone-induced osteolysis using a 64Cu-labeled RGD peptide", Journal of Nuclear Medicine, Society of Nuclear Medicine, vol. 48, No. 2, pp. 311-318, (2007).
Srinivasan, S.K, et al, "Review of in vivo pharmacokinetics and toxicology of phosphorothioate oligonucleotides", J Clin Lab Anal, vol. 9, No. 2, pp. 129-137, (1995).
Srivastava, et al. Cloning and sequencing of the human nucleolin cDNA. FEBS Lett. Jun. 19, 1989;250(1):99-105.
Srivastava, M. et al., "Genomic organization and chromosomal localization of the human nucleolin gene", The Journal of Biological Chemistry, vol. 265, No. 25, pp. 14922-14931, (1995).
Srivastava, M, et al, "Molecular dissection of nucleolin's role in growth and cell proliferation: new insights", FASEB J, vol. 13, No. 14, pp. 1911-1922, (1999).
Stange, D.E. et al., "Expression of an ASCL2 related stem cell signature and IGF2 in colorectal cancer liver metastases with 11p15.5 gain", Gut, vol. 59, pp. 1236-1244, (2010).
Stegh, A.H, et al, "DEDD, a novel death effector domain-containing protein, targeted to the nucleolus", EMBO J, vol. 17, No. 20, pp. 5974-5986, (1998).
Stein, C.A, et al, "Phosphorothioate oligodeoxynucleotides-antisense inhibitors of gene expression?", Pharmacol Ther, vol. 52, No. 3, pp. 365-384, (1991).
Stein, C.A, "Is irrelevant cleavage the price of antisense efficacy?", Pharmacol Ther, vol. 85, No. 3, pp. 231-236, (2000).
Stein, C.A. "Keeping the biotechnology of antisense in context", Nat. Biotechnol, vol. 17, No. 3, pp. 209, (1999).
Steube, et al. Expression of bcl-2 mRNA and protein in leukemia-lymphoma cell lines. Leukemia. Nov. 1995;9(11):1841-6.
Stone, K.R, et al, "Isolation of a human prostate carcinoma cell line (DU 145)", Int J Cancer, vol. 21, pp. 274-281, (1978).
Stroun, M, et al, "About the possible orgin and mechanism of circulating DNA apoptosis and active DNA release", Clin Chim Acta, vol. 313, No. 1-2, pp. 139-142, (2001).
Stryer, L, "Levels of structure in protein architecture", Biochemistry, Third Edition, chapter 2, pp. 31-33, W.H. Freeman Company, New York, (1988).
Subramanian, D. et al., "Cancer-selective induction of macropinocytosis and cell death in neuroblastoma cells treated with AS1411", Research Louisville 2011, University of Louisville, Louisville, Kentucky, Abstract #GRD-72.
Summerton, J, et al, "Morpholino antisense oligomers: design, preparation, and properties", Antisense Nucleic Acid Drug Development, vol. 7, No. 3, pp. 187-195, (1997).
Sundquist, W.I, et al, "Evidence for interstrand quadruplex formation in the dimerization of human immunodeficiency virus 1 genomic RNA", Proc Natl Acad Science USA, vol. 90, No. 8, pp. 3393-3397, (1993).
Sundquist, W.I, et al, "Telomeric DNA dimerizes by formation of guanine tetrads between hairpin loops", Nature, vol. 342, No. 6251, pp. 825-829, (1989).
Sutton, V.R, et al, "Initiation of apoptosis by granzyme B requires direct cleavage of bid, but not direct granzyme B-mediated caspase activation", J Exp Med, vol. 192, No. 10, pp. 1403-1413, (2000).
Symons, R.H. "Small catalytic RNAS", Annual Review Biochem, vol. 61, pp. 641-671, (1992).
Takafuji, Y. et al., "Simple PEG modification of DNA aptamer based on copper ion coordination for tumor targeting", Journal of Biomaterials Science, vol. 22, pp. 1179-1195, (2011).
Takahashi, T, et al, "p53: a frequent target for genetic abnormalities in lung cancer", Science, vol. 246, pp. 491-494, (1989).
Takekoshi, et al. Cloning and expression of human anti-tumor necrosis factor-alpha monoclonal antibodies from Epstein-Barr virus transformed oligoclonal libraries. J Biochem. Aug. 2001;130(2):299-303.
Tanaka, Y, et al, "Inhibition and down-regulation of poly(ADP-ribose) polymerase results in a marked resistance of HL-60 cells to various apoptosis-inducers", Cell Mol Biol, vol. 41, No. 6, pp. 771-781, (1995).
Templin, M.V, et al, "Pharmacokinetic and toxicity profile of a phosphorothioate oligonucleotide following inhalation delivery to lung in mice", Antisense Nucleic Acid Drug Dev, vol. 10, No. 5, pp, 359-368, (2000).
Tentori, L, et al, "Potential clinical applications of poly(ADP-ribose) polymerase (PARP) inhibitors", Pharmacol Res, vol. 45, No. 2, pp. 73-85, (2002).
Thayer, A.M. "Fabulous fluorine", Chemical and Engineering News, vol. 84, No. 23, pp. 15-24, (2006).
Thomsen, M.K. et al., "SOX9 elevation in the prostate promotes proliferation and cooperates with PTEN loss to drive tumor formation", Cancer Research, vol. 70, No. 3, pp. 979-987, (2010).
Thomsen, M.K. et al., "Sox9 is required for prostate development", Developmental Biology, vol. 316, No. 2, pp. 302-311, (2008).
Thomsen, M.K. et al., "The role of Sox9 in prostate development", Differentiation, vol. 76, pp. 728-735, (2008).
Thornberry, N.A, et al, "Caspases: enemies within", Science, vol. 281, pp. 1312-1316, (1998).

(56) References Cited

OTHER PUBLICATIONS

Tockman, M.S, et al, "Sensitive and specific monoclonal antibody recognition of human lung cancer antigen on preserved sputum cells: a new approach to early lung cancer detection", J Clin Oncol, vol. 6, No. 11, pp. 1685-1693, (1988).
Tockman, M.S, et al, "Prospective detection of preclinical lung cancer: results from two studies of heterogeneous nuclear ribonucleoprotein A2/B1 overexpression", Clin Cancer Research, vol. 3, No. 12, pt.1, pp. 2237-2246, (1997).
Tomayko, M.M. et al., "Determination of subcutaneous tumor size in athymic (nude) mice", Cancer Chemotherapy and Pharmacology, vol. 24, issue 3, pp. 148-154, (1989).
Tormanen, U, et al, "Enhanced apoptosis predicts shortened survival in non-small cell lung carcinoma", Cancer Research, vol. 55, No. 23, pp. 5595-5602, (1995).
Trere, D, "AgNOR staining and quantification", Micron, vol. 31, No. 2, pp. 127-131, (2000).
Tu, G.C, et al, "Tetranucleotide GGGA motif in primary RNA transcripts. Novel target site for antisense design", J Biol Chem, vol. 273, No. 39, pp. 25125-25131, (1998).
Tuteja, N, et al, "Human DNA helicase IV is nucleolin, an RNA helicase modulated by phosphorylation", Gene, vol. 160, No. 2, pp. 143-148, (1995).
Tuteja, R, et al, "Nucleolin: a multifunctional major nucleolar phosphoprotein", Crit Rrev Biochem Mol Biol, vol. 33, pp. 407-436, (1998).
Ugrinova I. et al., "Inactivation of nucleolin leads to nucleolar disruption, cell cycle arrest and defects in centrosome duplication", BMC Molecular Biology, pp. 1-16, (2007).
Umana, et al. Engineered glycoforms of an antineuroblastoma IgG1 with optimized antibody-dependent cellular cytotoxic activity. Nat Biotechnol. Feb. 1999;17(2):176-80.
Van de Loosdrecht, A.A, et al, "A tetrazolium-based colorimetric MTT assay to quantitate human monocyte mediated cytotoxicity against leukemic cells from cell lines and patients with acute myeloid leukemia", J Immunol Methods, vol. 174, pp. 311-320, (1994).
Van Dijk, et al. Human antibodies as next generation therapeutics. Curr Opin Chem Biol. Aug. 2001;5(4):368-74.
Vaswani, et al. Humanized antibodies as potential therapeutic drugs. Ann Allergy Asthma Immunol. Aug. 1998;81(2):105-15; quiz 115-6, 119.
Verma et al. Gene therapy—promises, problems and prospects. (Nature Sep. 1997;389:239-242).
Vermes, I. et al., "A novel assay for apoptosis. Flow cytometric detection of phosphatidylserine expression on early apoptotic cells using fluorescein labeled Annexin V", Journal of Immunological Methods, vol. 184, No. 1, pp. 39-51, (1995).
Vidal, V.P.I. et al., "SOX9 expression is a general marker of basal cell carcinoma and adnexal-related neoplasms", Journal of Cutaneous Pathology, vol. 35, pp. 373-379, (2008).
Vitetta, et al. Redesigning nature's poisons to create anti-tumor reagents. Science. Nov. 20, 1987;238(4830):1098-104.
Waggoner, S, et al, "Viral ribonucleoprotein complex formation and nucleolar-cytoplasmic relocalization of nucleolin in poliovirus-infected cells", J Virol, vol. 72, No. 8, pp. 6699-6709, (1998).
Waldmann, T.A. Immunotherapy: past, present and future. Nature Medicine, vol. 9, No. 3, pp. 269-277, (2003).
Walker, I. et al., "Do molecularly targeted agents in oncology have reduced attrition rates?", Nature Reviews, Drug Discovery, vol. 8, pp. 15-16, (2009).
Wang, H. et al., "SOX9 is expressed in human fetal prostate epithelium and enhances prostate cancer invasion", Cancer Research, vol. 68, No. 6, pp. 1625-1630, (2008).
Wang, H. et al., "SOX9 is expressed in normal prostate basal cells and regulates androgen receptor expression in prostate cancer cells", Cancer Research, vol. 67, No. 2, pp. 528-536, (2007).
Wang, W, et al, "A comparison of guanosine-quartet inhibitory effects versus cytidine homopolymer inhibitory effects on rat neointimal formation", Antisense Nucleic Acid Drug Development, vol. 8, No. 3, pp. 227-236, (1998).
Wang, Y, et al, "Solution structure of the human telomeric repeat d[AG3(T2AG3)3] G-tetraplex", Structure, vol. 1, No. 4, pp. 263-282, (1993).
Wang, Y, et al, "Regulation of dna replication after heat shock by replication protein a-nucleolin interactions", J Biol Chem, vol. 276, No. 23, pp. 20579-20588, (2001).
Wang, Z.Q, et al, "PARP is important for genomic stability but dispensable in apoptosis", Genes Dev, vol. 11, No. 18, pp. 2347-2358, (1997).
Weisenberger, D, et al, "A possible mechanism for the inhibition of ribosomal RNA gene transcription furing mitosis", J Cell Biology, vol. 129, No. 3, pp. 561-575, (1995).
Welschof, et al. Amino acid sequence based PCR primers for amplification of rearranged human heavy and light chain immunoglobulin variable region genes. J Immunol Methods. Feb. 27, 1995;179(2):203-14.
Westmark and Malter. Extracellular-regulated kinase controls beta-amyloid precursor protein mRNA decay. Brain Res. Mol. Brain Res. 2001; 90(2):193-201.
White, J.R, et al, "Phosphorothioate-capped antisense oligonucleotides to Ras GAP injibit cell proliferation and trigger apoptosis but fail to downregulate GAP gene expression", Biochem Biophys Res Commun, vol. 227, No. 1, pp. 118-124, (1996).
Whittles, C.E, et al, "Apoptotic and proliferative activity in the neoplastic progression of Barrett's oesophagus: a comparative study", The Journal of Pathology, vol. 187, issue 5, pp. 535-540, (1999).
Williamson, J.R, et al, "Monovalent cation-induced structure os telomeric DNA: the G-quartet model", Cell, vol. 59, No. 5, pp. 871-880, (1989).
Winer, I. et al., "F3-targeted cisplatin-hydrogel nanoparticles as an effective therapeutic that targets both murine and human ovarian tumor endothelial cells in vivo", Cancer Research, vol. 70, No. 21, pp. 8674-8683, (2010).
Winter, G, et al, "Making antibodies by phage display technology", Annu Rev Immunol, vol. 12, pp. 433-455, (1994).
Wittwer, et al. Glycosylation at Asn-184 inhibits the conversion of single-chain to two-chain tissue-type plasminogen activator by plasmin. Biochemistry. May 1, 1990;29(17):4175-80.
Wolters, D.A, et al, "An automated multidimensional protein identification technology for shotfun proteomics", Anal Chem, vol. 73, No. 23, pp. 5683-5690, (2001).
Workman, P. et al., "Minimally invasive pharmacokinetic and pharmacodynamic technologies in hypothesis-testing clinical trials of innovative therapies", Journal of the National Cancer Institute, vol. 98, No. 9, pp. 580-598, (2006).
Wright, et al. Effect of glycosylation on antibody function: implications for genetic engineering.Trends Biotechnol. Jan. 1997;15(1):26-32.
Wurzer, G, et al, "Increased resistance to anticancer therapy of mouse cells lacking the poly(ADP-ribose) polymerase attributable to up-regulation of the multidrug resistance gene product P-glycoprotein", Cancer Research, vol. 60, No. 15, pp. 4238-4244, (2000).
Wyatt, J.R, et al, "Combinatorially selected guanosine-quartet structure is a potent inhibitor of human immunodeficiency virus envelope-mediated cell fusion", Proc Natl Acad Science USA, vol. 91, No. 4, pp. 1356-1360, (1994).
Wyllie, A.H, et al, "Cell death: the significance of apoptosis", International Review of Cytology, vol. 68, pp. 251-306, (1980).
Wysocki, L.J, et al, ""Panning" for lymphocytes: a method for cell selection", Proc Natl Acad Sci USA, vol. 75, No. 6, pp. 2844-2848, (1978).
Wyss, et al. The structural role of sugars in glycoproteins. Curr Opin Biotechnol. Aug. 1996;7(4):409-16.
Xiao-Ming, Y., "Signal transduction mediated by Bid, a pro-death Bcl-2 family proteins, connects the death receptor and mitochondria apoptosis pathways", Cell Research, vol. 10, No. 3, pp. 161-167, (2000).

(56) References Cited

OTHER PUBLICATIONS

Xie, L., et al., "Bovine serum albumin nanoparticles modified with multilayers and aptamers for pH-responsive and targeted anti-cancer drug delivery", Journal of Materials Chemistry, vol. 22, pp. 6053-6060, (2012).
Xu, B. et al., "An efficient synthesis of difluoropropargyl bromides", Synthesis, vol. 5, pp. 803-806, (2006).
Xu, X, et al, "Inhibition of DNA replication and induction of S phase cell cycle arrest by G-rich oligonucleotides", The Journal of Biological Chemistry, vol. 276, No. 46, pp. 43221-43230, (2001).
Xue, Z, et al, "The amino terminus of mammalian nucleolin specifically recognizes SV40 T-antigen type nuclear localization sequences", Eur J Cell Biol, vol. 62, No. 1, pp. 13-21, (1993).
Yanagida, M, et al, "Isolation and proteomic characterization of the major proteins of the nucleolin-binding ribonucleoprotein complexes", Proteomics, vol. 1, No. 11, pp. 1390-1404, (2001).
Yang, et al. Identification of nucleolin and nucleophosmin as genotoxic stress-responsive RNA-binding proteins. Nucleic Acids Res. May 15, 2002;30(10):2251-60.
Yang, X. et al., "Near-infrared light-triggered, targeted drug delivery to cancer cells by aptamer gated nanovehicles", Advanced Materials, vol. 24, pp. 2890-2895, (2012).
Yao, G.Q, et al, "Identification of two oligodeoxyribonucleotide binding proteins on plasma membranes of human cell lines", Biochemical Pharmacology, vol. 51, pp. 431-436, (1996).
Yasui, W. et al., "Transcriptome dissection of gastric cancer: Identification of novel diagnostic and therapeutic targets from pathology specimens", Pathology International, vol. 59, pp. 121-136, (2009).
Yilmaz, O.H. et al., "Pten dependence distinguishes haematopoietic stem cells from leukaemia-initiating cells", Nature, vol. 441, pp. 475-482, (2006).
Yoo, C.B. et al., "Epigenetic therapy of cancer: past, present and future", Nature Reviews Drug Discovery, vol. 5, No. 1, pp. 37-50, (2006).
Zhang, Y. et al., "A surface-charge study on cellular-uptake behavior of F3-peptide-conjugated iron oxide nanoparticles", Small, vol. 5, No. 17,pp. 1990-1996, (2009).
Database Protein, [online], Genbank Accession No. NP_005372—nucleolin [*Homo sapiens*]. Available at www.ncbi.nlm.nih.gov/protein/55956788?sat=13&satkey=7538678, Uploaded Nov. 1, 2009. Accessed Feb. 8, 2017.

| Antibody | well | A450 |
|---|---|---|
| 3H11 | 1F8 | 0.629 |
| 3H11 | 3A3 | 0.593 |
| 3H11 | 4H12 | 0.299 |
| 5D1 | 2G3 | 0.457 |
| 5D1 | 3C10 | 0.575 |
| 5D1 | 4G2 | 0.336 |
| 5D1 | 4H12 | 0.589 |
| 8G4 | 1A11 | 0.633 |
| 8G4 | 2G2 | 0.308 |
| 8G4 | 4B6 | 0.698 |
| P1C6 | 1C7 | 0.636 |
| P1C6 | 2B9 | 0.685 |
| P1C6 | 4H7 | 0.660 |
| 7G7 | 1G9 | 0.579 |
| 7G7 | 3C2 | 0.711 |
| 7G7 | 4C7 | 0.657 |
| 7G7 | 4G9 | 0.389 |
| 7G7 | 5B1 | 0.526 |
| 9F9 | 1A7 | 0.707 |
| 9F9 | 3D4 | 0.624 |
| 9F9 | 5A8 | 0.702 |
| 9F9 | 5D2 | 0.662 |
| 2D3 | 2B1 | 0.642 |
| 2D3 | 3 E4 | 0.674 |
| 2H3 | 1C5 | 0.387 |
| 2H3 | 1H5 | 0.583 |
| 2H3 | 2H8 | 0.562 |
| 2H3 | 3F3 | 0.587 |
| 2H3 | 4C6 | 0.692 |
| 2H3 | 4C12 | 0.701 |
| 2H3 | 4 E3 | 0.399 |
| 2H3 | 5D3 | 0.793 |
| Negative Control | | 0.090 |
| Mouse anti-NCL MS3 | | 0.889 |

NUCLEOLIN ANTIBODIES

CROSS-REFERENCE

This application is a Divisional Application of U.S. application Ser. No. 13/510,270 filed Dec. 19, 2012, now U.S. Pat. No. 9,260,517, which is a 371 National Stage Entry of International Application No. PCT/US2010/057046 filed Nov. 17, 2010, which claims benefit of priority to U.S. Provisional Application Ser. No. 61/261,909, filed Nov. 17, 2009, each of which is incorporated herein by reference in its entirety.

STATEMENT AS TO FEDERALLY SPONSORED RESEARCH

This invention was made with the support of the United States government under grant number NCI CA109254-04S1 awarded by the National Cancer Institute, National Institutes of Health. The U.S. Government may have rights in this invention.

BACKGROUND OF THE INVENTION

The present invention relates generally to the fields of cell biology and immunology. More particularly, it concerns methods and compositions relating to the production and use of human monoclonal antibodies to human nucleolin (NCL).

Antibodies are a class of agents known as "biologicals." The source of antibodies can be a polyclonal supply, such as human or horse serum, or derived from a monoclonal source (single cell clone). With the technologic capability to control and select for specific antigen binding, monoclonal antibodies have yielded dramatic therapeutic benefits. However, the difficulty of generating specific antibodies for certain targets has limited the successes, and the potential for therapeutic and diagnostic agents remains largely untapped.

One impediment to the development of monoclonal antibodies for human therapy is the need to "humanize" such antibodies, which are generally made in mice, rats and rabbits. If human patients are administered such antibodies without humanized constant regions, they can suffer from "serum sickness," meaning that an endogenous immune response is mounted by the recipient against the non-human antibody sequences. Humanizing monoclonal antibodies produced in research animals can avoid this problem. However, the cost in time and expense for humanization of antibodies can be considerable.

Nucleolin is expressed on the cell surface of human chronic lymphocytic leukemia (CLL) cells, acute myeloid leukemia (AML) cells, some forms of breast carcinoma, as well as other tumors. As such, nucleolin constitutes a promising tumor antigen for targeting of therapeutics, including antibodies.

SUMMARY OF THE INVENTION

In one aspect of the invention a method is provided of producing an immortalized human B-cell that secrets an antibody that binds to human nucleolin comprising: obtaining a population of IgM-positive human B-cells; contacting said population with: Epstein-Barr virus (EBV) to immortalize said human B-cells, and a cytokine/growth factor/signaling agent cocktail to induce IgM-to-IgG immunoglobulin isotype class-switching; and culturing cells under conditions supporting said immortalization and immunoglobulin isotype class-switching. In one embodiment the method further comprises, selecting an immortalized human B-cell that expresses an antibody to human nucleolin. In another embodiment, selecting comprises an immunoassay performed on immortalized B-cell culture medium supernatants. In another embodiment, a cytokine cocktail comprises an agent that delivers a costimulatory signal to a human B-cell. In another embodiment, a cytokine cocktail comprises anti-IgM $F(ab')_2$ interleukin (IL)-2, IL-4, IL-5, IL-6, IL-9, IL-10, IL-13, INF$\alpha$, BAFF, soluble CD40L. In another embodiment, a population of IgM-positive human B-cells is obtained from peripheral blood, a tonsils bone marrow, a spleen, a lymph node, umbilical cord blood, a liver, an apheresis procedures or a buffy coat. In another embodiment, the method further comprises isolating a nucleic acid encoding an entire heavy and/or light chain from the immortalized human B-cell of step (d). In another embodiment, the method further comprises isolating a nucleic acid encoding a heavy and/or light chain antigen-binding region from the immortalized human B-cell of step (d). In another embodiment, the method further comprises cloning said nucleic acid into a nucleic acid encoding a framework region of a heavy and/or light chain. In another embodiment, contacting said population further comprises an EBV concentration step, a centrifugation step during infection, or both. In another embodiment, the method further comprises freezing said population of human B-cells following step (c). In another embodiment, contacting said population with a cytokine/growth factor/signaling agent cocktail is performed at about 0-96 hours following step (b)(ii). In another embodiment, contacting said population with a cytokine/growth factor/signaling agent cocktail is performed at about 16-20 hours following step (b)(ii). In another embodiment, about 50%-99% of said population are immortalized by EBV infection. In another embodiment, about 95%-99% of said population are immortalized by EBV infection. In another embodiment, selecting an immortalized human B-cell that expresses an antibody to human nucleolin occurs 1-4 weeks following infection. In another embodiment, selecting an immortalized human B-cell that expresses an antibody to human nucleolin occurs 2-3 weeks following infection. In another embodiment, selecting an immortalized human B-cell that expresses an antibody to human nucleolin occurs after thawing stored frozen immortalized B-cells, and/or after thawing stored frozen culture medium supernatants from said immortalized B-cells. In another embodiment, the B-cell is antigen naïve. In another embodiment, the B-cell is antigen experienced.

In another aspect the invention provides an immortalized human B-cell that expresses an IgG antibody that binds to human nucleolin. In one embodiment, the immortalized human B-cell is designated as T-5D1, V-3H11 (3G5), T-2D3, T-7G7 (1H9), T-2H3, T-9F9, T-8G4 or T-P1C6.

In another aspect the invention provides an immortalized human B-cell that expresses an IgG antibody or fragment thereof that binds to a protein of SEQ ID No. 2. In one embodiment, the IgG antibody is an IgG1, IgG2, IgG3, or IgG4 antibody. In another embodiment, the IgG antibody is an IgG1 antibody. In another embodiment, the IgG antibody comprises a kappa light chain. In another embodiment, the IgG antibody comprises a lambda light chain. In another embodiment, the B-cell is EBV immortalized. In another embodiment, the antibody or fragment thereof is a monoclonal antibody or fragment thereof. In another embodiment, the antibody or fragment thereof is substantially non-immunogenic to a human. In another embodiment, the antibody or fragment thereof is a human antibody or fragment thereof. In another embodiment, the antibody or fragment thereof kills at least 10% of a population of MCF-7 cells, when incubated with said MCF-7 cells and human AB serum for 48 hours. In another embodiment, the antibody or fragment thereof kills at least 20% of a population of MCF-7 cells, when incubated with said MCF-7 cells and human AB serum for 48 hours. In another embodiment, the antibody or fragment thereof kills at least 30% of a population of MCF-7 cells, when incubated with said MCF-7 cells and human AB serum for 48 hours. In another embodiment, the antibody or fragment thereof kills at least 40% of a population of MCF-7 cells, when incubated with said MCF-7 cells and human AB serum for 48 hours. In another embodiment, the antibody or fragment thereof kills at least 50% of a population of MCF-7 cells, when incubated with said MCF-7 cells and human AB serum for 48 hours. In another embodiment, the antibody or fragment thereof kills at least 60% of a population of MCF-7 cells, when incubated with said MCF-7 cells and human AB serum for 48 hours. In another embodiment, the antibody or fragment thereof kills at least 70% of a population of MCF-7 cells, when incubated with said MCF-7 cells and human AB serum for 48 hours. In another embodiment, the antibody or fragment thereof kills at least 80% of a population of MCF-7 cells, when incubated with said MCF-7 cells and human AB serum for 48 hours. In another embodiment, the antibody or fragment thereof kills at least 90% of a population of MCF-7 cells, when incubated with said MCF-7 cells and human AB serum for 48 hours. In another embodiment, the antibody or fragment thereof kills at least 100% of a population of MCF-7 cells, when incubated with said MCF-7 cells and human AB serum for 48 hours. In another embodiment, the antibody or fragment thereof kills at least 10% of a population of MV4-11 cells, when incubated with said MCF-7 cells and human AB serum for 48 hours. In another embodiment, the antibody or fragment thereof kills at least 20% of a population of MV4-11 cells, when incubated with said MCF-7 cells and human AB serum for 48 hours. In another embodiment, the antibody or fragment thereof kills at least 30% of a population of MV4-11 cells, when incubated with said MCF-7 cells and human AB serum for 48 hours. In another embodiment, the antibody or fragment thereof kills at least 40% of a population of MV4-11 cells, when incubated with said MCF-7 cells and human AB serum for 48 hours. In another embodiment, the antibody or fragment thereof kills at least 50% of a population of MV4-11 cells, when incubated with said MCF-7 cells and human AB serum for 48 hours. In another embodiment, the antibody or fragment thereof kills at least 60% of a population of MV4-11 cells, when incubated with said MCF-7 cells and human AB serum for 48 hours. In another embodiment, the antibody or fragment thereof kills at least 70% of a population of MV4-11 cells, when incubated with said MCF-7 cells and human AB serum for 48 hours. In another embodiment, the antibody or fragment thereof kills at least 80% of a population of MV4-11 cells, when incubated with said MCF-7 cells and human AB serum for 48 hours. In another embodiment, the antibody or fragment thereof kills at least 90% of a population of MV4-11 cells, when incubated with said MCF-7 cells and human AB serum for 48 hours. In another embodiment, the antibody or fragment thereof kills at least 100% of a population of MV4-11 cells, when incubated with said MCF-7 cells and human AB serum for 48 hours. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof induces complement-dependent cytotoxicity to a cancer cell. In another embodiment, the isolated antibody or fragment thereof induces complement-independent cytotoxicity to a cancer cell. In another embodiment, the isolated antibody or fragment thereof induces apoptosis in a cancer cell upon contact. In another embodiment, the isolated antibody or fragment thereof inhibits or kills an AML cancer cell, a CLL cancer cell or a breast cancer cell. In another embodiment, the isolated monoclonal antibody or fragment thereof reduces BCL-2 levels in a cancer cell.

In another aspect the invention provides an immortalized human B-cell that expresses an IgG antibody or fragment thereof that binds to a protein encoded by SEQ ID No. 1. In one embodiment, the IgG antibody is an IgG1, IgG2, IgG3, or IgG4 antibody. In another embodiment, the IgG antibody is an IgG1 antibody. In another embodiment, the IgG antibody comprises a kappa light chain. In another embodiment, the IgG antibody comprises a lambda light chain. In another embodiment, the B-cell is EBV immortalized. In another embodiment, the antibody or fragment thereof is a monoclonal antibody or fragment thereof. In another embodiment said antibody or fragment thereof is substantially non-immunogenic to a human. In another embodiment, the antibody or fragment thereof is a human antibody or fragment thereof. In another embodiment, the antibody or fragment thereof kills at least 10% of a population of MCF-7 cells, when incubated with said MCF-7 cells and human AB serum for 48 hours. In another embodiment, the antibody or fragment thereof kills at least 20% of a population of MCF-7 cells, when incubated with said MCF-7 cells and human AB serum for 48 hours. In another embodiment, the antibody or fragment thereof kills at least 30% of a population of MCF-7 cells, when incubated with said MCF-7 cells and human AB serum for 48 hours. In another embodiment, the antibody or fragment thereof kills at least 40% of a population of MCF-7 cells, when incubated with said MCF-7 cells and human AB serum for 48 hours. In another embodiment, the antibody or fragment thereof kills at least 50% of a population of MCF-7 cells, when incubated with said MCF-7 cells and human AB serum for 48 hours. In another embodiment, the antibody or fragment thereof kills at least 60% of a population of MCF-7 cells, when incubated with said MCF-7 cells and human AB serum for 48 hours. In another embodiment, the antibody or fragment thereof kills at least 70% of a population of MCF-7 cells, when incubated with said MCF-7 cells and human AB serum for 48 hours. In another embodiment, the antibody or fragment thereof kills at least 80% of a population of MCF-7 cells, when incubated with said MCF-7 cells and human AB serum for 48 hours. In another embodiment, the antibody or fragment thereof kills at least 90% of a population of MCF-7 cells, when incubated with said MCF-7 cells and human AB serum for 48 hours. In another embodiment, the antibody or fragment thereof kills at least 100% of a population of MCF-7 cells, when incubated with said MCF-7 cells and human AB serum for 48 hours. In another embodiment, the antibody or fragment thereof kills at least 10% of a population of MV4-11 cells, when incubated with said MCF-7 cells and human AB serum for 48 hours. In another embodiment, the antibody or fragment thereof kills at least 20% of a population of MV4-11 cells, when incubated with said MCF-7 cells and human AB serum for 48 hours. In another embodiment, the antibody or fragment thereof kills at least 30% of a population of MV4-11 cells, when incubated with said MCF-7 cells and human AB serum for 48 hours. In another embodiment, the antibody or fragment thereof kills at least 40% of a population of MV4-11 cells, when incubated with said MCF-7 cells and human AB serum for 48 hours. In another embodiment, the antibody or fragment thereof kills at least 50% of a population of MV4-11 cells, when incubated with said MCF-7 cells and human AB serum for 48 hours. In another embodiment, the antibody or fragment thereof kills at least 60% of a population of MV4-11 cells, when incubated with said MCF-7 cells and human AB serum for 48 hours. In another embodiment, the antibody or fragment thereof kills at least 70% of a population of MV4-11 cells, when incubated with said MCF-7 cells and human AB serum for 48 hours. In another embodiment, the antibody or fragment thereof kills at least 80% of a population of MV4-11 cells, when incubated with said MCF-7 cells and human AB serum for 48 hours. In another embodiment, the antibody or fragment thereof kills at least 90% of a population of MV4-11 cells, when incubated with said MCF-7 cells and human AB serum for 48 hours. In another embodiment, the antibody or fragment thereof kills at least 100% of a population of MV4-11 cells, when incubated with said MCF-7 cells and human AB serum for 48 hours. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof induces complement-dependent cytotoxicity to a cancer cell. In another embodiment, the isolated antibody or fragment thereof induces complement-independent cytotoxicity to a cancer cell. In another embodiment, the isolated antibody or fragment thereof induces apoptosis in a cancer cell upon contact. In another embodiment, the isolated antibody or fragment thereof inhibits or kills an AML cancer cell, a CLL cancer cell or a breast cancer cell. In another embodiment, the isolated monoclonal antibody or fragment thereof reduces BCL-2 levels in a cancer cell.

In another aspect the invention provides an immortalized human B-cell that expresses an IgG antibody or fragment thereof that binds to a protein comprising SEQ ID No. 4. In one embodiment, the IgG antibody is an IgG1, IgG2, IgG3, or IgG4 antibody. In another embodiment, the IgG antibody is an IgG1 antibody. In another embodiment, the IgG antibody comprises a kappa light chain. In another embodiment, the IgG antibody comprises a lambda light chain. In another embodiment, the B-cell is EBV immortalized. In another embodiment, said antibody or fragment thereof is a monoclonal antibody or fragment thereof. In another embodiment, the antibody or fragment thereof is substantially non-immunogenic to a human. In another embodiment, the antibody or fragment thereof is a human antibody or fragment thereof. In another embodiment, the antibody or fragment thereof kills at least 10% of a population of MCF-7 cells, when incubated with said MCF-7 cells and human AB serum for 48 hours. In another embodiment, the antibody or fragment thereof kills at least 20% of a population of MCF-7 cells, when incubated with said MCF-7 cells and human AB serum for 48 hours. In another embodiment, the antibody or fragment thereof kills at least 30% of a population of MCF-7 cells, when incubated with said MCF-7 cells and human AB serum for 48 hours. In another embodiment, the antibody or fragment thereof kills at least 40% of a population of MCF-7 cells, when incubated with said MCF-7 cells and human AB serum for 48 hours. In another embodiment, the antibody or fragment thereof kills at least 50% of a population of MCF-7 cells, when incubated with said MCF-7 cells and human AB serum for 48 hours. In another embodiment, the antibody or fragment thereof kills at least 60% of a population of MCF-7 cells, when incubated with said MCF-7 cells and human AB serum for 48 hours. In another embodiment, the antibody or fragment thereof kills at least 70% of a population of MCF-7 cells, when incubated with said MCF-7 cells and human AB serum for 48 hours. In another embodiment, the antibody or fragment thereof kills at least 80% of a population of MCF-7 cells, when incubated with said MCF-7 cells and human AB serum for 48 hours. In another embodiment, the antibody or fragment thereof kills at least 90% of a population of MCF-7 cells, when incubated with said MCF-7 cells and human AB serum for 48 hours. In another embodiment, the antibody or fragment thereof kills at least 100% of a population of MCF-7 cells, when incubated with said MCF-7 cells and human AB serum for 48 hours. In another embodiment, the antibody or fragment thereof kills at least 10% of a population of MV4-11 cells, when incubated with said MCF-7 cells and human AB serum for 48 hours. In another embodiment, the antibody or fragment thereof kills at least 20% of a population of MV4-11 cells, when incubated with said MCF-7 cells and human AB serum for 48 hours. In another embodiment, the antibody or fragment thereof kills at least 30% of a population of MV4-11 cells, when incubated with said MCF-7 cells and human AB serum for 48 hours. In another embodiment, the antibody or fragment thereof kills at least 40% of a population of MV4-11 cells, when incubated with said MCF-7 cells and human AB serum for 48 hours. In another embodiment, the antibody or fragment thereof kills at least 50% of a population of MV4-11 cells, when incubated with said MCF-7 cells and human AB serum for 48 hours. In another embodiment, the antibody or fragment thereof kills at least 60% of a population of MV4-11 cells, when incubated with said MCF-7 cells and human AB serum for 48 hours. In another embodiment, the antibody or fragment thereof kills at least 70% of a population of MV4-11 cells, when incubated with said MCF-7 cells and human AB serum for 48 hours. In another embodiment, the antibody or fragment thereof kills at least 80% of a population of MV4-11 cells, when incubated with said MCF-7 cells and human AB serum for 48 hours. In another embodiment, the antibody or fragment thereof kills at least 90% of a population of MV4-11 cells, when incubated with said MCF-7 cells and human AB serum for 48 hours. In another embodiment, the antibody or fragment thereof kills at least 100% of a population of MV4-11 cells, when incubated with said MCF-7 cells and human AB serum for 48 hours. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof induces complement-dependent cytotoxicity to a cancer cell. In another embodiment, the isolated antibody or fragment thereof induces complement-independent cytotoxicity to a cancer cell. In another embodiment, the isolated antibody or fragment thereof induces apoptosis in a cancer cell upon contact. In another embodiment, the isolated antibody or fragment thereof inhibits or kills an AML cancer cell, a CLL cancer cell or a breast cancer cell. In another embodiment, the isolated monoclonal antibody or fragment thereof reduces BCL-2 levels in a cancer cell.

In another aspect the invention provides an immortalized human B-cell that expresses an IgG antibody or fragment thereof that binds to a protein encoded by SEQ ID No. 3. In one embodiment, the IgG antibody is an IgG1, IgG2, IgG3, or IgG4 antibody. In another embodiment, the IgG antibody is an IgG1 antibody. In another embodiment, the IgG antibody comprises a kappa light chain. In another embodiment, the IgG antibody comprises a lambda light chain. In another embodiment, the B-cell is EBV immortalized. In another embodiment, the antibody or fragment thereof is a monoclonal antibody or fragment thereof. In another embodiment, the antibody or fragment thereof is substantially non-immunogenic to a human. In another embodiment, the antibody or fragment thereof is a human antibody or fragment thereof. In another embodiment, the antibody or fragment thereof kills at least 20% of a population of MCF-7 cells, when incubated with said MCF-7 cells and human AB serum for 48 hours. In another embodiment, the antibody or fragment thereof kills at least 20% of a population of MV4-11 cells, when incubated with said MCF-7 cells and human AB serum for 48 hours. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof induces complement-dependent cytotoxicity to a cancer cell. In another embodiment, the isolated antibody or fragment thereof induces complement-independent cytotoxicity to a cancer cell. In another embodiment, the isolated antibody or fragment thereof induces apoptosis in a cancer cell upon contact. In another embodiment, the isolated antibody or fragment thereof inhibits or kills an AML cancer cell, a CLL cancer cell or a breast cancer cell. In another embodiment, the isolated monoclonal antibody or fragment thereof reduces BCL-2 levels in a cancer cell.

In another aspect the invention provides an isolated human monoclonal antibody or fragment thereof that specifically binds to a protein of SEQ ID No. 4. In one embodiment, the antibody or fragment thereof is a human antibody or fragment thereof. In another embodiment, the antibody or fragment thereof kills at least 10% of a population of MCF-7 cells, when incubated with said MCF-7 cells and human AB serum for 48 hours. In another embodiment, the antibody or fragment thereof kills at least 20% of a population of MCF-7 cells, when incubated with said MCF-7 cells and human AB serum for 48 hours. In another embodiment, the antibody or fragment thereof kills at least 30% of a population of MCF-7 cells, when incubated with said MCF-7 cells and human AB serum for 48 hours. In another embodiment, the antibody or fragment thereof kills at least 40% of a population of MCF-7 cells, when incubated with said MCF-7 cells and human AB serum for 48 hours. In another embodiment, the antibody or fragment thereof kills at least 50% of a population of MCF-7 cells, when incubated with said MCF-7 cells and human AB serum for 48 hours. In another embodiment, the antibody or fragment thereof kills at least 60% of a population of MCF-7 cells, when incubated with said MCF-7 cells and human AB serum for 48 hours. In another embodiment, the antibody or fragment thereof kills at least 70% of a population of MCF-7 cells, when incubated with said MCF-7 cells and human AB serum for 48 hours. In another embodiment, the antibody or fragment thereof kills at least 80% of a population of MCF-7 cells, when incubated with said MCF-7 cells and human AB serum for 48 hours. In another embodiment, the antibody or fragment thereof kills at least 90% of a population of MCF-7 cells, when incubated with said MCF-7 cells and human AB serum for 48 hours. In another embodiment, the antibody or fragment thereof kills at least 100% of a population of MCF-7 cells, when incubated with said MCF-7 cells and human AB serum for 48 hours. In another embodiment, the antibody or fragment thereof kills at least 10% of a population of MV4-11 cells, when incubated with said MCF-7 cells and human AB serum for 48 hours. In another embodiment, the antibody or fragment thereof kills at least 20% of a population of MV4-11 cells, when incubated with said MCF-7 cells and human AB serum for 48 hours. In another embodiment, the antibody or fragment thereof kills at least 30% of a population of MV4-11 cells, when incubated with said MCF-7 cells and human AB serum for 48 hours. In another embodiment, the antibody or fragment thereof kills at least 40% of a population of MV4-11 cells, when incubated with said MCF-7 cells and human AB serum for 48 hours. In another embodiment, the antibody or fragment thereof kills at least 50% of a population of MV4-11 cells, when incubated with said MCF-7 cells and human AB serum for 48 hours. In another embodiment, the antibody or fragment thereof kills at least 60% of a population of MV4-11 cells, when incubated with said MCF-7 cells and human AB serum for 48 hours. In another embodiment, the antibody or fragment thereof kills at least 70% of a population of MV4-11 cells, when incubated with said MCF-7 cells and human AB serum for 48 hours. In another embodiment, the antibody or fragment thereof kills at least 80% of a population of MV4-11 cells, when incubated with said MCF-7 cells and human AB serum for 48 hours. In another embodiment, the antibody or fragment thereof kills at least 90% of a population of MV4-11 cells, when incubated with said MCF-7 cells and human AB serum for 48 hours. In another embodiment, the antibody or fragment thereof kills at least 100% of a population of MV4-11 cells, when incubated with said MCF-7 cells and human AB serum for 48 hours. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof induces complement-dependent cytotoxicity to a cancer cell. In another embodiment, the isolated antibody or fragment thereof induces complement-independent cytotoxicity to a cancer cell. In another embodiment, the isolated antibody or fragment thereof induces apoptosis in a cancer cell upon contact. In another embodiment, the isolated antibody or fragment thereof inhibits or kills an AML cancer cell, a CLL cancer cell or a breast cancer cell. In another embodiment, the isolated monoclonal antibody or fragment thereof reduces BCL-2 levels in a cancer cell.

In another aspect the invention provides an isolated antibody or fragment thereof that specifically binds to a human nucleolin protein, wherein said antibody or fragment thereof kills at least 20% of a population of MCF-7 cells, when incubated with said MCF-7 cells and human AB serum for 48 hours. In one embodiment, the amino acid sequence of said human nucleolin comprises SEQ ID No. 2. In another embodiment, the antibody or fragment thereof binds to an amino acid sequence consisting of amino acid residues 1 to 283 of SEQ ID No. 2. In another embodiment, the antibody or fragment thereof is a monoclonal antibody or fragment thereof. In another embodiment, the antibody or fragment thereof is substantially non-immunogenic to a human. In another embodiment, the antibody or fragment thereof is a human antibody or fragment thereof. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof is linked to a diagnostic or therapeutic agent. In another embodiment, the isolated antibody or fragment thereof exhibits complement-dependent cytotoxicity to a cancer cell. In another embodiment, the isolated antibody or fragment thereof exhibits complement-independent cytotoxicity to a cancer cell. In another embodiment, the isolated antibody or fragment thereof induces apoptosis in a cancer cell upon contact.

In another embodiment, the antibody or fragment thereof inhibits or kills an AML cancer cell, a CLL cancer cell or a breast cancer cell. In another embodiment, the isolated antibody or fragment thereof reduces BCL-2 levels in a cancer cell. In another embodiment, the antibody or fragment thereof is linked to a diagnostic agent. In another embodiment, the diagnostic agent is a radionuclide, a fluorophore, a chemilluminescent compound, a fluorescent compound, or an enzyme. In another embodiment, the antibody or fragment thereof is linked to a therapeutic agent. In another embodiment, the therapeutic agent is a radionuclide, a toxin or a chemotherapeutic moiety.

In another aspect the invention provides an isolated antibody or fragment thereof that specifically binds to a human nucleolin protein, wherein said antibody or fragment thereof kills at least 10-100% of a population of MV4-11 cells (such as 10, 20, 30, 40, 50, 60, 70, 80, 90 or 100% of a population of MV4-11 cells, when incubated with said MCF-7 cells and human AB serum for 48 hours. In another embodiment, the amino acid sequence of said human nucleolin comprises SEQ ID No. 2. In another embodiment, the antibody or fragment thereof binds to an amino acid sequence consisting of amino acid residues 1 to 283 of SEQ ID No. 2. In another embodiment, the antibody or fragment thereof is a monoclonal antibody or fragment thereof. In another embodiment, the antibody or fragment thereof is substantially non-immunogenic to a human. In another embodiment, the antibody or fragment thereof is a human antibody or fragment thereof. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof is linked to a diagnostic or therapeutic agent. In another embodiment, the isolated antibody or fragment thereof exhibits complement-dependent cytotoxicity to a cancer cell. In another embodiment, the isolated antibody or fragment thereof exhibits complement-independent cytotoxicity to a cancer cell. In another embodiment, the isolated antibody or fragment thereof induces apoptosis in a cancer cell upon contact. In another embodiment, the antibody or fragment thereof inhibits or kills an AML cancer cell, a CLL cancer cell or a breast cancer cell. In another embodiment, the isolated antibody or fragment thereof reduces BCL-2 levels in a cancer cell. In another embodiment, the said antibody or fragment thereof is linked to a diagnostic agent. In another embodiment, the diagnostic agent is a radionuclide, a fluorophore, a chemilluminescent compound, a fluorescent compound, or an enzyme. In another embodiment, the antibody or fragment thereof is linked to a therapeutic agent. In another embodiment, the therapeutic agent is a radionuclide, a toxin or a chemotherapeutic moiety.

In another aspect the invention provides an anti-nucleolin composition comprising one or more isolated antibodies or fragments thereof that specifically binds to a human nucleolin protein, wherein said one or more antibodies kills at least 10-100% of a population of MCF-7 cells (such as 10, 20, 30, 40, 40, 50, 60, 70, 80, 90, or 100%), when incubated with said MCF-7 cells and human AB serum for 48-96 (such as 48, 72 or 96 hours) hours. In one embodiment, the one or more isolated antibodies or fragments thereof is a monoclonal antibody or fragment thereof. In another embodiment, the one or more isolated antibodies or fragments thereof is substantially non-immunogenic to a human. In another embodiment, the one or more isolated antibodies or fragments thereof is a human antibody or fragment thereof. In another embodiment, the one or more isolated antibodies or fragments thereof binds to an RNA binding domain of human nucleolin. In another embodiment, the one or more isolated antibodies or fragments thereof inactivates an RNA binding domain of human nucleolin. In another embodiment, the amino acid sequence of said human nucleolin comprises SEQ ID No. 2. In another embodiment, the one or more isolated antibodies or fragments thereof binds to SEQ ID No. 4. In another embodiment, the anti-nucleolin composition further comprises a radionuclide, a fluorophore, a chemilluminescent compound, a fluorescent compound, an enzyme, a toxin or a chemotherapeutic agent. In another embodiment, the radionuclide, a fluorophore, a chemilluminescent compound, a fluorescent compound, an enzyme, a toxin or a chemotherapeutic agent is conjugated to said one or more isolated antibodies or fragments thereof. In another embodiment, the anti-nucleolin composition comprises two or more isolated antibodies or fragments thereof that specifically binds to said human nucleolin protein, wherein said one or more antibodies kills at least 20% of a population of MCF-7 cells, when incubated with said MCF-7 cells and human AB serum for 48 hours. In another embodiment, the anti-nucleolin composition comprises three or more isolated antibodies or fragments thereof that specifically binds to said human nucleolin protein, wherein said one or more antibodies kills at least 20% of a population of MCF-7 cells, when incubated with said MCF-7 cells and human AB serum for 48 hours.

In another aspect the invention provides a method of inhibiting or killing a cell expressing nucleolin on its surface comprising contacting said cell with an antibody or fragment thereof that binds to human nucleolin, wherein said antibody or fragment thereof kills at least 20% of a population of MCF-7 cells, when incubated with said MCF-7 cells and human AB serum for 48 hours. In one embodiment, the antibody or fragment thereof is a human antibody or fragment thereof. In another embodiment, the antibody or fragment thereof is a monoclonal antibody or fragment thereof. In another embodiment, the antibody or fragment thereof binds to SEQ ID No. 2. In another embodiment, the antibody or fragment thereof binds to an amino acid sequence encoded by SEQ ID No. 1. In another embodiment, the antibody or fragment thereof binds to SEQ ID No. 4. In another embodiment, the antibody or fragment thereof binds to an amino acid sequence encoded by SEQ ID No. 3. In another embodiment, the cell is a cancer cell. In another embodiment, the cancer cell is a lung cancer cell, a breast cancer cell, a prostate cancer cell, a colon cancer cell, a pancreatic cancer cell, a renal cell carcinoma cell, an ovarian cancer cell, a leukemia cell, a melanoma cell, a glioblastoma cell, a neuroblastoma cell, a sarcoma cell or a gastric cancer cell. In another embodiment, the cell is an immune cell. In another embodiment, the immune cell is a lymphocyte, dendritic cell, a peripheral blood monocyte, a macrophage or a glial cell. In another embodiment, the immune cell is an activated immune cell. In another embodiment, the immune cell is an activated B cell. In another embodiment, the immune cell is a memory B cell. In another embodiment, the immune cell is an activated T cell. In another embodiment, the immune cell is an activated CD4+ T cell. In another embodiment, the immune cell is an activated CD8+ T cell. In another embodiment, the cell a vascular smooth muscle cell or an endothelial cell. In another embodiment, the antibody or fragment thereof is linked to a therapeutic agent. In another embodiment, the therapeutic agent is a radionuclide, a toxin or a chemotherapeutic agent. In another embodiment, the inhibiting or killing comprises inducing apoptosis in said cell. In another embodiment, the cell is located in a human subject, and said contacting comprising administering said antibody or fragment thereof to said subject. In another embodiment, the method of further comprises contacting said cell with at least one additional inhibitory agent or treatment. In another embodiment, the additional treatment comprises one or more of surgery, radiotherapy, chemotherapy, toxin therapy, immunotherapy, hormone therapy, anti-angiogenic therapy or gene therapy orother biological therapies. In another embodiment, the additional inhibitory agent comprises one or more of radionuclides, chemotherapetic agents, toxins immunotherapeutics, hormones, nucleic acids or polypeptides. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the wherein said chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

In another aspect the invention provides a method of detecting a cell expressing nucleolin on its surface comprising contacting said cell with a human antibody or fragment thereof that binds immunologically to said nucleolin. In one embodiment, the cell is a cancer cell, an immune cell, or a vascular smooth muscle cell that expresses nucleolin on its surface, an endothelial cell that expresses nucleolin on its surface, or a virus infected cell. In another embodiment, the cell is a precancersous cell that expresses nucleolin on its surface. In another embodiment, the cancer cell selected from the group consisting of is a lung cancer cell, a breast cancer cell, a prostate cancer cell, a colon cancer cell, a pancreatic cancer cell, a renal cell carcinoma cell, an ovarian cancer cell, a leukemia cell, a melanoma cell, a glioblastoma cell, a neuroblastoma cell, a sarcoma cell and a gastric cancer cell. In another embodiment, the immune cell is a lymphocyte, dendritic cell, a peripheral blood monocyte, a macrophage and a glial cell. In another embodiment, the cell is an immune cell. In another embodiment, the immune cell is an activated immune cell. In another embodiment, the immune cell is an activated B cell. In another embodiment, the immune cell is a memory B cell. In another embodiment, the immune cell is an activated T cell. In another embodiment, the immune cell is an activated CD4+ T cell. In another embodiment, the immune cell is an activated CD8+ T cell. In another embodiment, the cell is a vascular smooth muscle cell or an endothelial cell. In another embodiment, the antibody or fragment thereof is linked to a diagnostic agent. In another embodiment, the diagnostic agent is a radionuclide, a fluorophore, a chemilluminescent compound, a fluorescent compound, a quantum dot, a nanoparticles or an enzyme. In another embodiment, the cell is located in a human subject and contacting comprises administering said antibody or fragment thereof to said subject. In another embodiment, the cell is located in an isolated, tissue sample or cell suspension.

In another aspect the invention provides a method of treating or preventing cancer in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof and said antibody or fragment thereof kills at least 10-100% (such as 10, 20, 30, 40, 50, 60, 70, 80, 90, or 100% of a population of MCF-7 cells, when incubated with said MCF-7 cells and human AB serum for 48 (such as 48, 72, or 96) hours. In one embodiment, the mammal is a human. In another embodiment, the treating cancer in a mammal comprises treating tumor hpoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

In another aspect the invention provides a method of treating or preventing cancer in a mammal comprising administering to said mammal a therapeutically effective amount of an anti-nucleolin antibody or fragment thereof, a toxin or chemotherapeutic agent and a pharmaceutically acceptable carrier, wherein said antibody or fragment thereof kills at least 10-100% (such as 10, 20, 30, 40, 50, 60, 70, 80, 90, or 100% of a population of MCF-7 cells, when incubated with said MCF-7 cells and human AB serum for 48 (such as 48, 72, or 96) hours. In one embodiment, the mammal is a human. In another embodiment, the treating cancer in a mammal comprises treating tumor hpoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine In another aspect the invention provides a method of treating or preventing cancer in a mammal comprising administering to said mammal a therapeutically effective amount of an anti-nucleolin antibody or fragment thereof and a pharmaceutically acceptable carrier, and further treating said mammal with radiation therapy, wherein said antibody or fragment thereof kills at least 10-100% (such as 10, 20, 30, 40, 50, 60, 70, 80, 90, or 100% of a population of MCF-7 cells, when incubated with said MCF-7 cells and human AB serum for 48 (such as 48, 72, or 96) hours. In one embodiment, the mammal is a human. In another embodiment, the treating cancer in a mammal comprises treating tumor hpoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

In another aspect the invention provides a method of treating or preventing cancer in a mammal comprising administering to said mammal a therapeutically effective amount of an anti-nucleolin agent and a pharmaceutically acceptable carrier; wherein said anti-nucleolin agent comprises a anti-nucleolin antibody or fragment thereof that specifically binds to a protein of SEQ ID No. 4. In one embodiment, the mammal is a human. In another embodiment, the treating cancer in a mammal comprises treating tumor hypoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

A method of treating or preventing cancer in a mammal comprising administering to said mammal a therapeutically effective amount of a anti-nucleolin antibody or fragment thereof, a toxin or chemotherapeutic agent and a pharmaceutically acceptable carrier, wherein said antibody or fragment thereof specifically binds to a protein of SEQ ID No. 4. In one embodiment, the mammal is a human. In another embodiment, the treating cancer in a mammal comprises treating tumor hpoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

In another aspect the invention provides a method of treating or preventing cancer in a mammal comprising administering to said mammal a therapeutically effective amount of a anti-nucleolin antibody or fragment thereof and a pharmaceutically acceptable carrier, and further treating said mammal with radiation therapy, wherein said antibody or fragment thereof specifically binds to a protein of SEQ ID No. 4. In one embodiment, the mammal is a human. In another embodiment, the treating cancer in a mammal comprises treating tumor hpoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

In another aspect the invention provides a method of treating an autoimmune disease in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof and said antibody or fragment thereof kills at least 10-100% (such as 10, 20, 30, 40, 50, 60, 70, 80, 90, or 100%) of a population of MCF-7 cells, when incubated with said MCF-7 cells and human AB serum for 48 (such as 48, 72, or 96) hours. In one embodiment, the autoimmune disease is alopecia greata, ankylosing spondylitis, antiphospholipid syndrome, autoimmune Addison's disease, asthma, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes mellitus (e.g., type 1), eosinophilic fascites, fibromyalgia-fibromyositis, glomerulonephritis, Graves' disease, Guillain-Barre, Hashimoto's thyroiditis, Henoch-Schonlein purpura, idiopathic pulmonary fibrosis, idiopathic/autoimmune thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus-related disorders (e.g., pemphigus vulgaris), myelodysplastic syndrome, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, or Vogt-Koyanagi-Hareda syndrome. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating an autoimmune disease in a mammal comprising administering to said mammal a therapeutically effective amount of an anti-nucleolin agent and a pharmaceutically acceptable carrier; wherein said anti-nucleolin agent comprises a human anti-nucleolin antibody or fragment thereof that specifically binds to a protein of SEQ ID No. 2. In one embodiment, the autoimmune disease is alopecia greata, ankylosing spondylitis, antiphospholipid syndrome, autoimmune Addison's disease, asthma, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes mellitus (e.g., type 1), eosinophilic fascites, fibromyalgia-fibromyositis, glomerulonephritis, Graves' disease, Guillain-Barre, Hashimoto's thyroiditis, Henoch-Schonlein purpura, idiopathic pulmonary fibrosis, idiopathic/autoimmune thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus-related disorders (e.g., pemphigus vulgaris), myelodysplastic syndrome, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, or Vogt-Koyanagi-Hareda syndrome. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating an autoimmune disease in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof that specifically binds to a protein of SEQ ID No. 4. In one embodiment, the autoimmune disease is alopecia greata, ankylosing spondylitis, antiphospholipid syndrome, autoimmune Addison's disease, asthma, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes mellitus (e.g., type 1), eosinophilic fascites, fibromyalgia-fibromyositis, glomerulonephritis, Graves' disease, Guillain-Barre, Hashimoto's thyroiditis, Henoch-Schonlein purpura, idiopathic pulmonary fibrosis, idiopathic/autoimmune thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus-related disorders (e.g., pemphigus vulgaris), myelodysplastic syndrome, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, or Vogt-Koyanagi-Hareda syndrome. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating an airway disease in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof and said antibody or fragment thereof kills at least 10-100% (10, 20, 30, 40, 50, 60, 70, 90, 100%) of a population of MCF-7 cells, when incubated with said MCF-7 cells and human AB serum for 48 (48, 72, or 96) hours. In another embodiment, the airway disease is asthma, chronic obstructive pulmonary disease, idiopathic pulmonary fibrosis, or inflammatory pneumonitis. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating an airway disease in a mammal comprising administering to said mammal a therapeutically effective amount of an anti-nucleolin agent and a pharmaceutically acceptable carrier; wherein said anti-nucleolin agent comprises a human anti-nucleolin antibody or fragment thereof that specifically binds to a protein of SEQ ID No. 2. In another embodiment, the airway disease is asthma, chronic obstructive pulmonary disease, idiopathic pulmonary fibrosis, or inflammatory pneumonitis. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating an airway disease in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof that specifically binds to a protein of SEQ ID No. 4. In another embodiment, the airway disease is asthma, chronic obstructive pulmonary disease, idiopathic pulmonary fibrosis, or inflammatory pneumonitis. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating a virally infected cell in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof and said antibody or fragment thereof kills at least 20% of a population of MCF-7 cells, when incubated with said MCF-7 cells and human AB serum for 48 hours. In another embodiment, the virally infected cell is infected with an HIV virus. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating a virally infected cell in a mammal comprising administering to said mammal a therapeutically effective amount of an anti-nucleolin agent and a pharmaceutically acceptable carrier; wherein said anti-nucleolin agent comprises a human anti-nucleolin antibody or fragment thereof that specifically binds to a protein of SEQ ID No. 2. In another embodiment, the virally infected cell is infected with an HIV virus. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating a virally infected cell in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof that specifically binds to a protein of SEQ ID No. 4. In another embodiment, the virally infected cell is infected with an HIV virus. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating or preventing a non-cancerous condition or disease in a mammal characterized by increased surface expression of nucleolin, comprising administering to said mammal a therapeutically effective amount of an anti-nucleolin agent and a pharmaceutically acceptable carrier; wherein said anti-nucleolin agent comprises an anti-nucleolin antibody or fragment thereof and said antibody or fragment thereof kills at least 10-100% (such as 10, 20, 30, 40, 50, 60, 70, 80, 90, or 100%) of a population of MCF-7 cells, when incubated with said MCF-7 cells and human AB serum for 48 (48, 72, or 96) hours. In one embodiment, the condition or disease in a mammal characterized by increased surface expression of nucleolin is macular degeneration, diabetic retinopathy, or inflammatory disease. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating or preventing a non-cancerous condition or disease in a mammal characterized by increased surface expression of nucleolin, comprising administering to said mammal a therapeutically effective amount of an anti-nucleolin agent and a pharmaceutically acceptable carrier; wherein said anti-nucleolin agent comprises a human anti-nucleolin antibody or fragment thereof that specifically binds to a protein of SEQ ID No. 2. In one embodiment, the condition or disease in a mammal characterized by increased surface expression of nucleolin is macular degeneration, diabetic retinopathy, or inflammatory disease. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating or preventing a non-cancerous condition or disease in a mammal characterized by increased surface expression of nucleolin, comprising administering to said mammal a therapeutically effective amount of an anti-nucleolin agent and a pharmaceutically acceptable carrier; wherein said anti-nucleolin agent comprises an anti-nucleolin antibody or fragment thereof that specifically binds to a protein of SEQ ID No. 4. In one embodiment, the condition or disease in a mammal characterized by increased surface expression of nucleolin is macular degeneration, diabetic retinopathy, or inflammatory disease. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides an anti-nucleolin agent that kills at least 50% of a population of MCF-7 cells, when incubated with said MCF-7 cells and human AB serum for 48 hours. In another embodiment, the said anti-nucleolin agent is substantially non-immunogenic to a human.

In another aspect the invention provides an anti-nucleolin agent that kills more MCF-7 cells than MCF10A cells when incubated with separate populations of MCF-7 cells and MCF10A cells and heat inactivated serum for 72 or 96 hours. In another embodiment, the said anti-nucleolin agent is substantially non-immunogenic to a human.

In another aspect the invention provides an anti-nucleolin agent that kills more MCF-7 cells than MCF10A cells when incubated with separate populations of MCF-7 cells and MCF10A cells and human AB serum for 96 hours. In another embodiment, the said anti-nucleolin agent is substantially non-immunogenic to a human.

In another aspect the invention provides an anti-nucleolin agent that specifically binds to a protein of SEQ ID No. 4 and inhibits or kills one or more cancer cells that express nucleolin on their cell surface. In another embodiment, the said anti-nucleolin agent is substantially non-immunogenic to a human.

In another aspect the invention provides a method of determining a liklihood that a subject will develop cancer by detecting increased cell surface nucleolin expression in one or more precancerous cells.

In another aspect the invention provides a antibody of any of the proceeding claims, wherein said antibody fragment is a Fab, Fab', F(ab').sub.2, or Fv fragment; diabodie; linear antibody; single-chain antibody; or a multispecific antibody formed from an antibody fragment.

In another aspect the invention provides a method of any of the proceeding claims comprising the use of an antibody fragment, wherein said antibody fragment is a Fab, Fab', F(ab').sub.2, or Fv fragment; diabodie; linear antibody; single-chain antibody; or a multispecific antibody formed from an antibody fragment.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A shows a comparison between CLL and normal B cells. FIG. 2B shows a comparison between MCF-7 and MCF-10A cells.

(FIG. 5A) Two well-defined nodular human leukemic infiltrates present in the mouse spleen. The leukemic infiltrates are positive for nucleolin (fuchsin immunostain). Surrounding mouse spleen lymphocytes are negative for nucleolin immunostaining (blue counterstain). Magnification was 40×. (FIG. 5B) A tissue array with 50 cases of paraffin embedded formalin fixed human breast tumor and adjacent normal tissue (Biomax BR1006) was stained with anti-nucleolin Mab MS3 (Santa Cruz 1:100) using Vectastain mouse kit, DAB substrate, and hematoxylin counterstain. Representative cases were imaged on an Olympus CKX41 at 100× magnification.

(FIG. 9A) Flow cytometric analysis of tonsil B cells 24 h post-infection with GFP-labeled EBV (EBfaV-GFP) compared with control after conventional supernatant infection (top panels) or after spinfection with concentrated virus (bottom panels). GFP fluorescence indicates infection. (FIG. 9B) Four B95-8 EBV-immortalized tonsil B cell libraries were cultured with or without anti-IgM F(ab')2, recombinant soluble CD40L and Baff. Cell supernatants were assayed for IgM and IgG by ELISA after 5 (top panel) or 15 (bottom panel) days.

(FIG. 10A) Culture supernatants obtained from six human B cell lines producing anti-nucleolin antibodies were screened by ELISA for binding to recombinant Δ1-283Nuc-$(His)_6$ nucleolin (nucleolin lacking the N-terminal amino acids 1 through 283), using HRP-labeled goat anti-human IgG and colorimetric substrate for detection. Binding was measured by spectrophotometry at 450 nm. Results were compared with that obtained from culture supernatants containing human anti-HA IgG or mouse anti-nucleolin MS3. (FIG. 10B) Eight B cell lines producing anti-nucleolin antibodies were subcloned by limiting dilution cloning. Three weeks later, fewer than 10% of wells on each 96-well plate contained small monoclonal colonies, which were then tested by ELISA for binding to recombinant nucleolin as described above. Nucleolin binding in the wells was assessed by measuring absorbance at 450 nm.

(FIG. 12A) Anti-nucleolin HuMabs or Rituxan® (5 μg/ml) were incubated with MV4-11 or normal tonsil cells for 30 min on ice, washed, then incubated with APC-labeled anti-human IgG (Miltenyi). Flow cytometry was performed on a FACSCaliber, and median fluorescence intensity (MFI) is shown.

(FIG. 14A) MCF-7 cells were incubated with anti-nucleolin HuMAbs (2 μg/ml) in the presence of human AB serum (+ complement) or heat inactivated serum (− complement). Viability was determined by MTS assay at 48-96 h. (FIG. 14B) MCF-7 and MCF10A cells were incubated with anti-nucleolin HuMAbs (2 μg/ml, top panels; or 1 mg/ml, bottom panels) or AS1411 (20 μM), in the presence of human AB serum (+ complement) or heat inactivated serum (− complement). Viability was determined by MTS assay at 72 h (top panels) and 96 h (bottom panels). (FIG. 14C) MV4-11 cells were incubated with anti-nucleolin HuMAbs (2 μg/ml) or AS1411 (20 μM), in the presence of human AB serum (+ complement) or heat inactivated serum (− complement). Viability was determined by MTS assay at 48-96 h.

DESCRIPTION OF ILLUSTRATIVE EMBODIMENTS

Figure 1:
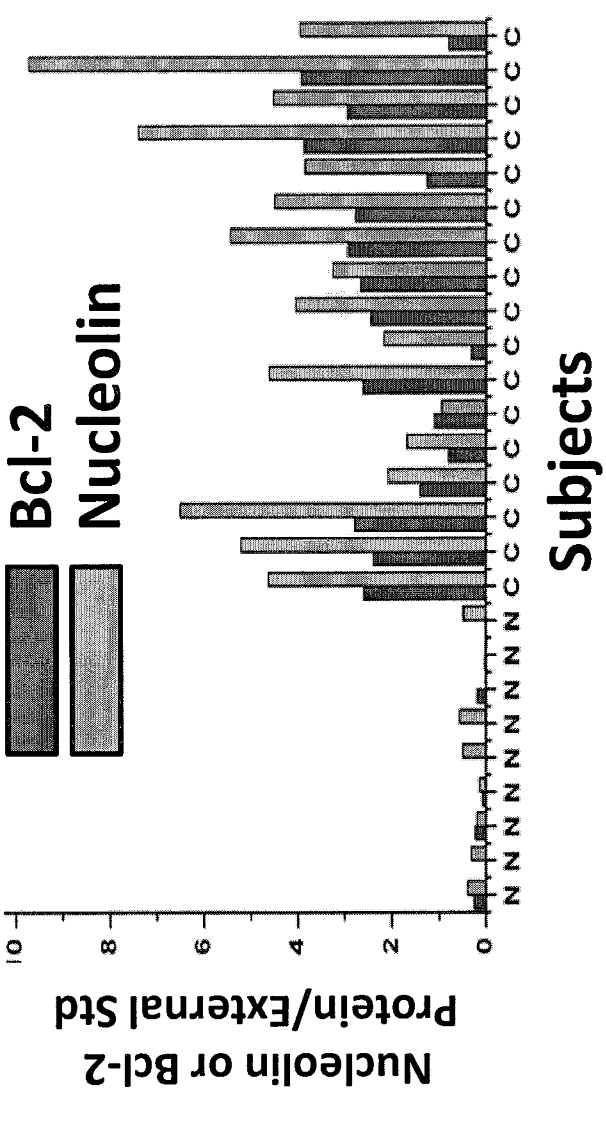
FIG. 1. Over-expression of nucleolin and Bcl-2 proteins in CLL cells vs. normal B cells. Peripheral-blood lymphocytes were isolated from CLL patients and healthy volunteers by density gradient centrifugation and the B cells were purified by positive selection with magnetic-activated cell separation (MACS) CD19 immunomagnetic beads. Nucleolin and Bcl-2 protein levels were measured in S10 extracts of the cells by Western blotting. The results were normalized to the values obtained from known amounts of nucleolin and Bcl-2 protein external standards. The labels N and C along the X-axis refer to normal B cells and CLL cells, respectively, from individual subjects. N=CD19+ B cells from healthy volunteers; C=CD19+ CLL cells.

The present invention provides, human monoclonal antibodies that bind specifically to human nucleolin, and methods of use thereof. These antibodies exhibit cytotoxicity towards cells expressing human nucleolin in the plasma membrane, such as cells involved in cancer, autoimmune disorders, viral disorders. Therefore, the antibodies have therapeutic potential for certain forms of cancer and autoimmune disorders and can also be used as diagnostic agents.

I. Nucleolin

A. General

Nucleolin is a multi-functional protein that binds to DNA, RNA and the external surface of the plasma membrane. The ability of nucleolin to perform numerous and diverse functions within the cell is related to the multiple structural domains within the protein. Its negatively charged N-terminal domain regulates rDNA transcription by inducing nucleolar chromatin decondensation (Srivastava et al., 1989), while the central globular domain contains four RNA binding domains (RBDs) (Serin et al., 1997). It has been proposed that nucleolin, via binding of its RBD and its RGG-rich C-terminal domains to pre-ribosomal RNA, functions as an assembly factor by bringing together the correctly folded rRNA and other components necessary for rRNA maturation and ribosome assembly (Ginisty et al., 2001). Nucleolin may also be involved in exporting ribosomes to the cytoplasm while shuttling between the cytoplasm and nucleus (Srivastava and Pollard, 1999). The nucleolin gene coding and protein sequences are listed in Table 1.

TABLE 1

Nucleolin Sequences

| SEQ ID NO: | Identity | Sequence |
|---|---|---|
| 1 | Human nucleolin coding sequence Accession number NM_005381 XM_002342 275 | CTTTCGCCTCAGTCTCGAGCTCTCGCTGGCCTTCGGGTGTACGTGCTCCGGGAT<br>CTTCAGCACCCGCGGCCGCCATCGCCGTCGCTTGGCTTCTTCTGGACTCATCTG<br>CGCCACTTGTCCGCTTCACACTCCGCCGCCATCATGGTGAAGCTCGCGAAGGCA<br>GGTAAAAATCAAGGTGACCCCAAGAAAATGGCTCCTCCTCCAAAGGAGGTAGAA<br>GAAGATAGTGAAGATGAGGAAATGTCAGAAGATGAAGAAGATGATAGCAGTGGA<br>GAAGAGGTCGTCATACCTCAGAAGAAAGGCAAGAAGGCTGCTGCAACCTCAGCA<br>AAGAAGGTGGTCGTTTCCCCAACAAAAAAGGTTGCAGTTGCCACACCAGCCAAG<br>AAAGCAGCTGTCACTCCAGGCAAAAAGGCAGCAGCAACACCTGCCAAGAAGACA<br>GTTACACCAGCCAAAGCAGTTACCACACCTGGCAAGAAGGGAGCCACACCAGGC<br>AAAGCATTGGTAGCAACTCCTGGTAAGAAGGGTGCTGCCATCCCAGCCAAGGGG<br>GCAAAGAATGGCAAGAATGCCAAGAAGGAAGACAGTGATGAAGAGGAGGATGAT<br>GACAGTGAGGAGGATGAGGAGGATGACGAGGACGAGGATGAGGATGAAGATGAA<br>ATTGAACCAGCAGCGATGAAAGCAGCAGCTGCTGCCCCTGCCTCAGAGGATGAG<br>GACGATGAGGATGACGAAGATGATGAGGATGACGATGACGATGAGGAAGATGAC<br>TCTGAAGAAGAAGCTATGGAGACTACACCAGCCAAAGGAAAGAAAGCTGCAAAA<br>GTTGTTCCTGTGAAAGCCAAGAACGTGGCTGAGGATGAAGATGAAGAAGAGGAT<br>GATGAGGACGAGGATGACGACGACGACGAAGATGATGAAGATGATGATGATGAA<br>GATGATGAGGAGGAGGAAGAAGAGGAGGAGGAAGAGCCTGTCAAAGAAGCACCT<br>GGAAAACGAAAGAAGGAAATGGCCAAACAGAAAGCAGCTCCTGAAGCCAAGAAA<br>CAGAAAGTGGAAGGCACAGAACCGACTACGGCTTTCAATCTCTTTGTTGGAAAC<br>CTAAACTTTAACAAATCTGCTCCTGAATTAAAAACTGGTATCAGCGATGTTTTT<br>GCTAAAAATGATCTTGCTGTTGTGGATGTCAGAATTGGTATGACTAGGAAATTT<br>GGTTATGTGGATTTTGAATCTGCTGAAGACCTGGAGAAAGCGTTGGAACTCACT |

TABLE 1-continued

Nucleolin Sequences

| SEQ ID NO: | Identity | Sequence |
|---|---|---|
| | | GGTTTGAAAGTCTTTGGCAATGAAATTAAACTAGAGAAACCAAAAGGAAAAGAC<br>AGTAAGAAAGAGCGAGATGCGAGAACACTTTTGGCTAAAAATCTCCCTTACAAA<br>GTCACTCAGGATGAATTGAAAGAAGTGTTTGAAGATGCTGCGGAGATCAGATTA<br>GTCAGCAAGGATGGGAAAAGTAAAGGGATTGCTTATATTGAATTTAAGACAGAA<br>GCTGATGCAGAGAAAACCTTTGAAGAAAAGCAGGGAACAGAGATCGATGGGCGA<br>TCTATTTCCCTGTACTATACTGGAGAGAAAGGTCAAAATCAAGACTATAGAGGT<br>GGAAAGAATAGCACTTGGAGTGGTGAATCAAAAACTCTGGTTTTAAGCAACCTC<br>TCCTACAGTGCAACAGAAGAAACTCTTCAGGAAGTATTTGAGAAAGCAACTTTT<br>ATCAAAGTACCCCAGAACCAAAATGGCAAATCTAAAGGGTATGCATTTATAGAG<br>TTTGCTTCATTCGAAGACGCTAAAGAAGCTTTAAATTCCTGTAATAAAAGGGAA<br>ATTGAGGGCAGAGCAATCAGGCTGGAGTTGCAAGGACCCAGGGGATCACCTAAT<br>GCCAGAAGCCAGCCATCCAAAACTCTGTTTGTCAAAGGCCTGTCTGAGGATACC<br>ACTGAAGAGACATTAAAGGAGTCATTTGACGGCTCCGTTCGGGCAAGGATAGTT<br>ACTGACCGGGAAACTGGGTCCTCCAAAGGGTTTGGTTTTGTAGACTTCAACAGT<br>GAGGAGGATGCCAAAGCTGCCAAGGAGGCCATGGAAGACGGTGAAATTGATGGA<br>AATAAAGTTACCTTGGACTGGGCCAAACCTAAGGGTGAAGGTGGCTTCGGGGGT<br>CGTGGTGGAGGCAGAGGCGGCTTTGGAGGACGAGGTGGTGGTAGAGGAGGCCGA<br>GGAGGATTTGGTGGCAGAGGCCGGGGAGGCTTTGGAGGGCGAGGAGGCTTCCGA<br>GGAGGCAGAGGAGGAGGAGGTGACCACAAGCCACAAGGAAAGAAGACGAAGTTT<br>GAATAGCTTCTGTCCCTCTGCTTTCCCTTTTCCATTTGAAAGAAAGGACTCTGG<br>GGTTTTTACTGTTACCTGATCAATGACAGAGCCTTCTGAGGACATTCCAAGACA<br>GTATACAGTCCTGTGGTCTCCTTGGAAATCCGTCTAGTTAACATTTCAAGGGCA<br>ATACCGTGTTGGTTTTGACTGGATATTCATATAAACTTTTTAAAGAGTTGAGTG<br>ATAGAGCTAACCCTTATCTGTAAGTTTTGAATTTATATTGTTTCATCCCATGTA<br>CAAAACCATTTTTTCCTACAAATAGTTTGGGTTTTGTTGTTGTTTCTTTTTTTT<br>GTTTTGTTTTTGTTTTTTTTTTTTTTGCGTTCGTGGGGTTGTAAAAGAAAAGAA<br>AGCAGAATGTTTTATCATGGTTTTTGCTTCAGCGGCTTTAGGACAAATTAAAAG<br>TCAACTCTGGTGCCAGAAAAAAAAAAAAAAAAA |
| 2 | Human nucleolin full length amino acid sequence Accession number NP_005372 XP_002342 316 | MVKLAKAGKNQGDPKKMAPPPKEVEEDSEDEEMSEDEEDDSSGEEVVIPQKKGK<br>KAAATSAKKVVVSPTKKVAVATPAKKAAVTPGKKAAATPAKKTVTPAKAVTTPG<br>KKGATPGKALVATPGKKGAAIPAKGAKNGKNAKKEDSDEEEDDDSEEDEEDDED<br>EDEDEDEIEPAAMKAAAAAPASEDEDDEDDEDDEDDDDDEEDDSEEEAMETTPA<br>KGKKAAKVVPVKAKNVAEDEDEEEDDEDEDDDDDEDDEDDDDEDDEEEEEEEEE<br>EPVKEAPGKRKKEMAKQKAAPEAKKQKVEGTEPTTAFNLFVGNLNFNKSAPELK<br>TGISDVFAKNDLAVVDVRIGMTRKFGYVDFESAEDLEKALELTGLKVFGNEIKL<br>EKPKGKDSKKERDARTLLAKNLPYKVTQDELKEVFEDAAEIRLVSKDGKSKGIA<br>YIEFKTEADAEKTFEEKQGTEIDGRSISLYYTGEKGQNQDYRGGKNSTWSGESK<br>TLVLSNLSYSATEETLQEVFEKATFIKVPQNQNGKSKGYAFIEFASFEDAKEAL<br>NSCNKREIEGRAIRLELQGPRGSPNARSQPSKTLFVKGLSEDTTEETLKESFDG<br>SVRARIVTDRETGSSKGFGFVDFNSEEDAKAAKEAMEDGEIDGNKVTLDWAKPK<br>GEGGFGGRGGGRGGFGGRGGGRGGRGGFGGRGRGGFGGRGGFRGGRGGGGDHKP<br>QGKKTKFE |
| 3 | Human nucleolin coding sequence for the deletion construct amino acid sequence Δ1-283Nuc (lacking residues 1-283) | aagaaggaaatggccaaacagaaagcagctcctgaagccaagaaacagaaagtg<br>gaaggcacagaaccgactacggctttcaatctctttgttggaaacctaaacttt<br>aacaaatctgctcctgaattaaaaactggtatcagcgatgtttttgctaaaaat<br>gatcttgctgttgtggatgtcagaattggtatgactaggaaatttggttatgtg<br>gattttgaatctgctgaagacctggagaaagcgttggaactcactggtttgaaa<br>gtctttggcaatgaaattaaactagagaaaccaaaaggaaaagacagtaagaaa<br>gagcgagatgcgagaacacttttggctaaaaatctcccttacaaagtcactcag<br>gatgaattgaaagaagtgtttgaagatgctgcggagatcagattagtcagcaag<br>gatgggaaaagtaaagggattgcttatattgaatttaagacagaagctgatgca<br>gagaaaacctttgaagaaaagcagggaacagagatcgatgggcgatctatttcc<br>ctgtactatactggagagaaaggtcaaaatcaagactatagaggtggaaagaat<br>agcacttggagtggtgaatcaaaaactctggttttaagcaacctctcctacagt<br>gcaacagaagaaactcttcaggaagtatttgagaaagcaacttttatcaaagta<br>ccccagaaccaaaatggcaaatctaaagggtatgcatttatagagtttgcttca<br>ttcgaagacgctaaagaagctttaaattcctgtaataaaagggaaattgagggc<br>agagcaatcaggctggagttgcaaggacccaggggatcacctaatgccagaagc<br>cagccatccaaaactctgtttgtcaaaggcctgtctgaggataccactgaagag<br>acattaaaggagtcatttgacggctccgttcgggcaaggatagttactgaccgg<br>gaaactgggtcctccaaagggtttggttttgtagacttcaacagtgaggaggat<br>gccaaagctgccaaggaggccatggaagacggtgaaattgatggaaataaagtt<br>accttggactgggccaaacctaagggtgaaggtggcttcgggggtcgtggtgga<br>ggcagaggcggctttggaggacgaggtggtggtagaggaggccgaggaggattt<br>ggtggcagaggccggggaggctttggagggcgaggaggcttccgaggaggcaga<br>ggaggaggaggtgaccacaagccacaaggaaagaagacgaagtttgaagtttaa<br>ac |
| 4 | Human nucleolin deletion construct amino acid | MAKQKAAPEAKKQKVEGTEPTTAFNLFVGNLNFNKSAPELKTGISDVFAKNDLA<br>VVDVRIGMTRKFGYVDFESAEDLEKALELTGLKVFGNEIKLEKPKGKDSKKERD<br>ARTLLAKNLPYKVTQDELKEVFEDAAEIRLVSKDGKSKGIAYIEFKTEADAEKT<br>FEEKQGTEIDGRSISLYYTGEKGQNQDYRGGKNSTWSGESKTLVLSNLSYSATE<br>ETLQEVFEKATFIKVPQNQNGKSKGYAFIEFASFEDAKEALNSCNKREIEGRAI |

TABLE 1-continued

| Nucleolin Sequences | | |
|---|---|---|
| SEQ ID NO: | Identity | Sequence |
| | sequence Δ1-283Nuc (lacking residues 1-283) | RLELQGPRGSPNARSQPSKTLFVKGLSEDTTEETLKESFDGSVRARIVTDRETG SSKGFGFVDFNSEEDAKAAKEAMEDGEIDGNKVTLDWAKPKGEGGFGGRGGGRG GFGGRGGGRGGRGGFGGRGRGGFGGRGGFRGGRGGGGDHKPQGKKTKFE |

Listed are the genomic coding region and protein sequence of human nucleolin and N-terminal deletion fragment of human nucleolin. Nucleolin is also known as C23, FLJ45706, FLJ59041, and NCL.

Human NCL gene consists of 14 exons with 13 introns and spans approximately 11 kb. The nucleolin protein contains several functional domains that mediate its functions. The N-terminal part contains multiple phosphorylation sites and is rich in acidic amino acids. The central part of nucleolin includes four RNA binding domains (RBD) and the C-terminal part contains glycine and arginine rich domain (termed RGG or GAR domain). (Farin et al., 2009)

In one embodiment, a region of nucleolin containing the RNA binding domain is used for generation of an isolated human anti-nucleolin antibody. In one embodiment, a region of nucleolin lacking residues 1-283 (SEQ ID NO:4) is used for generation of an isolated human anti-nucleolin antibody. In one embodiment, the invention provides for an human anti-nucleolin antibody that specifically targets a RNA domain-containing portion of nucleolin. In one embodiment, the invention provides for an isolated human anti-nucleolin monoclonal antibody that specifically targets a RNA domain-containing portion of nucleolin. In one embodiment, the invention provides for an isolated human anti-nucleolin monoclonal antibody produced by a human B cell that specifically targets a RNA domain-containing portion of nucleolin. In one embodiment, the interaction of a human anti-nucleolin antibody with nucleolin disrupts interactions of the nucleolin RNA domain with other molecules. In one embodiment, the interaction of a human anti-nucleolin antibody with nucleolin disrupts interactions of the nucleolin RNA domain with BCL-2.

A considerable body of evidence supports a role for nucleolin in mRNA stabilization. Nucleolin binds to the 3'-untranslated region (3'-UTR) of amyloid precursor protein mRNA and stabilizes this mRNA (Westmark and Malter, 2001). It is also required for the stabilization of IL-2 mRNA that occurs during T cell activation (Chen et al., 2000). More recent studies have demonstrated that nucleolin binds to an A-U rich element (ARE) in the 3'-UTR of bcl-2 mRNA in HL-60 cells (Sengupta et al., 2004), chronic lymphocytic leukemia (CLL) cells (Otake et al., 2007), and MCF-7 breast cancer cells (Soundararajan et al., 2008). Binding of nucleolin to the bcl-2 ARE stabilizes bcl-2 mRNA by protecting it from ribonuclease degradation, while shRNA knockdown of nucleolin in MCF-7 cells leads to bcl-2 mRNA instability and decreased levels of bcl-2 protein (Soundararajan et al., 2008).

Nucleolin is present on the external surface of various types of tumor cells Otake et al., 2007; Soundararajan et al., 2008; Chen et al., 2008; Hovanessian et al., 2000; Sinclair and O'Brien, 2002), despite its lack of a transmembrane domain or signal sequence (Srivastava et al., 1989; Lapeyre et al., 1987). Results show that nucleolin is not secreted from either MV4-11 cells or K-562 cells into the tissue culture medium (Soundararajan et al., 2009). This suggests that the presence of nucleolin on the cell surface is not the result of adsorption of secreted nucleolin by macromolecules on the cell surface of tumor cells. However, nucleolin undergoes extensive posttranslational modification (Srivastava et al., 1989; Lapeyre et al., 1987). It has been isolated as a glyco-phospho-protein from the surface of various types of proliferating cells (Hovanessian et al., 2000; Pfeifle and Anderer, 1983). It is also possible that palmitoylation, prenylation, or myristoylation of nucleolin may allow for insertion or anchoring of these hydrophobic regions of the protein into the plasma membrane. It is thought that nucleolin functions as a shuttling protein between the plasma membrane and nucleus (Hovanessian et al., 2000). In proliferating tumor cells, nucleolin is often associated with endocytotic vesicles that invaginate from the plasma membrane (Hovanessian et al., 2000). Nucleolin also acts as a cell surface receptor for various ligands, since ligands bound to nucleolin within these vesicles become internalized in a temperature-dependent process. For example, plasma membrane nucleolin has been reported to function as a receptor for intimin-γ of *E. coli* (Sinclair and O'Brien, 2002), the anti-HIV agent midkine (Said et al., 2002), laminin-1 (Kibbey et al., 1995), DNA nanoparticles (Chen et al., 2008), and the anti-angiogenic pseudopeptide HB-19 (Destouches et al., 2008). Nucleolin is an important protein in the nucleolus involved in ribosome biogenesis and maturation in exponentially growing eukaryotic cells. In this regard, one important function of nucleolin is as a shuttling protein between cytoplasm and nucleus involving RNA processing and other cell biological process. While in normal cellular physiology, nucleolin is localized predominantly in the nucleolus and cytoplasm, under certain conditions, especially in various disease states it has also been shown to be present in a phosphorylated form on the cell surface. In this regard, nucleolin in the cell membrane serves as a binding protein for a variety of ligands that drive cell proliferation, differentiation, adhesion, mitogenesis and angiogenesis.

B. Nucleolin in Cancer

Several lines of evidence suggest that nucleolin is an excellent tumor antigen for antibody-based immunotherapy. Nucleolin is overexpressed in the plasma membrane and cytoplasm a variety of human tumors including human chronic lymphocytic leukemia (CLL) (Otake et al., 2007), acute myeloid leukemia (AML) (Soundararajan et al., 2008), and breast cancer cells (Soundararajan et al., 2008), but not in normal CD19+ B cells (Otake et al., 2007), CD33+ myeloid cells (Gattoni-Celli et al., 2009), nor in normal mammary epithelial cells (Soundararajan et al., 2008). It is of interest that AML blast cells from patients that engraft in NOD/SCID mice show intense nucleolin staining in the plasma membrane and cytoplasm while the normal mouse bone marrow cells and spleen lymphocytes were negative for nucleolin (Gattoni-Celli et al., 2009).

The nucleolin targeting aptamer, AS1411, targets human nucleolin. Plasma membrane nucleolin was recently reported to be a receptor for AS1411 in human MV4-11 leukemia cells (Soundararajan et al., 2009).

AS1411 binds to nucleolin that is overexpressed on the external surface of tumor cells and gains intracellular access when nucleolin is shuttled from the plasma membrane to the cytoplasm and nucleus. AS1411 has been shown to exhibit antiproliferative activity in a broad set of cancer cell lines that over-express nucleolin (Table 2).

TABLE 2

Cancer Cell Lines That Over-express Nucleolin and/or are Killed Subsequent to Nucleolin Inhibition

| Cancer Type: | Cell Line: |
|---|---|
| Lung cancer | A549, NCI-H322M, NCI-H460, EKVX, HOP-92, NCI-H299, CaLu1, NCI-H1385, NCI-H82, CaLu6 |
| Breast cancer | MCF7, T-47D, BT-549, MDA-N, MDA-MB-231, ZR7S-1 |
| Prostate cancer | DU145, PC-3, CA-HPV-10 |
| Colon cancer | HCC 2998, HT-29, KM12, HCT-116, SW620, HCT-15, LS174T |
| Pancreatic cancer | PANC-1, MIA-PaCa-2, PANC-1 |
| Renal cell carcinoma | 786-0, CAKI-1, RXF393, TK10, A498, ACHN, SN12C |
| Ovarian cancer | IGROV, OVCAR-3, OVCAR-4, OVCAR-5 |
| Cervical cancer | HeLa |
| Leukemia & Lymphoma | CCRF-CEM, SR, HL60, K-562, RPMI-6226, U937, Meg0, MV4-11 |
| Melanoma | LOX-IMVI, SK-MEL-2, A375, SK-MEL-28, MDA-MB-435 |
| Glioblastoma | SF-268, U87-MG |
| Neuroblastoma | IMR 32, Lan 5 |
| Sarcoma | HT-1080 |
| Gastric cancer | KATOIII, HGC27 |

Data from NCI Tumor Cell Line Screen of AS1411 (>50% growth inhibition at 6.3 μM). (Bates et al., 2009).

Anti-nucleolin antibodies can also exploit the shuttling function of plasma membrane nucleolin and become internalized after binding to cell surface nucleolin. Of significance in the present application is the finding that the incubation of human tumor vascular endothelial cells, grown in nude mice or matrigel plugs, with a polyclonal anti-nucleolin antibody resulted in downregulation of bcl-2 mRNA levels and induction of apoptosis (Fogal et al., 2009). This suggests that anti-nucleolin antibodies can elicit anti-tumor effects through intracellular mechanisms, and/or to antibody-dependent cellular cytotoxicity (ADCC) and complement-dependent cellular cytotoxicity (CDCC).

C. Antibodies or Fragments Thereof

In one embodiment any of the methods disclosed herein can be practiced with an anti-nucleolin antibody or fragment thereof. In one embodiment an anti-nucleolin antibody or fragment thereof is used to detect a cell expressing nucleolin on its surface. In another embodiment an anti-nucleolin antibody or fragment thereof is used to inhibit or kill a cell expressing nucleolin on its surface. In another embodiment an anti-nucleolin antibody or fragment thereof is used to treat or prevent a neoplastic disease (e.g. cancer), an auto-immune disease, an inflammatory disease or condition, a respiratory disease, a viral infection, or macular degeneration.

In one embodiment an anti-nucleolin antibody or fragment thereof is conjugated, linked or fused to a toxin, chemotherapeutic, an immunostimulatory nucleic acid sequence (e.g., a CpG sequence), a radionuclide or an immunotherapeutic. In another embodiment an anti-nucleolin antibody or fragment thereof is conjugated, linked or fused to a radionuclide, a fluorophore, a chemilluminescent compound, a fluorescent compound, or an enzyme. In another embodiment anti-nucleolin antibody or fragment thereof is used to contact a cell expressing nucleolin on its surface. In one embodiment the cell is pre-cancerous cell, a cancer cell or an immune cell.

In one embodiment the anti-nucleolin antibody fragment thereof is a human anti-nucleolin antibody or fragment. In one embodiment the anti-nucleolin antibody fragment thereof is a non-human anti-nucleolin antibody fragment thereof. In one embodiment the anti-nucleolin antibody fragment thereof is a chimeric anti-nucleolin antibody fragment thereof. In one embodiment the anti-nucleolin antibody fragment thereof is a humanized anti-nucleolin antibody fragment thereof.

In one embodiment an anti-nucleolin antibody fragment thereof is generated from an anti-nucleolin antibody. In one embodiment the anti-nucleolin antibody fragment has the same binding specificity to human nucleolin as the parent antibody. In another embodiment the anti-nucleolin antibody fragment has improved binding specificity to human nucleolin as the parent antibody. In one embodiment the anti-nucleolin antibody fragment has the same binding affinity to human nucleolin as the parent antibody. In another embodiment the anti-nucleolin antibody fragment has improved affinity to human nucleolin as the parent antibody. In one embodiment an anti-nucleolin antibody or fragment thereof is a human anti-nucleolin antibody fragment.

Antibody fragments" comprise a portion of an intact antibody, preferably comprising the antigen binding region thereof. Examples of antibody fragments include Fab, Fab', F(ab').sub.2, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab').sub.2 fragment that has two antigen-combining sites and is still capable of cross-linking antigen.

"Fv" is a minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab').sub.2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthun, in The Pharmacology of Monoclonal Antibodies, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., Nat. Med. 9:129-134 (2003); and Hollinger et al., PNAS USA 90: 6444-6448 (1993). Triabodies and tetrabodies are also described in Hudson et al., Nat. Med. 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations can be advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, Nature, 256:495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, PNAS USA 101(34): 12467-12472 (2004); and Lee et al., J. Immunol. Methods 284 (1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., PNAS USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al, Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

The modifier "polyclonal" indicates the character of the antibody as being obtained from a source of a nonhomogeneous population of antibodies. A polyclonal antibody comprises more than one antibody, such as 1, 2, 3, 4, 5, 6, 7, 8, 9 or 10 antibodies.

The monoclonal antibodies herein include human, non-human, humanized and "chimeric" antibodies. "Chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., PNAS USA 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., PNAS USA, 103:3557-3562 (2006) regarding human antibodies generated via a human B-cell hybridoma technology.

II. Preparing Human Monoclonal Antibodies from $IgM^+$ B-Cells

The following are descriptions of the general procedures for obtaining a human monoclonal antibody against nucleolin. These procedures are exemplary and can be modified while retaining the essential aspects of the invention.

A. Obtaining $IgM^+$ B-Cell Populations

To prepare B-cells from tonsils, tonsil tissue is mixed with an antibiotic, chopped and minced to approximately 1 $mm^3$ pieces, followed by gentle grinding of tonsil pieces and straining through a nylon strainer. The suspension is then centrifuged on a Ficoll cushion. The boundary layer containing mononuclear cells is extracted, washed and re-suspended in DPBS. Further enrichment (>95%) can be achieved by negative selection using antibodies and magnetic beads Non-human mammalian, chimeric, polyclonal (e.g., sera) and/or monoclonal antibodies (Mabs) and fragments (e.g., proteolytic digestion or fusion protein products thereof) are potential therapeutic agents are often used in an attempt to treat certain diseases. However, such antibodies or fragments can elicit an immune response when administered to humans. Such an immune response can result in an immune complex-mediated clearance of the antibodies or fragments from the circulation, and make repeated administration unsuitable for therapy, thereby reducing the therapeutic benefit to the patient and limiting the readministration of the antibody or fragment. For example, repeated administration of antibodies or fragments comprising non-human portions can lead to serum sickness and/or anaphalaxis. In order to avoid these and other problems, a number of approaches have been taken to reduce the immunogenicity of such antibodies and portions thereof, including chimerization and humanization. These and other approaches, however, still can result in antibodies or fragments having some immunogenicity, low affinity, low avidity, or with problems in cell culture, scale up, production, and/or low yields. Thus, such antibodies or fragments can be less than ideally suited for manufacture or use as therapeutic proteins. Thus, an antibody expressed from human cells can avoid many of these issues and be substantially non-immunogenic to a human. "Immunogenic" as used herein refers to possessing the ability to elicit an immune response.

In one embodiment, a human anti-nucleolin antibody expressed by a human B cell is substantially non-immunogenic a human. In one embodiment, an isolated human anti-nucleolin monoclonal antibody expressed by a human B cell is substantially non-immunogenic a human.

To prepare B-cells from peripheral blood, venous blood is drawn into syringes containing heparin sodium to prevent coagulation, diluted, and centrifuged on a Ficoll cushion. The boundary layer containing mononuclear cells is extracted, washed and re-suspended in DPBS. Further enrichment can be achieved as stated above.

B. EBV Immortalization

For infection by inoculation with EBV supernatant, B-cells are resuspended at $10^6$ to $10^7$ cells per ml in complete RPMI media, and mixed with an equal volume of filtered EBV supernatant, then incubated for 4 hours at 37° C. and 5% $CO_2$. The culture volume can be adjusted by the addition of complete RPMI media, such that infected cells were resuspended for cell culture at a desired concentration (generally $10^5$ to $10^6$ cells per ml). Cells are then dispensed into multi-well plates and transferred to a tissue culture incubator at 37° C. and 5% $CO_2$.

For spin-fection, B-cells are resuspended at $10^6$ to 10' cells per ml in complete RPMI media, and mixed with an equal volume of 10-fold ultrafiltration concentrated EBV and placed in a well of a 6-well tissue culture plate. The plate is then centrifuged at 900 g for 1 hr at ambient temperature, at which time infected cells are re-suspended in complete RPMI media at a desired concentration (generally $10^5$ to $10^6$ cells per ml), dispensed into multi-well plates and transferred to a tissue culture incubator at 37° C. and 5% $CO_2$.

Optionally, B-cells may be contacted with Toll Like Receptor (TLR) ligands at the time of or subsequent to the infection. The ligands may be added at the following final concentrations: Pam3CSK4 (0.1-1 μg/ml), Zymosan (1-10 μg/ml), poly I:C (1-25 μg/ml), LPS (1-5 μg/ml), Imiquimod (1 μg/ml), and/or CpG (1-10 μg/ml).

Infectivity varies based upon route of infection. Infection of tonsil B cells by inoculation with EBV supernatant results in immortalization of approximately 1-5% of B cells. Addition of TLR ligands approximately doubles infection efficiency. Infection of tonsil B cells by spin-fection with concentrated virus increases infection efficiency to virtually 100% after 24 hours.

C. Culturing to Induce Immunoglobulin Isotype Class Switching and IgG Secretion To induce B-cell differentiation, immunoglobulin isotype class switching, and/or IgG secretion, cytokines and other signaling agents are added to EBV infected B-cells immediately after infection, 16 to 20 hr after infection, and/or sequentially at weekly intervals (2, 3, 4 or 5 times). Agents may be diluted in media and added to cells at the following final concentrations: recombinant human interleukins (IL) IL-4, 0.2 ng/ml; IL-5, 0.2 ng/ml; IL-6, 0.1 ng/ml; IL-9, 0.2 ng/ml; IL-10, 0.24 ng/ml; IL-13, 1 ng/ml; recombinant human interferon-α2a (IFN-α2a), 2,000 IU/ml; recombinant human BAFF, 1 ng/ml; recombinant human soluble CD40L, 5 ng/ml; goat anti-human IgM $F(ab')_2$, 1.4 μg/ml (amounts are approximate). Particular combinations comprise anti-IgM $F(ab')_2$, CD40L+/−BAFF; anti-IgM $F(ab')_2$, IL-6+/−BAFF; anti-IgM $F(ab')_2$, CD40L, IL-6+/−BAFF; anti-IgM $F(ab')_2$, CD40L, IL-6+/−IL4; and anti-IgM $F(ab')_2$, CD40L, and IL-9+/−IL-13.

The initiation of immunoglobulin isotype class switching can be detected as early as 5 days following exposure to the cytokine/growth factor/signaling agent cocktail, and the process continues for the following 10 days.

D. Selection of Immortalized B-Cells

Following exposure to the cytokine/growth factor/signaling agent cocktail, culture supernatants are collected about once a week or at days 10-20 post-infection from immortalized tonsil and blood B-cell cultures, pooled, and tested using an ELISA or other screening format, such as dot blot, or flow cytometry, Western blotting, or inhibition/promotion of functional activity. Antigen may be bound directly or through capture antibodies onto the wells of a polystyrene (e.g., 96-well) plate and allowed to bind, e.g., overnight. Plates are then washed, blocked, and contacted with immortalized B cell culture supernatant samples or controls in triplicate or other replicates. Subsequently, the plate is washed extensively, and then e.g., alkaline phosphatase (AP)-coupled goat anti-human IgG or other labeled secondary antibody is added for detection of bound IgG by e.g. AP conversion of colorimetric substrate p-nitrophenyl phosphate disodium salt.

Based upon the discussion above, immunoglobulin isotype class switching and/or IgG secretion starts immediately after and can be detected as early as 5 days following exposure to the cytokine/growth factor/signaling agent cocktail. IgG levels increase in the supernatant over the next 10 days. Thus, from about 7-21 days, about 10-21 days, about 7-10 days or about 10-14 days, or at 7, 8, 9, 10, 11, 12, 13, 14, 15, 16, 17, 18, 19, 20 or 21 days, one will select B-cells that have undergone immunoglobulin isotype class switching and secrete IgG.

III. Cloning and Expression of Human Ig Light and Heavy Chains

Various methods can be employed for the cloning and expression of human immunoglobulin light and heavy chain sequences. Weltschof et al. (1995), incorporated herein by reference, describes in detail the methods used by the inventors. The variable regions, or variable+constant regions, can be cloned.

Other techniques, such as those described by Takekoshi et al. (2001), are also useful. In that reference, total cellular RNA was isolated from pelleted cells using a commercial kit (RNeasy mini kit, Qiagen). Using random 9-mers, nucleotides and reverse transcriptase (Takara, RNA-PCR kit, Ohtsu), cDNAs were synthesized and were amplified by the polymerase chain reaction (PCR), with heavy and light chain primers specific for human immunoglobulins (Ig). A "touchdown" PCR protocol was employed, i.e., three cycles each of denaturation at 95° C. for 1 min, annealing for 1 min, and elongation at 72° C. for 2 min, for a total of 11 cycles. The annealing temperature was varied from 65-55° C. in steps of 1° C. The touchdown cycles were followed by 25 cycles using an annealing temperature of 55° C. The resultant PCR product was gel-purified in agarose and extracted using Qiaquick spin-columns (Qiagen). The light chain and heavy chain Fc genes were then cloned into the NheI/AscI and the SfiI/NotI sites of the expression vector pFab1-His2. The ligated pFab1-His2 vectors with the light chain (κ and λ) and Fc heavy chain genes (γ and μ) were introduced into competent *E. coli* JM109 cells (Toyobo, Osaka). After transformation, the *E. coli* cells were plated onto Luria-Bertani (LB)/ampicillin (50 μg/ml) plates. Isolated bacterial colonies were incubated at 30° C. in 2 ml of Super Broth (SB) with ampicillin (50 μg/ml) and $MgCl_2$ (1.5 mM). Isopropyl-β-D-thiogalactopyranoside (IPTG) was used to induce production of the Fab protein. Cells from the bacterial cultures were pelleted, resuspended in 0.3 ml of B-PER (Pierce) with a protease inhibitor cocktail (Complete, Boehringer Mannheim), and shaken for 5 min at room temperature. Cell lysates were centrifuged at 15,000G for 10 min, and the resultant supernatant containing the Fab antibody portion was collected.

The foregoing is purely exemplary and other methods can be employed.

IV. Antibody Production

Once cloned, the nucleic acids for the human light and heavy chains can be inserted into appropriate expression vectors and transferred into host cells (e.g., antibody-producing cells) that support production of antibodies. Particular cell lines contemplated for production are 293 cells, CHO cells, COS cells or various forms of myeloma cells, some lacking IgG. These cells can be exploited for human MAb production in two basic ways. First, myelomas or immortalized cells can be injected (often into the peritoneal cavity) into a histocompatible animal of the type that was used to provide the somatic and myeloma cells for the original fusion (e.g., a syngeneic mouse), or into an immunodeficient animal for injection of noncompatible cells. Optionally, the animals are primed with a hydrocarbon, especially oils such as pristane (tetramethylpentadecane) prior to injection. The injected animal develops tumors secreting the specific monoclonal antibody produced by the transfected myeloma. The body fluids of the animal, such as serum or ascites fluid, can then be tapped to provide human MAbs in high concentration. Second, the individual cell lines could be cultured in vitro, where the human MAbs are naturally secreted into the culture medium from which they can be readily obtained in high concentrations.

Human MAbs produced by either means can be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction.

In one embodiment a human anti-nucleolin antibody is produced from an immortalized human B cell. In one embodiment a human anti-nucleolin antibody is produced using a method such as one set forth in PCT/US2008/072124 or U.S. patent application Ser. No. 12/671,936, which are herein incorporated by reference in their entirety.

In one embodiment, the cDNA of an isolated human anti-nucleolin antibody may be produced by cloning cDNA or genomic DNA encoding the immunoglobulin light and heavy chains of the anti-nucleolin antibody from a hybridoma cell (by fusing a specific antibody-producing B cell with a myeloma) that produces an antibody homolog according to this invention. In one embodiment, an isolated human anti-nucleoline antibody is produced by a human B cell. In one embodiment, a cell is transfected by one or more polynucleotide sequences isolated from a human B cell where the polynucleotide sequence encodes for human anti-nucleolin antibody. The cDNA or genomic DNA encoding the polypeptides can be inserted into expression vectors so that both genes are operatively linked to their own transcriptional and translational expression control sequences. The expression vector and expression control sequences can then be chosen to be compatible with the expression host cell used. Typically, both genes are inserted into the same expression vector.

Prokaryotic or eukaryotic cells can be used as expression hosts. Expression in eukaryotic host cells is preferred because such cells are more likely than prokaryotic cells to assemble and secrete a properly folded and immunologically active antibody. However, any antibody produced that is inactive due to improper folding may be renaturable according to well known methods (Kim and Baldwin, 1982). It is possible that the host cells will produce portions of intact antibodies, such as light chain dimers or heavy chain dimers, which also are antibody homologs according to the present invention.

It will be understood that variations on the above procedure are within the scope of the present invention. In one embodiment, a host cell is transformed with DNA encoding either the light chain or the heavy chain (but not both) of an antibody homolog of this invention. Recombinant DNA technology may also be used to remove some or all of the DNA encoding either or both of the light and heavy chains that is not necessary for nucleolin binding. The molecules expressed from such truncated DNA molecules are antibody homologs according to this invention. In one embodiment, bifunctional antibodies are produced in which one heavy and one light chain are homologs of a human anti-nucleolin antibody and the other heavy and light chain are specific for an antigen other than nucleolin, or another epitope of nucleolin.

In one embodiment, DNA encoding an isolated human anti-nucleolin antibody is transferred to a preferred mammalian cell line for expression in "production" or commercial amounts. It has long been recognized that Chinese Hamster Ovary cells (CHO cells) make excellent expression vehicles for recombinant or non-endogenous DNA. See U.S. Pat. No. 4,816,567. There has been developed a series of DHFR deficient CHO cell strains, which permit the amplification of inserted DNA encoding specific proteins or DNA sequences, as set forth in U.S. Pat. No. 5,981,214. Examples of additional mammalian cell lines for expression in "production" or commercial amounts include, but are not limited to 293HEK cells, HeLa cells, COS cells, NIH3T3 cells, Jurkat Cells., NSO cells and HUVEC cells. Other mammalian cell lines suitable for the expression of recombinant proteins have been identified in the literature, and can be equally suitable for use in the invention of this application.

A. Amino Acid Sequence Variants of Antibodies

In one embodiment, the anti-nucleolin antibody of the invention comprises a modified amino acid sequence compared to wild type. For example, it can be desirable to improve the binding affinity and/or other biological properties of the antibody. Amino acid sequence variants of the anti-nucleolin antibodies are prepared by introducing appropriate nucleotide changes into the nucleic acid encoding the anti-nucleolin antibody chains, or by peptide synthesis. Such modifications include, for example, deletions from, and/or insertions into and/or substitutions of, residues within the amino acid sequences of the anti-nucleolin antibody. Any combination of deletion, insertion, and substitution is made to arrive at the final construct, provided that the final construct possesses the desired characteristics. The amino acid changes also may alter post-translational processes of the anti-nucleolin antibody, such as changing the number or position of glycosylation sites.

A useful method for identification of certain residues or regions of the anti-nucleolin antibody that are preferred locations for mutagenesis is called "alanine scanning mutagenesis," as described by Cunningham and Wells Science (1989). Here, a residue or group of target residues are identified (e.g., charged residues such as arg, asp, his, lys, and glu and replaced by a neutral or negatively charged amino acid (most preferably alanine or polyalanine) to affect the interaction of the amino acids with the antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed anti-nucleolin antibody variants are screened for the desired activity.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an anti-nucleolin antibody with an N-terminal methionyl residue or the antibody fused to an epitope tag. Other insertional variants of the anti-nucleolin antibody molecule include the fusion to the N- or C-terminus of the antibody of an enzyme or a polypeptide which increases the serum half-life of the antibody.

Another type of variant is an amino acid substitution variant. These variants have at least one amino acid residue in the anti-nucleolin antibody molecule removed and a different residue inserted in its place. Substantial modifications in the biological properties of the anti-nucleolin antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe.

Non-conservative substitutions may also be done and entail exchanging a member of one of these classes for another class. Any cysteine residue not involved in maintaining the proper conformation of the antagonist also may be substituted, generally with serine, to improve the oxidative stability of the molecule and prevent aberrant crosslinking. Conversely, cysteine bond(s) may be added to the antagonist to improve its stability (particularly where the anti-nucleolin antibody is an antibody fragment such as an Fv fragment).

A type of substitution variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitution variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., antagonist activity) as herein disclosed. In order to identify candidate hypervariable region sites for modification, alanine scanning mutagenesis can be performed to identify hypervariable region residues contributing significantly to antigen binding. Alternatively, or in addition, it may be beneficial to analyze a crystal structure of the antigen-antibody complex to identify contact points between the antibody and nucleolin. Such contact residues and neighboring residues are candidates for substitution according to the techniques elaborated herein. Once such variants are generated, the panel of variants is subjected to screening as described herein and antibodies with superior properties in one or more relevant assays may be selected for further development.

B. Glycosylation Variants of Antibodies

In one embodiment, the anti-nucleolin antibody is modified to have altered glycosylation compared to wild type antibody. Antibodies are glycosylated at conserved positions in their constant regions (Jefferis and Lund, 1997; Wright and Morrison, 1997). The oligosaccharide side chains of the inmunoglobulins affect the protein's function (Boyd et al., 1996; Wittwe and Howard, 1990), and the intramolecular interaction between portions of the glycoprotein which can affect the conformation and presented three-dimensional surface of the glycoprotein (Jefferis and Lund, 1996). Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., 1995). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., 1996), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al. 1999).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. Nucleic acid molecules encoding amino acid sequence variants of the anti-nucleolin antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-nucleolin antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected (see, e.g., Hse et al., 1997). In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered, e.g. make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

C. Other Modifications of Antibodies

In one embodiment, an anti-nucleolin antibody is formulated as immunoliposomes. Liposomes containing the antibody are prepared by methods known in the art, such as described in Epstein et al. (1985); Hwang et al. (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. (1982) via a disulfide interchange reaction. A chemotherapeutic agent (such as Doxorubicin) is optionally contained within the liposome. See Gabizon et al. (1989).

In one embodiment, an anti-nucleolin antibody is used in ADEPT by conjugating the antibody to a prodrug-activating enzyme which converts a prodrug (e.g., a peptidyl chemotherapeutic agent, see WO 81/01145) to an active drug. See, for example, WO 88/07378 and U.S. Pat. No. 4,975,278.

The enzyme component of the immunoconjugate useful for ADEPT includes any enzyme capable of acting on a prodrug in such a way so as to covert it into its more active form exhibiting the desired biological properties.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes," can be used to convert the prodrugs of the invention into free active drugs (see, e.g., Massey, 1987). Antibody-abzyme conjugates can be prepared as described herein for delivery of the abzyme to a desired cell population.

The enzymes can be covalently bound to the anti-nucleolin antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., 1984).

In one embodiment of the invention, an anti-nucleolin antibody comprises an antibody fragment, rather than an intact antibody. In this case, the antibody fragment may be modified in order to increase its serum half-life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis). See WO 96/32478 published Oct. 17, 1996.

The salvage receptor binding epitope generally constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

In one embodiment, an anti-nucleolin antibody is modified by covalent linkages. Covalent linkages may include but are not limited to by chemical synthesis or by enzymatic or chemical cleavage of the antibody. Other types of covalent modifications of the antibody are introduced into the molecule by reacting targeted amino acid residues of the antibody with an organic derivatizing agent that is capable of reacting with selected side chains or the N- or C-terminal residues. Exemplary covalent modifications of polypeptides are described in U.S. Pat. No. 5,534,615, specifically incorporated herein by reference. One type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or U.S. Pat. No. 4,179,337.

In another embodiment, an anti-nucleolin antibody (such as a human antibody) is modified by fusing, or conjugating it to another, heterologous polypeptide or amino acid sequence.

In one embodiment, an human anti-nucleolin antibody is modified to comprise targeted immunoconjugate moieties which enable the effective generation of innate and adaptive immune responses against tumors or pathogens. In one embodiment, an isolated human anti-nucleolin monoclonal antibody is modified to comprise targeted immunoconjugate moieties which enable the effective generation of innate and adaptive immune responses against tumors or pathogens. In one embodiment, an isolated human anti-nucleolin monoclonal antibody produced by a human B cell is modified to comprise targeted immunoconjugate moieties which enable the effective generation of innate and adaptive immune responses against tumors or pathogens. The immunoconjugates can be capable of simultaneously satisfying multiple key requirements for mounting effective antibody- and/or cell-mediated immune responses against the targeted tumor or pathogen, which include but are not limited to: (i) Inducing or augmenting uptake and cross-presentation of tumor- or pathogen antigen(s) or antigenic determinant(s) by antigen presenting cells (APC)/dendritic cells (DC); (ii) promoting the maturation of dendritic cells (DCs) in the target cell milieu; (iii) providing CD4+ T cell help to generate CD8+ T cell memory and antibodies against the tumor or pathogen; (iv) sensitizing the targeted tumor cell to antibody dependent cell cytotoxicity (ADCC) and T-cell mediated death. Such immunoconjugated antibodies can be used for targeted immunotherapy or immunoprophylaxis of neoplastic diseases, infectious diseases, and other disorders. For example, pattern recognition receptors (PRRs), such as Toll Like Receptors, recognize pathogen-associated molecular patterns (PAMPs) expressed by diverse infectious microorganisms (bacteria, fungi, protozoa, viruses) and molecules released by damaged host tissues (damage associated molecular patterns/alarmins). The addition of a PAMP conjugated to a isolated human anti-nucleolin antibody provides a moiety comprising a nucleic acid or protein that is recognized by a PRR, ultimately leading to an immune response which eliminates the target cell with the anti-nucleolin antibody bound to it. Examples of PAMPS that can be conjugated to an anti-nucleolin antibody include but are limited to known viral and pathogenic epitopes, such as polyinosine-polycytidylic acid, lipopolysaccharide (LPS), lipid A, flagellin, GU-rich short single-stranded RNA, unmethylated CpG-oligodeoxynucleotides.

In one embodiment an anti-nucleolin antibody (such as a human antibody) is fused or conjugated with a tag polypeptide which provides an epitope to which an anti-tag antibody can selectively bind. The epitope tag can be placed at the amino- or carboxyl-terminus of the anti-nucleolin antibody. The presence of such epitope-tagged forms of an anti-nucleolin antibody can be detected using an antibody against the tag polypeptide. Also, provision of the epitope tag enables the anti-nucleolin antibody to be readily purified by affinity purification using an anti-tag antibody or another type of affinity matrix that binds to the epitope tag. Various tag polypeptides and their respective antibodies are well known in the art. A non-limiting summary of example epitope tags that may be fused to an anti-nucleolin antibody of the invention is listed in Table 3. Examples include poly-histidine (poly-his) or poly-histidine-glycine (poly-his-gly) tags; the flu HA tag and its antibody 12CA5 (Field et al., 1988); the c-myc tag and the 8F9, 3C7, 6E10, G4, B7 and 9E10 antibodies thereto (Evan et al., 1985); and the Herpes Simplex virus glycoprotein D (gD) tag and its antibody (Paborsky et al., 1990). Other tag polypeptides include the Flag-peptide (Hopp et al., 1988); the KT3 epitope peptide (Martin et al., 1992); an α-tubulin epitope peptide (Skinner et al., 1991); and the T7 gene 10 protein peptide tag (Lutz-Freyermuth et al., 1990).

TABLE 3

Sequence of Affinity Tags

| SEQ ID NO: | Tag: | Amino Acid Sequence: |
|---|---|---|
| 5 | Poly-Arg | RRRRR (SEQ ID NO: 5) |
| 6 | Poly-Lys | KKKK (SEQ ID NO: 6) |
| 7 | Poly-His | HHHHHH (SEQ ID NO: 7) |
| 8 | FLAG | DYKDDDDK (SEQ ID NO: 8) |
| 9 | Strep-tag II | WSHPQFEK (SEQ ID NO: 9) |
| 10 | c-myc | EQKLISEEDL (SEQ ID NO: 10) |
| 11 | S | KETAAAKFERQHMDS (SEQ ID NO: 11) |
| 12 | HAT | KDHLIHNVHKEFHAHAHNK (SEQ ID NO: 12) |
| 13 | 3x FLAG | DYKDHDGDYKDHDIDYKDDDDK (SEQ ID NO: 13) |
| 14 | Calmodulin-binding peptide | KRRWKKNFIAVSAANRFKKISSSGAL (SEQ ID NO: 14) |
| 15 | SBP | MDEKTTGWRGGHVVEGLAGELEQLRARLEHHPQGQREP (SEQ ID NO: 15) |
| 16 | Chitin-binding domain | TNPGVSAWQVNTAYTAGQLVTYNGKTYKCLQPHTSLAGWEPSNVPALWQLQ (SEQ ID NO: 16) |
| 17 | Glutathione S-transferase | Protein |
| 18 | Maltose-binding protein | Protein |

In one embodiment, a human anti-nucleolin antibody is linked to a nanoparticle. In one embodiment, an isolated human anti-nucleolin monoclonal antibody is linked to a nanoparticle. In one embodiment, a human anti-nucleolin antibody produced by a human B cell is linked to a nanoparticle. Cell surface nucleolin has been reported to serve as receptor for DNA nanoparticles composed of pegylated polylysine and DNA (Chen et al., 2008). In one embodiment, the antibody-nanoparticle conjugate can penetrate a cell expressing nucleolin on its surface more rapidly and extensively than the uncongugated antibody. In one embodiment, the cell is a cancer cell, tumor cell, virally infected cell, lymphocyte, or activated lymphocyte.

D. Deposit of Cell Lines

Cell lines that express antibodies that immunospecifically bind one or more nucleolin (NCL) polypeptides (e.g., SEQ ID NO:4 or fragments thereof) were deposited on Nov. 17, 2010, with the American Type Culture Collection (10801 University Boulevard, Manassas, Va. 20110-2209 U.S.A.) as an original deposit and were given the accession numbers ATCC PTA-11490, ATCC PTA-11491, ATCC PTA-11492, ATCC PTA-11493, ATCC PTA-11494, ATCC PTA-11495, ATCC PTA-11496, and ATCC PTA-11497. The deposit was made under Budapest Treaty, and all restrictions on the availability to the public of the deposited material will be irrevocably removed upon the granting of the patent, except for the requirements specified in 36 C.F.R. 1.808(b), and the term of the deposit will comply with 37 C.F.R. 1.806.

V. Diagnostics

In one embodiment, a human anti-nucleolin antibody is used to determine the presence of cancer cells in a human. In one embodiment, an isolated human anti-nucleolin monoclonal antibody is used to determine the presence of cancer cells in a human. In one embodiment, an isolated human anti-nucleolin monoclonal antibody produced by a human B cell is used to determine the presence of cancer cells in a human.

In one embodiment, a human anti-nucleolin antibody is used to determine the presence of cancer cells in a human sample. In one embodiment, an isolated human anti-nucleolin monoclonal antibody is used to determine the presence of cancer cells in a human sample. In one embodiment, an isolated anti-nucleolin monoclonal antibody expressed by a human B cell is provided and used to determine the presence of cancer cells in a human sample. The term human sample as used refers to biological collections from a subject that include but are not limited to a cell, tissue, plasma, serum, whole blood, sputum, or saliva. In one embodiment, the detection results from a human subject sample are compared to those from a control sample. In one embodiment, an isolated human anti-nucleolin monoclonal antibody is used to determine the presence of cancer cells in a subject. In one embodiment, an isolated human anti-nucleolin monoclonal antibody expressed by a human B cell is used to determine the presence of cancer cells in a subject. In one embodiment the determination is made by binding ahuman anti-nucleolin antibody to nucleolin on the surface of a human cancer cell. The terms "cancer" and "cancerous" refer to or describe a physiological condition in mammals that is typically characterized by unregulated cell growth. Examples of cancer include, but are not limited to: Acute Lymphoblastic Leukemia; Myeloid Leukemia; Acute Myeloid Leukemia; Chronic Myeloid Leukemia; Adrenocortical Carcinoma Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma; Bile Duct Cancer, Extrahepatic; Bladder Cancer; Bladder Cancer; Bone Cancer, osteosarcoma/Malignant Fibrous Histiocytoma; Brain Stem Glioma; Brain Tumor; Brain Tumor, Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer, Female; Breast Cancer, Male; Bronchial Adenomas/Carcinoids; Burkitt's Lymphoma; Carcinoid Tumor; Central Nervous System Lymphoma; Cerebellar Astrocytoma; Cerebral Astrocytoma/ Malignant Glioma; Cervical Cancer; Chronic Lymphocytic Leukemia; Chronic Myelogenous Leukemia; Chronic Myeloproliferative Disorders; Colon Cancer; Colorectal Cancer; Cutaneous T-Cell Lymphoma; B-Cell Lymphoma Endometrial Cancer; Ependymoma; Esophageal Cancer; Esophageal Cancer; Ewing's Family of Tumors; Extracranial Germ Cell Tumor; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Leukemia, Acute Lymphoblastic; Leukemia, Acute Lymphoblastic; Leukemia, Acute Myeloid; Leukemia, Acute Myeloid; Leukemia, Chronic Lymphocytic; Leukemia; Chronic Myelogenous; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt's; Lymphoma, Cutaneous T-Cell, see Mycosis Fungoides and Sezary Syndrome; Lymphoma, Hodgkin's; Lymphoma, Hodgkin's During Pregnancy; Lymphoma, Non-Hodgkin's; Lymphoma, Non-Hodgkin's During Pregnancy; Lymphoma, Primary Central Nervous System; Macroglobulinemia, Waldenstrom's; Malignant Fibrous Histiocytoma of Bone/Osteosarcoma; Medulloblastoma; Melanoma; Melanoma, Intraocular (Eye); Merkel Cell Carcinoma; Mesothelioma, Adult Malignant; Mesothelioma; Metastatic Squamous Neck Cancer with Occult Primary; Multiple Endocrine Neoplasia Syndrome; Multiple Myeloma/Plasma Cell Neoplasm' Mycosis Fungoides; Myelodysplastic Syndromes; Myelodysplastic/ Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Hodgkin's Lymphoma During Pregnancy; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer; Pancreatic Cancer, Islet Cell; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Prostate Cancer; Rectal Cancer; Renal Cell (Kidney) Cancer; Renal Cell (Kidney) Cancer; Renal Pelvis and Ureter, Transitional Cell Cancer; Retinoblastoma; Rhabdomyosarcoma; Salivary Gland Cancer; Salivary Gland Cancer; Sarcoma, Ewing's Family of Tumors; Sarcoma, Kaposi's; Sarcoma, Soft Tissue; Sarcoma, Soft Tissue; Sarcoma, Uterine; Sezary Syndrome; Skin Cancer (non-Melanoma); Skin Cancer; Skin Cancer (Melanoma); Skin Carcinoma, Merkel Cell; Small Cell Lung Cancer; Small Intestine Cancer; Soft Tissue Sarcoma; Soft Tissue Sarcoma; Squamous Cell Carcinoma, see Skin Cancer (non-Melanoma); Squamous Neck Cancer with Occult Primary, Metastatic; Stomach (Gastric) Cancer; Stomach (Gastric) Cancer; Supratentorial Primitive Neuroectodermal Tumors; T-Cell Lymphoma, Cutaneous, see Mycosis Fungoides and Sezary Syndrome; Testicular Cancer; Thymoma; Thymoma and Thymic Carcinoma; Thyroid Cancer; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; and Wilms' Tumor.

In one embodiment, a human anti-nucleolin antibody is used determine the presence of a proliferative disorder. In one embodiment, an isolated human anti-nucleolin monoclonal antibody is used determine the presence of a proliferative disorder. In one embodiment, a human anti-nucleolin antibody produced from a human B cell is used determine the presence of a proliferative disorder. The terms "cell proliferative disorder," "proliferative disorder" and "neoplastic disorder," as used herein, refer to disorders that are associated with some degree of abnormal cell proliferation.

In one embodiment, a human anti-nucleolin antibody is used determine the presence of a malignant disease wherein nucleolin is expressed on the cell surface or in the cytoplasm. In one embodiment, an isolated human anti-nucleolin monoclonal antibody is used determine the presence of a malignant disease wherein nucleolin is expressed on the cell surface or in the cytoplasm. In one embodiment, an isolated anti-nucleolin monoclonal antibody expressed by a human B cell is provided and used to determine the presence of a malignant disease wherein nucleolin is expressed on the cell surface or in the cytoplasm. The term "malignant diseases" as used hereing refers to progressive or metastatic diseases or diseases characterized by small tumor burden such as minimal residual disease. Examples of malignant diseases that a human anti-nucleolin antibody is used determine the presence of include, but are not limited to leukemias (e.g., acute myeloid, acute lymphocytic and chronic myeloid) and cancers (e.g., breast, lung, thyroid or gastrointestinal cancer or a melanoma).

In one embodiment, a human anti-nucleolin antibody is used to determine the presence of a non-malignant cell proliferative disorders wherein nucleolin is expressed on the cell surface or in the cytoplasm. In one embodiment, an isolated human anti-nucleolin monoclonal antibody is used to determine the presence of a non-malignant cell proliferative disorders wherein nucleolin is expressed on the cell surface or in the cytoplasm. In one embodiment, an isolated anti-nucleolin monoclonal antibody expressed by a human B cell is provided and used to determine the presence of a non-malignant cell proliferative disorders wherein nucleolin is expressed on the cell surface or in the cytoplasm. For example, specific non-limiting examples of non-malignant cell proliferative disorders that can be used to determine the presence of a non-malignant cell proliferative disorder with an isolated human anti-nucleolin monoclonal antibody include but are not limited to warts, benign prostatic hyperplasia, skin tags, and non-malignant tumors. For example, an isolated human anti-nucleolin monoclonal antibody can be used to determine such cell proliferative disorders as benign prostatic hyperplasia or unwanted genital warts by targeting the undesirable cells that characterize such conditions for removal. In one embodiment, an isolated human anti-nucleolin monoclonal antibody is used determine the presence of a angiogenic tumor cell wherein nucleolin is expressed on the cell surface or in the cytoplasm.

In one embodiment, a human anti-nucleolin is to determine the presence of a tumor. "Tumor", as used herein, refers to all neoplastic cell growth and proliferation, whether malignant or benign, and all pre-cancerous and cancerous cells and tissues.

In one embodiment, a human anti-nucleolin antibody is used to determine the presence of a cell expressing human nucleolin on its surface or in its cytoplasm in a subject with an autoimmune disorder. In one embodiment, an isolated human anti-nucleolin monoclonal antibody is used to determine the presence of a cell expressing human nucleolin on its surface or in its cytoplasm in a subject with an autoimmune disorder. In one embodiment, an isolated anti-nucleolin monoclonal antibody expressed by a human B cell is provided and used to determine the presence of a cell expressing human nucleolin on its surface or in its cytoplasm in a subject with an autoimmune disorder. In one embodiment, a human anti-nucleolin antibody is used to determine the presence of a cell expressing human nucleolin on its surface or in its cytoplasm in lymphocytes. In one embodiment, a isolated human anti-nucleolin monoclonal antibody is used to determine the presence of a cell expressing human nucleolin on its surface or in its cytoplasm in lymphocytes. In one embodiment, an isolated human anti-nucleolin monoclonal antibody expressed by a human B cell is provided and used to determine the presence of a cell expressing human nucleolin on its surface or in its cytoplasm in lymphocytes. In one embodiment, the lymphocyte comprises a B cell, T cell, or natural killer cell. In one embodiment, the lymphocyte comprises a CD4-positive or CD8-positive cells.

In one embodiment, a human anti-nucleolin antibody is used to determine the presence of a cell expressing human nucleolin on its surface or in its cytoplasm in activated lymphocytes or memory cells. In one embodiment, an isolated human anti-nucleolin monoclonal antibody is used to determine the presence of a cell expressing human nucleolin on its surface or in its cytoplasm in activated lymphocytes or memory cells. In one embodiment, an isolated anti-nucleolin monoclonal antibody expressed by a human B cell is provided and used to determine the presence of a cell expressing human nucleolin on its surface or in its cytoplasm in activated lymphocytes or memory cells. In one embodiment, the activated lymphocyte comprises an activated B cell, T cell, or natural killer cell.

The term "autoimmune disease or disorder" refers to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders. Exemplary autoimmune diseases or disorders which may be diagnosed with the use of a human anti-nucleolin antibody include, but are not limited to: alopecia greata, ankylosing spondylitis, antiphospholipid syndrome, autoimmune Addison's disease, asthma, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes, type I diabetes mellitus, diabetic retinopathy, eosinophilic fascites, fibromyalgia-fibromyositis, glomerulonephritis, Graves' disease, Guillain-Barre, Hashimoto's thyroiditis, Henoch-Schonlein purpura, idiopathic pulmonary fibrosis, idiopathic/autoimmune thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus-related disorders (e.g., pemphigus vulgaris), myelodysplastic syndrome, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, Vogt-Koyanagi-Hareda syndrome, chronic inflammatory pneumonitis, and chronic inflammation resulting from chronic viral or bacteria infections.

In one embodiment, a human anti-nucleolin antibody is used to determine the presence of a cell expressing human nucleolin on its surface or in its cytoplasm in viral infected cells. In one embodiment, an isolated human anti-nucleolin monoclonal antibody is used to determine the presence of a cell expressing human nucleolin on its surface or in its cytoplasm in viral infected cells. In one embodiment, an isolated anti-nucleolin monoclonal antibody expressed by a human B cell is provided and used determine the presence of a cell expressing human nucleolin on its surface or in its cytoplasm in viral infected cells. Nucleolin is expressed at the cell surface of virus infected cells (Hovanessian et al., 2006; Bose et al., 2004; Izumi et al., 2001). Examples of virus which can infect cells include but are not limited to: Retroviridae (e.g. human immunodeficiency viruses, such as HIV-1 (also referred to as HTLV-III, LAV or HTLV-III/LAV, or HIV-III); and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Rous sarcoma virus (RSV), avian leukemia virus (ALV), and avian myeloblastosis virus (AMV)) and C-type group B (including feline leukemia virus (FeLV), gibbon ape leukemia virus (GALV), spleen necrosis virus (SNV), reticuloendotheliosis virus (RV) and simian sarcoma virus (SSV)), D-type retroviruses include Mason-Pfizer monkey virus (MPMV) and simian retrovirus type 1 (SRV-1), the complex retroviruses including the subgroups of lentiviruses, T-cell leukemia viruses and the foamy viruses, lentiviruses including HIV-1, HIV-2, SIV, Visna virus, feline immunodeficiency virus (FIV), and equine infectious anemia virus (EIAV), simian T-cell leukemia virus (STLV), and bovine leukemia virus (BLV), the foamy viruses including human foamy virus (HFV), simian foamy virus (SFV) and bovine foamy virus (BFV), Poxyiridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses), *Mycobacterium* (*Mycobacterium tuberculosis, M bovis, M. avium-intracellulare, M. leprae*), *Pneumococcus, Streptococcus, Staphylcococcus, Diphtheria, Listeria, Erysipelothrix, Anthrax, Tetanus, Clostridium*, Mixed Anaerobes, *Neisseria, Salmonella, Shigella, Hemophilus, Escherichia coli, Klebsiella, Enterobacter, Serratia, Pseudomonas, Bordatella, Francisella tularensis, Yersinia, Vibrio cholerae, Bartonella, Legionella, Spirochaetes* (*Treponema, Leptospira, Borrelia*), Fungi, *Actinomyces, Rickettsia, Mycoplasma, Chlamydia, Protozoa* (including *Entamoeba, Plasmodium, Leishmania, Trypanosoma, Toxoplasma, Pneumocystis, Babasia, Giardia, Cryptosporidium, Trichomonas*), *Helminths* (*Trichinella, Wucheraria, Onchocerca, Schistosoma, Nematodes, Cestodes, Trematodes*), and viral pneumonias. Additional examples of antigens which can be targets for compositions of the invention are known, such as those disclosed in U.S. Patent Publication No. 2007/0066554. In another embodiment, a conjugate can comprise an antigen or cellular component as described herein, but in addition to a targeting moiety and an immunostimulatory nucleic acid molecule.

In one embodiment, detectable labels are used in a therapeutic and/or diagnostic application using an anti-nucleolin antibody. "Detectable labels" are compounds and/or elements that permit detection of bound antibody. Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging agents. Other agents include enzymes, haptens, fluorescent labels, phosphorescent molecules, chemilluminescent molecules, chromophores, photoaffinity molecules, colored particles or ligands, such as biotin.

In one aspect, the detectable labels comprise paramagnetic ions. Examples of paramagnetic ions include, but are not limited to, chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and bismuth (III). In one aspect, the detectable lables comprise radioactive isotopes. Examples of radioactive isotope include, but are not limited to, $^{124}$antimony, $^{125}$antimony, $^{74}$arsenic, $^{211}$astatine, $^{103}$barium, $^{140}$barium, $^{7}$beryllium, $^{206}$bismuth, $^{207}$bismuth, $^{109}$cadmium, $^{115}$cadmium, $^{45}$calcium, $^{14}$carbon, $^{139}$cerium, $^{141}$cerium, $^{144}$cerium, $^{137}$cesium, $^{51}$chromium, $^{36}$chlorine, $^{56}$cobalt, $^{57}$cobalt, $^{58}$cobalt, $^{60}$cobalt, $^{67}$copper, $^{169}$erbium, $^{152}$eurpium, $^{67}$gallium, $^{153}$gadolinium, $^{195}$gold, $^{199}$gold, $^{175}$hafnium, $^{175+181}$hafnium, $^{181}$hafnium, $^{3}$hydrogen, $^{123}$iodine, $^{125}$iodine, $^{131}$iodine, $^{111}$indium, $^{192}$iridium, $^{55}$iron, $^{59}$iron, $^{85}$krypton, $^{210}$lead, $^{177}$lutecium, $^{54}$manganese, $^{197}$mercury, $^{203}$mercury, $^{99}$molybdenum, $^{147}$neodynium, $^{237}$neptunium, $^{63}$nickel, $^{95}$niobium, $^{185+191}$osmium, $^{103}$palladium, $^{32}$phosphorus, $^{184}$platinum, $^{143}$praseodymium, $^{147}$promethium, $^{233}$protactinium, $^{226}$radium, rhenium$^{186}$, $^{188}$rhenium, $^{86}$rubidium, $^{130}$ruthenium, $^{106}$ruthenium, $^{44}$scandium, $^{46}$scandium, $^{45}$selenium, $^{75}$selenium, $^{110m}$silver, $^{111}$ silver, $^{22}$sodium, $^{85}$strontium, $^{89}$strontium, $^{90}$strontium, $^{35}$sulphur, $^{182}$tantalum, $^{99m}$technicium, $^{125m}$tellurium, $^{132}$tellurium, $^{160}$terbium, $^{204}$thallium, $^{228}$thorium, $^{232}$thorium, $^{170}$thullium, $^{113}$tin, $^{44}$titanium, $^{185}$tungsten, $^{48}$vanadlum, $^{49}$vanadium, $^{88}$yttrium, $^{90}$yttrium, $^{91}$yttrium, $^{169}$ytterbium, $^{65}$zinc, and $^{95}$zirconium.

In one embodiment $^{125}$Iodine technicium$^{99m}$ and/or indium$^{111}$ are used due to their low energy and suitability for long range detection. Radioactively labeled monoclonal antibodies of the present invention can be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention can be labeled with technetium$^{99m}$ by ligand exchange process, for example, by reducing pertechnate with stannous solution, chelating the reduced technetium onto a Sephadex column and applying the antibody to this column. Alternatively, direct labeling techniques can be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

In one embodiment, a detectable labelcomprises a fluorescent label. Examples of fluorescent labels include but are not limited to Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include but are not limited to urease, alkaline phosphatase, (horseradish) hydrogen peroxidase or glucose oxidase. Particular secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this can not be advantageous since it results in loss of antigen binding by the antibody conjugate.

Molecules containing azido groups can also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and can be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies can also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

In one embodiment, the present invention provides a method of transmitting data from a diagnostic result using a human anti-nucleolin antibody. The diagnostic assay may be used to detect cancer or an autoimmune disorder. An example of transmitting data can be disclosing the result of any of the methods and assays described herein across the internet. In one embodiment, the results from diagnostic methods using a human anti-nucleolin antibody with biological samples or a subject is collected and the information is transmitted by digital means, such as by facsimile, electronic mail, telephone, or a global communications network, such as the World Wide Web. For example, data can be transmitted via website posting, such as by subscription or select/secure access thereto and/or via electronic mail and/or via telephone, IR, radio, television or other frequency signal, and/or via electronic signals over cable and/or satellite transmission and/or via transmission of disks, compact discs (CDs), computers, hard drives, or other apparatus containing the information in electronic form, and/or transmission of written forms of the information, e.g., via facsimile transmission and the like. Thus, the invention comprehends a user performing according to the invention and transmitting information therefrom; for instance, to one or more parties who then further utilize some or all of the data or information, e.g., in the manufacture of products, such as therapeutics, assays and diagnostic tests and etc. This invention comprehends disks, CDs, computers, or other apparatus or means for storing or receiving or transmitting data or information containing information from methods and/or use of methods of the invention. Thus, the invention comprehends a method for transmitting information comprising performing a method as discussed herein and transmitting a result thereof.

In one aspect, the invention provides methods of doing business comprising performing or using some or all of the herein methods, and communicating or transmitting or divulging a result of a diagnostic assay using a human anti-nucleolin antibody, advantageously in exchange for compensation, e.g., a fee. Advantageously, the communicating, transmitting or divulging of information is via electronic means, e.g., via internet or email, or by any other transmission means herein discussed. Thus, the invention comprehends methods of doing business.

For example, a first party, a "client," can request information, e.g., via any of the herein mentioned transmission means—either previously prepared information or information specially ordered as to the results of the methods and assays of the invention—of a second party, "vendor", e.g., requesting information via electronic means such as via internet (for instance request typed into website) or via email. The vendor can transmit that information, e.g., via any of the transmission means herein mentioned, advantageously via electronic means, such as internet (for instance secure or subscription or select access website) or email. The information can come from performing some or all of a herein method or use of a herein method in response to the request, or from performing some or all of a herein method, and generating a library of information from performing some or all of a herein method or use of a herein algorithm. Meeting the request can then be by allowing the client access to the library or selecting data from the library that is responsive to the request.

Accordingly, the invention even further comprehends collections of information, e.g., in electronic form (such as forms of transmission discussed above), from performing or using a herein invention.

For example, a client hospital can find itself in need of determining the presence of a disease, such as cancer. A vendor proficient at the methods of the present invention can be contacted by the hospital to quickly test or screen a sample form a subject using any of the herein described methods or any other method contemplated by the invention. The results of the screen can be transmitted back to the client hospital for a fee.

VI. Therapeutic Use of MAbs

A. Human Monoclonal Anti-Nucleolin Antibodies

In one embodiment, a human anti-nucleolin antibody is provided that can be used to inhibit or kill a cancer cell. In another embodiment, an isolated human anti-nucleolin monoclonal antibody is provided that can be used to inhibit or kill a cancer cell. In another embodiment, an isolated anti-nucleolin monoclonal antibody expressed by a human B cell is provided that can be used to inhibit or kill a cancer cell. In one embodiment the cancer cell expresses human nucleolin on its surface or in it cytoplasm. Examples of cancer cells that can be inhibited or killed by a human anti-nucleolin antibody include but are not limited to: Acute Lymphoblastic Leukemia; Myeloid Leukemia; Acute Myeloid Leukemia; Chronic Myeloid Leukemia; Adrenocortical Carcinoma Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma; Bile Duct Cancer, Extrahepatic; Bladder Cancer; Bladder Cancer; Bone Cancer, osteosarcoma/Malignant Fibrous Histiocytoma; Brain Stem Glioma; Brain Tumor; Brain Tumor, Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer, Female; Breast Cancer, Male; Bronchial Adenomas/Carcinoids; Burkitt's Lymphoma; Carcinoid Tumor; Central Nervous System Lymphoma; Cerebellar Astrocytoma; Cerebral Astrocytoma/Malignant Glioma; Cervical Cancer; Chronic Lymphocytic Leukemia; Chronic Myelogenous Leukemia; Chronic Myeloproliferative Disorders; Myelodysplastic Syndromes; Colon Cancer; Colorectal Cancer; Cutaneous T-Cell Lymphoma; B-Cell Lymphoma Endometrial Cancer; Ependymoma; Esophageal Cancer; Esophageal Cancer; Ewing's Family of Tumors; Extracranial Germ Cell Tumor; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Leukemia, Acute Lymphoblastic; Leukemia, Acute Lymphoblastic; Leukemia, Acute Myeloid; Leukemia, Acute Myeloid; Leukemia, Chronic Lymphocytic; Leukemia; Chronic Myelogenous; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt's; Lymphoma, Cutaneous T-Cell, see Mycosis Fungoides and Sezary Syndrome; Lymphoma, Hodgkin's; Lymphoma, Hodgkin's During Pregnancy; Lymphoma, Non-Hodgkin's; Lymphoma, Non-Hodgkin's During Pregnancy; Lymphoma, Primary Central Nervous System; Macroglobulinemia, Waldenstrom's; Malignant Fibrous Histiocytoma of Bone/Osteosarcoma; Medulloblastoma; Melanoma; Melanoma, Intraocular (Eye); Merkel Cell Carcinoma; Mesothelioma, Adult Malignant; Mesothelioma; Metastatic Squamous Neck Cancer with Occult Primary; Multiple Endocrine Neoplasia Syndrome; Multiple Myeloma/Plasma Cell Neoplasm' Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Hodgkin's Lymphoma During Pregnancy; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer; Pancreatic Cancer, Islet Cell; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Prostate Cancer; Rectal Cancer; Renal Cell (Kidney) Cancer; Renal Cell (Kidney) Cancer; Renal Pelvis and Ureter, Transitional Cell Cancer; Retinoblastoma; Rhabdomyosarcoma; Salivary Gland Cancer; Salivary Gland Cancer; Sarcoma, Ewing's Family of Tumors; Sarcoma, Kaposi's; Sarcoma, Soft Tissue; Sarcoma, Soft Tissue; Sarcoma, Uterine; Sezary Syndrome; Skin Cancer (non-Melanoma); Skin Cancer; Skin Cancer (Melanoma); Skin Carcinoma, Merkel Cell; Small Cell Lung Cancer; Small Intestine Cancer; Soft Tissue Sarcoma; Soft Tissue Sarcoma; Squamous Cell Carcinoma, see Skin Cancer (non-Melanoma); Squamous Neck Cancer with Occult Primary, Metastatic; Stomach (Gastric) Cancer; Stomach (Gastric) Cancer; Supratentorial Primitive Neuroectodermal Tumors; T-Cell Lymphoma, Cutaneous, see Mycosis Fungoides and Sezary Syndrome; Testicular Cancer; Thymoma; Thymoma and Thymic Carcinoma; Thyroid Cancer; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; and Wilms' Tumor.

In one embodiment, a human anti-nucleolin antibody is used to reduce cell viability of a cancer cell in a subject sample by 30 to 80% as compared to cells not exposed to a human anti-nucleolin antibody. In one embodiment, an isolated human monoclonal anti-nucleolin antibody is used to reduce cell viability of a cancer cell in a subject sample by 30 to 80% as compared cells not exposed to a human anti-nucleolin antibody. In one embodiment, an isolated human monoclonal anti-nucleolin antibody produced from a human B cell is is provided and used to reduce cell viability of a cancer cell in a subject sample by 30 to 80% as compared cells not exposed to a human anti-nucleolin antibody.

In one embodiment, a human anti-nucleolin antibody is used to reduce cell viability of a cancer cell in a subject by 30 to 80% as compared cells not exposed to a human anti-nucleolin antibody. In one embodiment, an isolated human anti-nucleolin monoclonal antibody is used to reduce cell viability of a cancer cell in a subject by 30 to 80% as compared cells not exposed to a human anti-nucleolin antibody. In one embodiment, an isolated human anti-nucleolin monoclonal antibody produced from a human B cell is provided and used to reduce cell viability of a cancer cell in a subject by 30 to 80% as compared cells not exposed to a human anti-nucleolin antibody.

In one embodiment a human anti-nucleolin antibody is administered to a human subject with one or more forms of cancer. In one embodiment an isolated human anti-nucleolin monoclonal antibody is administered to a human subject with one or more forms of cancer. In one embodiment at least one of the forms of cancer is inhibited or killed by a human anti-nucleolin antibody. In one embodiment an isolated human anti-nucleolin monoclonal antibody is administered to a human subject where the cancer is resistant to other cancer treatments. In one embodiment an isolated human anti-nucleolin monoclonal antibody produced from a human B cell is provided is administered to a human subject where the cancer is resistant to other cancer treatments. For example, cancers can be resistant to radition therapy, chemotherapy, or biological therapy. In one embodiment the immune system of the human subject is more tolerant to the isolated human anti-nucleolin antibody than to an isolated non human anti-nucleolin antibody. In another embodiment the immune system of the human subject is more tolerant to the isolated human anti-nucleolin antibody than to an isolated humanized anti-nucleolin antibody. In another embodiment the immune system of the human subject is more tolerant to the isolated human anti-nucleolin antibody than to an isolated chimeric anti-nucleolin antibody.

In one embodiment, a human anti-nucleolin antibody is used to inhibit or kill a cell as part of an adjuvant therapy. In one embodiment, an isolated human anti-nucleolin monoclonal antibody is used to inhibit or kill a cell as part of an adjuvant therapy. In one embodiment, an isolated anti-nucleolin monoclonal antibody expressed by a human B cell is provided and used as part of an adjuvant therapy. Adjuvant therapy can include chemotherapy, radiation therapy, hormone therapy, targeted therapy, or biological therapy. Adjuvant therapy as used herein refers to treatment given after the primary treatment to lower the risk that the cancer will come back.

In one embodiment, a human anti-nucleolin antibody is used to inhibit or kill a cell used in combination with an adjuvant therapy. In one embodiment, an isolated human anti-nucleolin monoclonal antibody is used to inhibit or kill a cell used in combination with an adjuvant therapy. In one embodiment, an isolated anti-nucleolin monoclonal antibody expressed by a human B cell is provided as part of an adjuvant therapy. Adjuvant therapy may include chemotherapy, radiation therapy, hormone therapy, targeted therapy, or biological therapy.

In one embodiment, a human anti-nucleolin antibody is used to inhibit or kill a cell of a non-malignant cell proliferative disorder wherein nucleolin is expressed on the cell surface or in the cytoplasm. In one embodiment, an isolated human anti-nucleolin monoclonal antibody is used to inhibit or kill a cell of a non-malignant cell proliferative disorder wherein nucleolin is expressed on the cell surface or in the cytoplasm. In one embodiment, the isolated anti-nucleolin monoclonal antibody is expressed by a human B cell. For example, specific non-limiting examples of non-malignant cell proliferative disorders that can treated or inhibited with an anti-nucleolin antibody include but are not limited to warts, benign prostatic hyperplasia, skin tags, and non-malignant tumors. For example, an isolated human anti-nucleolin monoclonal antibody can be used to determine such cell proliferative disorders as benign prostatic hyperplasia or unwanted genital warts by targeting the undesirable cells that characterize such conditions for removal. Expression of nucleolin on the cell surface of endothelial cells in tumors has been shown to be a unique marker of tumor angiogenesis (Christian et al., 2003). In one embodiment, a human anti-nucleolin antibody is used to inhibit or kill in a subject a cell comprising anangiogenic tumor. In one embodiment, an isolated human anti-nucleolin monoclonal antibody is used to inhibit or kill in a subject a cell comprising an angiogenic tumor. In one embodiment, an isolated anti-nucleolin monoclonal antibody expressed by a human B cell is provided that can inhibit or kill in a subject a cell comprising an angiogenic tumor. An angiogenic tumor as used herein a tumor cell with a proliferation of a network of blood vessels that penetrate into cancerous growths, supplying nutrients and oxygen and removing waste products.

In one embodiment, a human anti-nucleolin antibody is used to inhibit or kill in a subject a tumor cell under conditions of tumor hypoxia. In one embodiment, an isolated human anti-nucleolin monoclonal antibody is used to inhibit or kill in a subject a tumor cell under conditions of tumor hypoxia. In one embodiment, an isolated anti-nucleolin monoclonal antibody expressed by a human B cell is provided that can inhibit or kill in a subject a tumor cell under conditions of tumor hypoxia. Tumor hypoxia occurs in the situation where tumor cells have been deprived of oxygen. Tumor hypoxia can be a result of the high degree of cell proliferation undergone in tumor tissue, causing a higher cell density, and thus taxing the local oxygen supply.

In one embodiment, a human anti-nucleolin antibody is used to inhibit or kill in subject a lymphocyte cell expressing human nucleolin on its surface. In one embodiment, a isolated human anti-nucleolin monoclonal antibody is used to inhibit or kill in subject a lymphocyte cell expressing human nucleolin on its surface. In one embodiment, an isolated human anti-nucleolin monoclonal antibody expressed by a human B cell is provided that is used to inhibit or kill in subject a lymphocyte cell expressing human nucleolin on its surface. In one embodiment, the lymphocyte cell comprises a B cell, T cell, or natural killer cell. In one embodiment, the lymphocyte cell comprises a CD4-positive or CD8-positive cells.

In one embodiment, a human anti-nucleolin antibody is used to inhibit or kill in a subject an activated lymphocyte or memory cell expressing human nucleolin on its surface. In one embodiment, an isolated human anti-nucleolin monoclonal antibody is used to inhibit or kill in a subject an activated lymphocyte or memory cell expressing human nucleolin on its surface. In one embodiment, an isolated anti-nucleolin monoclonal antibody expressed by a human B cell is provided that is used to inhibit or kill in subject an activated lymphocyte cell or memory cell expressing human nucleolin on its surface. In a further embodiment, the activated lymphocyte comprises an activated B cell, T cell, or natural killer cell. In one embodiment, a human anti-nucleolin antibody is used to inhibit or kill a cell in a subject having an autoimmune disorder. In one embodiment, an isolated human anti-nucleolin monoclonal antibody is used to inhibit or kill a cell in a subject having an autoimmune disorder. In one embodiment, an isolated anti-nucleolin monoclonal antibody expressed by a human B cell is provided that is used to inhibit or kill a cell in a subject having an autoimmune disorder.

In one embodiment, a human anti-nucleolin antibody is used to inhibit or kill a cell in a subject having an autoimmune disorder. In one embodiment, an isolated human anti-nucleolin monoclonal antibody is used to inhibit or kill a cell in a subject having an autoimmune disorder. In one embodiment, an isolated anti-nucleolin monoclonal antibody expressed by a human B cell is provided that can inhibit or kill cell in a subject having an autoimmune disorder. CD40 and CD40 ligand are interactions mediate T-dependent B cell response and efficient T cell priming and nucleolin has been shown to interact with CD40 ligand. (Geahlen et al., 1984) In one embodiment, an isolated human anti-nucleolin monoclonal antibody is used to inhibit or kill a cell in a subject having an autoimmune disorder wherein the cell is characterized by activated CD40 receptors. In one embodiment the cell expresses human nucleolin on its surface or in its cytoplasm. In one embodiment the cell is a lymphocyte. In one embodiment the lymphocyte is a B cell or T cell. In one embodiment the lymphocyte is activated. Exemplary autoimmune diseases or disorders which may be diagnosed with the use of a human anti-nucleolin antibody include, but are not limited to: alopecia greata, ankylosing spondylitis, antiphospholipid syndrome, autoimmune Addison's disease, asthma, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes, type 1 diabetes mellitus, diabetic retinopathy, eosinophilic fascites, fibromyalgia-fibromyositis, glomerulonephritis, Graves' disease, Guillain-Barre, Hashimoto's thyroiditis, Henoch-Schonlein purpura, idiopathic pulmonary fibrosis, idiopathic/autoimmune thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus-related disorders (e.g., pemphigus vulgaris), pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, Vogt-Koyanagi-Hareda syndrome, chronic inflammatory pneumonitis, and chronic inflammation resulting from chronic viral or bacteria infections.

In another embodiment, an human anti-nucleolin antibody is used to inhibit or kill a cell in a subject infected by a virus. In another embodiment, an isolated human anti-nucleolin monoclonal antibody is used to inhibit or kill a cell in a subject infected by a virus. In one embodiment, an isolated anti-nucleolin monoclonal antibody expressed by a human B cell is provided that can inhibit or kill cell in a subject infected by a virus. Examples of virus which can infect cells include but are not limited to: Retroviridae (e.g., human immunodeficiency viruses, such as HIV-1 (also referred to as HTLV-III, LAV or HTLV-III/LAV, or HIV-III); and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviradae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g. influenza viruses); Bungaviridae (e.g., Hantaan viruses, bunga viruses, phleboviruses and Nairo viruses); Arenaviridae (hemorrhagic fever viruses); Reoviridae (e.g., reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Rous sarcoma virus (RSV), avian leukemia virus (ALV), and avian myeloblastosis virus (AMV)) and C-type group B (including feline leukemia virus (FeLV), gibbon ape leukemia virus (GALV), spleen necrosis virus (SNV), reticuloendotheliosis virus (RV) and simian sarcoma virus (SSV)), D-type retroviruses include Mason-Pfizer monkey virus (MPMV) and simian retrovirus type 1 (SRV-1), the complex retroviruses including the subgroups of lentiviruses, T-cell leukemia viruses and the foamy viruses, lentiviruses including HIV-1, HIV-2, SIV, Visna virus, feline immunodeficiency virus (FIV), and equine infectious anemia virus (EIAV), simian T-cell leukemia virus (STLV), and bovine leukemia virus (BLV), the foamy viruses including human foamy virus (HFV), simian foamy virus (SFV) and bovine foamy virus (BFV), Poxyiridae (variola viruses, vaccinia viruses, pox viruses); and Iridoviridae (e.g. African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses), *Mycobacterium* (*Mycobacterium tuberculosis, M bovis, M. avium-intracellulare, M. leprae*), *Pneumococcus, Streptococcus, Staphylcococcus, Diphtheria, Listeria, Erysipelothrix, Anthrax, Tetanus, Clostridium*, Mixed Anaerobes, *Neisseria, Salmonella, Shigella, Hemophilus, Escherichia coli, Klebsiella, Enterobacter, Serratia, Pseudomonas, Bordatella, Francisella tularensis, Yersinia, Vibrio cholerae, Bartonella, Legionella, Spirochaetes* (*Treponema, Leptospira, Borrelia*), Fungi, *Actinomyces, Rickettsia, Mycoplasma, Chlamydia, Protozoa* (including *Entamoeba, Plasmodium, Leishmania, Trypanosoma, Toxoplasma, Pneumocystis, Babasia, Giardia, Cryptosporidium, Trichomonas*), *Helminths* (*Trichinella, Wucheraria, Onchocerca, Schistosoma, Nematodes, Cestodes, Trematodes*), and viral pneumonias. Additional examples of antigens which can be targets for compositions of the invention are known, such as those disclosed in U.S. Patent Publication No. 2007/0066554. In a further aspect of the invention, a conjugate can comprise an antigen or cellular component as described herein, but in addition to a targeting moiety and an immunostimulatory nucleic acid molecule.

In one embodiment, a human anti-nucleolin antibody is used to inhibit or kill a cell in a sample from a subject as a indicator for the presence of a disease. In one embodiment, an isolated human anti-nucleolin monoclonal antibody is used to inhibit or kill a cell in a sample from a subject as a prognostic indicator for a disease. In one embodiment, an isolated anti-nucleolin monoclonal antibody expressed by a human B cell is provided that is used to inhibit or kill a cell in a sample from a subject as a prognostic indicator for a disease. Examples of diseases tested include but are not limited to malignant tumor, non-malignant tumor, cancer, autoimmune disease, inflammatory disease, and infectious disease.

B. Antibody Conjugates

In one embodiment, the present invention provides for an isolated human anti-nucleolin antibody linked to at least one therapeutic agent to form an antibody conjugate. In one embodiment efficacy of an isolated human anti-nucleolin antibody, is linked, or covalently bound, or complexed to at least one therapeutic agent, such as a molecule or moiety. Therapeutic agents comprise molecules having a desired activity, e.g., cytotoxic activity. In one embodiment a therapeutic agent which can be attached to an antibody includes but is not limited to a toxin (such as a peptide immunotoxin that catalytically inhibit the elongation step of protein synthesis) an anti-tumor agent, a therapeutic enzyme, a radionuclide, an antiviral agent, a chelating agent as described herein, a cytokine, a growth factor, or a oligo- or polynucleotide. Conjugation methodologies are similar to those described above for diagnostic agents.

In one embodiment, an isolated human anti-nucleolin antibody is conjugated to an enzymatically active toxin or fragment thereof. Examples of enzymatically active toxins and fragments thereof include, but are not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), pokeweed antiviral protein, *momordica charantia* inhibitor, curcin, crotin, *sapaonaria officinalis* inhibitor, gelonin, mitogellin, restrictocin, phenomycin, enomycin, calicheamicins or the tricothecenes.

In another embodiment, an isolated human anti-nucleolin antibody is conjugated to an a radionuclide. Examples of suitable radionuclides include, but are not limited to, $^{124}$antimony, $^{125}$antimony, $^{74}$arsenic, $^{211}$ astatine, $^{103}$barium, $^{140}$barium, $^{7}$beryllium, $^{206}$bismuth, $^{207}$bismuth, $^{212}$Bi, $^{109}$cadmium, $^{115}$cadmium, $^{45}$calcium, $^{14}$carbon, $^{139}$cerium, $^{141}$cerium, $^{144}$cerium, $^{137}$cesium, $^{51}$chromium, $^{36}$chlorine, $^{56}$cobalt, $^{57}$cobalt, $^{58}$cobalt, $^{60}$cobalt, $^{67}$copper, $^{169}$erbium, $^{152}$eurpium, $^{67}$gallium, $^{153}$gadolinium, $^{195}$gold, $^{199}$gold, $^{175}$hafnium, $^{175+181}$hafnium, $^{181}$hafnium, $^{3}$hydrogen, $^{123}$iodine, $^{125}$iodine, $^{131}$iodine, $^{111}$indium, $^{131}$In, $^{192}$iridium, $^{55}$iron, $^{59}$iron, $^{85}$krypton, $^{210}$lead, $^{177}$lutecium, $^{54}$manganese, $^{197}$mercury, $^{203}$mercury, $^{99}$molybdenum, $^{147}$neodynium, $^{237}$neptunium, $^{63}$nickel, $^{95}$niobium, $^{185+191}$osmium, $^{103}$palladium, $^{32}$phosphorus, $^{184}$platinum, $^{143}$praseodymium, $^{147}$promethium, $^{233}$protactinium, $^{226}$radium, rhenium$^{186}$, $^{188}$rhenium, $^{86}$rubidium, $^{130}$ruthenium, $^{106}$ruthenium, $^{44}$scandium, $^{46}$scandium, $^{45}$selenium, $^{75}$selenium, $^{110m}$silver, $^{111}$silver, $^{22}$sodium, $^{85}$strontium, $^{89}$strontium, $^{90}$strontium, $^{35}$sulphur, $^{182}$tantalum, $^{99m}$technicium, $^{125m}$tellurium, $^{132}$tellurium, $^{160}$terbium, $^{204}$thallium, $^{228}$thorium, $^{232}$thorium, $^{170}$thullium, $^{113}$tin, $^{44}$titanium, $^{185}$tungsten, $^{48}$vanadlum, $^{49}$vanadium, $^{88}$yttrium, $^{90}$yttrium, $^{91}$yttrium, $^{169}$ytterbium, $^{65}$zinc, and/or $^{95}$zirconium.

Conjugates of the antibody and cytotoxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

In one embodiment, an isolated human anti-nucleolin antibody is conjugated to an a cytokine. The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; and other polypeptide factors including LIF and kit ligand (KL). As used herein, the term cytokine includes proteins from natural sources or from recombinant cell culture and biologically active equivalents of the native sequence cytokines.

In another embodiment, an isolated human anti-nucleolin antibody is conjugated to an chemotherapeutic agent. A variety of chemical compounds, also described as "chemotherapeutic agents," function to induce DNA damage. Categories of chemotherapeutic agents suitable for conjugation with a an isolated human anti-nucleolin antibody include, but are not limited to, alkylating agents, anthracyclines, cytoskeletal disruptors, epothilones, inhibitors of topoisomerase I, inhibitors of topoisomerase II, nucleoside and nucleotide analogs and precursor analogs, peptide antibiotics, platinum-based agents, retinoids, or vinca alkaloids and derivatives. Specific chemotherapeutic agents within these groups include, but are not limited to, actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, vinorelbine. The invention also encompasses the use of a combination of one or more DNA damaging agents, whether radiation-based or actual compounds, such as the use of X-rays with cisplatin or the use of cisplatin with etoposide.

In another embodiment, an isolated human anti-nucleolin antibody is conjugated to an anti-viral agent. Example of anti-viral agents that can be used with an isolated human anti-nucleolin antibody include, but are not limited to, substrates and substrate analogs, inhibitors and other agents that severely impair, debilitate or otherwise destroy virus-infected cells. Substrate analogs include amino acid and nucleoside analogs. Substrates can be conjugated with toxins or other viricidal substances Inhibitors include integrase inhibitors, protease inhibitors, polymerase inhibitors and transcriptase inhibitors such as reverse transcriptase inhibitors.

Specific antiviral agents that can be used with an isolated human anti-nucleolin antibody include, but are not limited to, ganciclovir, valganciclovir, oseltamivir (Tamiflu), zanamivir (Relenza), abacavir, aciclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, fusion inhibitors (e.g., enfuvirtide), ibacitabine, imunovir, idoxuridine, imiquimod, indinavir, inosine, integrase inhibitor, interferon type III, interferon type II, interferon type I, interferon, lamivudine, lopinavir, loviride, maraviroc, moroxydine, nelfinavir, nevirapine, nexavir, nucleoside analogues, peginterferon alfa-2a, penciclovir, peramivir, pleconaril, podophyllotoxin, protease inhibitor, raltegravir, reverse transcriptase inhibitor, ribavirin, rimantadine, ritonavir, pyrimidine antiviral, saquinavir, stavudine, synergistic enhancer (antiretroviral), tenofovir, tenofovir disoproxil, tipranavir, trifluridine, trizivir, tromantadine, truvada, valaciclovir (Valtrex), vicriviroc, vidarabine, viramidine, zalcitabine, and zidovudine.

Examples of nucleoside analogs thatcan be used with an isolated human anti-nucleolin antibody include acyclovir (ACV), ganciclovir (GCV), famciclovir, foscarnet, ribavirin, zalcitabine (ddC), zidovudine (AZT), stavudine (D4T), lamivudine (3TC), didanosine (ddI), cytarabine, dideoxyadenosine, edoxudine, floxuridine, idozuridine, inosine pranobex, 2'-deoxy-5-(methylamino)uridine, trifluridine and vidarabine.

C. Pharmaceutical Compositions and Administration

It is envisioned that, for administration to a subject in need thereof, a antibody will be suspended in a formulation suitable for administration to a host. In one embodiment the antibody is a monoclonal antibody. In one embodiment the monoclonal antibody is an anti-nucleolin antibody. In one embodiment the monoclonal anti-nucleolin antibody is a human monoclonal anti-nucleolin antibody. Aqueous compositions of the present invention comprise an effective amount of an antibody dispersed in a pharmaceutically acceptable formulation and/or aqueous medium. The phrases "pharmaceutically and/or pharmacologically acceptable" refer to compositions that do not produce an adverse, allergic and/or other untoward reaction when administered to an animal, and specifically to humans, as appropriate.

As used herein, "pharmaceutically acceptable carrier" includes any solvents, dispersion media, coatings, antibacterial and/or antifungal agents, isotonic and/or absorption delaying agents and the like. The use of such media or agents for pharmaceutical active substances is well known in the art. Except insofar as any conventional media or agent is incompatible with the active ingredient, its use in the therapeutic compositions is contemplated. Supplementary active ingredients can also be incorporated into the compositions. For administration to humans, preparations should meet sterility, pyrogenicity, general safety and/or purity standards as required by FDA Office of Biologics standards.

In one embodiment, a human anti-nucleolin antibody of the invention can be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with suitable excipient(s), adjuvants, and/or pharmaceutically acceptable carriers. In one embodiment of the present invention, the pharmaceutically acceptable carrier is pharmaceutically inert.

Administration of pharmaceutical compositions is accomplished orally or parenterally. Methods of parenteral delivery include topical, intra-arterial (e.g., directly to a tumor), intramuscular, subcutaneous, intramedullary, intrathecal, intraventricular, intravenous, intraperitoneal, or intranasal administration. In addition to the active ingredients, these pharmaceutical compositions can contain suitable pharmaceutically acceptable carriers comprising excipients and other compounds that facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, etc., suitable for ingestion by the patient. See PCT publication WO 93/23572.

Pharmaceutical preparations for oral use may be obtained through combination of active compounds with solid excipient, optionally grinding a resulting mixture, and processing the mixture of granules, after adding suitable additional compounds, if desired, to obtain tablets or dragee cores. Suitable excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner similar to that known in the art (e.g., by means of conventional mixing, dissolving, granulating, dragee-making, levigating, emulsifying, encapsulating, entrapping or lyophilizing processes).

The pharmaceutical composition may be provided as a salt and can be formed with many acids, including but not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectible compositions can be brought about by the use in the compositions of agents delaying absorption, for example, aluminum monostearate and gelatin.

After pharmaceutical compositions comprising a compound of the invention formulated in an acceptable carrier have been prepared, they can be placed in an appropriate container and labeled for treatment of an indicated condition. For administration of human telomerase proteins and nucleic acids, such labeling would include amount, frequency and method of administration.

Pharmaceutical compositions suitable for use in the present invention include compositions wherein the active ingredients are contained in an effective amount to achieve the intended purpose. "Therapeutically effective amount" or "pharmacologically effective amount" are well recognized phrases and refer to that amount of an agent effective to produce the intended pharmacological result. Thus, a therapeutically effective amount is an amount sufficient to ameliorate the symptoms of the disease being treated. One useful assay in ascertaining an effective amount for a given application (e.g., a therapeutically effective amount) is measuring the effect on cell survival. The amount actually administered will be dependent upon the individual to which treatment is to be applied, and will preferably be an optimized amount such that the desired effect is achieved without significant side-effects.

For any compound, the therapeutically effective dose can be estimated initially either in cell culture assays or in any appropriate animal model. The animal model is also used to achieve a desirable concentration range and route of administration. Such information can then be used to determine useful doses and routes for administration in humans.

In an animal, a "therapeutically effective amount" is the quantity of compound which results in an improved clinical outcome as a result of the treatment compared with a typical clinical outcome in the absence of the treatment. An "improved clinical outcome" refers, for, example, to a longer life expectancy, fewer complications, fewer symptoms, less physical discomfort and/or fewer hospitalizations as a result of the treatment. Improved clinical outcome can be quantified as a certain percent of subjects receiving administration and improving in their disease state over certain period of time. The certain percent of subjects receiving administration and improving in their disease state may be about 1%, 2%, 3%, 4%, 5%, 6%, 7%, 8%, 9%, or 10%. The certain percent of subjects receiving administration and improving in their disease state may be about 10%, 20%, 30%, 40%, 50%, 60%, 70%, 80%, or 85%. The certain percent of subjects receiving administration and improving in their disease state may be about 85%, 86%, 87%, 88%, 89%, 90%, 91%, 92%, 93%, 94%, 95%, 96%, 97%, 98%, 99%, or 100%. The certain period of time to measure improved clinical outcome may be 1, 2, 3, 4, 5, 6, or 7 days. The certain period of time to measure improved clinical outcome may be 1, 2, 3, or 4 weeks. The certain period of time to measure improved clinical outcome may be 1, 2, 3, 4, 5, 6, 7, 8, 9, 10 or more years.

With respect to cancer, an "improved clinical outcome" includes a longer life expectancy. It can also include slowing or arresting the rate of growth of a tumor, causing a shrinkage in the size of the tumor, a decreased rate of metastasis or an improved quality of life (e.g., a decrease in physical discomfort or an increase in mobility).

With respect to modulation of the immune system, "an improved clinical outcome" refers to an increase in the magnitude of the immune response in the individual, if the individual has a disease involving immune suppression. "An improved clinical outcome" for individuals with suppressed immune systems can also refer to a lesser susceptibility to infectious diseases. For diseases involving an overactive immune system, "an improved clinical outcome" can refer to a decrease in the magnitude of the immune response. In both cases, an improved clinical outcome can also involve an improvement in the quality of life, as described above.

A therapeutically effective amount refers to that amount of protein, polypeptide, peptide, antibody, oligo- or polynucleotide, agonist or antagonists which ameliorates the symptoms or condition. Therapeutic efficacy and toxicity of such compounds can be determined by standard pharmaceutical procedures in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio, $ED_{50}/LD_{50}$ Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state (e.g., tumor size and location; age, weight and gender of the patient; diet, time and frequency of administration, drug combination(s), reaction sensitivities, and tolerance/response to therapy). Administration may be every day, every other day, every week, every other week, every month, every other month, or any variation thereof. Administration of a dosage form comprising a human anti-nucleolin antibody may be for at least 1, 2, 3, 4, 5, 6, 7, 8, 9, or 10 days. Administration of a dosage form comprising a human anti-nucleolin antibody may be for at least 1, 2, 3, 4, 5, 6, 7, 8, 9, or 10 weeks. Administration of a dosage form comprising a human anti-nucleolin antibody may be for at least 1, 2, 3, 4, 5, 6, 7, 8, 9, 10, 11, or 12 months. Administration of a dosage form comprising a human anti-nucleolin antibody may be for at least 1, 2, 3, 4, 5, 6, 7, 8, 9, 10, 11, or 12 years. Administration of one or more agents (e.g., a human anti-nucleolin antibody and an other agent) can be intermittent; for example, administration can be once every two days, every three days, every five days, once a week, once or twice a month, and the like. Long acting pharmaceutical compositions may be administered every 3 to 4 days, every week, or once every two weeks depending on half-life and clearance rate of the particular formulation. Guidance as to particular dosages and methods of delivery is provided in the literature (see, U.S. Pat. Nos. 4,657,760; 5,206,344; and 5,225,212, herein incorporated by reference). In one embodiment, the dosage of a composition comprising human anti-nucleolin antibody is administered to a patient is about 0.1 mg/kg to 500 mg/kg of the patient's body weight. The amount, forms, and/or amounts of the different forms can be varied at different times of administration. In one embodiment, a human anti-nucleolin antibody is administered to a subject. The subjects can be male or female and may be of any race or ethnicity, including, but not limited to, Caucasian, African-American, African, Asian, Hispanic, Indian, etc. The subjects can be of any age, including newborn, neonate, infant, child, adolescent, adult, and geriatric. Subjects can also include animal subjects, particularly mammalian subjects such as dog, cat, horse, mouse, rat, etc., screened for veterinary medicine or pharmaceutical drug development purposes. Subjects further include, but are not limited, to those who have, have been exposed to, or have been previously diagnosed as afflicted with a proliferative disorder, such as cancer, or an autoimmune disorder, such as a viral disorder such as HIV or AIDS.

D. Nucleolin-Expressing Cancers and Non-Malignant Cells

In one embodiment, an isolated human anti-nucleolin antibody produced in accordance with the present invention is used in treating a variety of cells, including both cancerous and non-cancerous cells. In one embodiment the isolated human anti-nucleolin antibody is a monoclonal antibody. In another embodiment the isolated human anti-nucleolin antibody is a polyclonal antibody. The term "cancer" is described previously herein. Examples of types cancer that can be inhibited or treated with an isolated human antinucleolin antibody include, but are not limited to: Acute Lymphoblastic Leukemia; Myeloid Leukemia; Acute Myeloid Leukemia; Chronic Myeloid Leukemia; Adrenocortical Carcinoma Adrenocortical Carcinoma; AIDS-Related Cancers; AIDS-Related Lymphoma; Anal Cancer; Astrocytoma, Childhood Cerebellar; Astrocytoma, Childhood Cerebral; Basal Cell Carcinoma; Bile Duct Cancer, Extrahepatic; Bladder Cancer; Bladder Cancer; Bone Cancer, osteosarcoma/Malignant Fibrous Histiocytoma; Brain Stem Glioma; Brain Tumor; Brain Tumor, Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer, Female; Breast Cancer, Male; Bronchial Adenomas/Carcinoids; Burkitt's Lymphoma; Carcinoid Tumor; Central Nervous System Lymphoma; Cerebellar Astrocytoma; Cerebral Astrocytoma/Malignant Glioma; Cervical Cancer; Chronic Lymphocytic Leukemia; Chronic Myelogenous Leukemia; Chronic Myeloproliferative Disorders; Colon Cancer; Colorectal Cancer; Cutaneous T-Cell Lymphoma; B-Cell Lymphoma Endometrial Cancer; Ependymoma; Esophageal Cancer; Esophageal Cancer; Ewing's Family of Tumors; Extracranial Germ Cell Tumor; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma; Hodgkin's Lymphoma During Pregnancy; Hypopharyngeal Cancer; Hypothalamic and Visual Pathway Glioma; Intraocular Melanoma; Islet Cell Carcinoma (Endocrine Pancreas); Kaposi's Sarcoma; Kidney (Renal Cell) Cancer; Kidney Cancer; Laryngeal Cancer; Leukemia, Acute Lymphoblastic; Leukemia, Acute Lymphoblastic; Leukemia, Acute Myeloid; Leukemia, Acute Myeloid; Leukemia, Chronic Lymphocytic; Leukemia; Chronic Myelogenous; Lip and Oral Cavity Cancer; Liver Cancer, Adult (Primary); Liver Cancer, Childhood (Primary); Lung Cancer, Non-Small Cell; Lung Cancer, Small Cell; Lymphoma, AIDS-Related; Lymphoma, Burkitt's; Lymphoma, Cutaneous T-Cell, see Mycosis Fungoides and Sezary Syndrome; Lymphoma, Hodgkin's; Lymphoma, Hodgkin's During Pregnancy; Lymphoma, Non-Hodgkin's; Lymphoma, Non-Hodgkin's During Pregnancy; Lymphoma, Primary Central Nervous System; Macroglobulinemia, Waldenstrom's; Malignant Fibrous Histiocytoma of Bone/Osteosarcoma; Medulloblastoma; Melanoma; Melanoma, Intraocular (Eye); Merkel Cell Carcinoma; Mesothelioma, Adult Malignant; Mesothelioma; Metastatic Squamous Neck Cancer with Occult Primary; Multiple Endocrine Neoplasia Syndrome; Multiple Myeloma/Plasma Cell Neoplasm' Mycosis Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Hodgkin's Lymphoma During Pregnancy; Oral Cancer; Oral Cavity Cancer, Lip and; Oropharyngeal Cancer; Osteosarcoma/Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer; Pancreatic Cancer, Islet Cell; Parathyroid Cancer; Penile Cancer; Pheochromocytoma; Pineoblastoma and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Prostate Cancer; Rectal Cancer; Renal Cell (Kidney) Cancer; Renal Cell (Kidney) Cancer; Renal Pelvis and Ureter, Transitional Cell Cancer; Retinoblastoma; Rhabdomyosarcoma; Salivary Gland Cancer; Salivary Gland Cancer; Sarcoma, Ewing's Family of Tumors; Sarcoma, Kaposi's; Sarcoma, Soft Tissue; Sarcoma, Soft Tissue; Sarcoma, Uterine; Sezary Syndrome; Skin Cancer (non-Melanoma); Skin Cancer; Skin Cancer (Melanoma); Skin Carcinoma, Merkel Cell; Small Cell Lung Cancer; Small Intestine Cancer; Soft Tissue Sarcoma; Soft Tissue Sarcoma; Squamous Cell Carcinoma, see Skin Cancer (non-Melanoma); Squamous Neck Cancer with Occult Primary, Metastatic; Stomach (Gastric) Cancer; Stomach (Gastric) Cancer; Supratentorial Primitive Neuroectodermal Tumors; T-Cell Lymphoma, Cutaneous, see Mycosis Fungoides and Sezary Syndrome; Testicular Cancer; Thymoma; Thymoma and Thymic Carcinoma; Thyroid Cancer; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Cancer, Endometrial; Uterine Sarcoma; Vaginal Cancer; Visual Pathway and Hypothalamic Glioma; Vulvar Cancer; Waldenstrom's Macroglobulinemia; and Wilms' Tumor.

Cancer cells known to express nucleolin include lung cancers (e.g., non-small cell lung cancers), breast cancers, prostate cancers, colon cancers, pancreatic cancers, renal cell carcinomas, ovarian cancers, leukemias (e.g., AML, CLL), melanomas, glioblastomas, neuroblastomas, sarcomas and gastric cancers. In addition, non-cancer cells that express nucleolin include immune cells such as dendritic cells, peripheral blood monocytes, macrophages, and glial cells, as well as vascular smooth muscle cells and endothelial cells. In one embodiment, a antibody of the present invention is used in a treatment for subjects with hyper-immune and hyper-angiogenic diseases, the latter being described in U.S. Patent Publication No. 2009/0191244, incorporated herein by reference.

i. Acute Myeloid Leukemia

Acute myeloid leukemia (AML), also known as acute myelogenous leukemia, is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for approximately 1.2% of cancer deaths in the United States, its incidence is expected to increase as the population ages.

The symptoms of AML are caused by replacement of normal bone marrow with leukemic cells, which causes a drop in red blood cells, platelets, and normal white blood cells. These symptoms include fatigue, shortness of breath, easy bruising and bleeding, and increased risk of infection. Although several risk factors for AML have been identified, the specific cause of the disease remains unclear. As an acute leukemia, AML progresses rapidly and is typically fatal within weeks or months if left untreated.

AML has several subtypes; treatment and prognosis varies among subtypes. Five-year survival varies from 5-70%, and relapse rate varies from 30-95%, depending on subtype. AML is treated initially with chemotherapy aimed at inducing a remission; patients can go on to receive additional chemotherapy or a hematopoietic stem cell transplant. Recent research into the genetics of AML has developed tests that better predict how long a patient is likely to survive and whether a drug is likely to be effective.

The first symptom leading to a diagnosis of AML is typically non-specific, related to one or more of the cytopenias, e.g., anemia, neutropenia, and/or thrombocytopenia. While an excess of abnormal white blood cells (leukocytosis) with immature blood cells (blasts) in the peripheral blood are a common finding, and leukemic blasts are sometimes seen, AML can also present with isolated decreases in platelets, red blood cells, or even with a low white blood cell count (leukopenia). While a presumptive diagnosis of AML can be made via examination of the peripheral blood smear when there are circulating leukemic blasts, a definitive diagnosis usually requires an examination of the cells taken from a bone marrow aspiration and biopsy.

Marrow or blood is examined via light microscopy as well as flow cytometry to diagnose the presence of leukemia, to differentiate AML from other types of leukemia (e.g., acute lymphoblastic leukemia), and to classify the subtype of disease (see below). A sample of marrow or blood is typically also tested for various chromosomal aberrations by routine cytogenetics or fluorescent in situ hybridization. Genetic studies can also be performed to look for specific mutations in genes such as FLT3, nucleophosmin, and bcr/able among others, which can influence the outcome of the disease.

Cytochemical stains on blood and bone marrow smears are helpful in the distinction of AML from ALL and in subclassification of AML. The combination of a myeloperoxidase or Sudan black stain and a non specific esterase stain will provide the desired information in most cases. The myeloperoxidase or Sudan black reactions are most useful in establishing the identity of AML and distinguishing from ALL. The non-specific esterase stain is used to identify a monocytic component in AMLs and to distinguish a poorly differentiated monoblastic leukemia from ALL.

The diagnosis and classification of AML can be challenging, and should be performed by a qualified hematopathologist or hematologist. In straightforward cases, the presence of certain morphologic features (such as Auer rods) or specific flow cytometry results can distinguish AML from other leukemias; however, in the absence of such features, diagnosis can be more difficult.

According to the widely used WHO criteria, the diagnosis of AML is established by demonstrating involvement of more than 20% of the blood and/or bone marrow by leukemic myeloblasts. AML must be carefully differentiated from "pre-leukemic" conditions such as myelodysplastic or myeloproliferative syndromes, which are treated differently.

Because acute promyelocytic leukemia (APL) has the highest curability and requires a unique form of treatment, it is important to quickly establish or exclude the diagnosis of this subtype of leukemia. Fluorescent in situ hybridization performed on blood or bone marrow is often used for this purpose, as it readily identifies the chromosomal translocation (t[15; 17]) that characterizes APL.

The malignant cell in AML is the myeloblast. In normal hematopoiesis, the myeloblast is an immature precursor of myeloid white blood cells; a normal myeloblast will gradually mature into a mature white blood cell. However, in AML, a single myeloblast accumulates genetic changes which "freeze" the cell in its immature state and prevent differentiation. Such a mutation alone does not cause leukemia; however, when such a "differentiation arrest" is combined with other mutations which disrupt genes controlling proliferation, the result is the uncontrolled growth of an immature clone of cells, leading to the clinical entity of AML.

Much of the diversity and heterogeneity of AML stems from the fact that leukemic transformation can occur at a number of different steps along the differentiation pathway. Modern classification schemes for AML recognize that the characteristics and behavior of the leukemic cell (and the leukemia) can depend on the stage at which differentiation was halted.

Specific cyto genetic abnormalities can be found in many patients with AML; the types of chromosomal abnormalities often have prognostic significance. The chromosomal translocations encode abnormal fusion proteins, usually transcription factors whose altered properties can cause the "differentiation arrest." For example, in acute promyelocytic leukemia, the t(15; 17) translocation produces a PML-RARα fusion protein which binds to the retinoic acid receptor element in the promoters of several myeloid-specific genes and inhibits myeloid differentiation.

The clinical signs and symptoms of AML result from the fact that, as the leukemic clone of cells grows, it tends to displace or interfere with the development of normal blood cells in the bone marrow. This leads to neutropenia, anemia, and thrombocytopenia. The symptoms of AML are in turn often due to the low numbers of these normal blood elements. In rare cases, patients can develop a chloroma, or solid tumor of leukemic cells outside the bone marrow, which can cause various symptoms depending on its location.

Treatment of AML consists primarily of chemotherapy, and is divided into two phases: induction and postremission (or consolidation) therapy. The goal of induction therapy is to achieve a complete remission by reducing the amount of leukemic cells to an undetectable level; the goal of consolidation therapy is to eliminate any residual undetectable disease and achieve a cure.

All FAB subtypes except M3 are usually given induction chemotherapy with cytarabine (ara-C) and an anthracycline (such as daunorubicin or idarubicin). This induction chemotherapy regimen is known as "7+3" (or "3+7"), because the cytarabine is given as a continuous IV infusion for seven consecutive days while the anthracycline is given for three consecutive days as an IV push. Up to 70% of patients will achieve a remission with this protocol. Other alternative induction regimens, including high-dose cytarabine alone or investigational agents, can also be used. Because of the toxic effects of therapy, including myelosuppression and an increased risk of infection, induction chemotherapy can not be offered to the very elderly, and the options can include less intense chemotherapy or palliative care.

The M3 subtype of AML, also known as acute promyelocytic leukemia, is almost universally treated with the drug *ATRA* (all-trans-retinoic acid) in addition to induction chemotherapy. Care must be taken to prevent disseminated intravascular coagulation (DIC), complicating the treatment of APL when the promyelocytes release the contents of their granules into the peripheral circulation. APL is eminently curable with well-documented treatment protocols.

The goal of the induction phase is to reach a complete remission. Complete remission does not mean that the disease has been cured; rather, it signifies that no disease can be detected with available diagnostic methods. Complete remission is obtained in about 50%-75% of newly diagnosed adults, although this can vary based on the prognostic factors described above. The length of remission depends on the prognostic features of the original leukemia. In general, all remissions will fail without additional consolidation therapy.

Even after complete remission is achieved, leukemic cells likely remain in numbers too small to be detected with current diagnostic techniques. If no further post-remission or consolidation therapy is given, almost all patients will eventually relapse. Therefore, more therapy is necessary to eliminate non-detectable disease and prevent relapse—that is, to achieve a cure.

The specific type of postremission therapy is individualized based on a patient's prognostic factors (see above) and general health. For good-prognosis leukemias (i.e., inv(16), t(8; 21), and t(15; 17)), patients will typically undergo an additional 3-5 courses of intensive chemotherapy, known as consolidation chemotherapy. For patients at high risk of relapse (e.g. those with high-risk cytogenetics, underlying MDS, or therapy-related AML), allogeneic stem cell transplantation is usually recommended if the patient is able to tolerate a transplant and has a suitable donor. The best postremission therapy for intermediate-risk AML (normal cytogenetics or cytogenetic changes not falling into good-risk or high-risk groups) is less clear and depends on the specific situation, including the age and overall health of the patient, the patient's personal values, and whether a suitable stem cell donor is available.

Despite aggressive therapy, however, only 20%-30% of patients enjoy long-term disease-free survival. For patients with relapsed AML, the only proven potentially curative therapy is a stem cell transplant, if one has not already been performed. In 2000, the monoclonal antibody-linked cytotoxic agent gemtuzumab ozogamicin (Mylotarg) was approved in the United States for patients aged more than 60 years with relapsed AML who are not candidates for high-dose chemotherapy.

Patients with relapsed AML who are not candidates for stem cell transplantion, or who have relapsed after a stem cell transplant, can be offered treatment in a clinical trial, as conventional treatment options are limited. Agents under investigation include cytotoxic drugs such as clofarabine as well as targeted therapies such as farnesyl transferase inhibitors, decitabine, and inhibitors of MDR1 (multidrug-resistance protein). Since treatment options for relapsed AML are so limited, another option which can be offered is palliative care.

For relapsed acute promyelocytic leukemia (APL), arsenic trioxide has been tested in trials and approved by the Food and Drug Administration. Like ATRA, arsenic trioxide does not work with other subtypes of AML.

Acute myeloid leukemia is a curable disease; the chance of cure for a specific patient depends on a number of prognostic factors. The single most important prognostic factor in AML is cytogenetics, or the chromosomal structure of the leukemic cell. Certain cytogenetic abnormalities are associated with very good outcomes (for example, the t(15; 17) translocation in acute promyelocytic leukemia). About half of AML patients have "normal" cytogenetics; they fall into an intermediate risk group. A number of other cytogenetic abnormalities are known to associate with a poor prognosis and a high risk of relapse after treatment.

AML which arises from a pre-existing myelodysplastic syndrome or myeloproliferative disease (so-called secondary AML) has a worse prognosis, as does treatment-related AML arising after chemotherapy for another previous malignancy. Both of these entities are associated with a high rate of unfavorable cytogenetic abnormalities.

In some studies, age >60 years and elevated lactate dehydrogenase level were also associated with poorer outcomes. As with most forms of cancer, performance status (i.e., the general physical condition and activity level of the patient) plays a major role in prognosis as well.

FLT3 internal tandem duplications (ITDs) have been shown to confer a poorer prognosis in AML. Treating these patients with more aggressive therapy, such as stem-cell transplantation in first remission, has not been shown to enhance long-term survival, so this prognostic feature is of uncertain clinical significance at this point. ITDs of FLT3 can be associated with leukostasis.

Researchers are investigating the clinical significance of c-KIT mutations in AML. These are prevalent, and clinically relevant because of the availability of tyrosine kinase inhibitors, such as imatinib and sunitinib that can block the activity of c-KIT pharmacologically. Other genes being investigated as prognostic factors or therapeutic targets include CEBPA, BAALC, ERG, and NPM1.

Cure rates in clinical trials have ranged from 20-45%; however, it should be noted that clinical trials often include only younger patients and those able to tolerate aggressive therapies. The overall cure rate for all patients with AML (including the elderly and those unable to tolerate aggressive therapy) is likely lower. Cure rates for promyelocytic leukemia can be as high as 98%.

ii. Chronic Lymphocytic Leukemia

B-cell chronic lymphocytic leukemia (B-CLL), also known as chronic lymphoid leukemia (CLL), is the most common type of leukemia. Leukemias are abnormal and malignant neoplastic proliferations of the white blood cells (leukocytes). CLL involves a particular subtype of white blood cells, which is a lymphocyte called a B cell. B cells originate in the bone marrow, develop in the lymph nodes, and normally fight infection. In CLL, the DNA of a B cell is damaged, so that it can't fight infection by producing antibodies. Additionally, they grow out of control and accumulate in the bone marrow and blood, where they crowd out healthy blood cells.

CLL is a disease of adults, but in rare cases it can occur in teenagers and occasionally in children (inherited). Most (>75%) people newly diagnosed with CLL are over the age of 50, and the majority are men. Most people are diagnosed without symptoms as the result of a routine blood test that returns a high white blood cell count, but as it advances CLL results in swollen lymph nodes, spleen, and liver, and eventually anemia and infections. Early CLL is not treated, and late CLL is treated with chemotherapy and monoclonal antibodies. Survival varies from 5 years to more than 25 years. It is now possible to predict survival length more precisely by examining the DNA mutations; patients with slowly-progressing disease can be reassured and can not need any treatment in their lifetimes.

Although not originally appreciated, CLL is now felt to be identical to a disease called small lymphocytic lymphoma (SLL), a type of non-Hodgkin's lymphoma which presents primarily in the lymph nodes. The World Health Organization considers CLL and SLL to be one disease at different stages, not two separate entities.

Staging, determining the extent of the disease, is done with the Rai staging system or the Binet classification and is based primarily on the presence, or not, of a low platelet or red cell count. Early stage disease does not need to be treated.

Recent publications suggest that two or three prognostic groups of CLL exist based on the maturational state of the cell. This distinction is based on the maturity of the lymphocytes as discerned by the immunoglobulin variable-region heavy chain ($IgV_H$) gene mutation status. High risk patients have an immature cell pattern with few mutations in the DNA in the $IgV_H$ antibody gene region whereas low risk patients show considerable mutations of the DNA in the antibody gene region indicating mature lymphocytes.

Since assessment of the $IgV_H$ antibody DNA changes is difficult to perform, the presence of either cluster of differentiation 38 (CD38) or Z-chain-associated protein kinase-70 (ZAP-70) can be surrogate markers of high risk subtype of CLL. Their expression correlates with a more immature cellular state and a more rapid disease course.

In addition to the maturational state, the prognosis of patients with CLL is dependent on the genetic changes within the neoplastic cell population. These genetic changes can be identified by fluorescent probes to chromosomal parts using a technique referred to as fluorescent in situ hybridization (FISH). Four main genetic aberrations are recognized in CLL cells that have a major impact on disease behavior.

Deletions of part of the short arm of chromosome 17 (del 17p) which target the cell cycle regulating protein p53 are particularly deleterious. Patients with this abnormality have significantly short interval before they require therapy and a shorter survival. This abnormality is found in 5-10% of patients with CLL. Deletions of the long arm on chromosome 11 (del 11q) are also unfavorable although not to the degree seen with del 17p. The abnormality targets the ATM gene and occurs infrequently in CLL (5-10%). Trisomy 12, an additional chromosome 12, is a relatively frequent finding occurring in 20-25% of patients and imparts an intermediate prognosis. Deletion of the long arm of chromosome 13 (del 13q) is the most common abnormality in CLL with roughly 50% of patients with cells containing this defect. These patients have the best prognosis and most will live many years, even decades, without the need for therapy. The gene targeted by this deletion is a segment that likely produces small inhibitory RNA molecules that affect expression of important death inhibiting gene products.

Most people are diagnosed without symptoms as the result of a routine blood test that returns a high white blood cell count. Uncommonly, CLL presents as enlargement of the lymph nodes without a high white blood cell count or no evidence of the disease in the blood. This is referred to as small lymphocytic lymphoma. In some individuals the disease comes to light only after the neoplastic cells overwhelm the bone marrow resulting in anemia producing tiredness or weakness.

The disease is easily diagnosed. CLL is usually first suspected by the presence of a lymphocytosis, an increase in one type of the white blood cell, on a complete blood count (CBC) test. This frequently is an incidental finding on a routine physician visit. Most often the lymphocyte count is greater than 4000 cells per $mm^3$ (microliter) of blood but can be much higher. The presence of a lymphocytosis in an elderly individual should raise strong suspicion for CLL and a confirmatory diagnostic test, in particular flow cytometry, should be performed unless clinically unnecessary.

The diagnosis of CLL is based on the demonstration of an abnormal population of B lymphocytes in the blood, bone marrow, or tissues that display an unusual but characteristic pattern of molecules on the cell surface. This atypical molecular pattern includes the co-expression of cells surface markers cluster of differentiation 5 (CD5) and cluster of differentiation 23 (CD23). In addition, all the CLL cells within one individual are clonal, that is genetically identical. In practice, this is inferred by the detection of only one of the mutually exclusive antibody light chains, kappa or lambda, on the entire population of the abnormal B cells. Normal B lymphocytes consist of a stew of different antibody producing cells resulting in a mixture of both kappa and lambda expressing cells. The lack of the normal distribution of kappa and lambda producing B cells is one basis for demonstrating clonality, the key element for establishing a diagnosis of any B cell malignancy (B cell Non-Hodgkin's lymphoma).

The combination of the microscopic examination of the peripheral blood and analysis of the lymphocytes by flow cytometry to confirm clonality and marker molecule expression is needed to establish the diagnosis of CLL. Both are easily accomplished on a small amount of blood. A flow cytometer is an instrument that can examine the expression of molecules on individual cells in fluids. This requires the use of specific antibodies to marker molecules with fluorescent tags recognized by the instrument. In CLL, the lymphocytes are genetically clonal, of the B cell lineage (express marker molecules cluster of differentiation 19 (CD19) and CD20), and characteristically express the marker molecules CD5 and CD23. Morphologically, the cells resemble normal lymphocytes under the microscope, although slightly smaller, and are fragile when smeared onto a glass slide giving rise to many broken cells (smudge cells).

CLL treatment focuses on controlling the disease and its symptoms rather than on an outright cure. CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes).

Initial CLL treatments vary depending on the exact diagnosis and the progression of the disease, and even with the preference and experience of the health care practitioner. There are dozens of agents used for CLL therapy, and there is considerable research activity studying them individually or in combination with each other.

While generally considered incurable, CLL progresses slowly in most cases. Many people with CLL lead normal and active lives for many years—in some cases for decades. Because of its slow onset, early-stage CLL is generally not treated since it is believed that early CLL intervention does not improve survival time or quality of life. Instead, the condition is monitored over time to detect any change in the disease pattern.

The decision to start CLL treatment is taken when the patient's clinical symptoms or blood counts indicate that the disease has progressed to a point where it can affect the patient's quality of life. Determining when to start treatment and by what means is often difficult; studies have shown there is no survival advantage to treating the disease too early. The National Cancer Institute Working Group has issued guidelines for treatment, with specific markers that should be met before it is initiated.

Although the purine analogue fludarabine was shown to give superior response rates than chlorambucil as primary therapy, there is no evidence that early use of fludarabine improves overall survival, and some clinicians prefer to reserve fludarabine for relapsed disease. Mab therapies include alemtuzumab (directed against CD52) and rituximab (directed against CD20).

Combination chemotherapy options are effective in both newly-diagnosed and relapsed CLL. Recently, randomized trials have shown that combinations of purine analogues (fludarabine) with alkylating agents (cyclophosphamide) produce higher response rates and a longer progression-free survival than single agents:

FC (fludarabine with cyclophosphamide)

FR (fludarabine with rituximab)

FCR (fludarabine, cyclophosphamide, and rituximab)

CHOP (cyclophosphamide, doxorubicin, vincristine and prednisolone)

Allogeneic bone marrow (stem cell) transplantation is rarely used as a first-line treatment for CLL due to its risk. There is increasing interest in the use of reduced intensity allogeneic stem cell transplantation, which offers the prospect of cure for selected patients with a suitable donor.

Current research is comparing different forms of bone marrow transplants to determine which patients are the best candidates and which approach is best in different situations. Younger patients that are at high risk for dying from CLL might consider hematopoietic stem cell transplantation (HSCT). Autologous stem cell transplantation, a lower-risk form of treatment using the patient's own blood cells, is not curative. Myeloablative (bone marrow killing) forms of allogeneic stem cell transplantation, a high-risk treatment using blood cells from a healthy donor, can be curative for some patients, but most patients cannot tolerate the treatment. An intermediate level, called reduced-intensity conditioning allogeneic stem cell transplantation, can be better tolerated by older or frail patients. "Refractory" CLL is a disease that no longer responds favorably to treatment.

In this case more aggressive therapies, including lenalidomide, flavopiridol, and bone marrow (stem cell) transplantation, are considered. The monoclonal antibody, alemtuzumab (directed against CD52), can be used in patients with refractory, bone marrow-based disease.

iii. Breast Cancer

Breast cancer is a cancer that starts in the breast, usually in the inner lining of the milk ducts or lobules. There are different types of breast cancer, with different stages (spread), aggressiveness, and genetic makeup. With best treatment, 10-year disease-free survival varies from 98% to 10%. Treatment is selected from surgery, drugs (chemotherapy), and radiation. In the United States, there were 216,000 cases of invasive breast cancer and 40,000 deaths in 2004. Worldwide, breast cancer is the second most common type of cancer after lung cancer (10.4% of all cancer incidence, both sexes counted) and the fifth most common cause of cancer death. In 2004, breast cancer caused 519,000 deaths worldwide (7% of cancer deaths; almost 1% of all deaths). Breast cancer is about 100 times as frequent among women as among men, but survival rates are equal in both sexes.

The first symptom, or subjective sign, of breast cancer is typically a lump that feels different from the surrounding breast tissue. According to the The Merck Manual, more than 80% of breast cancer cases are discovered when the woman feels a lump. According to the American Cancer Society, the first medical sign, or objective indication of breast cancer as detected by a physician, is discovered by mammogram. Lumps found in lymph nodes located in the armpits can also indicate breast cancer. Indications of breast cancer other than a lump can include changes in breast size or shape, skin dimpling, nipple inversion, or spontaneous single-nipple discharge. Pain ("mastodynia") is an unreliable tool in determining the presence or absence of breast cancer, but can be indicative of other breast health issues.

When breast cancer cells invade the dermal lymphatics—small lymph vessels in the skin of the breast—its presentation can resemble skin inflammation and thus is known as inflammatory breast cancer (IBC). Symptoms of inflammatory breast cancer include pain, swelling, warmth and redness throughout the breast, as well as an orange-peel texture to the skin referred to as "peau d'orange." Another reported symptom complex of breast cancer is Paget's disease of the breast. This syndrome presents as eczematoid skin changes such as redness and mild flaking of the nipple skin. As Paget's advances, symptoms can include tingling, itching, increased sensitivity, burning, and pain. There can also be discharge from the nipple. Approximately half of women diagnosed with Paget's also have a lump in the breast.

Occasionally, breast cancer presents as metastatic disease, that is, cancer that has spread beyond the original organ. Metastatic breast cancer will cause symptoms that depend on the location of metastasis. Common sites of metastasis include bone, liver, lung and brain. Unexplained weight loss can occasionally herald an occult breast cancer, as can symptoms of fevers or chills. Bone or joint pains can sometimes be manifestations of metastatic breast cancer, as can jaundice or neurological symptoms. These symptoms are "non-specific," meaning they can also be manifestations of many other illnesses.

The primary risk factors that have been identified are sex, age, childbearing, hormones, a high-fat diet, alcohol intake, obesity, and environmental factors such as tobacco use, radiation and shiftwork. No etiology is known for 95% of breast cancer cases, while approximately 5% of new breast cancers are attributable to hereditary syndromes. In particular, carriers of the breast cancer susceptibility genes, BRCA1 and BRCA2, are at a 30-40% increased risk for breast and ovarian cancer, depending on in which portion of the protein the mutation occurs. Experts believe that 95% of inherited breast cancer can be traced to one of these two genes. Hereditary breast cancers can take the form of a site-specific hereditary breast cancer-cancers affecting the breast only- or breast-ovarian and other cancer syndromes. Breast cancer can be inherited both from female and male relatives.

Breast cancer subtypes are categorized on an immunohistochemical basis.

Subtype definitions are generally as follows:

normal (ER+, PR+, HER2+, cytokeratin 5/6+, and HER1+)

luminal A (ER+ and/or PR+, HER2−)

luminal B (ER+ and/or PR+, HER2+)

triple-negative (ER−, PR−, HER2−)

HER2+/ER−(ER−, PR−, and HER2+)

unclassified (ER−, PR−, HER2−, cytokeratin 5/6−, and HER1−)

In the case of triple-negative breast cancer cells, the cancer's growth is not driven by estrogen or progesterone, or by growth signals coming from the HER2 protein. By the same token, such cancer cells do not respond to hormonal therapy, such as tamoxifen or aromatase inhibitors, or therapies that target HER2 receptors, such as Herceptin®. About 10-20% of breast cancers are found to be triple-negative. It is important to identify these types of cancer to that one can avoid costly and toxic effects of therapies that are unlike to succeed, and to focus on treatments that can be used to treat triple-negative breast cancer. Like other forms of breast cancer, triple-negative breast cancer can be treated with surgery, radiation therapy, and/or chemotherapy. One particularly promosing approach is "neoadjuvant" therapy, where chemo- and/or radiotherapy is provided prior to sugery. Another new drug therapy is the use of poly (ADP-ribose) polymerase, or PARP inhibitors.

While screening techniques discussed above are useful in determining the possibility of cancer, a further testing is necessary to confirm whether a lump detected on screening is cancer, as opposed to a benign alternative such as a simple cyst. In a clinical setting, breast cancer is commonly diagnosed using a "triple test" of clinical breast examination (breast examination by a trained medical practitioner), mammography, and fine needle aspiration cytology. Both mammography and clinical breast exam, also used for screening, can indicate an approximate likelihood that a lump is cancer, and can also identify any other lesions. Fine Needle Aspiration and Cytology (FNAC), which can be done in a GP's office using local anaesthetic if required, involves attempting to extract a small portion of fluid from the lump. Clear fluid makes the lump highly unlikely to be cancerous, but bloody fluid can be sent off for inspection under a microscope for cancerous cells. Together, these three tools can be used to diagnose breast cancer with a good degree of accuracy. Other options for biopsy include core biopsy, where a section of the breast lump is removed, and an excisional biopsy, where the entire lump is removed.

Breast cancer screening is an attempt to find cancer in otherwise healthy individuals. The most common screening method for women is a combination of x-ray mammography and clinical breast exam. In women at higher than normal risk, such as those with a strong family history of cancer, additional tools can include genetic testing or breast Magnetic Resonance Imaging.

Breast self-examination was a form of screening that was heavily advocated in the past, but has since fallen into disfavour since several large studies have shown that it does not have a survival benefit for women and often causes considerably anxiety. This is thought to be because cancers that could be detected tended to be at a relatively advanced stage already, whereas other methods push to identify the cancer at an earlier stage where curative treatment is more often possible.

X-ray mammography uses x-rays to examine the breast for any uncharacteristic masses or lumps. Regular mammograms is recommended in several countries in women over a certain age as a screening tool.

Genetic testing for breast cancer typically involves testing for mutations in the BRCA genes. This is not generally a recommended technique except for those at elevated risk for breast cancer.

The mainstay of breast cancer treatment is surgery when the tumor is localized, with possible adjuvant hormonal therapy (with tamoxifen or an aromatase inhibitor), chemotherapy, and/or radiotherapy. At present, the treatment recommendations after surgery (adjuvant therapy) follow a pattern. Depending on clinical criteria (age, type of cancer, size, metastasis) patients are roughly divided to high risk and low risk cases, with each risk category following different rules for therapy. Treatment possibilities include radiation therapy, chemotherapy, hormone therapy, and immune therapy.

Targeted cancer therapies are treatments that target specific characteristics of cancer cells, such as a protein that allows the cancer cells to grow in a rapid or abnormal way. Targeted therapies are generally less likely than chemotherapy to harm normal, healthy cells. Some targeted therapies are antibodies that work like the antibodies made naturally by our immune systems. These types of targeted therapies are sometimes called immune-targeted therapies.

There are currently 3 targeted therapies doctors use to treat breast cancer. Herceptin® (trastuzumab) works against HER2-positive breast cancers by blocking the ability of the cancer cells to receive chemical signals that tell the cells to grow. Tykerb® (lapatinib) works against HER2-positive breast cancers by blocking certain proteins that can cause uncontrolled cell growth. Avastin® (bevacizumab) works by blocking the growth of new blood vessels that cancer cells depend on to grow and function.

Hormonal (anti-estrogen) therapy works against hormone-receptor-positive breast cancer in two ways: first, by lowering the amount of the hormone estrogen in the body, and second, by blocking the action of estrogen in the body. Most of the estrogen in women's bodies is made by the ovaries. Estrogen makes hormone-receptor-positive breast cancers grow. So reducing the amount of estrogen or blocking its action can help shrink hormone-receptor-positive breast cancers and reduce the risk of hormone-receptor-positive breast cancers coming back (recurring). Hormonal therapy medicines are not effective against hormone-receptor-negative breast cancers. There are several types of hormonal therapy medicines, including aromatase inhibitors, selective estrogen receptor modulators, and estrogen receptor downregulators. In some cases, the ovaries and fallopian tubes can be surgically removed to treat hormone-receptor-positive breast cancer or as a preventive measure for women at very high risk of breast cancer. The ovaries also can be shut down temporarily using medication.

In planning treatment, doctors can also use PCR tests like Oncotype DX or microarray tests that predict breast cancer recurrence risk based on gene expression. In February 2007, the first breast cancer predictor test won formal approval from the Food and Drug Administration. This is a new gene test to help predict whether women with early-stage breast cancer will relapse in 5 or 10 years, this could help influence how aggressively the initial tumor is treated.

Radiation therapy is also used to help destroy cancer cells that can linger after surgery. Radiation can reduce the risk of recurrence by 50-66% when delivered in the correct dose.

E. Combination Therapy

Tumor cell resistance to single agents represents a major problem in clinical oncology. One goal of current cancer research is to find ways to improve the efficacy of existing therapies. One way is by combining therapies in what is known as combination therapy. In one embodiment, the present invention provides a combination therapy wherein an anti-nucleolin antibody and at least one other agent comprise a composition for use in contacting a "target cell." In one aspect, the combination of anti-nucleolin antibody and at least one other agent are used in a combined amount effective to kill or inhibit proliferation of the cell.

In one embodiment, the method further comprisescancontacting the cells with a human anti-nucleolin antibody and one or more additional agent(s) or factor(s). In one embodiment, the method further comprises contacting the cell with a single composition or pharmacological formulation that includes both agents, or by contacting the cell with two distinct compositions or formulations, at the same time, wherein one composition includes the anti-nucleolin antibody and the other includes the agent.

In another embodiment, the method comprises contact by the anti-nucleolin antibody before or after contact by the other agent by intervals ranging from minutes to weeks. In embodiments where the other agent and anti-nucleolin antibody are applied separately to the cell, one would generally ensure that a significant period of time did not expire between the time of each delivery, such that the agent and anti-nucleolin antibody would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it can be desirable to extend the time period for treatment significantly, however, where several days (2, 3, 4, 5, 6 or 7) to several weeks (1, 2, 3, 4, 5, 6, 7 or 8) lapse between the respective administrations.

In another embodiment, the method comprises more than one administration of either the anti-nucleolin antibody or the other agent. Combinations of the anti-nucleolin antibody or the other agent, include, where the anti-nucleolin antibody is "A" and the other agent is "B," as exemplified below:

| | | | | | |
|---|---|---|---|---|---|
| A/B/A | B/A/B | B/B/A | A/A/B | B/A/A | A/B/B |
| B/B/B/A | B/B/A/B | A/A/B/B | A/B/A/B | A/B/B/A | B/B/A/A |
| B/A/B/A | B/A/A/B | B/B/B/A | A/A/A/B | B/A/A/A | A/B/A/A |
| A/A/B/A | A/B/B/B | B/A/B/B | B/B/A/B | | |

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. In particular, such agents are those discussed in Section VI(C)(i)-(iii) above. In treating cancer according to the invention, one would contact the tumor cells with an agent in addition to the anti-nucleolin antibody. This can be achieved by irradiating the localized tumor site with radiation or administering to the subject a therapeutically effective amount of a pharmaceutical composition comprising a chemotherapeutic compound.

A variety of chemical compounds, also described as "chemotherapeutic agents," function to induce DNA damage, all of which are intended to be of use in the combined treatment methods disclosed herein. In one embodiment, the "other agents" comprise chemotherapeutic agents. Categories of chemotherapeutic agents of the invention include, but are not limited to, alkylating agents, anthracyclines, cytoskeletal disruptors, epothilones, inhibitors of topoisomerase II, nucleotide analogs and precursor analogs, peptide antibiotics, platinum-based agents, retinoids, or vinca alkaloids and derivatives. Specific chemotherapeutic agents within these groups include, but are not limited to, actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, vinorelbine. The invention also encompasses the use of a combination of one or more DNA damaging agents, whether radiation-based or actual compounds, such as the use of X-rays with cisplatin or the use of cisplatin with etoposide.

Agents that directly cross-link nucleic acids, specifically DNA, are envisaged to facilitate DNA damage leading to a synergistic, antineoplastic combination with anti-nucleolin antibody. Agents such as cisplatin, and other DNA alkylating agents can be used. Cisplatin has been widely used to treat cancer, with efficacious doses used in clinical applications of 20 $mg/m^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 $mg/m^2$ at 21 day intervals for adriamycin, to 35-50 $mg/m^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

F. Immunodetection Kits

In still further embodiments, the present invention concerns immunodetection kits for use with the immunodetection methods described above. The immunodetection kits will comprise, in suitable container means, a human anti-nucleolin antibody, and optionally an immunodetection reagent.

In certain embodiments, the antibody can be pre-bound to a solid support, such as a column matrix and/or well of a microtitre plate. The immunodetection reagents of the kit can take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels can be employed in connection with the present invention.

The kits can further comprise a suitably aliquoted composition of the nucleolin, whether labeled or unlabeled, as can be used to prepare a standard curve for a detection assay. The kits can contain antibody-label conjugates either in fully conjugated form, in the form of intermediates, or as separate moieties to be conjugated by the user of the kit. The components of the kits can be packaged either in aqueous media or in lyophilized form.

The container means of the kits will generally include at least one vial, test tube, flask, bottle, syringe or other container means, into which the antibody can be placed, or preferably, suitably aliquoted. The kits of the present invention will also typically include a means for containing the antibody, antigen, and any other reagent containers in close confinement for commercial sale. Such containers can include injection or blow-molded plastic containers into which the desired vials are retained.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In one aspect of the invention a method is provided of producing an immortalized human B-cell that secrets an antibody that binds to human nucleolin comprising: obtaining a population of IgM-positive human B-cells; contacting said population with: Epstein-Barr virus (EBV) to immortalize said human B-cells, and a cytokine/growth factor/signaling agent cocktail to induce IgM-to-IgG immunoglobulin isotype class-switching; and culturing cells under conditions supporting said immortalization and immunoglobulin isotype class-switching. In one embodiment the method further comprises, selecting an immortalized human B-cell that expresses an antibody to human nucleolin. In another embodiment, selecting comprises an immunoassay performed on immortalized B-cell culture medium supernatants. In another embodiment, a cytokine cocktail comprises an agent that delivers a costimulatory signal to a human B-cell. In another embodiment, a cytokine cocktail comprises anti-IgM F(ab')$_2$ interleukin (IL)-2, IL-4, IL-5, IL-6, IL-9, IL-10, IL-13, INFα, BAFF, soluble CD40L. In another embodiment, a population of IgM-positive human B-cells is obtained from peripheral blood, a tonsils bone marrow, a spleen, a lymph node, umbilical cord blood, a liver, an apheresis procedures or a buffy coat. In another embodiment, the method further comprises isolating a nucleic acid encoding an entire heavy and/or light chain from the immortalized human B-cell of step (d). In another embodiment, the method further comprises isolating a nucleic acid encoding a heavy and/or light chain antigen-binding region from the immortalized human B-cell of step (d). In another embodiment, the method further comprises cloning said nucleic acid into a nucleic acid encoding a framework region of a heavy and/or light chain. In another embodiment, contacting said population further comprises an EBV concentration step, a centrifugation step during infection, or both. In another embodiment, the method further comprises freezing said population of human B-cells following step (c). In another embodiment, contacting said population with a cytokine/growth factor/signaling agent cocktail is performed at about 0-96 hours following step (b)(ii). In another embodiment, contacting said population with a cytokine/growth factor/signaling agent cocktail is performed at about 16-20 hours following step (b)(ii). In another embodiment, about 50%-99% of said population are immortalized by EBV infection. In another embodiment, about 95%-99% of said population are immortalized by EBV infection. In another embodiment, selecting an immortalized human B-cell that expresses an antibody to human nucleolin occurs 1-4 weeks following infection. In another embodiment, selecting an immortalized human B-cell that expresses an antibody to human nucleolin occurs 2-3 weeks following infection. In another embodiment, selecting an immortalized human B-cell that expresses an antibody to human nucleolin occurs after thawing stored frozen immortalized B-cells, and/or after thawing stored frozen culture medium supernatants from said immortalized B-cells. In another embodiment, the B-cell is antigen naïve. In another embodiment, the B-cell is antigen experienced.

In another aspect the invention provides an immortalized human B-cell that expresses an IgG antibody that binds to human nucleolin. In one embodiment, the immortalized human B-cell is designated as T-5D1, V-3H11 (3G5), T-2D3, T-7G7 (1H9), T-2H3, T-9F9, T-8G4 or T-P1C6.

In another aspect the invention provides an immortalized human B-cell that expresses an IgG antibody or fragment thereof that binds to a protein of SEQ ID No. 2. In one embodiment, the IgG antibody is an IgG1, IgG2, IgG3, or IgG4 antibody. In another embodiment, the IgG antibody is an IgG1 antibody. In another embodiment, the IgG antibody comprises a kappa light chain. In another embodiment, the IgG antibody comprises a lambda light chain. In another embodiment, the B-cell is EBV immortalized. In another embodiment, the antibody or fragment thereof is a monoclonal antibody or fragment thereof. In another embodiment, the antibody or fragment thereof is substantially non-immunogenic to a human. In another embodiment, the antibody or fragment thereof is a human antibody or fragment thereof. In another embodiment, the antibody or fragment thereof kills at least 10% of a population of MCF-7 cells, when incubated with said MCF-7 cells and human AB serum for 48 hours. In another embodiment, the antibody or fragment thereof kills at least 20% of a population of MCF-7 cells, when incubated with said MCF-7 cells and human AB serum for 48 hours. In another embodiment, the antibody or fragment thereof kills at least 30% of a population of MCF-7 cells, when incubated with said MCF-7 cells and human AB serum for 48 hours. In another embodiment, the antibody or fragment thereof kills at least 40% of a population of MCF-7 cells, when incubated with said MCF-7 cells and human AB serum for 48 hours. In another embodiment, the antibody or fragment thereof kills at least 50% of a population of MCF-7 cells, when incubated with said MCF-7 cells and human AB serum for 48 hours. In another embodiment, the antibody or fragment thereof kills at least 60% of a population of MCF-7 cells, when incubated with said MCF-7 cells and human AB serum for 48 hours. In another embodiment, the antibody or fragment thereof kills at least 70% of a population of MCF-7 cells, when incubated with said MCF-7 cells and human AB serum for 48 hours. In another embodiment, the antibody or fragment thereof kills at least 80% of a population of MCF-7 cells, when incubated with said MCF-7 cells and human AB serum for 48 hours. In another embodiment, the antibody or fragment thereof kills at least 90% of a population of MCF-7 cells, when incubated with said MCF-7 cells and human AB serum for 48 hours. In another embodiment, the antibody or fragment thereof kills at least 100% of a population of MCF-7 cells, when incubated with said MCF-7 cells and human AB serum for 48 hours. In another embodiment, the antibody or fragment thereof kills at least 10% of a population of MV4-11 cells, when incubated with said MCF-7 cells and human AB serum for 48 hours. In another embodiment, the antibody or fragment thereof kills at least 20% of a population of MV4-11 cells, when incubated with said MCF-7 cells and human AB serum for 48 hours. In another embodiment, the antibody or fragment thereof kills at least 30% of a population of MV4-11 cells, when incubated with said MCF-7 cells and human AB serum for 48 hours. In another embodiment, the antibody or fragment thereof kills at least 40% of a population of MV4-11 cells, when incubated with said MCF-7 cells and human AB serum for 48 hours. In another embodiment, the antibody or fragment thereof kills at least 50% of a population of MV4-11 cells, when incubated with said MCF-7 cells and human AB serum for 48 hours. In another embodiment, the antibody or fragment thereof kills at least 60% of a population of MV4-11 cells, when incubated with said MCF-7 cells and human AB serum for 48 hours. In another embodiment, the antibody or fragment thereof kills at least 70% of a population of MV4-11 cells, when incubated with said MCF-7 cells and human AB serum for 48 hours. In another embodiment, the antibody or fragment thereof kills at least 80% of a population of MV4-11 cells, when incubated with said MCF-7 cells and human AB serum for 48 hours. In another embodiment, the antibody or fragment thereof kills at least 90% of a population of MV4-11 cells, when incubated with said MCF-7 cells and human AB serum for 48 hours. In another embodiment, the antibody or fragment thereof kills at least 100% of a population of MV4-11 cells, when incubated with said MCF-7 cells and human AB serum for 48 hours. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof induces complement-dependent cytotoxicity to a cancer cell. In another embodiment, the isolated antibody or fragment thereof induces complement-independent cytotoxicity to a cancer cell. In another embodiment, the isolated antibody or fragment thereof induces apoptosis in a cancer cell upon contact. In another embodiment, the isolated antibody or fragment thereof inhibits or kills an AML cancer cell, a CLL cancer cell or a breast cancer cell. In another embodiment, the isolated monoclonal antibody or fragment thereof reduces BCL-2 levels in a cancer cell.

In another aspect the invention provides an immortalized human B-cell that expresses an IgG antibody or fragment thereof that binds to a protein encoded by SEQ ID No. 1. In one embodiment, the IgG antibody is an IgG1, IgG2, IgG3, or IgG4 antibody. In another embodiment, the IgG antibody is an IgG1 antibody. In another embodiment, the IgG antibody comprises a kappa light chain. In another embodiment, the IgG antibody comprises a lambda light chain. In another embodiment, the B-cell is EBV immortalized. In another embodiment, the antibody or fragment thereof is a monoclonal antibody or fragment thereof. In another embodiment, said antibody or fragment thereof is substantially non-immunogenic to a human. In another embodiment, the antibody or fragment thereof is a human antibody or fragment thereof. In another embodiment, the antibody or fragment thereof kills at least 10% of a population of MCF-7 cells, when incubated with said MCF-7 cells and human AB serum for 48 hours. In another embodiment, the antibody or fragment thereof kills at least 20% of a population of MCF-7 cells, when incubated with said MCF-7 cells and human AB serum for 48 hours. In another embodiment, the antibody or fragment thereof kills at least 30% of a population of MCF-7 cells, when incubated with said MCF-7 cells and human AB serum for 48 hours. In another embodiment, the antibody or fragment thereof kills at least 40% of a population of MCF-7 cells, when incubated with said MCF-7 cells and human AB serum for 48 hours. In another embodiment, the antibody or fragment thereof kills at least 50% of a population of MCF-7 cells, when incubated with said MCF-7 cells and human AB serum for 48 hours. In another embodiment, the antibody or fragment thereof kills at least 60% of a population of MCF-7 cells, when incubated with said MCF-7 cells and human AB serum for 48 hours. In another embodiment, the antibody or fragment thereof kills at least 70% of a population of MCF-7 cells, when incubated with said MCF-7 cells and human AB serum for 48 hours. In another embodiment, the antibody or fragment thereof kills at least 80% of a population of MCF-7 cells, when incubated with said MCF-7 cells and human AB serum for 48 hours. In another embodiment, the antibody or fragment thereof kills at least 90% of a population of MCF-7 cells, when incubated with said MCF-7 cells and human AB serum for 48 hours. In another embodiment, the antibody or fragment thereof kills at least 100% of a population of MCF-7 cells, when incubated with said MCF-7 cells and human AB serum for 48 hours. In another embodiment, the antibody or fragment thereof kills at least 10% of a population of MV4-11 cells, when incubated with said MCF-7 cells and human AB serum for 48 hours. In another embodiment, the antibody or fragment thereof kills at least 20% of a population of MV4-11 cells, when incubated with said MCF-7 cells and human AB serum for 48 hours. In another embodiment, the antibody or fragment thereof kills at least 30% of a population of MV4-11 cells, when incubated with said MCF-7 cells and human AB serum for 48 hours. In another embodiment, the antibody or fragment thereof kills at least 40% of a population of MV4-11 cells, when incubated with said MCF-7 cells and human AB serum for 48 hours. In another embodiment, the antibody or fragment thereof kills at least 50% of a population of MV4-11 cells, when incubated with said MCF-7 cells and human AB serum for 48 hours. In another embodiment, the antibody or fragment thereof kills at least 60% of a population of MV4-11 cells, when incubated with said MCF-7 cells and human AB serum for 48 hours. In another embodiment, the antibody or fragment thereof kills at least 70% of a population of MV4-11 cells, when incubated with said MCF-7 cells and human AB serum for 48 hours. In another embodiment, the antibody or fragment thereof kills at least 80% of a population of MV4-11 cells, when incubated with said MCF-7 cells and human AB serum for 48 hours. In another embodiment, the antibody or fragment thereof kills at least 90% of a population of MV4-11 cells, when incubated with said MCF-7 cells and human AB serum for 48 hours. In another embodiment, the antibody or fragment thereof kills at least 100% of a population of MV4-11 cells, when incubated with said MCF-7 cells and human AB serum for 48 hours. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof induces complement-dependent cytotoxicity to a cancer cell. In another embodiment, the isolated antibody or fragment thereof induces complement-independent cytotoxicity to a cancer cell. In another embodiment, the isolated antibody or fragment thereof induces apoptosis in a cancer cell upon contact. In another embodiment, the isolated antibody or fragment thereof inhibits or kills an AML cancer cell, a CLL cancer cell or a breast cancer cell. In another embodiment, the isolated monoclonal antibody or fragment thereof reduces BCL-2 levels in a cancer cell.

In another aspect the invention provides an immortalized human B-cell that expresses an IgG antibody or fragment thereof that binds to a protein comprising SEQ ID No. 4. In one embodiment, the IgG antibody is an IgG1, IgG2, IgG3, or IgG4 antibody. In another embodiment, the IgG antibody is an IgG1 antibody. In another embodiment, the IgG antibody comprises a kappa light chain. In another embodiment, the IgG antibody comprises a lambda light chain. In another embodiment, the B-cell is EBV immortalized. In another embodiment, said antibody or fragment thereof is a monoclonal antibody or fragment thereof. In another embodiment, the antibody or fragment thereof is substantially non-immunogenic to a human. In another embodiment, the antibody or fragment thereof is a human antibody or fragment thereof. In another embodiment, the antibody or fragment thereof kills at least 10% of a population of MCF-7 cells, when incubated with said MCF-7 cells and human AB serum for 48 hours. In another embodiment, the antibody or fragment thereof kills at least 20% of a population of MCF-7 cells, when incubated with said MCF-7 cells and human AB serum for 48 hours. In another embodiment, the antibody or fragment thereof kills at least 30% of a population of MCF-7 cells, when incubated with said MCF-7 cells and human AB serum for 48 hours. In another embodiment, the antibody or fragment thereof kills at least 40% of a population of MCF-7 cells, when incubated with said MCF-7 cells and human AB serum for 48 hours. In another embodiment, the antibody or fragment thereof kills at least 50% of a population of MCF-7 cells, when incubated with said MCF-7 cells and human AB serum for 48 hours. In another embodiment, the antibody or fragment thereof kills at least 60% of a population of MCF-7 cells, when incubated with said MCF-7 cells and human AB serum for 48 hours. In another embodiment, the antibody or fragment thereof kills at least 70% of a population of MCF-7 cells, when incubated with said MCF-7 cells and human AB serum for 48 hours. In another embodiment, the antibody or fragment thereof kills at least 80% of a population of MCF-7 cells, when incubated with said MCF-7 cells and human AB serum for 48 hours. In another embodiment, the antibody or fragment thereof kills at least 90% of a population of MCF-7 cells, when incubated with said MCF-7 cells and human AB serum for 48 hours. In another embodiment, the antibody or fragment thereof kills at least 100% of a population of MCF-7 cells, when incubated with said MCF-7 cells and human AB serum for 48 hours. In another embodiment, the antibody or fragment thereof kills at least 10% of a population of MV4-11 cells, when incubated with said MCF-7 cells and human AB serum for 48 hours. In another embodiment, the antibody or fragment thereof kills at least 20% of a population of MV4-11 cells, when incubated with said MCF-7 cells and human AB serum for 48 hours. In another embodiment, the antibody or fragment thereof kills at least 30% of a population of MV4-11 cells, when incubated with said MCF-7 cells and human AB serum for 48 hours. In another embodiment, the antibody or fragment thereof kills at least 40% of a population of MV4-11 cells, when incubated with said MCF-7 cells and human AB serum for 48 hours. In another embodiment, the antibody or fragment thereof kills at least 50% of a population of MV4-11 cells, when incubated with said MCF-7 cells and human AB serum for 48 hours. In another embodiment, the antibody or fragment thereof kills at least 60% of a population of MV4-11 cells, when incubated with said MCF-7 cells and human AB serum for 48 hours. In another embodiment, the antibody or fragment thereof kills at least 70% of a population of MV4-11 cells, when incubated with said MCF-7 cells and human AB serum for 48 hours. In another embodiment, the antibody or fragment thereof kills at least 80% of a population of MV4-11 cells, when incubated with said MCF-7 cells and human AB serum for 48 hours. In another embodiment, the antibody or fragment thereof kills at least 90% of a population of MV4-11 cells, when incubated with said MCF-7 cells and human AB serum for 48 hours. In another embodiment, the antibody or fragment thereof kills at least 100% of a population of MV4-11 cells, when incubated with said MCF-7 cells and human AB serum for 48 hours. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof induces complement-dependent cytotoxicity to a cancer cell. In another embodiment, the isolated antibody or fragment thereof induces complement-independent cytotoxicity to a cancer cell. In another embodiment, the isolated antibody or fragment thereof induces apoptosis in a cancer cell upon contact. In another embodiment, the isolated antibody or fragment thereof inhibits or kills an AML cancer cell, a CLL cancer cell or a breast cancer cell. In another embodiment, the isolated monoclonal antibody or fragment thereof reduces BCL-2 levels in a cancer cell.

In another aspect the invention provides an immortalized human B-cell that expresses an IgG antibody or fragment thereof that binds to a protein encoded by SEQ ID No. 3. In one embodiment, the IgG antibody is an IgG1, IgG2, IgG3, or IgG4 antibody. In another embodiment, the IgG antibody is an IgG1 antibody. In another embodiment, the IgG antibody comprises a kappa light chain. In another embodiment, the IgG antibody comprises a lambda light chain. In another embodiment, the B-cell is EBV immortalized. In another embodiment, the antibody or fragment thereof is a monoclonal antibody or fragment thereof. In another embodiment, the antibody or fragment thereof is substantially non-immunogenic to a human. In another embodiment, the antibody or fragment thereof is a human antibody or fragment thereof. In another embodiment, the antibody or fragment thereof kills at least 20% of a population of MCF-7 cells, when incubated with said MCF-7 cells and human AB serum for 48 hours. In another embodiment, the antibody or fragment thereof kills at least 20% of a population of MV4-11 cells, when incubated with said MCF-7 cells and human AB serum for 48 hours. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof induces complement-dependent cytotoxicity to a cancer cell. In another embodiment, the isolated antibody or fragment thereof induces complement-independent cytotoxicity to a cancer cell. In another embodiment, the isolated antibody or fragment thereof induces apoptosis in a cancer cell upon contact. In another embodiment, the isolated antibody or fragment thereof inhibits or kills an AML cancer cell, a CLL cancer cell or a breast cancer cell. In another embodiment, the isolated monoclonal antibody or fragment thereof reduces BCL-2 levels in a cancer cell.

In another aspect the invention provides an isolated human monoclonal antibody or fragment thereof that specifically binds to a protein of SEQ ID No. 4. In one embodiment, the antibody or fragment thereof is a human antibody or fragment thereof. In another embodiment, the antibody or fragment thereof kills at least 10% of a population of MCF-7 cells, when incubated with said MCF-7 cells and human AB serum for 48 hours. In another embodiment, the antibody or fragment thereof kills at least 20% of a population of MCF-7 cells, when incubated with said MCF-7 cells and human AB serum for 48 hours. In another embodiment, the antibody or fragment thereof kills at least 30% of a population of MCF-7 cells, when incubated with said MCF-7 cells and human AB serum for 48 hours. In another embodiment, the antibody or fragment thereof kills at least 40% of a population of MCF-7 cells, when incubated with said MCF-7 cells and human AB serum for 48 hours. In another embodiment, the antibody or fragment thereof kills at least 50% of a population of MCF-7 cells, when incubated with said MCF-7 cells and human AB serum for 48 hours. In another embodiment, the antibody or fragment thereof kills at least 60% of a population of MCF-7 cells, when incubated with said MCF-7 cells and human AB serum for 48 hours. In another embodiment, the antibody or fragment thereof kills at least 70% of a population of MCF-7 cells, when incubated with said MCF-7 cells and human AB serum for 48 hours. In another embodiment, the antibody or fragment thereof kills at least 80% of a population of MCF-7 cells, when incubated with said MCF-7 cells and human AB serum for 48 hours. In another embodiment, the antibody or fragment thereof kills at least 90% of a population of MCF-7 cells, when incubated with said MCF-7 cells and human AB serum for 48 hours. In another embodiment, the antibody or fragment thereof kills at least 100% of a population of MCF-7 cells, when incubated with said MCF-7 cells and human AB serum for 48 hours. In another embodiment, the antibody or fragment thereof kills at least 10% of a population of MV4-11 cells, when incubated with said MCF-7 cells and human AB serum for 48 hours. In another embodiment, the antibody or fragment thereof kills at least 20% of a population of MV4-11 cells, when incubated with said MCF-7 cells and human AB serum for 48 hours. In another embodiment, the antibody or fragment thereof kills at least 30% of a population of MV4-11 cells, when incubated with said MCF-7 cells and human AB serum for 48 hours. In another embodiment, the antibody or fragment thereof kills at least 40% of a population of MV4-11 cells, when incubated with said MCF-7 cells and human AB serum for 48 hours. In another embodiment, the antibody or fragment thereof kills at least 50% of a population of MV4-11 cells, when incubated with said MCF-7 cells and human AB serum for 48 hours. In another embodiment, the antibody or fragment thereof kills at least 60% of a population of MV4-11 cells, when incubated with said MCF-7 cells and human AB serum for 48 hours. In another embodiment, the antibody or fragment thereof kills at least 70% of a population of MV4-11 cells, when incubated with said MCF-7 cells and human AB serum for 48 hours. In another embodiment, the antibody or fragment thereof kills at least 80% of a population of MV4-11 cells, when incubated with said MCF-7 cells and human AB serum for 48 hours. In another embodiment, the antibody or fragment thereof kills at least 90% of a population of MV4-11 cells, when incubated with said MCF-7 cells and human AB serum for 48 hours. In another embodiment, the antibody or fragment thereof kills at least 100% of a population of MV4-11 cells, when incubated with said MCF-7 cells and human AB serum for 48 hours. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof induces complement-dependent cytotoxicity to a cancer cell. In another embodiment, the isolated antibody or fragment thereof induces complement-independent cytotoxicity to a cancer cell. In another embodiment, the isolated antibody or fragment thereof induces apoptosis in a cancer cell upon contact. In another embodiment, the isolated antibody or fragment thereof inhibits or kills an AML cancer cell, a CLL cancer cell or a breast cancer cell. In another embodiment, the isolated monoclonal antibody or fragment thereof reduces BCL-2 levels in a cancer cell.

In another aspect the invention provides an isolated antibody or fragment thereof that specifically binds to a human nucleolin protein, wherein said antibody or fragment thereof kills at least 20% of a population of MCF-7 cells, when incubated with said MCF-7 cells and human AB serum for 48 hours. In one embodiment, the amino acid sequence of said human nucleolin comprises SEQ ID No. 2. In another embodiment, the antibody or fragment thereof binds to an amino acid sequence consisting of amino acid residues 1 to 283 of SEQ ID No. 2. In another embodiment, the antibody or fragment thereof is a monoclonal antibody or fragment thereof. In another embodiment, the antibody or fragment thereof is substantially non-immunogenic to a human. In another embodiment, the antibody or fragment thereof is a human antibody or fragment thereof. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof is linked to a diagnostic or therapeutic agent. In another embodiment, the isolated antibody or fragment thereof exhibits complement-dependent cytotoxicity to a cancer cell. In another embodiment, the isolated antibody or fragment thereof exhibits complement-independent cytotoxicity to a cancer cell. In another embodiment, the isolated antibody or fragment thereof induces apoptosis in a cancer cell upon contact. In another embodiment, the antibody or fragment thereof inhibits or kills an AML cancer cell, a CLL cancer cell or a breast cancer cell. In another embodiment, the isolated antibody or fragment thereof reduces BCL-2 levels in a cancer cell. In another embodiment, the antibody or fragment thereof is linked to a diagnostic agent. In another embodiment, the diagnostic agent is a radionuclide, a fluorophore, a chemilluminescent compound, a fluorescent compound, or an enzyme. In another embodiment, the antibody or fragment thereof is linked to a therapeutic agent. In another embodiment, the therapeutic agent is a radionuclide, a toxin or a chemotherapeutic moiety.

In another aspect the invention provides an isolated antibody or fragment thereof that specifically binds to a human nucleolin protein, wherein said antibody or fragment thereof kills at least 10-100% of a population of MV4-11 cells (such as 10, 20, 30, 40, 50, 60, 70, 80, 90 or 100% of a population of MV4-11 cells, when incubated with said MCF-7 cells and human AB serum for 48 hours. In another embodiment, the amino acid sequence of said human nucleolin comprises SEQ ID No. 2. In another embodiment, the antibody or fragment thereof binds to an amino acid sequence consisting of amino acid residues 1 to 283 of SEQ ID No. 2. In another embodiment, the antibody or fragment thereof is a monoclonal antibody or fragment thereof. In another embodiment, the antibody or fragment thereof is substantially non-immunogenic to a human. In another embodiment, the antibody or fragment thereof is a human antibody or fragment thereof. In another embodiment, the antibody or fragment thereof binds to an RNA binding domain of human nucleolin. In another embodiment, the antibody or fragment thereof inactivates an RNA binding domain of human nucleolin. In another embodiment, the isolated antibody or fragment thereof is linked to a diagnostic or therapeutic agent. In another embodiment, the isolated antibody or fragment thereof exhibits complement-dependent cytotoxicity to a cancer cell. In another embodiment, the isolated antibody or fragment thereof exhibits complement-independent cytotoxicity to a cancer cell. In another embodiment, the isolated antibody or fragment thereof induces apoptosis in a cancer cell upon contact. In another embodiment, the antibody or fragment thereof inhibits or kills an AML cancer cell, a CLL cancer cell or a breast cancer cell. In another embodiment, the isolated antibody or fragment thereof reduces BCL-2 levels in a cancer cell. In another embodiment, the said antibody or fragment thereof is linked to a diagnostic agent. In another embodiment, the diagnostic agent is a radionuclide, a fluorophore, a chemilluminescent compound, a fluorescent compound, or an enzyme. In another embodiment, the antibody or fragment thereof is linked to a therapeutic agent. In another embodiment, the therapeutic agent is a radionuclide, a toxin or a chemotherapeutic moiety.

In another aspect the invention provides an anti-nucleolin composition comprising one or more isolated antibodies or fragments thereof that specifically binds to a human nucleolin protein, wherein said one or more antibodies kills at least 10-100% of a population of MCF-7 cells (such as 10, 20, 30, 40, 40, 50, 60, 70, 80, 90, or 100%), when incubated with said MCF-7 cells and human AB serum for 48-96 (such as 48, 72 or 96 hours) hours. In one embodiment, the one or more isolated antibodies or fragments thereof is a monoclonal antibody or fragment thereof. In another embodiment, the one or more isolated antibodies or fragments thereof is substantially non-immunogenic to a human. In another embodiment, the one or more isolated antibodies or fragments thereof is a human antibody or fragment thereof. In another embodiment, the one or more isolated antibodies or fragments thereof binds to an RNA binding domain of human nucleolin. In another embodiment, the one or more isolated antibodies or fragments thereof inactivates an RNA binding domain of human nucleolin. In another embodiment, the amino acid sequence of said human nucleolin comprises SEQ ID No. 2. In another embodiment, the one or more isolated antibodies or fragments thereof binds to SEQ ID No. 4. In another embodiment, the anti-nucleolin composition further comprises a radionuclide, a fluorophore, a chemilluminescent compound, a fluorescent compound, an enzyme, a toxin or a chemotherapeutic agent. In another embodiment, the radionuclide, a fluorophore, a chemilluminescent compound, a fluorescent compound, an enzyme, a toxin or a chemotherapeutic agent is conjugated to said one or more isolated antibodies or fragments thereof. In another embodiment, the anti-nucleolin composition comprises two or more isolated antibodies or fragments thereof that specifically binds to said human nucleolin protein, wherein said one or more antibodies kills at least 20% of a population of MCF-7 cells, when incubated with said MCF-7 cells and human AB serum for 48 hours. In another embodiment, the anti-nucleolin composition comprises three or more isolated antibodies or fragments thereof that specifically binds to said human nucleolin protein, wherein said one or more antibodies kills at least 20% of a population of MCF-7 cells, when incubated with said MCF-7 cells and human AB serum for 48 hours.

In another aspect the invention provides a method of inhibiting or killing a cell expressing nucleolin on its surface comprising contacting said cell with an antibody or fragment thereof that binds to human nucleolin, wherein said antibody or fragment thereof kills at least 20% of a population of MCF-7 cells, when incubated with said MCF-7 cells and human AB serum for 48 hours. In one embodiment, the antibody or fragment thereof is a human antibody or fragment thereof. In another embodiment, the antibody or fragment thereof is a monoclonal antibody or fragment thereof. In another embodiment, the antibody or fragment thereof binds to SEQ ID No. 2. In another embodiment, the antibody or fragment thereof binds to an amino acid sequence encoded by SEQ ID No. 1. In another embodiment, the antibody or fragment thereof binds to SEQ ID No. 4. In another embodiment, the antibody or fragment thereof binds to an amino acid sequence encoded by SEQ ID No. 3. In another embodiment, the cell is a cancer cell. In another embodiment, the cancer cell is a lung cancer cell, a breast cancer cell, a prostate cancer cell, a colon cancer cell, a pancreatic cancer cell, a renal cell carcinoma cell, an ovarian cancer cell, a leukemia cell, a melanoma cell, a glioblastoma cell, a neuroblastoma cell, a sarcoma cell or a gastric cancer cell. In another embodiment, the cell is an immune cell. In another embodiment, the immune cell is a lymphocyte, dendritic cell, a peripheral blood monocyte, a macrophage or a glial cell. In another embodiment, the immune cell is an activated immune cell. In another embodiment, the immune cell is an activated B cell. In another embodiment, the immune cell is a memory B cell. In another embodiment, the immune cell is an activated T cell. In another embodiment, the immune cell is an activated CD4+ T cell. In another embodiment, the immune cell is an activated CD8+ T cell. In another embodiment, the cell a vascular smooth muscle cell or an endothelial cell. In another embodiment, the antibody or fragment thereof is linked to a therapeutic agent. In another embodiment, the therapeutic agent is a radionuclide, a toxin or a chemotherapeutic agent. In another embodiment, the inhibiting or killing comprises inducing apoptosis in said cell. In another embodiment, the cell is located in a human subject, and said contacting comprising administering said antibody or fragment thereof to said subject. In another embodiment, the method of further comprises contacting said cell with at least one additional inhibitory agent or treatment. In another embodiment, the additional treatment comprises one or more of surgery, radiotherapy, chemotherapy, toxin therapy, immunotherapy, hormone therapy, anti-angiogenic therapy or gene therapy orother biological therapies. In another embodiment, the additional inhibitory agent comprises one or more of radionuclides, chemotherapetic agents, toxins immunotherapeutics, hormones, nucleic acids or polypeptides. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the wherein said chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

In another aspect the invention provides a method of detecting a cell expressing nucleolin on its surface comprising contacting said cell with a human antibody or fragment thereof that binds immunologically to said nucleolin. In one embodiment, the cell is a cancer cell, an immune cell, or a vascular smooth muscle cell that expresses nucleolin on its surface, an endothelial cell that expresses nucleolin on its surface, or a virus infected cell. In another embodiment, the cell is a precancersous cell that expresses nucleolin on its surface. In another embodiment, the cancer cell selected from the group consisting of is a lung cancer cell, a breast cancer cell, a prostate cancer cell, a colon cancer cell, a pancreatic cancer cell, a renal cell carcinoma cell, an ovarian cancer cell, a leukemia cell, a melanoma cell, a glioblastoma cell, a neuroblastoma cell, a sarcoma cell and a gastric cancer cell. In another embodiment, the immune cell is a lymphocyte, dendritic cell, a peripheral blood monocyte, a macrophage and a glial cell. In another embodiment, the cell is an immune cell. In another embodiment, the immune cell is an activated immune cell. In another embodiment, the immune cell is an activated B cell. In another embodiment, the immune cell is a memory B cell. In another embodiment, the immune cell is an activated T cell. In another embodiment, the immune cell is an activated CD4+ T cell. In another embodiment, the immune cell is an activated CD8+ T cell. In another embodiment, the cell is a vascular smooth muscle cell or an endothelial cell. In another embodiment, the antibody or fragment thereof is linked to a diagnostic agent. In another embodiment, the diagnostic agent is a radionuclide, a fluorophore, a chemilluminescent compound, a fluorescent compound, a quantum dot, a nanoparticles or an enzyme. In another embodiment, the cell is located in a human subject and contacting comprises administering said antibody or fragment thereof to said subject. In another embodiment, the cell is located in an isolated, tissue sample or cell suspension.

In another aspect the invention provides a method of treating or preventing cancer in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof and said antibody or fragment thereof kills at least 10-100% (such as 10, 20, 30, 40, 50, 60, 70, 80, 90, or 100% of a population of MCF-7 cells, when incubated with said MCF-7 cells and human AB serum for 48 (such as 48, 72, or 96) hours. In one embodiment, the mammal is a human. In another embodiment, the treating cancer in a mammal comprises treating tumor hpoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin.

In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

In another aspect the invention provides a method of treating or preventing cancer in a mammal comprising administering to said mammal a therapeutically effective amount of an anti-nucleolin antibody or fragment thereof, a toxin or chemotherapeutic agent and a pharmaceutically acceptable carrier, wherein said antibody or fragment thereof kills at least 10-100% (such as 10, 20, 30, 40, 50, 60, 70, 80, 90, or 100% of a population of MCF-7 cells, when incubated with said MCF-7 cells and human AB serum for 48 (such as 48, 72, or 96) hours. In one embodiment, the mammal is a human. In another embodiment, the treating cancer in a mammal comprises treating tumor hpoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine In another aspect the invention provides a method of treating or preventing cancer in a mammal comprising administering to said mammal a therapeutically effective amount of an anti-nucleolin antibody or fragment thereof and a pharmaceutically acceptable carrier, and further treating said mammal with radiation therapy, wherein said antibody or fragment thereof kills at least 10-100% (such as 10, 20, 30, 40, 50, 60, 70, 80, 90, or 100% of a population of MCF-7 cells, when incubated with said MCF-7 cells and human AB serum for 48 (such as 48, 72, or 96) hours. In one embodiment, the mammal is a human. In another embodiment, the treating cancer in a mammal comprises treating tumor hpoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

In another aspect the invention provides a method of treating or preventing cancer in a mammal comprising administering to said mammal a therapeutically effective amount of an anti-nucleolin agent and a pharmaceutically acceptable carrier; wherein said anti-nucleolin agent comprises a anti-nucleolin antibody or fragment thereof that specifically binds to a protein of SEQ ID No. 4. In one embodiment, the mammal is a human. In another embodiment, the treating cancer in a mammal comprises treating tumor hypoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

A method of treating or preventing cancer in a mammal comprising administering to said mammal a therapeutically effective amount of a anti-nucleolin antibody or fragment thereof, a toxin or chemotherapeutic agent and a pharmaceutically acceptable carrier, wherein said antibody or fragment thereof specifically binds to a protein of SEQ ID No. 4. In one embodiment, the mammal is a human. In another embodiment, the treating cancer in a mammal comprises treating tumor hpoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

In another aspect the invention provides a method of treating or preventing cancer in a mammal comprising administering to said mammal a therapeutically effective amount of a anti-nucleolin antibody or fragment thereof and a pharmaceutically acceptable carrier, and further treating said mammal with radiation therapy, wherein said antibody or fragment thereof specifically binds to a protein of SEQ ID No. 4. In one embodiment, the mammal is a human. In another embodiment, the treating cancer in a mammal comprises treating tumor hpoxia. In another embodiment, the treating cancer in a mammal comprises inhibiting tumor angiogenesis. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin monoclonal antibody or fragment thereof is a monoclonal antibody or fragment thereof. In another embodiment, the toxin is diphtheria toxin, exotoxin A chain, ricin A chain, abrin A chain, modeccin A chain, alpha-sarcin, *Aleurites fordii* proteins, dianthin proteins, *phytolaca americana* protein, pokeweed antiviral protein, *momordica charantia* inhibitor, curcin, crotin, *sapaonaria officinalis* inhibitor, gelonin, mitogellin, restrictocin, phenomycin, enomycin, calicheamicins or tricothecenes toxin. In another embodiment, the chemotherapeutic agent is an alkylating agent, anthracycline, cytoskeletal disruptor, epothilone, inhibitor of topoisomerase I, inhibitor of topoisomerase II, nucleoside or nucleotide analog, precursor analogs, peptide antibiotic, platinum-based agents retinoids, vinca alkaloids or derivatives thereof. In another embodiment, the chemotherapeutic agent is actinomycin-D, all-trans retinoic acid azacitidine, adriamycin azathioprine, bleomycin, camptothecin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, 5-fluorouracil (5FU), gemcitabine, hydroxyurea, hydrogen peroxide, idarubicin, imatinib, mechlorethamine, mercaptopurine, methotrexate, mitomycin C, mitoxantrone, oxaliplatin, paclitaxel, pemetrexed, teniposide, tioguanine, valrubicin, vinblastine, vincristine, vindesine, or vinorelbine.

In another aspect the invention provides a method of treating an autoimmune disease in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof and said antibody or fragment thereof kills at least 10-100% (such as 10, 20, 30, 40, 50, 60, 70, 80, 90, or 100%) of a population of MCF-7 cells, when incubated with said MCF-7 cells and human AB serum for 48 (such as 48, 72, or 96) hours. In one embodiment, the autoimmune disease is alopecia greata, ankylosing spondylitis, antiphospholipid syndrome, autoimmune Addison's disease, asthma, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes mellitus (e.g., type 1), eosinophilic fascites, fibromyalgia-fibromyositis, glomerulonephritis, Graves' disease, Guillain-Barre, Hashimoto's thyroiditis, Henoch-Schonlein purpura, idiopathic pulmonary fibrosis, idiopathic/autoimmune thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus-related disorders (e.g., pemphigus vulgaris), myelodysplastic syndrome, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, or Vogt-Koyanagi-Hareda syndrome. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating an autoimmune disease in a mammal comprising administering to said mammal a therapeutically effective amount of an anti-nucleolin agent and a pharmaceutically acceptable carrier; wherein said anti-nucleolin agent comprises a human anti-nucleolin antibody or fragment thereof that specifically binds to a protein of SEQ ID No. 2. In one embodiment, the autoimmune disease is alopecia greata, ankylosing spondylitis, antiphospholipid syndrome, autoimmune Addison's disease, asthma, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes mellitus (e.g., type 1), eosinophilic fascites, fibromyalgia-fibromyositis, glomerulonephritis, Graves' disease, Guillain-Barre, Hashimoto's thyroiditis, Henoch-Schonlein purpura, idiopathic pulmonary fibrosis, idiopathic/autoimmune thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus-related disorders (e.g., pemphigus vulgaris), myelodysplastic syndrome, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, or Vogt-Koyanagi-Hareda syndrome. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating an autoimmune disease in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof that specifically binds to a protein of SEQ ID No. 4. In one embodiment, the autoimmune disease is alopecia greata, ankylosing spondylitis, antiphospholipid syndrome, autoimmune Addison's disease, asthma, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, diabetes mellitus (e.g., type 1), eosinophilic fascites, fibromyalgia-fibromyositis, glomerulonephritis, Graves' disease, Guillain-Barre, Hashimoto's thyroiditis, Henoch-Schonlein purpura, idiopathic pulmonary fibrosis, idiopathic/autoimmune thrombocytopenia purpura (ITP), IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus-related disorders (e.g., pemphigus vulgaris), myelodysplastic syndrome, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosis (SLE), Sweet's syndrome, Still's disease, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, graft versus host disease, urticaria, or Vogt-Koyanagi-Hareda syndrome. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating an airway disease in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof and said antibody or fragment thereof kills at least 10-100% (10, 20, 30, 40, 50, 60, 70, 90, 100%) of a population of MCF-7 cells, when incubated with said MCF-7 cells and human AB serum for 48 (48, 72, or 96) hours. In another embodiment, the airway disease is asthma, chronic obstructive pulmonary disease, idiopathic pulmonary fibrosis, or inflammatory pneumonitis. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating an airway disease in a mammal comprising administering to said mammal a therapeutically effective amount of an anti-nucleolin agent and a pharmaceutically acceptable carrier; wherein said anti-nucleolin agent comprises a human anti-nucleolin antibody or fragment thereof that specifically binds to a protein of SEQ ID No. 2. In another embodiment, the airway disease is asthma, chronic obstructive pulmonary disease, idiopathic pulmonary fibrosis, or inflammatory pneumonitis. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating an airway disease in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof that specifically binds to a protein of SEQ ID No. 4. In another embodiment, the airway disease is asthma, chronic obstructive pulmonary disease, idiopathic pulmonary fibrosis, or inflammatory pneumonitis. In another embodiment, the mammal is a human. In another embodiment, the anti-nucleolin antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating a virally infected cell in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof and said antibody or fragment thereof kills at least 20% of a population of MCF-7 cells, when incubated with said MCF-7 cells and human AB serum for 48 hours. In another embodiment, the virally infected cell is infected with an HIV virus. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating a virally infected cell in a mammal comprising administering to said mammal a therapeutically effective amount of an anti-nucleolin agent and a pharmaceutically acceptable carrier; wherein said anti-nucleolin agent comprises a human anti-nucleolin antibody or fragment thereof that specifically binds to a protein of SEQ ID No. 2. In another embodiment, the virally infected cell is infected with an HIV virus. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating a virally infected cell in a mammal comprising administering to said mammal a therapeutically effective amount of an anti-nucleolin agent and a pharmaceutically acceptable carrier; wherein said anti-nucleolin agent comprises an anti-nucleolin antibody or fragment thereof that specifically binds to a protein of SEQ ID No. 4. In another embodiment, the virally infected cell is infected with an HIV virus. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating or preventing a non-cancerous condition or disease in a mammal characterized by increased surface expression of nucleolin, comprising administering to said mammal a therapeutically effective amount of an anti-nucleolin agent and a pharmaceutically acceptable carrier; wherein said anti-nucleolin agent comprises an anti-nucleolin antibody or fragment thereof and said antibody or fragment thereof kills at least 10-100% (such as 10, 20, 30, 40, 50, 60, 70, 80, 90, or 100%) of a population of MCF-7 cells, when incubated with said MCF-7 cells and human AB serum for 48 (48, 72, or 96) hours. In one embodiment, the condition or disease in a mammal characterized by increased surface expression of nucleolin is macular degeneration, diabetic retinopathy, or inflammatory disease. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating or preventing a non-cancerous condition or disease in a mammal characterized by increased surface expression of nucleolin, comprising administering to said mammal a therapeutically effective amount of an anti-nucleolin agent and a pharmaceutically acceptable carrier; wherein said anti-nucleolin agent comprises a human anti-nucleolin antibody or fragment thereof that specifically binds to a protein of SEQ ID No. 2. In one embodiment, the condition or disease in a mammal characterized by increased surface expression of nucleolin is macular degeneration, diabetic retinopathy, or inflammatory disease. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides a method of treating or preventing a non-cancerous condition or disease in a mammal characterized by increased surface expression of nucleolin, comprising administering to said mammal a therapeutically effective amount of an anti-nucleolin agent and a pharmaceutically acceptable carrier; wherein said anti-nucleolin agent comprises an anti-nucleolin antibody or fragment thereof that specifically binds to a protein of SEQ ID No. 4. In one embodiment, the condition or disease in a mammal characterized by increased surface expression of nucleolin is macular degeneration, diabetic retinopathy, or inflammatory disease. In another embodiment, the mammal is a human. In another embodiment, the anti-nucleolin monoclonal antibody or fragment thereof is substantially non-immunogenic to a human. In another embodiment, the anti-nucleolin antibody or fragment thereof is a human antibody or fragment thereof. In another embodiment, the anti-nucleolin antibody or fragment thereof is a monoclonal antibody or fragment thereof.

In another aspect the invention provides an anti-nucleolin agent that kills at least 50% of a population of MCF-7 cells, when incubated with said MCF-7 cells and human AB serum for 48 hours. In another embodiment, the said anti-nucleolin agent is substantially non-immunogenic to a human.

In another aspect the invention provides an anti-nucleolin agent that kills more MCF-7 cells than MCF10A cells when incubated with separate populations of MCF-7 cells and MCF10A cells and heat inactivated serum for 72 or 96 hours. In another embodiment, the said anti-nucleolin agent is substantially non-immunogenic to a human.

In another aspect the invention provides an anti-nucleolin agent that kills more MCF-7 cells than MCF10A cells when incubated with separate populations of MCF-7 cells and MCF10A cells and human AB serum for 96 hours. In another embodiment, the said anti-nucleolin agent is substantially non-immunogenic to a human.

In another aspect the invention provides an anti-nucleolin agent that specifically binds to a protein of SEQ ID No. 4 and inhibits or kills one or more cancer cells that express nucleolin on their cell surface. In another embodiment, the said anti-nucleolin agent is substantially non-immunogenic to a human.

In another aspect the invention provides a method of determining a liklihood that a subject will develop cancer by detecting increased cell surface nucleolin expression in one or more precancerous cells.

In another aspect the invention provides a antibody of any of the proceeding claims, wherein said antibody fragment is a Fab, Fab', F(ab').sub.2, or Fv fragment; diabodie; linear antibody; single-chain antibody; or a multispecific antibodt formed from an antibody fragment.

In another aspect the invention provides a method of any of the proceeding claims comprising the use of an antibody fragment, wherein said antibody fragment is a Fab, Fab', F(ab').sub.2, or Fv fragment; diabodie; linear antibody; single-chain antibody; or a multispecific antibody formed from an antibody fragment.

Example 1—Materials & Methods

Isolation and culture of tonsil B cells. To prepare B cells from tonsils, tonsil tissue was placed inside a sterile Petri dish (VWR International, cat. #25384-088) containing 20-30 ml Dulbecco's phosphate buffered saline (DPBS, without $CaCl_2$ or $MgCl_2$; Gibco/Invitrogen, Grand Island, N.Y. cat. #14190144) supplemented with 1× Antibiotic-Antimycotic (Gibco/Invitrogen cat. #15240-062). The tissue was chopped and minced with scalpels to approximately 1 $mm^3$ pieces. Additional lymphocytes were released by gentle grinding of tonsil pieces between the frosted glass surfaces of two sterile microscope slides (VWR cat. #12-550-34), and single cell preparation was made by straining through 70 μm nylon strainer (BD Falcon, cat. #352350, BD Biosciences, Two Oak Park, Bedford, Mass.). This suspension was layered onto a Ficoll (Amersham Biosciences cat. #17-1440-03, Uppsala, Sweden) cushion (35 ml sample over 15 ml Ficoll) and resolved at 1500G for 20 min. The boundary layer containing mononuclear cells was extracted, washed 2× with DPBS (1300G for 7 min), counted, and re-suspended in DPBS at $10^8$ cells/ml. A highly enriched (>95%) B-cell population was obtained with the use of StemSep Negative Selection Human B-cell Enrichment Kit antibody cocktail (cat. #14064A) and magnetic beads (cat. #19150) from StemCell Technologies Inc., Vancouver, Canada, according to manufacturer's instructions, with the following modifications for use on a "The Big Easy" EasySep magnet (StemCell Tech. cat. #18001). All steps were performed in a laminar flow biohazard hood at ambient temperature. The cell suspension was placed in a sterile round bottom 14 ml polypropylene tube (VWR cat. #60818-689), mixed with an equal volume of the StemSep Negative Selection Human B-cell Enrichment Kit antibody cocktail, and incubated for 10 minutes. Then, a volume of magnetic bead suspension equal to the antibody cocktail volume was added, followed by 10 minute incubation. The volume inside the tube was brought to 10 ml with DPBS and the tube (minus the cap) was placed inside the magnet for 10 minutes, at which time the contents of the tube (still inside the magnet) were gently decanted in a single pour into a second sterile 14 ml tube. The original tube with non-B cells adhering to its walls was removed from the magnet, and the second tube was inserted for 10 minute clean-up incubation. The enriched B-cell suspension obtained after the first and second negative selection steps was poured into a 15 ml Falcon tube, counted, washed with DPBS (1300G for 7 min) and resuspended in an appropriate volume of complete RPMI media for in vitro culture (generally $10^5$ to $10^6$ cells/ml) in a 37° C., 5% $CO_2$ tissue culture incubator. Complete RPMI media contains RPMI 1640 (Gibco/Invitrogen cat. #11875-093) supplemented with 10% fetal bovine serum (FBS, HyClone cat. #SH30088.03, lot. #AQC23460, Logan, Utah), and 100 U/ml Penicillin, 100 μg/ml Streptomycin (cat. #15140-122), 2 mM L-Glutamine (cat. #25030-081), 1 mM Sodium Pyruvate (cat. #11360-070), 10 mM HEPES (cat. #15630-080), 0.1% 2-mercaptoethanol (cat. #21985.023), and 0.1% Falk's Cloning Cocktail, which consists of 50 mM α-thioglycerol (Sigma, cat.# M6145), 20 μM bathocuproinedisulfonic acid (Sigma, cat. #B1125), 100 mM Na pyruvate (cat. #11360-070), 1M HEPES pH 7.4 (cat. #15630-080). L-glutamine, Sodium Pyruvate, Penicillin/Streptomycin and HEPES were obtained from Gibco/Invitrogen. Alternatively, cells were resuspended in complete RPMI media at $10^8$ cells/ml for spinfection with concentrated Epstein-Barr virus stocks to make immortalized tonsil B cell libraries as described below.

Isolation and Culture of Peripheral Blood B Cells.

To prepare B cells from peripheral blood, venous blood (up to 180 ml) was drawn into 60 ml syringes containing 1-5 ml citric acid or heparin sulfate, which prevent coagulation, diluted with equal volume of DPBS, layered onto a Ficoll cushion (35 ml of diluted sample over 15 ml Ficoll) and resolved at 2000 rpm for 20 min. Serum (from upper layer) was collected and stored in aliquots. The boundary layer containing mononuclear cells was extracted, washed 2× with DPBS (1300G for 7 min), counted, and re-suspended in DPBS at $10^8$ cells/ml. Highly pure populations of B-cells were obtained with the use of StemSep Negative Human B-cell Enrichment Kit (StemCell Technologies Inc.) as described above for isolation of tonsil B-cells. Isolated B-cells were washed (1300G for 7 min) and re-suspended at $10^5$-$10^6$ cells per ml of complete RPMI media (described above), and cultured in a 37° C., 5% $CO_2$ tissue culture incubator. Alternatively, cells were resuspended in complete RPMI media at $10^8$ cells/ml for spinfection with concentrated Epstein-Barr virus stocks to make immortalized peripheral blood B cell libraries as described below.

EBV Stock Preparation.

To prepare infectious Epstein-Barr virus (EBV) stocks, B95-8 cells, a marmoset lymphoblastoid cell line (LCL) chronically-infected with B95-8 strain EBV (Miller & Lipman, 1973), or EBfaV-GFP cells (Speck et al., 1999; described below), were cultured in complete RPMI media (described above) at a cell density of approximately $10^5$-2×$10^5$ cells/ml, in a 37° C., 5% $CO_2$ tissue culture incubator.

Approximately 140 ml of cell culture (containing either B95-8 EBV or recombinant EBfaV-GFP) was induced to enter lytic virus production phase by treatment with phorbol myristate acetate (PMA, 10 ng/ml, Calbiochem, cat. #524400). After a four hour incubation with PMA, the PMA was removed from the culture supernatant and replaced with complete RPMI media. The cells were cultured for 3 to 4 days until highly confluent, at which point cells were removed by centrifugation (1300G for 7 min), and culture supernatant was filtered through 150 ml Nalgene 0.45 μm vacuum filter (Corning cat. #430320) to remove cell debris. Filtered supernatant was either flash-frozen in liquid nitrogen in 1 ml-1.8 ml aliquots for storage at −80° C. in 1.5 ml Eppendorf tubes or 2 ml cryovials, or concentrated by ultrafiltration as described below.

EBV Concentration.

Viral concentration was performed by loading the filtered virus supernatant (140 ml) into two Centricon Plus-70 (100K MW cut-off) units (Millipore, Billerica, Mass.), which have a 70 ml capacity, or by sequentially loading 60 ml of viral supernatant onto a single JumboSep 300K unit (Pall Corp., Ann Arbor, Mich.), which has a 60 ml capacity and was loaded three times to concentrate up to 150 ml of filtered virus stock. All steps were performed on ice or at 4° C. according to manufacturers' instructions. The Centricon filter units were centrifuged (2000G) for between 15 and 45 minutes (monitored each 15 minutes), until the minimal retentate volume (approximately 0.5 ml per filtration unit) was achieved. The filtrate was discarded, and virus-containing concentrates were re-suspended with complete RPMI media up to a total volume of 14 ml (or 1/10 of the original culture supernatant volume). The JumboSep units were centrifuged at 3000G, and yielded about 15 ml of retentate or 10× concentrated virus stocks. One ml-1.8 ml aliquots of concentrated virus stocks were transferred into cryovials, flash-frozen in liquid nitrogen, and transferred to −80° C. freezer for storage.

B Cell Infection by Inoculation.

B cells were resuspended at $10^6$ to $10^7$ cells/ml in complete RPM' media, and were mixed with an equal volume or up to 2 volumes of filtered EBV supernatant, then placed in a T-25 flask and incubated for 4-6 hours in a tissue culture incubator at 37° C. and 5% $CO_2$. The culture volume was then adjusted by the addition of complete RPMI media, such that infected cells were resuspended for cell culture at the desired concentration (generally $10^5$ to $10^6$ cells per ml), dispensed into multi-well plates and transferred to a tissue culture incubator at 37° C. and 5% $CO_2$.

B Cell Infection by Spinfection with Concentrated EBV Stocks.

B cells were resuspended at $10^6$ to $10^7$ cells/ml in complete RPMI media, and were mixed with an equal volume or up to two volumes of 10× concentrated EBV, or were resuspended directly in 10× concentrated EBV stocks at $2\times10^6$ up to $2\times10^7$ cells per ml, and placed in wells of a 6-well tissue culture plate (Greiner bio-one, cat. #65760). (Concentration of EBV stocks more than 10× resulted in decreased infection efficiencies.) The plate was then centrifuged at 900G for 1-2 hours at ambient temperature, at which time infected cells were re-suspended in complete RPMI media, or complete RPMI media containing cytokines and signaling agents for induction of differentiation, at a desired concentration (generally $10^5$ to $10^6$ cells per ml). Infected cells were dispensed into multi-well plates and transferred to a tissue culture incubator at 37° C. and 5% $CO_2$. For generation of immortalized B cell libraries, generally ~$10^7$ cells were resuspended in 200 ml of media containing cytokines and signaling agents, and plated into ten round bottom 96-well plates (~$10^4$ cells per 200 μL per well).

Infection in the Presence of TLR Ligands.

B cells were infected with B95-8 strain EBV as described above, with the addition of Toll-Like Receptor (TLR) ligands at the time of the infection. The ligands were added at the following final concentrations: lipoprotein Pam3CSK4 (0.5 μg/ml), zymosan (1 μg/ml), polyinosine, polycitadylic acid (poly I:C) (25 μg/ml), lipopolysaccharide (LPS) (5 μg/ml), Imiquimod (1 μg/ml), unmethylated CpG DNA (1 μg/ml). All TLR ligands (from InVivoGen Inc) were generously donated by Dr. Mohamed Salem (MUSC).

Evaluation of B Cell Immortalization Efficiency by Lymphoblastoid Cell Outgrowth.

At 12 hours post-infection, B cells were counted and dispensed into wells of 96-well round bottom plates (Greiner cat#650180) as a 2-fold dilution series, with each consecutive row of wells containing half the number of cells found in the previous row. The initial rows contained 50,000 cells per well, and final rows in the dilution series contained 24 cells per well. Cells were incubated for 9 days in a tissue culture incubator at 37° C. and 5% $CO_2$, at which point lymphoblastoid cell outgrowth was visible by microscopy. Immortalization efficiency was estimated based upon the assumption that lymphoblastoid cell proliferation resulted from EBV immortalization of at least one B cell in the well. Thus, the efficiency was calculated from rows containing wells with the lowest number of cells per well in which lymphoblastoid cell proliferation was consistently observed by microscopy, and expressed as 1 immortalization event per number of cells originally dispensed into the well.

Flow Cytometry analysis was performed using a Becton Dickinson FACSCalibur instrument at the MUSC Flow Cytometry Facility, according to established methods. Infection efficiency of B cells infected with EBfaV-GFP was assessed by measuring fluorescence of Green Fluorescent Protein 24 h post-infection. Antibodies used to characterize human B cells were obtained from BD Biosciences and are specific for human CD20, CD19, CD23, CD27, CD30, CD38, IgD, IgM, and IgG.

Induction of B Cell Differentiation and IgG Secretion.

To determine their effect on B cell differentiation during the immortalization process, cytokines and other signaling agents were added to EBV infected B cells either immediately after infection, or 16 to 20 hours after infection, and twice more at weekly intervals. All agents were diluted in complete RPMI media and added to cells at the following final concentrations: recombinant human interleukins (IL) IL-4, 0.2 ng/ml; IL-5, 0.2 ng/ml; IL-6, 0.1 ng/ml; IL-9, 0.2 ng/ml; IL-10, 2.4 ng/ml; IL-13, 1 ng/ml; recombinant human interferon-α (IFN-α2a), 2,000 IU/ml; recombinant human BAFF, 1 ng/ml; recombinant human soluble CD40L, 5 ng/ml; goat anti-human IgM $(Fab')_2$, 1.4 μg/ml. IL-4 (cat. #200-04), IL-5 (cat. #200-05), IL-6 (cat. #200-06), IL-9 (cat. #200-09), IL-10 (cat. #200-10), IL-13 (cat. #200-13), CD40L (cat. #310-02) and BAFF (cat. #310-13) were obtained from PeproTech (Rocky Hill, N.J.). IFN-α2a (Roferon®-A) was from Roche Pharmaceuticals, and goat anti-human IgM $(Fab')_2$ (cat. #109-006-129) was from Jackson Immune Research Laboratories Inc.

Creation of Immortalized B Cell Repertoires Used in Nucleolin Binding studies.

Tonsil or peripheral blood B cells were infected by spinfection with 10× concentrated B95-8 virus as described above. Immediately following spinfection, cells were resuspended in complete RPMI media to which CD40L (5 ng/mL), BAFF (1 ng/ml), and goat anti-human IgM $(Fab')_2$ (1.4 μg/ml) (for twelve samples) were added. Generally tonsil libraries consisted of ~$10^7$ infected B cells that were resuspended in 200 ml of media containing the cytokines and signaling agents cocktail, and plated into ten round bottom 96-well plates (~$10^4$ cells per 200 μL per well). Peripheral blood libraries were resuspended at $10^6$ B cells per 20 ml media plus cocktail, and were plated into round bottom 96-well plates at ~$10^4$ cells per 200 μL per well.

Measurement of Human Immunoglobulin IgM and IgG Production by ELISA.

Culture supernatants were collected at various time points beginning 5 days after infection and stored frozen at −20° C. until quantitative assay by capture ELISA for IgM and IgG. Costar EIA/RIA 96-well plates were coated with goat anti-human IgG UNLB or anti-human IgM UNLB (Southern Biotech) at 2 μg/ml in 0.05M carbonate-bicarbonate buffer, pH 9.6, using 100 μL/well. Covered plates are incubated overnight at 4° C. Next day, plates are washed 4 times with 1×PBS/0.05% Tween-20 (200 μl/well), and blocked with 1×PBS/1% BSA (300 μl/well) for 1 hr at room temperature with shaking at 450 rpm. Plates are then washed 2 times with 1×PBS/0.05% Tween-20 (350 μl/well), and samples and standards (human IgG and human IgM standards (Sigma) are diluted in 1×PBS/1% BSA and applied to plates (100 μl/well). A 10-point standard curve with 2-fold dilutions ranging from 3.9 ng/mL to 1000 ng/mL, and media only is created. Plates are then incubated for 1 hour at room temperature, with shaking at 450 rpm. After washing, plates are washed 4 times with 200 μl/well of 1×PBS/0.05% Tween-20, and detection antibody is then added (goat anti-human IgG or IgM AP-conjugate (Southern Biotech #2040-04 or 2020-04) diluted 1:4000 in 1×PBS/1% BSA (100 μl/well). Plates are incubated for 1 hour at room temperature, with shaking at 450 rpm. After washing, AP conversion of colorimetric substrate p-nitrophenyl phosphate disodium salt (PNPP, Peirce cat #37620) was detected by measuring absorbance at $OD_{405}$ using a Multiskan Spectrum plate reader (ThermoLabsystems). Levels of human immunoglobulin in culture supernatant samples were calculated following standard curve calibration of purified human IgG and IgM standards using MultiSkan software.

Nucleolin Binding ELISA.

Screening by ELISA for recombinant nucleolin binding was performed by coating plates overnight at 4° C. with recombinant nucleolin (0.5-2 μg/ml) in 1× Dulbeccos PBS Ca/Mg-free. Next day, plates are washed 3 times with 1×PBS/0.05% Tween-20 (300 μL per well) and blocked with 1× SuperBlock protein (Thermo Scientific #37545) in 2.5 mM Tris, 0.15 M NaCl, pH 7.4, for 1 h at room temperature with shaking at 450 rpm. After washing, primary antibody is added, consisting of either control mouse anti-nucleolin MS-3 MAb (Santa Cruz Biotechnology, Inc. #sc-8031) diluted 1:100 in blocking buffer, or B cell culture supernatants containing anti-nucleolin antibodies (neat, 100 μL/well). After 2 h incubation at room temperature with shaking at 450 rpm, plates are washed and detection antibody is added, consisting of either goat anti-human IgG-HRP MAb (Southern Biotech, #2040-05) used at 1:5000 dilution in blocking buffer for culture supernatants, or for MS3 goat anti-mouse IgG-HRP MAb (Santa Cruz Biotechnology, Inc. #sc-2055) used at 1:2000 dilution in blocking buffer for detection of control mouse MS3 MAb. Plates were developed using TMB+ chromagen (Dako, Denmark S1599) used at 100 μL/well, and quantified by spectrophotometry at absorbance $OD_{450}$.

Production and Isolation of Recombinant Human Nucleolin Protein.

*E. coli* was transformed with a recombinant pET21a plasmid carrying a truncated nucleolin gene encoding residues 284-707 and six histidines [pET Δ1-283 Nuc-$(His)_6$] (Yang et al., 2002), and lysed by sonication. Recombinant human nucleolin was produced and purified as described previously (Sengupta et al., 2004). Briefly, *E. coli* were cultured until A600=0.6, then induced overnight with 0.4 mM isopropyl-1-thio-β-D-galactopyranoside at 30° C. After induction, cell pellets were resuspended in buffer A (20 mM sodium phosphate buffer, pH 7.4, 500 mM NaCl, 10 mM imidazole, 1 mM phenylmethylsulfonyl fluoride) and lysed by sonication. The lysate was centrifuged at 12,000 g for 30 min. The supernatant was loaded onto a 1.7 ml metal chelate (POROS MC-M) column (BioCAD SPRINT perfusion chromatography system) equilibrated and washed with buffer A, then eluted with a linear gradient of 0-200 mM imidazole in buffer C. The imidazole was removed by dialysis, and the protein concentrated in a Microcon concentrator. The protein concentration was measured by Bradford assay, and protein purity was assessed by SDS-PAGE analysis.

Isolation of Endogenous Nucleolin from MV4-11 Cells.

A human nucleolin affinity column was created by coupling mouse anti-human nucleolin MAb MS-3 (Santa Cruz) to Ultralink Biosupport medium (Pierce) according to the manufacturer's instructions. Briefly, 1 mg of MS-3 MAb was dialyzed against 0.1 M carbonate buffer, pH 9.0, and sodium citrate was added to a final concentration of 0.6 M. Dry beads (0.25 g) were added and mixed for 2 h at RT, poured into a column and washed with PBS. The eluate and washings were collected to determine the coupling efficiency, which is typically ~94%. Six ml of 3 M ethanolamine, pH 9.0, was added to the column to block residual binding sites, and then the column was closed at both ends and mixed end-over-end for 2.5 h at RT. The column was then washed sequentially with PBS, 1 M NaCl, then PBS, and the MV4-11 cell extract was loaded. To make the cell extract, MV4-11 cells were washed with PBS, pelleted and resuspended in lysis buffer containing protease and phosphatase inhibitors and incubated for 15 min on ice. The lysate was centrifuged at 10,000 g for 20 min and the supernatant loaded onto the MS-3 MAb-affinity column. The column was washed with 20 volumes of Tris-buffer (pH 7.5) and the bound proteins eluted with antigen/antibody elution buffer (Pierce). One ml fractions were collected and desalted using PD10 columns. The protein fraction was concentrated and analyzed by SDS-page followed by silver staining and western blotting with MS-3 anti-nucleolin MAb.

Clone 5D1.

Initial Screening and Primary Subcloning.

Tonsil sample was received processed into 5×96-well plates: repertoire (T031009). Plate pools were screened for plate pools and well pools (well pools for P031109 and T031009 combined). Putative positive wells (T031009-5D1 and -5G5, P030909-3D1 and -3G5) were expanded from 1 well into 3 wells each. ELISA confirmation was conducted, identifying reactive wells (T031009-5D1 and P031109-3G5). The wells were subcloned into 1 plate of 1000 cells/well and 2 plates of 100 cells/well.

Secondary Subcloning.

The 3 subclone plates (1×1000 cells/well and 2×100 cells/well) were screened as a single plate pool without reactivity, and rescreened. Reactive wells were confirmed. T031009-5D1 wells 1E7 and 1G7 had the highest reactivity and were each subcloned into 60 wells on individual 96-well plates.

Tertiary Subcloning.

The 2 subclone plates (T031009-5D1-1E7 and T031009-5D1-1G7) were screened as a single plate pool three times, without reactivity; however the positive control mouse monoclonal antibody (MS-3) was also non-reactive indicating that the nucleolin antigen had degraded, and unfortunately there was none remaining for further screening. Plates were split twice with the excess cells separately pooled and outgrown and aliquots were frozen. The plate pools and outgrown replicate pools were retested against new stocks of non-degraded nucleolin. Wells 1C11 and 1G2 (both from T031009-5D1-1G7) were weakly reactive, and selected for subcloning.

Quaternary Subcloning.

The 2 subclone plates were screened 2 weeks later as a plate pool without reactivity, and were rescreened one week later showing weak reactivity in multiple wells. Individual wells were screened, and T031009-5D1-1G7 wells 1F10 and 1G2 had the highest reactivity and were each subcloned into 60 wells on individual 96-well plates.

$5^{th}$ Round Subcloning.

The subclone plates were screened 2 weeks later as single column pools with very weak reactivity in 1 and 2 wells each, and were rescreened a week later, and the full plate pool was rescreened 2 days after that with individual wells confirmed 2 days later. T031009-5D1-1G7-1F10 well 1D10 had the highest reactivity and was subcloned into 60 wells on a single 96-well plate.

$6^{th}$ Round Subcloning.

The subclone plate was screened 16 days later as an individual column pool with 3 reactive wells. Screening of the full plate was done 4 days later and T031009-5D1-1G7-

1F10-1D10 well 1B4 had the highest reactivity and was subcloned 2 days later into 60 wells on a single 96-well plate.

7th Round Subcloning.

The subclone plate was screened 17 days later as an individual column pool without reactivity, and rescreened 10 days later with moderate reactivity in 4 wells and weak reactivity in the other 2 wells. Screening of the entire plate was done 2 days later and T031009-5D1-1G7-1F10-1D10-1B4 well 1C7 had the highest reactivity and was subcloned into 60 wells on a single 96-well plate 2 days later. The remainder of the reactive wells was pooled, expanded and frozen at −80° C. (T031009-5D1-1G7-1F10-1D10-1B4).

8th Round Subcloning.

Three weeks later, the subclone plate was screened as an individual column pool with all 6 wells moderately reactive. Screening of the entire plate was done with many strongly or moderately reactive wells. T031009-5D1-1G7-1F10-1D10-1B4-1C7 well 1G10 had the highest reactivity and was subcloned into 60 wells on a single 96-well plate. The remainder of the reactive wells was pooled. Eleven days later, the subcloned plates showed evidence of fungal contamination and were discarded. Reactive cells from the pooled remainder (T031009-5D1-1G7-1F10-1D10-1B4-1C7) were expanded and 4 days later subcloned into ten 96-well plates. Two weeks later these subclone plates were screened, and T031009-5D1-1G7-1F10-1D10-1B4-1C7 wells 8B9 and 8E10 had the highest nucleolin reactivity and were subcloned the next day into 60 wells each on single 96-well plates. Nine days later, the subcloned plates again showed evidence of fungal contamination and were discarded. Frozen pooled T031009-5D1-1G7-1F10-1D10-1B4 cells were thawed and expanded, and ten days later, subcloned into five 96-well plates. Two weeks later, the plates were screened for nucleolin reactivity, and T031009-5D1-1G7-1F10-1D10-1B4 wells 2E3 and 4C9 were confirmed positive on the following day, and were subcloned into 60 wells each on single 96-well plates. Ten days later, the plates were screened for nucleolin reactivity, and T031009-5D1-1G7-1F10-1D10-1B4-2E3 wells 2D10 and 2G5 had the highest reactivity, and were subcloned the next day into 60 wells each on single 96-well plates.

9th Round Subcloning.

Seventeen days later, the subclone plates were screened for nucleolin reactivity, and T031009-5D1-1G7-1F10-1D10-1B4-2E3-2D10 well 1F7 had the highest nucleolin reactivity, and was subcloned the next day by limiting dilution cloning into ten 96-well plates. Clonal colonies appeared slowly over time, and were screened for nucleolin reactivity between weeks 4 and 6. Three wells (6G10, 2F8, 6B3) had reactivity. Clone T031009-5D1-1G7-1F10-1D10-1B4-2E3-2D10-1F7-6B3 was expanded for functional antibody testing because of its superior growth properties.

Clone 3H11.

Initial Screening and Primary Subcloning.

Volunteer peripheral blood sample received, processed into 5×96-well plates: repertoire (P031109). Screened for plate pools and well pools (well pools for P031109 and T031009 combined). Putative positive wells (T031009-5D1 and -5G5, P031109-3D1 and -3G5) were expanded from 1 well into 3 wells each and P031109-3G5 was identified as the reactive well. It was subcloned into 1 plate of 500 cells/well and 2 plates of 50 cells/well.

Secondary Subcloning.

The 3 subclone plates (1×500 cell/well and 2×50 cell/well) were screened for reactivity as a single plate pool without reactivity. Plate pool was rescreened. Reactive wells were confirmed and P031109-3G5 wells 1D9 and 1D11 had the highest reactivity and each were subcloned into 60 wells on single 96-well plates.

Tertiary Subcloning, Loss and Recovery.

The 2 subclone plates (P031109-3G5-1D9 and P031109-3G5-1D11) were screened as a single plate pool twice without reactivity; however, the positive control mouse monoclonal antibody (MS-3) was also non-reactive suggesting that the nucleolin antigen had degraded, and unfortunately there was none remaining for further screening. Plates were split twice with the excess cells separately pooled and outgrown, and aliquots were frozen. The plate pools and outgrown replicate pools were tested against new stocks of non-degraded nucleolin. The original subclone plates lost reactivity while the outgrown replicate supernatants tested positive. These cells expanded from P031109-3G5-1D9 were subcloned into 10×96-well plates and cultured.

Quaternary Subcloning.

The 10 subclone plates (P031109-3G5-1D9) were screened as a single plate pool, which was poorly reactive. The plate pool supernatant was re-screened with weak reactivity. Individual wells were tested. P031109-3G5-1D9 well 3H11 had the highest reactivity and was subcloned into 60 wells on a single 96-well plate.

5th Round Subcloning.

The subclone plate was screened as a single column pool without any reactivity, and rescreened with 2 positive wells. Screening of the full plate was done. P031109-3G5-1D9-3H11 well 1F8 had the highest reactivity and was subcloned into 60 wells on a single 96-well plate.

6th Round Subcloning.

The subclone plate was screened as an individual column pool with 4 wells indicating reactivity. Screening of the full plate was done and P031109-3G5-1D9-3H11-1F8 well 1C7 had the highest reactivity and was subcloned into 60 wells on a single 96-well plate.

7th Round Subcloning.

The subclone plate was screened as a column pool with weak reactivity in 2 wells. Rescreening was done with moderate reactivity in 5 wells. Screening of the entire plate was done and P031109-3G5-1D9-3H11-1F8-1C7 well 1F8 had the highest reactivity and was subcloned into 60 wells on a single 96-well plate. The remainder of the reactive wells was pooled, expanded and frozen at −80° C. (P031109-3G5-1D9-3H11-1F8-1C7).

8th Round Subcloning.

The subclone plate was screened as an individual column pool with 2 highly reactive and 4 moderately reactive wells. Screening of the entire plate was done with multiple strongly reactive wells. P031109-3G5-1D9-3H11-1F8-1C7-1F8 well 1C3 had the highest reactivity and was subcloned into 60 wells on a single 96-well plate. The remainder of the reactive wells was pooled. Eleven days later, the subcloned plates showed evidence of fungal contamination and were discarded. Reactive cells from the pooled remainder (P031109-3G5-1D9-3H11-1F8-1C7-1F8) were expanded and 7 days later subcloned into ten 96-well plates. Two weeks later these subclone plates were screened, and P031109-3G5-1D9-3H11-1F8-1C7-1F8 wells 8B9 and 8E10 had the highest nucleolin reactivity and were subcloned the next day into 60 wells each on single 96-well plates. Nine days later, the subcloned plates again showed evidence of fungal contamination and were discarded. Frozen pooled P031109-3G5-1D9-3H11-1F8-1C7 cells were thawed and expanded, and ten days later, subcloned into five 96-well plates. Two weeks later, the plates were screened for nucleolin reactivity, and P031109-3G5-1D9-3H11-1F8-1C7 wells 2D2 and 2G9 were confirmed positive on the following day, and were subcloned into 60 wells each on single 96-well plates. Ten days later, the plates were screened for nucleolin reactivity, and P031109-3G5-1D9-3H11-1F8-1C7-2G9 wells 2E4 and 2G3 had the highest reactivity, and were subcloned the next day into 60 wells each on single 96-well plates.

9$^{th}$ Round Subcloning.

Seventeen days later, the subclone plates were screened for nucleolin reactivity, and P031109-3G5-1D9-3H11-1F8-1C7-2G9-2E4 well 1B9 had the highest nucleolin reactivity, and was subcloned the next day by limiting dilution cloning into ten 96-well plates. Clonal colonies appeared slowly over time, and were screened for nucleolin reactivity between weeks 4 and 6. Four wells (8D2, 3F3, 2C6, 9B7) had reactivity. Clone P031109-3G5-1D9-3H11-1F8-1C7-2G9-2E4-1B9-2C6 was expanded for functional antibody testing because of its superior growth properties.

Clone 2D3.

Initial Screening and Primary Subcloning.

Tonsil sample received and processed into 10×96-well plates: repertoire (T031609A). Eleven days later these were screened for plate pools and well pools. ELISA confirmation was conducted 3 days later, and reactive well (T031609A-2D3) was identified and subcloned into 1 plate of 1000 cells/well and 2 plates of 100 cells/well 2 days later.

Secondary Subcloning.

The 3 subclone plates (1×1000 cells/well and 2×100 cells/well) were screened as a single plate pool without reactivity, and rescreened again 1 week later. Reactive wells were confirmed. T031609A-2D3 wells 1C7 and 1E3 had the highest reactivity and were each subcloned into 60 wells on individual 96-well plates.

Tertiary Subcloning.

The 2 subcloned plates (T031609A-2D3-1C7 and T031609A-2D3-1E3) were screened as a single plate pool, and repeated without reactivity; however, the positive control mouse monoclonal antibody (MS-3) was also non-reactive, indicating that the nucleolin antigen was degraded, and unfortunately there was none remaining for further screening. Plates were split twice with the excess cells separately pooled and outgrown and aliquots frozen. The plates and outgrown replicate pools were tested against new stocks of non-degraded nucleolin. Reactive well 1F4 (from T031609A-2D3-1C7) was selected and subcloned.

Quaternary Subcloning.

The subclone supernatants (T031609A-2D3-1C7-1F4) were screened without reactivity, and rescreened with weak reactivity. Wells 1B11 and 1F3 had the highest reactivity and were selected for subcloning. Each well was subcloned into 60 wells on individual 96-well plates.

5$^{th}$ Round Subcloning.

The subclone plates were screened as single column pools without reactivity, and rescreened, with plate pools rescreened, and confirmation done. Well 1C9 from plate T031609A-2D3-1C7-1F4-1B11 had the highest reactivity and was subcloned into 60 wells on a single 96-well plate.

6$^{th}$ Round Subcloning.

The subclone plate was screened as an individual column pool with 3 wells indicating reactivity. Screening of the full plate was done. T031609A-2D3-1C7-1F4-1B11-1C9 well 1G6 had the highest reactivity and was subcloned into 60 wells on a single 96-well plate.

7$^{th}$ Round Subcloning.

The subclone plate was screened as an individual column pool with weak reactivity in 1 well. Rescreening was done with moderate reactivity in two wells. Screening of the entire plate was done and T031609A-2D3-1C7-1F4-1B11-1C9-1G6 well 1E10 had the highest reactivity and was subcloned into 60 wells on a single 96-well plate. The remainder of the reactive wells was pooled, expanded and frozen at −80° C. (T031609A-2D3-1C7-1F4-1B11-1C9-1G6).

8$^{th}$ Round Subcloning.

The subclone plate was screened as an individual column pool with 4 reactive wells. Screening of the entire plate was done with moderate reactivity. T031609A-2D3-1C7-1F4-1B11-1C9-1G6-1E10 well 1F3 had the highest reactivity and was subcloned into 60 wells on a single 96-well plate. The remainder of the reactive wells was pooled. Eleven days later, the subcloned plates showed evidence of fungal contamination and were discarded. Reactive cells from the pooled remainder (T031609A-2D3-1C7-1F4-1B11-1C9-1G6-1E10) were expanded and 7 days later subcloned into ten 96-well plates. Two weeks later these subclone plates were screened, and T031609A-2D3-1C7-1F4-1B11-1C9-1G6-1E10 wells 10F7 and 10G7 had the highest nucleolin reactivity and were subcloned the next day into 60 wells each on single 96-well plates. Nine days later, the subcloned plates again showed evidence of fungal contamination and were discarded. Frozen pooled T031609A-2D3-1C7-1F4-1B11-1C9-1G6 cells were thawed and expanded, and ten days later, subcloned into five 96-well plates. Two weeks later, the plates were screened for nucleolin reactivity, and T031609A-2D3-1C7-1F4-1B11-1C9-1G6 wells 1B6 and 5F4 were confirmed positive on the following day, and were subcloned into 60 wells each on single 96-well plates. Ten days later, the plates were screened for nucleolin reactivity, and T031609A-2D3-1C7-1F4-1B11-1C9-1G6-5F4 wells 2F10 and 2G6 had the highest reactivity, and were subcloned the next day into 60 wells each on single 96-well plates.

9$^{th}$ Round Subcloning.

Seventeen days later, the subclone plates were screened for nucleolin reactivity, and T031609A-2D3-1C7-1F4-1B11-1C9-1G6-5F4-2F10 well 1D8 had the highest nucleolin reactivity, and was subcloned the next day by limiting dilution cloning into ten 96-well plates. Clonal colonies appeared slowly over time, and were screened for nucleolin reactivity between weeks 4 and 6. Three wells (9D7, 2A12, 3E4) had reactivity. Clone T031609A-2D3-1C7-1F4-1B11-1C9-1G6-5F4-2F10-1D8-2A12 was expanded for functional antibody testing because of its superior growth properties.

Clone 7G7.

Initial Screening and Primary Subcloning.

Tonsil sample received and processed into 10×96-well plates: repertoire (T031609B). These were screened for plate pools and well pools. ELISA confirmation was conducted, identifying reactive well T031609B-1H9, which was subcloned into 3 plates (1 plate of 1000 cells/well and 2 plates of 100 cells/well).

Secondary Subcloning.

The 3 subclone plates (1×1000 cell/well and 2×100 cell/well) were screened as a single plate pool without reactivity, and rescreened later. Reactive wells were confirmed. T031609B-1H9 wells 1G2 and 1G9 had the highest reactivity and were each subcloned into 60 wells on individual 96-well plates.

Tertiary Subclones Loss and Recovery.

The 2 subclone plates (T031609B-1H9-1G2 and T031609B-1H9-1G9) were screened as a single plate pool three times without reactivity; however, the positive control mouse monoclonal antibody (MS-3) was also non-reactive indicating that the nucleolin antigen had degraded, and unfortunately there was none remaining for further screening. Plates were split twice with the excess cells separately pooled and outgrown and aliquots were frozen. The plate pools and outgrown replicate pools were tested against new stocks of non-degraded nucleolin, but were non-reactive. Frozen aliquots from T031609B-1H9-1G2 were thawed on Jun. 3, 2009, and plated into 10×96-well plates for reculture.

Quaternary Subcloning.

The 10 subclone plates (T031609B-1H9-1G2) were screened as a column pool without reactivity. Supernatants from the 10 pooled plates were rescreened with weak reactivity. Individual wells were tested. T031609B-1H9-1G2 well 7G7 had the highest reactivity and was subcloned into 60 wells on a single 96-well plate.

$5^{th}$ Round Subcloning.

The subclone plate was screened as a single column pool without any reactivity, and rescreened later with 1 reactive well. The full plate pool was rescreened, and T031609B-1H9-1G2-7G7 well 1B9 had the highest reactivity and was subcloned into 60 wells on a single 96-well plate.

$6^{th}$ Round Subcloning.

The subclone plate was screened as an individual column pool with 2 reactive wells. Screening of the full plate was done and T031609B-1H9-1G2-7G7-1B9 well 1D6 had the highest reactivity and was subcloned into 60 wells on a single 96-well plate.

$7^{th}$ Round Subcloning.

The subclone plate was screened as a column pool with weak reactivity in 4 wells, and rescreened on with moderate reactivity in 4 wells. Screening of the entire plate was done and T031609B-1H9-1G2-7G7-1B9-1D6 well 1E3 had the highest reactivity and was subcloned into 60 wells on a single 96-well plate. The remainder of the reactive wells was pooled, expanded and frozen at −80° C. (T031609B-1H9-1G2-7G7-1B9-1D6).

$8^{th}$ Round Subcloning.

The subclone plate was screened as an individual column pool with 5 moderately reactive wells. Screening of the entire plate was done with multiple moderately reactivity. T031609B-1H9-1G2-7G7-1B9-1D6-1E3 well 1D9 had the highest reactivity and was subcloned into 60 wells on a single 96-well plate. The remainder of the reactive wells was pooled. Eleven days later, the subcloned plates showed evidence of fungal contamination and were discarded. Reactive cells from the pooled remainder (T031609B-1H9-1G2-7G7-1B9-1D6-1E3) were expanded and 7 days later subcloned into ten 96-well plates. Two weeks later these subclone plates were screened, and T031609B-1H9-1G2-7G7-1B9-1D6-1E3 wells 3G10 and 3G11 had the highest nucleolin reactivity and were subcloned the next day into 60 wells each on single 96-well plates. Nine days later, the subcloned plates again showed evidence of fungal contamination and were discarded. Frozen pooled T031609B-1H9-1G2-7G7-1B9-1D6 cells were thawed and expanded, and ten days later, subcloned into five 96-well plates. Two weeks later, the plates were screened for nucleolin reactivity, and T031609B-1H9-1G2-7G7-1B9-1D6 wells 3D9 and 4B7 were confirmed positive on the following day, and were subcloned into 60 wells each on single 96-well plates. Ten days later, the plates were screened for nucleolin reactivity, and T031609B-1H9-1G2-7G7-1B9-1D6-4B7 wells 2C10 and 2F11 had the highest reactivity, and were subcloned the next day into 60 wells each on single 96-well plates.

$9^{th}$ Round Subcloning.

Seventeen days later, the subclone plates were screened for nucleolin reactivity, and T031609B-1H9-1G2-7G7-1B9-1D6-4B7-2F11 well 2E6 had the highest nucleolin reactivity, and was subcloned the next day by limiting dilution cloning into ten 96-well plates. Clonal colonies appeared slowly over time, and were screened for nucleolin reactivity between weeks 4 and 6. Four wells (2B9, 7F2, 1C4, 10G11) had reactivity. Clone T031609B-1H9-1G2-7G7-1B9-1D6-4B7-2F11-2E6-7F2 was expanded for functional antibody testing because of its superior growth properties.

Clone 2H3.

Initial Screening and Primary Subcloning.

2 tonsil samples were received, pooled and processed into a single repertoire consisting of 10×96-well plates (T060809). This was screened 10 days later for plate pools and well pools. ELISA confirmation screening was conducted the next day and reactive well T060809-2H3 was identified and subcloned 3 days later into 60 wells of a single plate.

Secondary Subcloning.

The subclone plate was screened as a single column pool without substantial reactivity, and column pools were rescreened, with the full plate rescreened. T060809-2H3 wells 1B8 and 1E7 had the highest reactivity and were each subcloned into 60 wells on individual 96-well plates.

Tertiary Subcloning.

The subclone plates were screened as individual column pools with multiple wells indicating reactivity. Screening of full plates was done. Reactive wells T060809-2H3-1B8 1C10 and T060809-2H3-1E7 1F5 had the highest reactivity and were each subcloned into 60 wells on individual 96-well plates.

Quaternary Subcloning.

The subclone plates were screened as individual column pools with multiple reactive wells for T060809-2H3-1B8-1C10. Screening of the full plate was done and well 1F9 had the highest reactivity and was subcloned into 60 wells on a single 96-well plate. The remainder of the reactive wells was pooled, expanded and frozen at −80° C. (T060809-2H3-1B8-1C10).

$5^{th}$ Round Subcloning.

The subclone plate was screened as an individual column pool without reactivity, and rescreened later, while the entire plate was done with moderate reactivity in many wells. T060809-2H3-1B8-1C10-1F9 well 1G3 had the highest reactivity was subcloned into 60 wells on a single 96-well plate. The remainder of the reactive wells was pooled. Eleven days later, the subcloned plates showed evidence of fungal contamination and were discarded. Reactive cells from the pooled remainder (T060809-2H3-1B8-1C10-1F9) were expanded and 7 days later subcloned into ten 96-well plates. Two weeks later these subclone plates were screened, and T060809-2H3-1B8-1C10-1F9 wells 2D8 and 3F9 had the highest nucleolin reactivity and were subcloned the next day into 60 wells each on single 96-well plates. Nine days later, the subcloned plates again showed evidence of fungal contamination and were discarded. Frozen pooled T060809-2H3-1B8-1C10 cells were thawed and expanded, and ten days later, subcloned into five 96-well plates. Two weeks later, the plates were screened for nucleolin reactivity, and T060809-2H3-1B8-1C10 wells 1B7 and 1D6 were confirmed positive on the following day, and were subcloned into 60 wells each on single 96-well plates. Ten days later, the plates were screened for nucleolin reactivity, and T060809-2H3-1B8-1C10-1D6 wells 2D11 and 2E9 had the highest reactivity, and were subcloned the next day into 60 wells each on single 96-well plates.

$6^{th}$ Round Subcloning.

Seventeen days later, the subclone plates were screened for nucleolin reactivity, and T060809-2H3-1B8-1C10-1D6-2D11 well 2C7 had the highest nucleolin reactivity, and was subcloned the next day by limiting dilution cloning into ten 96-well plates. Clonal colonies appeared slowly over time, and were screened for nucleolin reactivity between weeks 4 and 6. Four wells (3D8, 10C3, 7G9, 1H4) had reactivity. Clone T060809-2H3-1B8-1C10-1D6-2D11-2C7-1H4 was expanded for functional antibody testing because of its superior growth properties.

Clone 9F9.

Initial Screening and Primary Subcloning.

2 tonsil samples were received, pooled and processed into a single repertoire consisting of 10×96-well plates (T061509). These were screened for plate pools and well pools 10 days later. ELISA confirmation was conducted the next day, identifying reactive well T061509-9F9, which was subcloned into 60 wells on 1 plate the following day.

Secondary Subcloning.

The subclone plate was screened as a single column pool without any reactivity, and was rescreened later. Then the full plate was rescreened. T061509-9F9 well 1D11 had the highest reactivity and was subcloned into 60 wells on a single 96-well plate.

Tertiary Subcloning.

The subclone plate was screened as an individual column pool with one reactive well. Screening of the full plate was done later and T061509-9F9-1D11 well 1D10 had the highest reactivity and was subcloned into 60 wells on a single 96-well plate.

Quaternary Subcloning.

The subclone plates were screened as individual column pools without reactivity, and rescreened again without reactivity. Screening of the entire plate was done later with moderate reactivity. T061509-9F9-1D11-1D10 well 1F9 had the highest reactivity and was subcloned into 60 wells on a single 96-well plate. The remainder of the reactive wells was pooled, expanded and frozen at −80° C. (T061509-9F9-1D11-1D10).

$5^{th}$ Round Subcloning.

The subclone plates were screened as individual column pools with multiple reactive wells. Screening of the entire plate was done with moderate reactivity. T061509-9F9-1D11-1D10-1F9 well 1B6 had the highest reactivity and was subcloned into 60 wells on a single 96-well plate. The remainder of the reactive wells was pooled. Eleven days later, the subcloned plates showed evidence of fungal contamination and were discarded. Reactive cells from the pooled remainder (T061509-9F9-1D11-1D10-1F9) were expanded and 7 days later subcloned into ten 96-well plates. Two weeks later these subclone plates were screened, and T061509-9F9-1D11-1D10-1F9 wells 6B9 and 9D3 had the highest nucleolin reactivity and were subcloned the next day into 60 wells each on single 96-well plates. Nine days later, the subcloned plates again showed evidence of fungal contamination and were discarded. Frozen pooled T061509-9F9-1D11-1D10 cells were thawed and expanded, and ten days later, subcloned into five 96-well plates. Two weeks later, the plates were screened for nucleolin reactivity, and T061509-9F9-1D11-1D10 wells 2C7 and 2F8 were confirmed positive on the following day, and were subcloned into 60 wells each on single 96-well plates. Ten days later, the plates were screened for nucleolin reactivity, and T061509-9F9-1D11-1D10-2F8 wells 2D11 and 2B6 had the highest reactivity, and were subcloned the next day into 60 wells each on single 96-well plates.

$6^{th}$ Round Subcloning.

Seventeen days later, the subclone plates were screened for nucleolin reactivity, and T061509-9F9-1D11-1D10-2F8-2D11 well 1F4 had the highest nucleolin reactivity, and was subcloned the next day by limiting dilution cloning into ten 96-well plates. Clonal colonies appeared slowly over time, and were screened for nucleolin reactivity between weeks 4 and 6. Three wells (4E8, 1C7, 8A6) had reactivity. Clone T061509-9F9-1D11-1D10-2F8-2D11-1F4-4E8 was expanded for functional antibody testing because of its superior growth properties.

Clone 8G4.

Initial Screening and Primary Subcloning.

A tonsil sample was received and processed into an immortalized repertoire consisting of 10×96-well plates (T081009). Eleven days later, the library was screened for reactivity to nucleolin. ELISA confirmation was conducted, identifying reactive well (T081009-8G4), which was subcloned into 60 wells on a single plate.

Secondary Subcloning.

The subclone plate was screened 19 days later and 2 wells were identified with nucleolin reactivity (T081009-8G4 wells 1C9 and 1F3). Well 1F3 had the highest reactivity and was subcloned into 60 wells on a single 96-well plate 3 days later.

Tertiary Subcloning.

Three weeks later, the subclone plate was screened and multiple wells had nucleolin reactivity. T081009-8G4-1F3 wells 2G4 and 2H3 had the highest reactivity and were subcloned the next day into 60 wells each on single 96-well plates. The remainder of the reactive wells were pooled. Five days later, the subcloned plates showed evidence of fungal contamination and were discarded. Reactive cells from the pooled remainder (T081009-8G4-1F3) were expanded and two weeks later subcloned into ten 96-well plates. Thirteen days later these subclone plates were screened, and T081009-8G4-1F3 wells 4G2 and 5B9 had the highest nucleolin reactivity and were subcloned two days later into 60 wells each on single 96-well plates.

Quaternary Subcloning.

Three weeks later, the subclone plates were screened, and T081009-8G4-1F3-4G2 wells 1E9 and 2F5 had the highest nucleolin reactivity and were subcloned the next day into 60 wells each on single 96-well plates.

$5^{th}$ Round Subcloning.

Thirteen days later, the subclone plates were screened, and T081009-8G4-1F3-4G2-2F5 wells 2C10 and 2E8 had the highest nucleolin reactivity and were subcloned the next day into 60 wells each on single 96-well plates.

$6^{th}$ Round Subcloning.

Twenty-five days later, the subclone plates were screened, and T081009-8G4-1F3-4G2-2F5-2E8 well 2D11 had the highest nucleolin reactivity. Four days later, well 2D11 was subcloned by limiting dilution cloning into ten 96-well plates. Clonal colonies appeared slowly over time, and were screened for nucleolin reactitvity between days 17 and 33. Multiple wells (7E9, 4C9, 4D9, 6A3, 10F8, 8B3) had reactivity. Clone T081009-8G4-1F3-4G2-2F5-2E8-2D11-8B3 was expanded for functional antibody testing because of its superior growth properties.

Clone P1C6.

Initial Screening and Primary Subcloning.

A peripheral blood sample was received and processed into an immortalized repertoire consisting of 10×96-well plates (PB120909). Nine days later, the library was screened for reactivity to nucleolin. ELISA confirmation was conducted, identifying reactive well (PB120909-106), which was subcloned 3 days later into 60 wells on a single plate.

Secondary Subcloning.

The subclone plate was screened three weeks later, and 2 wells were identified with nucleolin reactivity (PB120909-

106 wells 1H2 and 1H9). Both were subcloned into 60 wells each on single 96-well plates.

Tertiary Subcloning.

Seventeen days later, the subclone plates were screened and PB120909-1C6-1H9 wells 2F4 and 2G3 had the highest nucliolin reactivity and were subcloned into 60 wells each on single 96-well plates.

Quaternary Subcloning.

Three weeks later, the subclone plates were screened, and PB120909-1C6-1H9-2G3 wells 2E7 and 2C9 had the highest nucleolin reactivity and were subcloned into 60 wells each on single 96-well plates.

5th Round Subcloning.

Seventeen days later, the subclone plates were screened, and PB120909-1C6-1H9-2G3-2C9 wells 1G6 and 1H10 had the highest nucleolin reactivity and were subcloned the next day into 60 wells each on single 96-well plates.

$6^{th}$ Round Subcloning.

Two weeks later, the subclone plates were screened, and PB120909-1C6-1H9-2G3-2C9-1G6 well 1F5 had the highest nucleolin reactivity. Three days later, well 1F5 was subcloned by limiting dilution cloning into ten 96-well plates. Clonal colonies appeared slowly over time, and were screened for nucleolin reactitvity between days 22 and 28. Multiple wells (3C7, 7D6, 10F9, 10G10) had reactivity. Clone PB120909-1C6-1H9-2G3-2C9-1G6-1F5-3C7 was expanded for functional antibody testing because of its superior growth properties.

Example 2—Results

Nucleolin and Bcl-2 Protein are Overexpressed in the Plasma Membrane and Cytoplasm of B-CLL Cells Compared to B Cells from Normal Human Volunteers.

CLL is indolent during most of its clinical course and the clonal B cells accumulate in the bone marrow and circulation during the indolent phase by avoiding apoptosis (Klein et al., 2000). CLL cells circumvent apoptosis by overexpressing the anti-apoptotic protein Bcl-2. High-level expression of bcl-2 mRNA and protein is seen in the absence of gene rearrangements that are known to enhance bcl-2 transcription (Bakhshi et al., 1985; Robertson et al., 1996; Steube et al., 1995). One of the inventors discovered that bcl-2 mRNA is highly stabilized in CLL cells from patients compared to normal CD19+ B cells from healthy volunteers (Otake et al., 2007). In addition, the inventors showed that the enhanced stability of bcl-2 mRNA in CLL cells was a direct result of binding of the stabilizing protein nucleolin to an ARE element in the 3'-UTR of bcl-2 mRNA. Furthermore, nucleolin was over-expressed in the cytoplasm of CLL cells from all of the patients examined (FIG. 1).

Peripheral blood samples were obtained from 17 patients with untreated CLL and 9 healthy volunteers. Mononuclear cells were isolated from each blood sample and the B cells were purified from this fraction by immuno-magnetic separation using positive selection for CD19, a pan-B cell marker. The cytosolic levels of nucleolin and Bcl-2 protein were then compared in CD19+ CLL cells from the patients to the levels in CD19+ B cells from the healthy volunteers (Otake et al., 2007). Cytoplasmic levels of nucleolin were examined because that is postulated to be the site of stabilization of bcl-2 mRNA. The non-nuclear (cytoplasmic) levels of nucleolin and Bcl-2 protein were determined by immunoblots of S10 extracts. To accurately compare the immuno-blot results from different patients, the integrated density values (IDV) of the nucleolin and Bcl-2 protein bands in the immunoblots were normalized to the IDV values obtained from known amounts of nucleolin and Bcl-2 external standards. This analysis revealed that Bcl-2 levels were 11-fold elevated ($p<0.001$) and nucleolin levels were 26-fold elevated ($p<0.001$) in CLL cells from 17 patients compared to B cells from 9 normal volunteers (FIG. 1). In addition, the enhanced Bcl-2 protein levels positively correlated with the increased nucleolin levels (Pearson's correlation=0.83, $p<0.001$). No significant difference was observed in the levels of nucleolin in nuclear fractions between CLL and normal B cells. The fact that nucleolin was uniformly over-expressed in all of the CLL patients, including those in early stages of disease without prior therapy, suggests that nucleolin stabilization of bcl-2 mRNA is an early event in CLL pathogenesis, rather than a feature of disease evolution or an epiphenomenon of chemotherapy.

Nucleolin and Bcl-2 Protein are Overexpressed in the Plasma Membrane and Cytoplasm of B-CLL Cells Compared to B Cells from Normal Human Volunteers.

Figure 2A:
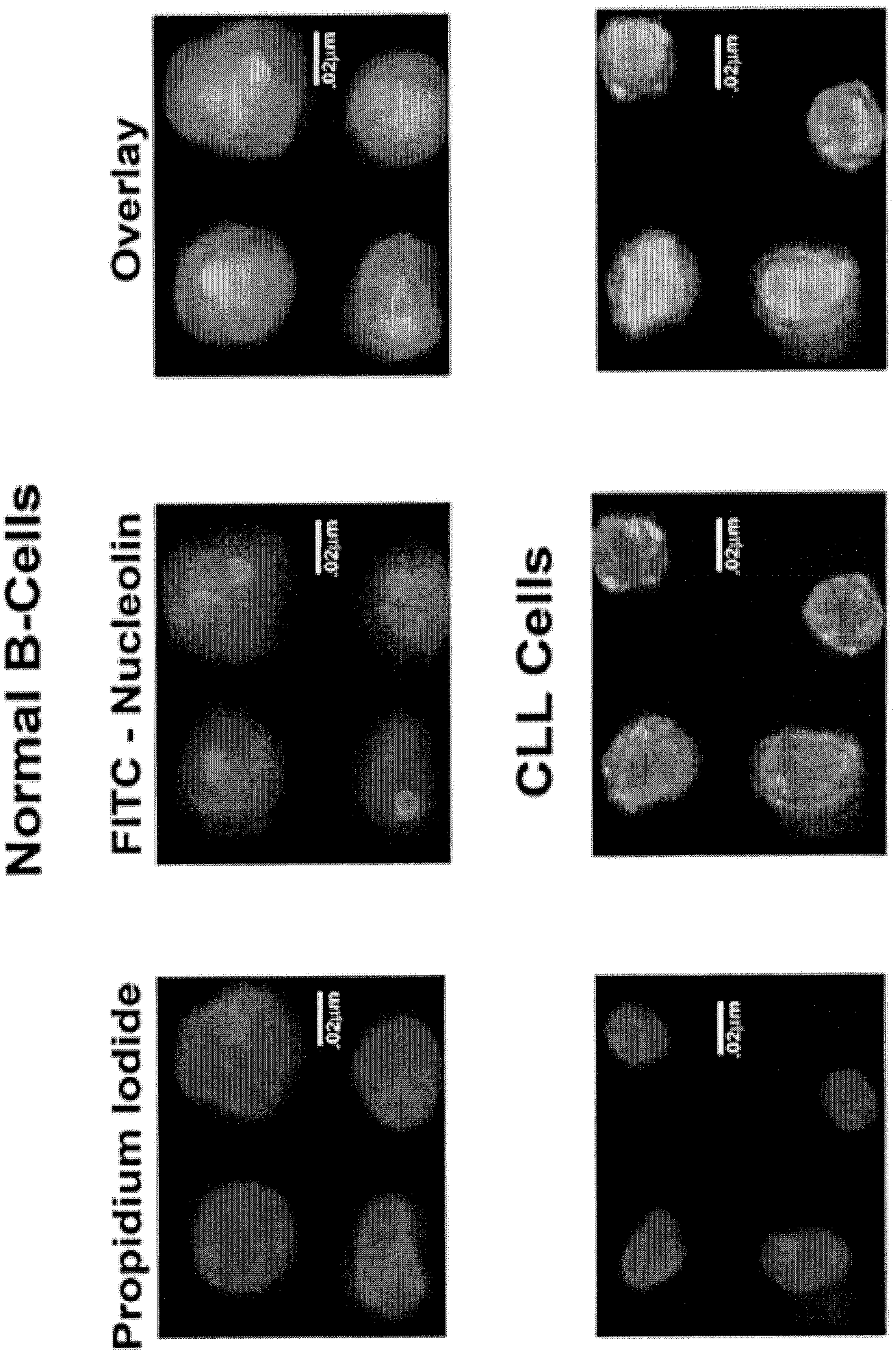
FIGS. 2A-B. Subcellular localization of nucleolin in CLL vs normal B cells and MCF-7 vs MCF-10A cells. The intracellular localization of nucleolin was determined by indirect immunofluorescence using mouse anti-human nucleolin mAb and a secondary FITC-conjugated anti-mouse IgG. Nuclei were counterstained with propidium iodide.

Confocal microscopy studies of CLL cells from patients and B cells from healthy volunteers were performed to confirm the results obtained by immuno-blotting. The localization of nucleolin was determined by indirect immunofluorescence using anti-nucleolin MAb and a FITC-anti-mouse IgG secondary antibody. The DNA was stained with propidium iodide. The overlay images in FIG. 2A indicate that nucleolin was present in the plasma membrane, cytoplasm and nucleus of CLL cells, but was only present in the nucleus of B cells. These results were consistent with the immunoblots indicating localization of nucleolin in the plasma membrane and cytoplasm of CLL cells but not in normal B cells.

Nucleolin is Also Highly Overexpressed in MCF-7 Breast Cancer Cells Compared to MCF-10A Normal Mammary Epithelial Cells.

Figure 2B:
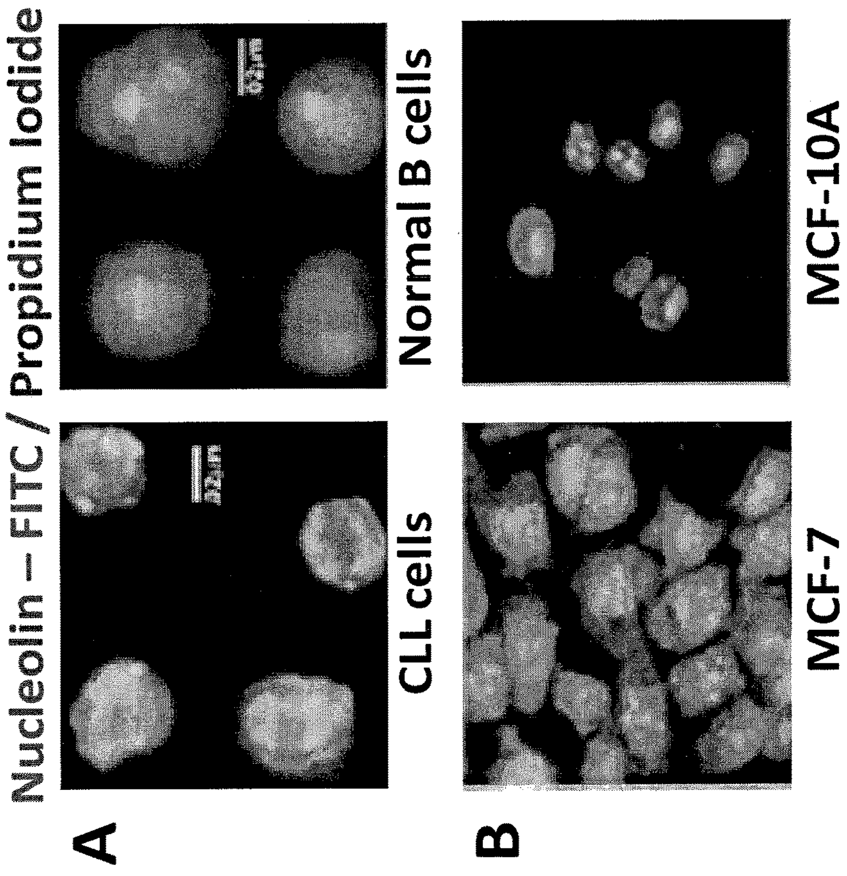

The intracellular localization of nucleolin in MCF-7 and MDA-MB-231 breast cancer cells and MCF-10A normal mammary epithelial cells was determined by indirect immunofluorescence as described above (Soundararajan et al., 2008). The overlay images in FIG. 2B indicate that nucleolin was present throughout the nucleus, plasma membrane and cytoplasm (green fluorescence) of MCF-7 cells, while in normal MCF-10A cells nucleolin was detected only in the nucleus. This was also true for MDA-MB-231 breast cancer cells (Soundararajan et al., 2008)

Nucleolin and Bcl-2 Protein are also Overexpressed in the Plasma Membrane and Cytoplasm of MCF-7 and MDA-MB-231 Breast Cancer Cells Compared to MCF-10A Normal Mammary Epithelial Cells.

Figure 3:
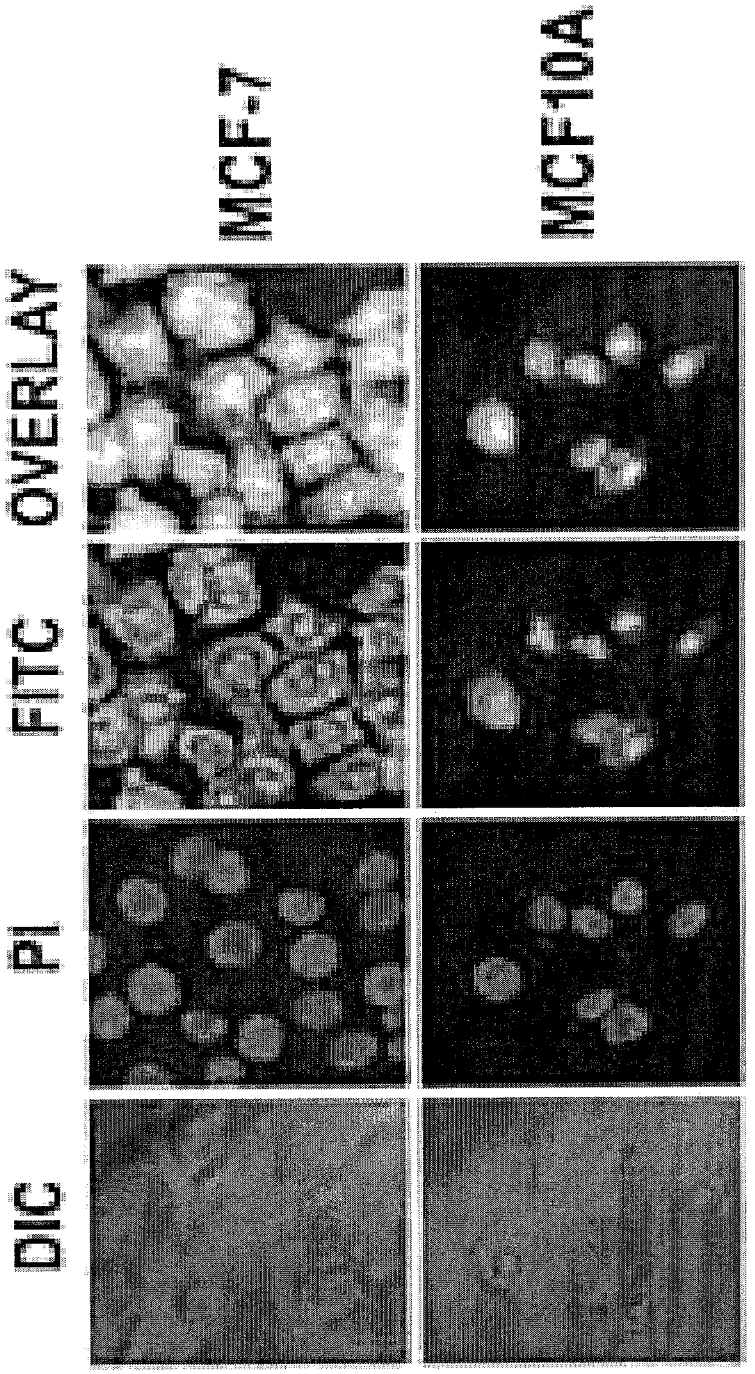
FIG. 3. Subcellular localization of nucleolin in MCF-7 and MCF-10A cells. The intracellular localization of nucleolin was determined by indirect immunofluorescence using a monoclonal antibody against human nucleolin and a secondary FITC-conjugated anti-mouse IgG. Nuclei were counterstained with propidium iodide. Cell morphology is shown as DIC images. Results are representatives of three separate experiments.

The intracellular localization of nucleolin was determined by indirect immunofluorescence using primary antibody against nucleolin and a FITC-conjugated anti-mouse IgG secondary antibody (green fluorescence). The DNA was stained with propidium iodide (red fluorescence). The overlay images in FIG. 3 indicate that nucleolin was present throughout the nucleus (yellow fluorescence), plasma membrane and cytoplasm (green fluorescence) of MCF-7 cells, while in normal MCF-10A cells nucleolin was detected only in the nucleus. The intracellular localization of nucleolin in MDA-MB-231 breast cancer cells (Soundararajan et al., 2008) was similar to that of MCF-7 cells.

AML Blast Cells from Patients that Engraft in NOD/SCID Mice Show Intense Nucleolin Staining.

Figure 4:
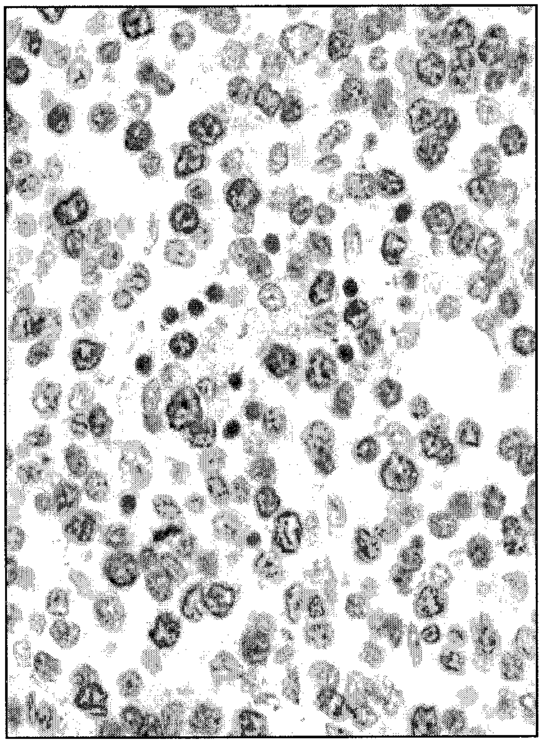
FIG. 4. Bone marrow biopsy from a patient with AML-M1 stained with anti-nucleolin antibody (fuchsin stain) shows intense nuclear staining. Interspersed non-leukemic marrow elements are either negative (dark blue counterstain) or show only a nuclear blush. Magnification was 40×.

Further evidence that nucleolin is a tumor-specific antigen and also has a role in human AML pathogenesis comes from human AML xenograft studies. Biopsy specimens from the bone marrow were assessed for expression of nucleolin in the blast cytoplasm and/or nucleus. Immunohistochemical analysis was performed on glass slides of paraffin-embedded tissue sections of archived bone marrow biopsies. In all cases, the AML blasts were compared to the surrounding normal bone marrow elements. The inventors observed that anti-nucleolin staining was intense in the AML blast cells (fuchsin stain), while normal elements of the bone marrow (dark blue counterstain) were either weakly positive or outright negative (FIG. 4). Strong expression of nucleolin has been observed in all AML samples tested to date.

Figure 5A:
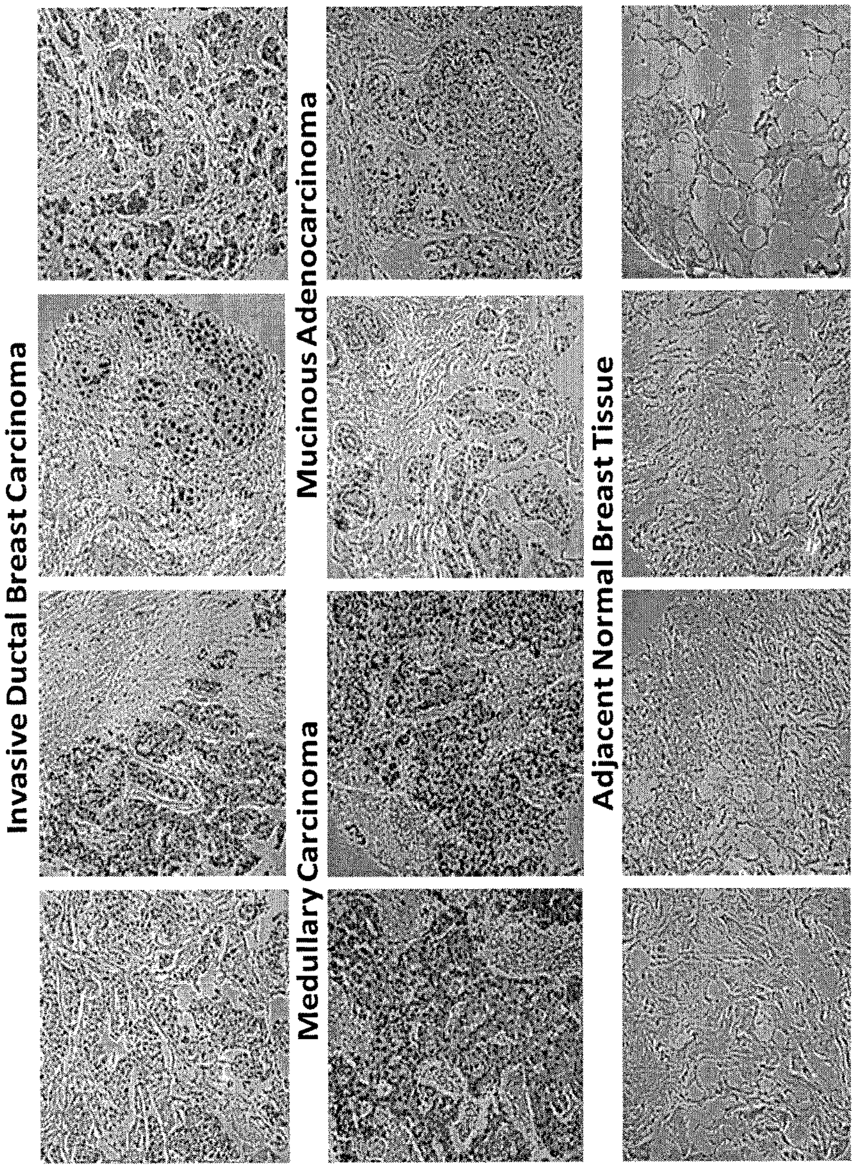
FIGS. 5A-B. Nucleolin overexpression in spleen sections from human AML-engrafted mice and from human breast cancer cells.

Ten NOD-SCID male mice (eleven weeks of age) were each injected i.p. with 25 μg of anti-asialo GM antibody and exposed to 2.3 Gy in a Cs137 irradiator. The same day, five of the ten mice were each injected i.p. with $2\times10^7$ PBMC from a human subject diagnosed with AML. At least 60% of the PBMC in this subject were AML blasts. Four months after the i.p. injection of PBMC all mice were euthanized. In two of five mice injected i.p. with AML cells, the spleens were enlarged and showed nodular lesions on the surface of the spleen as well as within it Part of the spleen of each mouse was processed to dissociate splenocytes and analyzed by flow cytometry for the presence of human CD45+ cells. In mice with abnormal spleens, some of the spleenocytes were stained with anti-human CD45 antibodies, demonstrating that these mice had been engrafted with human AML cells. The inventors next carried out histopathology and immunohistochemistry analyses on the spleen of engrafted and control NOD/SCID mice (FIG. 5A). Nodular areas of leukemic engraftment in the spleen were strikingly positive for nucleolin expression.

Nucleolin is Also Highly Overexpressed in Human Breast Carcinomas Compared to Normal Mammary Tissue.

Figure 5B:
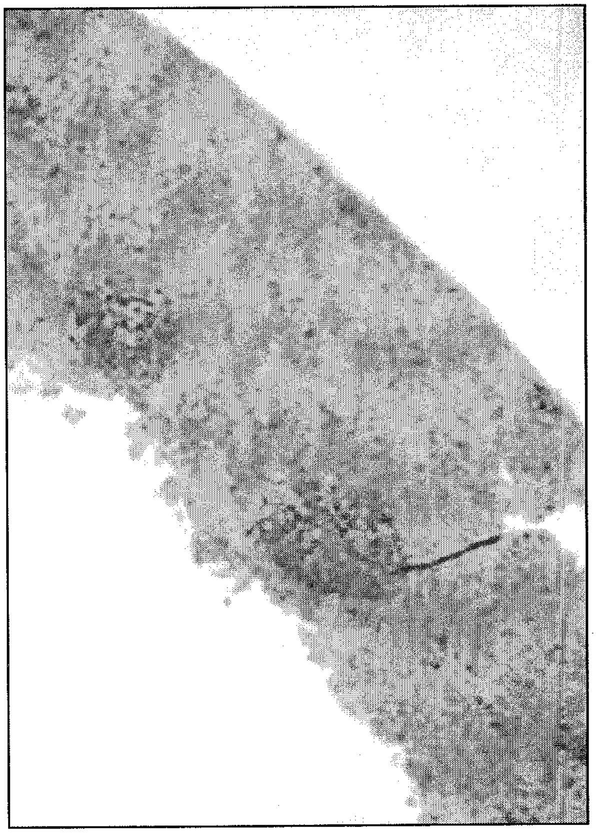

Furthermore, nucleolin immuno-histochemistry performed on a human breast carcinoma tissue array comprising tumor and normal adjacent breast tissue from 50 patients indicated that nucleolin was overexpressed in the tumors compared to the normal adjacent tissue. Representative results are depicted for the most common forms of breast cancer (FIG. 5B). Nucleolin was highly expressed in invasive ductal carcinoma (8/8 cases tested) and medullary carcinoma (6/6 cases), and was moderately expressed in mucinous adenocarcinoma (8/8 cases), but was not detected in adjacent normal tissue (FIG. 5B).

The results presented in FIGS. 1-5B above provide strong evidence that nucleolin is overexpressed on the cell surface of certain human tumor cells as a tumor-specific antigen. For human CLL (and possibly AML and breast cancer), nucleolin overexpression is an early event in the pathogenesis of this disease. The nucleolin-targeting aptamer AS1411, which is considered a ““chemical”” anti-nucleolin antibody (Soundararajan et al., 2008; Soundararajan et al., 2009) showed promising activity in phase II clinical trials for refractory and relapsed AML (Clinical Trials.gov Identifier NCT00512083). Thus, when taken together these results indicate that nucleolin is an excellent target for the development of therapeutic antibodies.

Bcl-2 mRNA Stability is Increased in CLL Cells Relative to Normal Bc Cells.

Figure 6:
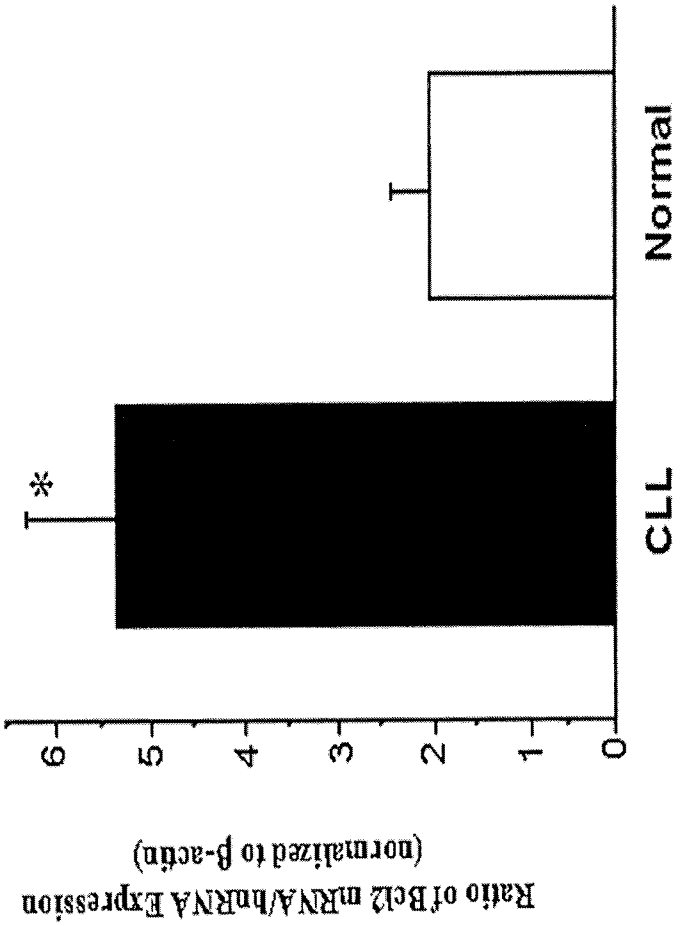
FIG. 6. Relative expression levels of bcl-2 hnRNA and bcl-2 mRNA in CLL and normal B cells. The levels of bcl2 hnRNA and bcl2 mRNA in CLL cells from 4CLL patients and normal B cells from 4 healthy volunteers were determined by RT-PCR. Results are expressed as the means of 4 determinations per group SEM. *P<0.001 compared with normal B cells.

The overexpression of Bcl-2 in CLL cells compared to normal B cells could result either from enhanced bcl-2 mRNA transcription, increased bcl-2 mRNA stability, or increased efficiency of bcl-2 mRNA translation. It is difficult to measure mRNA stability in primary CLL cells with the standard method using actinomycin D to block transcription, since bcl-2 mRNA is very stable in CLL cells requiring long incubation times with actinomycin D, which is toxic to the cells. To circumvent this problem, the inventors measured the levels of nascent, unspliced heterogeneous nuclear bcl-2 mRNA (hnRNA) and mature bcl-2 mRNA in CLL cells and normal B cells from healthy volunteers. This method has been used successfully to determine the relative rate of mRNA transcription and mRNA decay in a variety of cells. Equal amounts of total RNA from each sample were reverse-transcribed and real-time PCR was performed with two sets of primers. One reaction contained primers that anneal to the first intron (to selectively amplify hnRNA) and one with primers that anneal to sequences in two adjacent exons (to selectively amplify spliced, mature RNA). The inventors found that the ratio of bcl-2 mRNA to bcl-2 hnRNA was about 3-fold higher for CLL cells compared to normal B cells ($p<0.001$) (FIG. 6). The 3-fold higher ratio of bcl-2 mRNA/bcl-2 hnRNA for CLL cells was entirely due to increased levels of bcl-2 mRNA in CLL cells (3.3±0.4 SEM relative to β-actin mRNA) compared to bcl-2 mRNA levels in normal B cells (1.1±0.2 SEM relative to β-actin mRNA). No significant difference was observed in the level of bcl-2 hnRNA in CLL cells (6.5±1.4 SEM relative to β-actin mRNA) versus normal B cells (5.5±1.4 SEM relative to β-actin mRNA). These results indicate that bcl-2 mRNA is relatively more stable in CLL cells compared to normal B cells. Furthermore, the rate of bcl-2 mRNA transcription was not relatively higher in CLL cells because the bcl-2 mRNA/hnRNA ratio would have been lower in CLL versus normal B cells if that were true.

Mechanism by which Nucleolin Overexpression Upregulates Bcl-2 mRNA.

Figure 7:
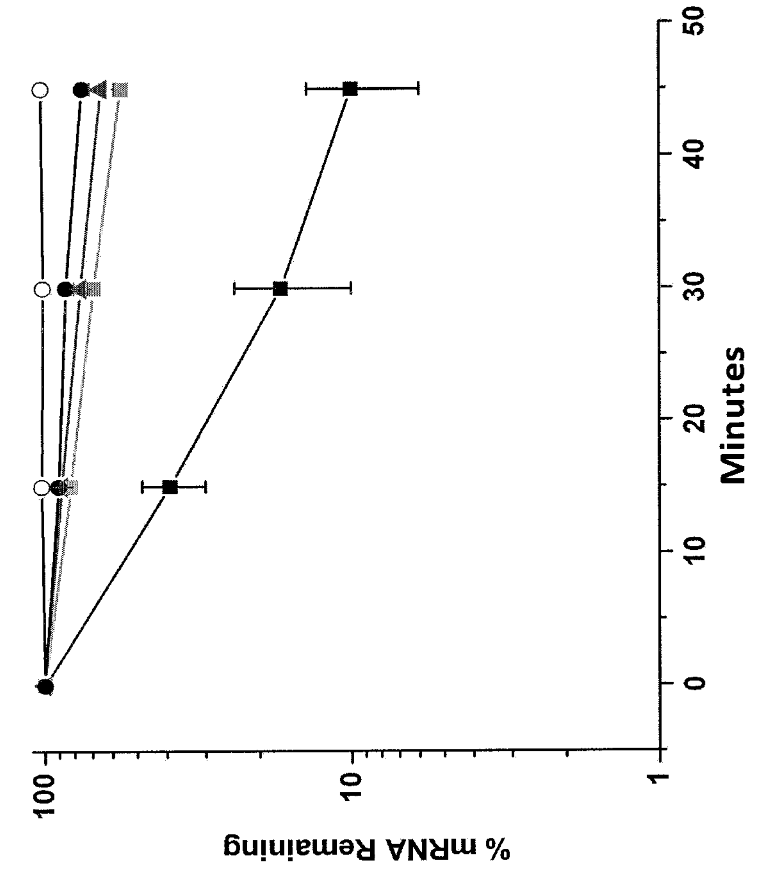
FIG. 7. Decay of bcl-2 mRNA in extracts of CLL and normal B cells. 5'-capped and polyadenylated [$^{32}$P]bcl-2-CR RNA and [$^{32}$P]bcl-2-CR-ARE RNA were incubated with 5100 extracts prepared from either CLL cells from 4 patients or normal B cells from 3 human volunteers. At the indicated times aliquots of the reaction mixtures were removed and analyzed by PAGE and phosphorimaging. The results are expressed as the mean percentage of full-length RNA remaining±SEM as a function of time. Symbols: -○-CLL cell extract+[$^{32}$P]bcl-2-CR RNA; -●-, CLL cell extract+[$^{32}$P]bcl-2-CR-ARE RNA; -□-, normal B cell extract+[$^{32}$P]bcl-2-CR RNA; -■-, normal B cell extract+[$^{32}$P]bcl-2-CR-ARE RNA; -▲-, normal cell extract+[$^{32}$P]bcl-2-CR-ARE RNA+280 nM purified recombinant nucleolin.

The mechanism of bcl-2 mRNA stabilization by nucleolin was examined by following the decay rate of bcl-2 RNA transcripts in extracts prepared from purified CLL cells and normal B cells, using an in vitro RNA decay system (Sengupta et al., 2004). Capped and polyadenylated mRNAs were used in these assays to mimic in vivo decay, which involves cap-stimulated deadenylation by poly (A)-specific ribonuclease (PARN), followed by rapid decay of the mRNA body by the exosome (Chen et al., 2001; Mukherjee et al., 2002). $^{32}P$-labeled bcl-2-ARE transcripts were incubated with cytoplasmic S100 extracts from CLL and normal B cells in the presence of poly(A) to activate deadenylation. As shown in FIG. 7, bcl-2 transcripts decayed more rapidly in extracts of normal B cells than in extracts of CLL cells. The average half-life of bcl-2 RNA in cytoplasmic extracts of CLL cells from 4 patients was estimated to be 72 min by extrapolation of the data, while the average half-life of the transcript in normal B cell extracts was 12 min (FIG. 7). The rapid decay of the bcl-2-CR (coding region)-ARE RNA transcripts in normal B cell extracts was highly ARE-dependent, since the rates of decay of bcl-2 mRNA coding region transcripts lacking the ARE (bcl-2-CR RNA) were similar in normal B cell and CLL cell extracts. It is also important to note that addition of 280 nM purified recombinant nucleolin [Δ1-283 Nuc-(His)6] to extracts of normal B cells greatly slowed the decay rate of bcl-2-ARE (extrapolated half-life of 62 min). When taken together, these results indicate that nucleolin stabilizes bcl-2 mRNA by binding to an ARE in the 3'-UTR of bcl-2 mRNA and protecting the mRNA from degradation.

Development of Nucleolin-Specific Human Antibodies.

Figure 8:
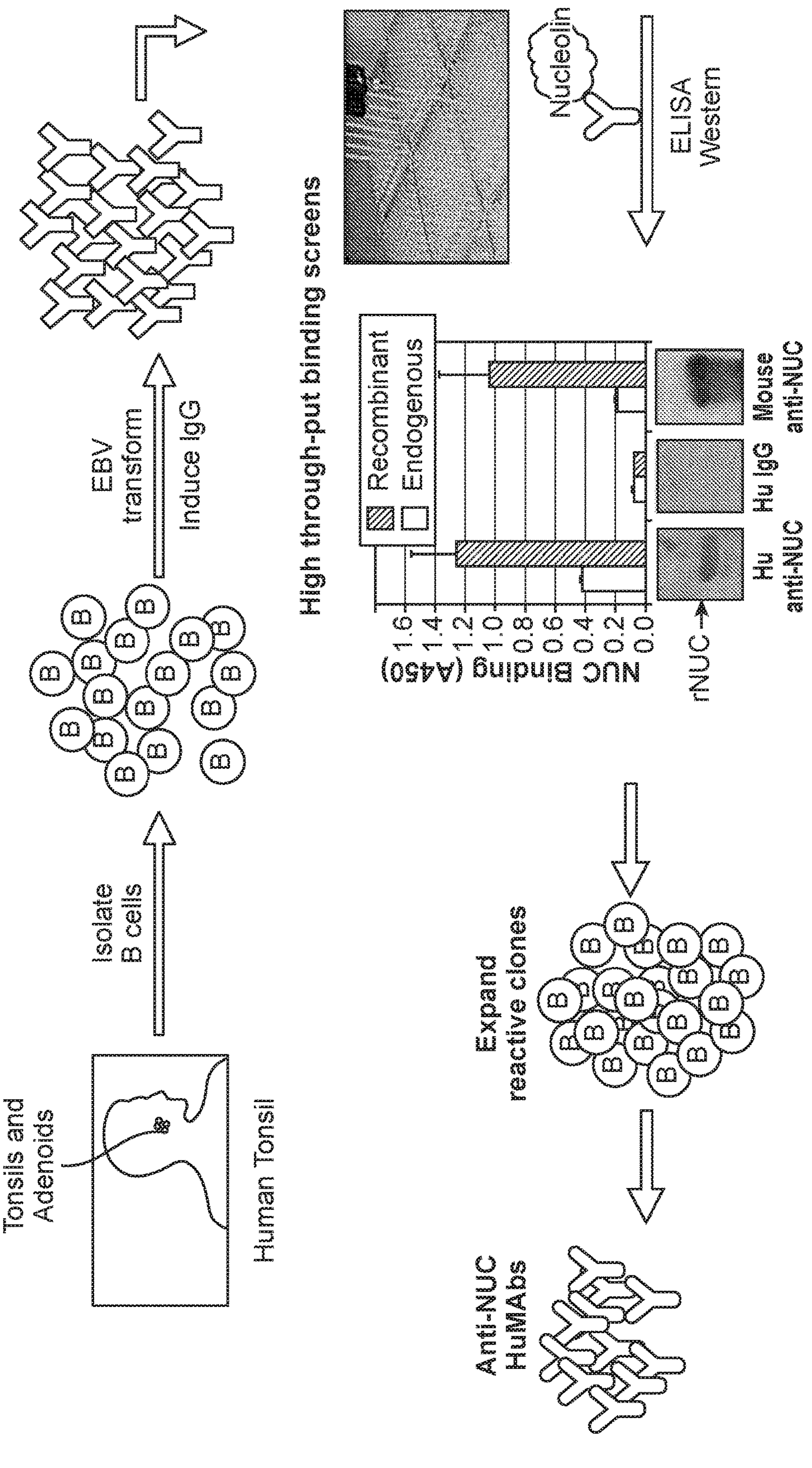
FIG. 8. Producing human mAbs in vitro. Tonsil B cells are isolated and efficiently immortalized with EBV, then induced to differentiate into antibody-producing cells. Immortalized B cell libraries are plated into multiple wells, then cell supernatants containing IgG are screened for binding to recombinant nucleolin. Reactive cells are cloned by limiting dilution, expanded, and the IgG purified from the culture supernatant. Ig genes can be subcloned into producer cell lines for large scale recombinant IgG production. See PCT/US2008/072124.
Figures 9A, 9B:
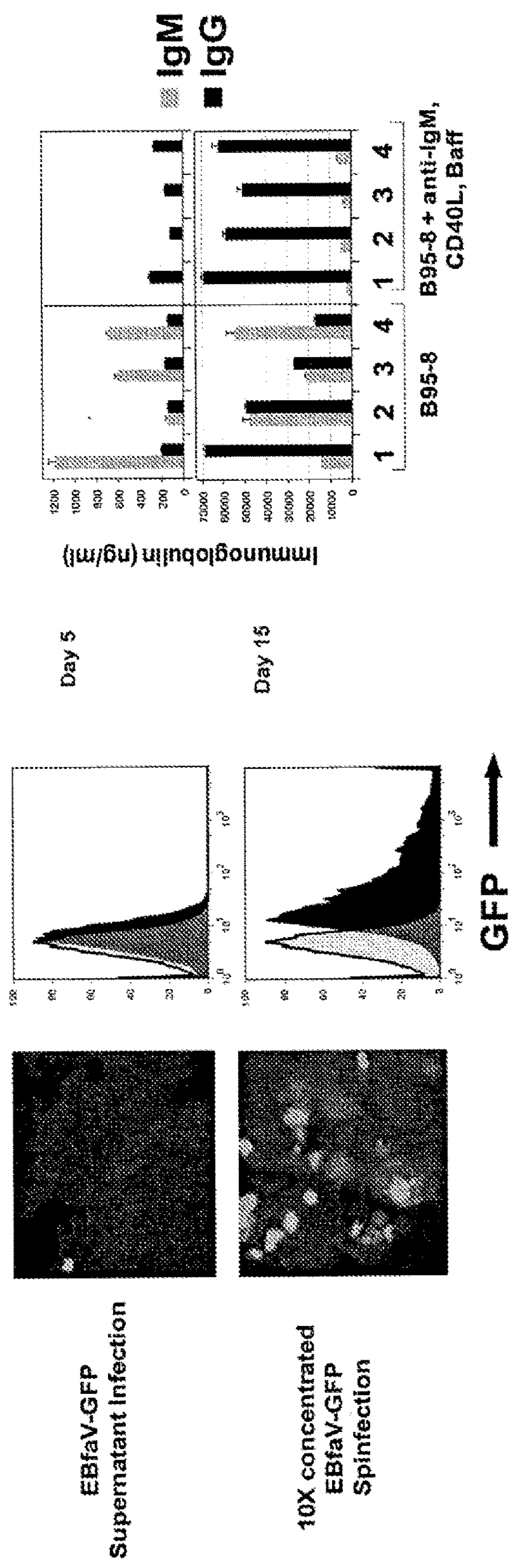
FIGS. 9A-B. Efficient EBV infection and induction of differentiation in tonsil B cell libraries.

Cumulatively, the preliminary studies described above indicate that nucleolin is a promising tumor antigen target for antibody based immunotherapy of CLL and AML, and possibly for certain forms of breast cancer. The inventors therefore set out to create therapeutic human MAbs specific for nucleolin, using a novel in vitro method for producing human MAbs from immortalized B cell libraries created from human tonsil. The technology holds several advantages including 1) rapid antibody production with all steps in vitro; 2) human immunization is not required, 3) the resulting antibodies are fully human and therefore should not be rejected, nor cause serum sickness. This technology was invented with support of the National Cancer Institute and the Federal Government has certain rights in the invention. A worldwide patent application (PCT/US2008/072124) was filed in August, 2008. An overview of the technology is depicted in FIG. 8. Human B cells were isolated from tonsillectomy specimens from healthy children, then efficiently infected with Epstein-Barr virus (EBV) resulting in wide scale B cell transformation. Infected B cells were induced to differentiate with agents that mimic B cell receptor signaling and T cell help. Since tonsil is a rich source of B cells, this process typically allowed for the isolation of $10^7$-$10^8$ B cells, each with unique antibody specificity. The efficient infection process is demonstrated in FIG. 9A, which shows that after spinfection of tonsil B cells with 10× concentrated viral stocks of recombinant EBV containing a green fluorescent protein marker gene (EBfaV-GFP (Speck et al., 1999a; Speck et al., 1999b), nearly 100% of the tonsil B cells were infected after 24 h. The infected cells were then plated into 96-well plates at $10^3$-$10^4$ cells per well in the presence of a proprietary differentiation cocktail (Diff-Cktl) consisting of recombinant CD40L, Baff and anti-human IgM $(Fab')_2$, that induced immunoglobulin (Ig) isotype class switching from IgM to IgG over a 2 week period. As can be seen in FIG. 9B, IgG was secreted into the culture supernatant at levels typically ranging from 1-4 μg/ml. This process reproducibly creates EBV immortalized tonsil B cell libraries secreting polyclonal IgG with an estimated $10^6$-$10^7$ antibody specificities, depending upon the number of B cells isolated from an individual tonsil. Cell culture supernatants from the libraries can then be screened for specific binding to various antigens of interest. B cells producing IgG with the desired specificity can then be isolated by limiting dilution cloning, and the IgG purified from the culture supernatant. For larger scale production, recombinant IgG can be produced by subcloning the clonal B cells' Ig genes into mammalian expression vectors and transducing cell lines commonly used for the production of biologicals. To date, the inventors have created more than 40 libraries (data not shown), which have been screened for reactivity to various antigenic targets.

Figures 10A, 10B:
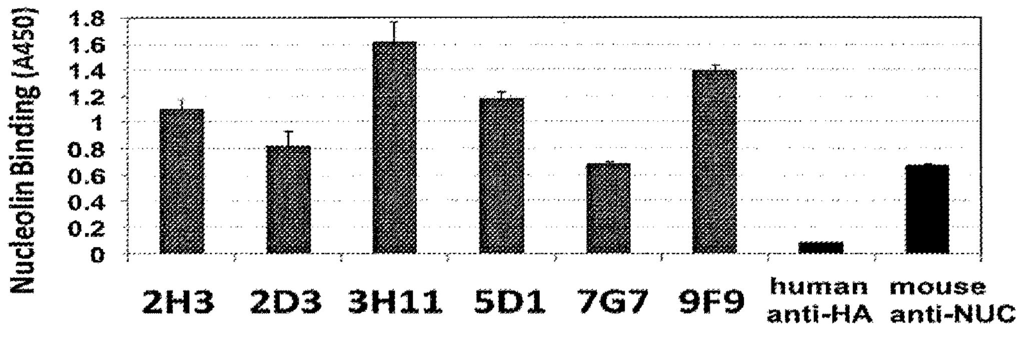
FIGS. 10A-B. Isolation of eight immortalized B cell lines producing nucleolin-specific human antibodies.

This platform technology is ideal for producing autoantibodies with therapeutic implications, such as antibodies to tumor antigens like nucleolin. Ordinarily, healthy children would not be expected to make strong secondary antibody responses to self-proteins such as nucleolin, because autoreactive B cells do not normally receive sufficient T cell help required for their survival and differentiation into IgG secreting plasma cells. Instead, the autoreactive B cells become tolerized or are deleted in vivo. However, these data indicate that it is possible to rescue rare nucleolin reactive B cells from tonsil or peripheral blood, using EBV to immortalize the autoreactive B cells, and the differentiation cocktail to artificially force them to undergo Ig isotype class switching and secretion of nucleolin specific IgG in vitro. Using this approach, the inventors screened twelve immortalized tonsil libraries for nucleolin specific IgG by enzyme linked immunosorbent assay (ELISA). As can be seen in FIG. 10, six human B cell lines have been isolated that produce IgG antibodies that react strongly with recombinant human nucleolin (Δ1-283Nuc-$(His)_6$) produced in bacteria. As a positive control, binding was compared to that obtained with mouse anti-nucleolin MAb MS3 (Santa Cruz Biotech), while culture supernatant from a human B cell line raised in the same manner, but producing IgG1 antibodies specific for H5 hemagglutinin (human anti-HA) served as a negative control.

Preliminary Characterization of Human Anti-Nucleolin Antibodies.

Figure 11:
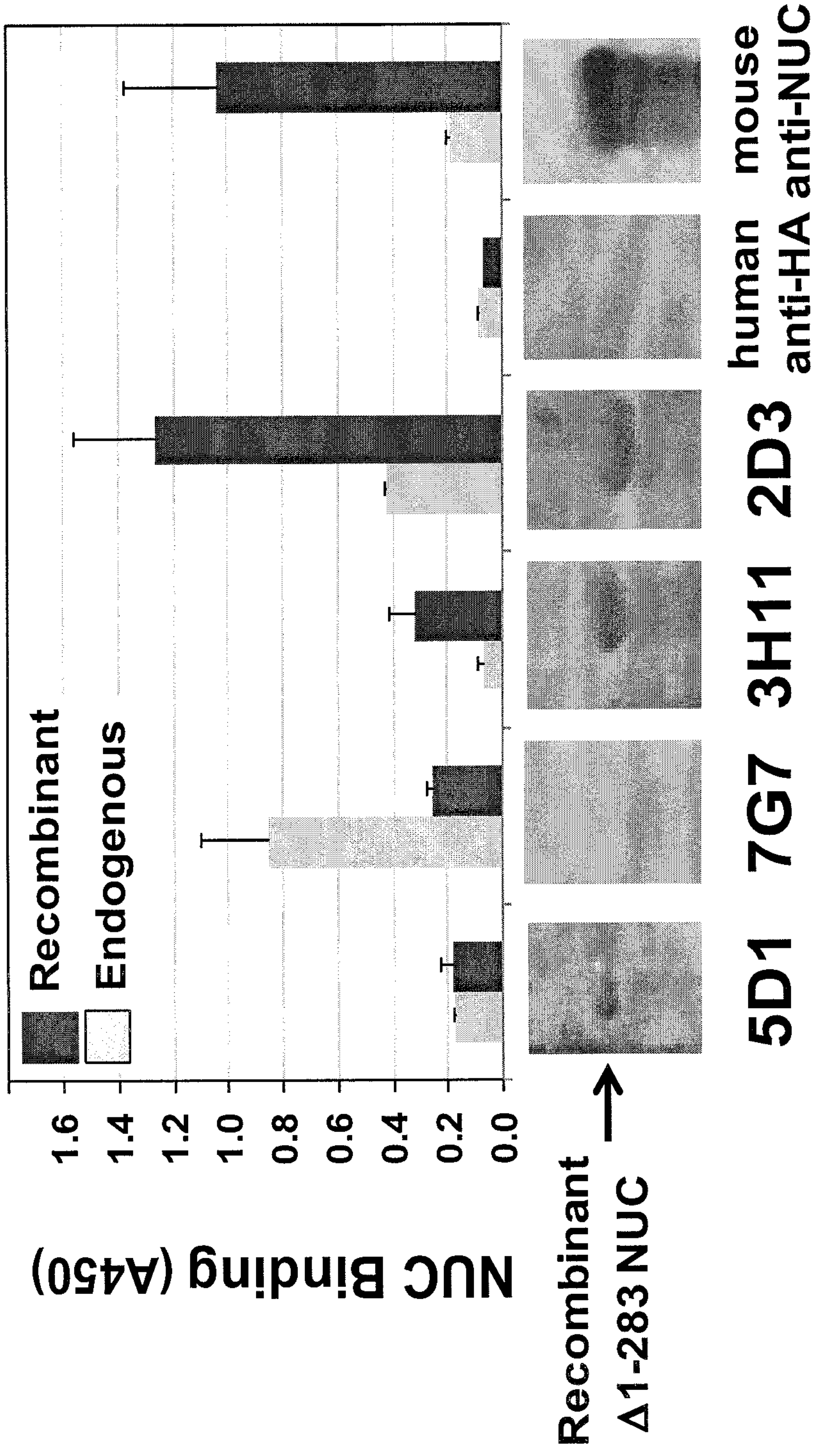
FIG. 11. Isolation of human anti-nucleolin antibodies. Supernatants from immortalized human B cell libraries were screened by ELISA (top) and Western blotting (bottom) for IgG binding to recombinant Δ1-283Nuc-$(His)_6$ nucleolin and/or endogenous nucleolin isolated from MV411 leukemic cells.

In order to test whether any or all of these anti-nucleolin antibodies might have therapeutic potential, the inventors have begun characterizing the antibodies by further ELISA analyses, Western blotting, flow cytometry, immunohistochemistry and cytotoxic killing of MV4-11 cells. Four of the antibodies were initially screened further by ELISA in order to test whether they recognize endogenous nucleolin purified from MV4-11 human leukemia cells, and to recombinant His-tagged nucleolin (Δ1-283 Nuc-(His)6 produced in bacteria; Ishimaru et al., 2009). As can be seen in FIG. 11, top panel, supernatants from three out of four of the B cell lines (SDI, 7G7 and 2D3) reacted with endogenous nucleolin with similar (or higher) intensity as mouse anti-nucleolin MS3, while all bound the his-tagged recombinant to varying degrees. In addition, three of the four culture supernatants (5D1, 3H11, and 2D3) reacted to the his-tagged recombinant nucleolin by Western blotting (FIG. 11, bottom). Thus, the antibodies had distinct patterns of binding to the endogenous and his-tagged proteins, and reacted differently in the Western blotting analysis, possibly indicating that each recognizes distinct protein epitopes.

Anti-Nucleolin Cytotoxicity to MV4-11 AML Cells and MCF-7 Breast Cancer Cells in the Absence of CDCC or ADCC.

Figure 12:
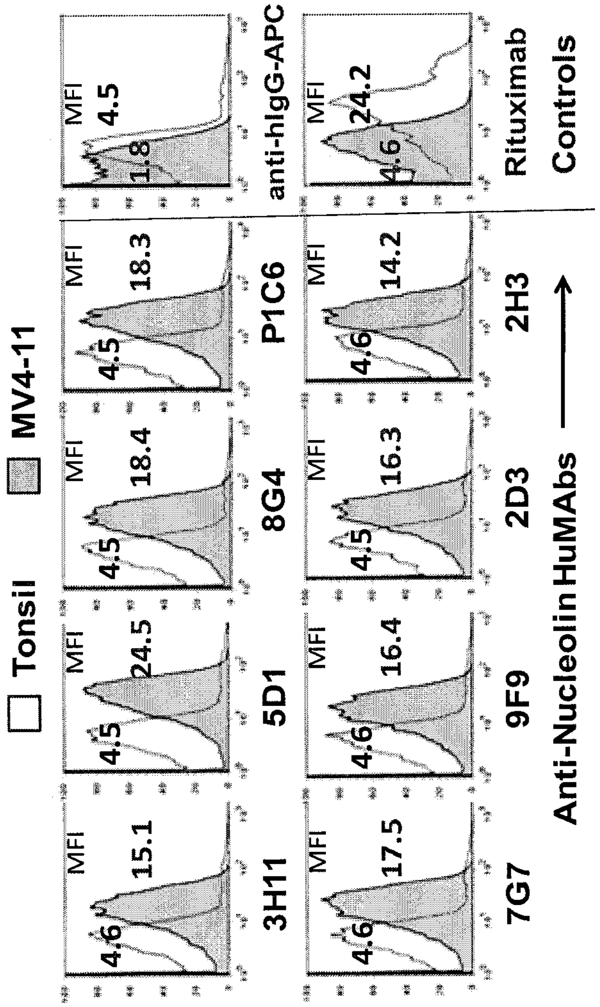
FIG. 12. Binding of HuMAbs to cell surface nucleolin and cytotoxicity to MV4-11 leukemia cells.
Figure 14A:
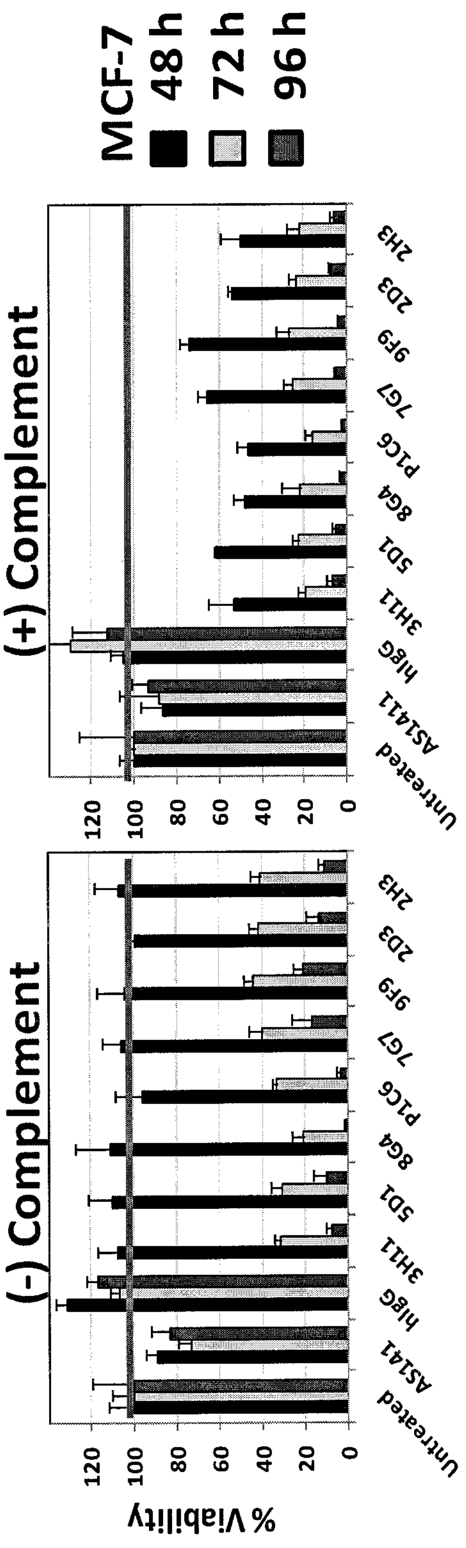
FIGS. 14A-C. Nucleolin specific killing of MCF-7 and MV4-11 AML cells occurs through complement dependent and independent mechanisms.
Figure 14B:
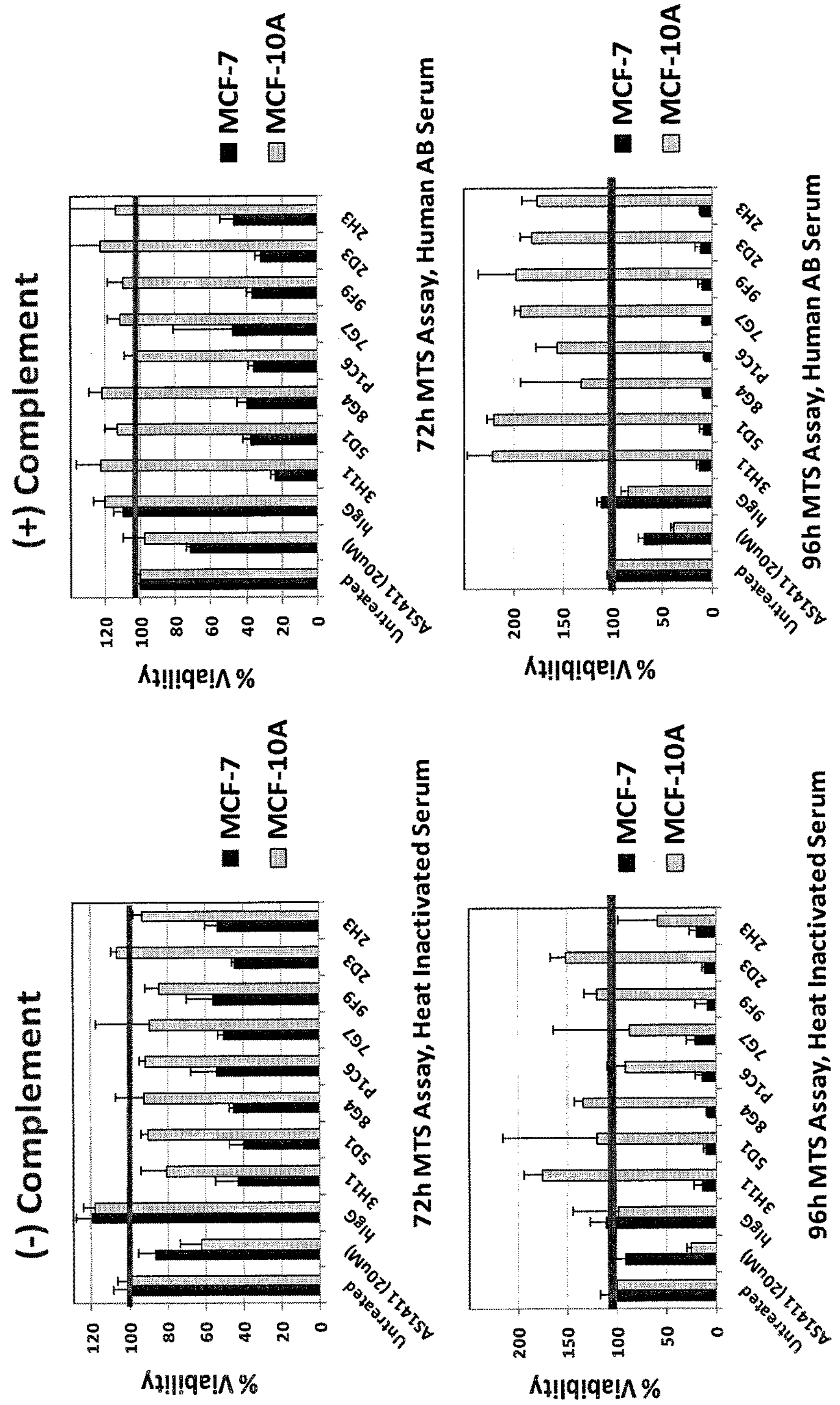
Figure 14C:
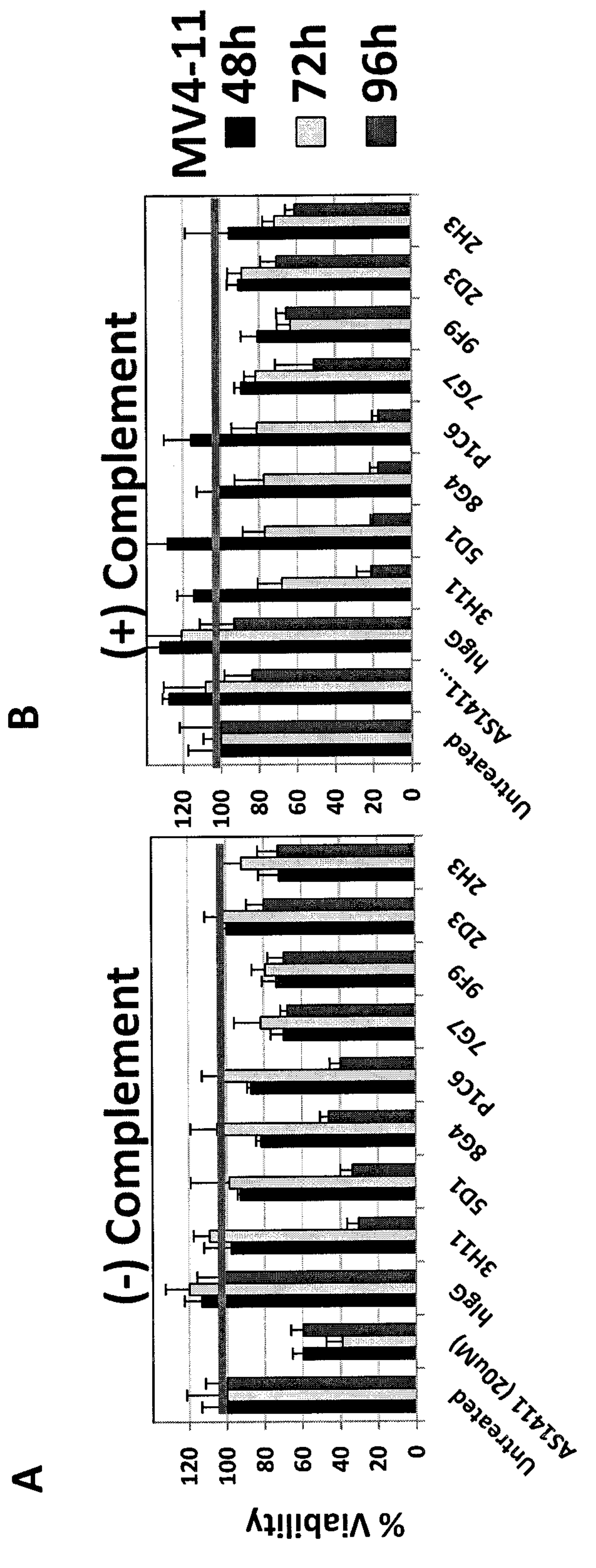

FIG. 12 further demonstrates that all of the anti-NUC HuMAbs bind to cell surface nucleolin on MV4-11 AML cells, but they do not bind to normal tonsil cells, which do not express nucleolin on the cell surface. In contrast, Rituximab bound to normal tonsil cells but not to MV4-11 cells. Furthermore, the anti-NUC HuMAbs were cytotoxic to MV4-11 cells (FIG. 14C). After incubation of MV4-11 cells with each antibody (2 μg/ml), mitochondrial function was measured by MTS assay at 48, 72 and 96 h. FIG. 14C demonstrates that by 96 h, cell viability decreased in response to each antibody, ranging from ~30-80% of untreated cells. By comparison, after incubation with nucleolin-targeting aptamer AS1411 (20 μM), cell viability decreased to ~40-60% of untreated cells, and was unchanged by incubation with control human IgG. This assay was performed in the absence of complement and without the effector cells required for ADCC, indicating that the anti-nucleolin HuMAbs acted independently of CDCC and ADCC. A summary of these findings is presented in Table 4. Taken together, these data provide strong evidence that each of the six antibodies isolated have distinct binding characteristics and are either binding to different epitopes on human nucleolin, and/or have distinct affinities for the protein.

Figure 13:
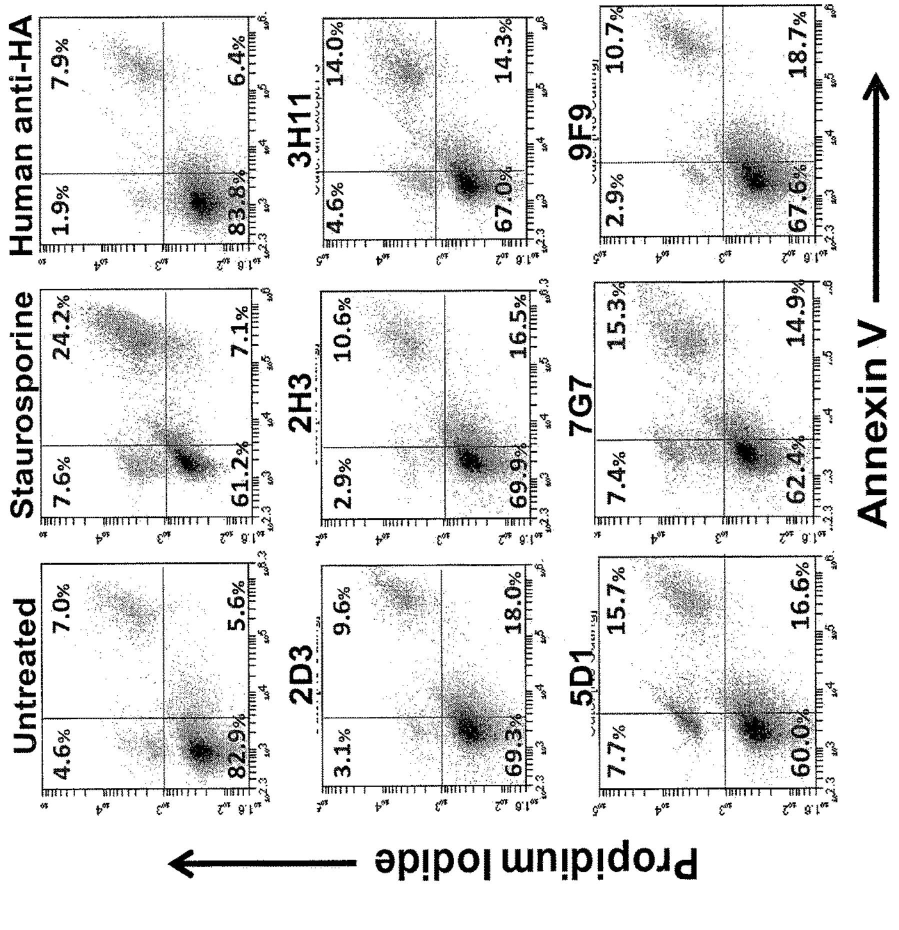
FIG. 13. Complement-mediated killing of MV4-11 cells. Supernatants from antibody-producing B cell lines were incubated with MV411 cells (50% v/v) for 16 h in the presence of human serum (25% v/v). Controls were treated with staurosporine (25 μM) or media (untreated). Cells were then stained with propidium iodide and annexin V-FITC, and analyzed by flow cytometry.

While the binding analysis has fundamental significance, from a therapeutic standpoint the most important criterion is that the antibodies mediate cytotoxicity. For this reason, the inventors set up a simple flow cytometric based assay measuring induction of apoptosis and/or cell death by propidium iodide (PI) and annexin-V staining Annexin-V binds to phoshatidyl serine residues, which become exposed on the cell membrane as an early event during induction of apoptosis. At later stages of apoptosis or during necrotic cell death, disruption of membrane integrity makes the cells permeable to the non-vital dye PI, which can be detected through flow cytometry. MV4-11 cells were cultured for 16 h in the presence of each antibody and human serum, which was used as a source of complement and is required for detecting complement dependent cellular cytotoxicity (CDCC), after which they were stained with PI and annexin V-FITC. As can be seen in FIG. 13, MV4-11 cells treated with human anti-HA antibodies (negative control) showed no significant differences in either annexin-V or PI staining compared with untreated cells. In contrast, each of the anti-nucleolin antibodies induced about a 3-fold shift in the mean fluorescence intensity of annexin-V staining compared to untreated or anti-HA treated cells. A similar shift was also seen in cells treated with staurosporine (25 μM), a chemical inducer of apoptosis. Anti-nucleolin antibodies 5D1 and 7G7 were the most cytotoxic antibodies, with 38-40% of cells staining positive for PI and/or annexin-V after 16 h, compared to just 16% for control anti-HA treatment, while the other anti-nucleolin antibodies induced cytotoxicity in ~30% of cells. The relative cytotoxic activities of each antibody against MV4-11 leukemia cells are summarized in Table 4. These preliminary data indicate that more comprehensive cytotoxicity testing is warranted, particularly for antibodies 5D1 and 7G7.

Similar experiments were performed with MCF-7 breast carcinoma cells, which were found to be more sensitive to the anti-nucleolin HuMAbs than were the MV4-11 cells. In the absence of complement, the anti-nucleolin HuMabs inhibited cell viability to less than 20% of untreated cells after 96 h, while AS1411 reduced cell viability to just 80% of untreated cells, and control human IgG had no effect (FIG. 14A, left panel). Complement dependent cytotoxicity was assayed in parallel experiments with the addition of human AB serum (25% vol/vol) as a source of complement. As can be seen in FIG. 14A, right panel, the addition of complement potentiated the cytotoxic effects of the antibodies, significantly inhibiting cell viability as early as 48 h, with complete inhibition by 96 h. FIG. 14B shows that the cytotoxic effects were selective for MCF-7 cells, since the HuMAbs had no effect on cell viability of MCF-10A normal mammary epithelial cells that do not express cell surface nucleolin. Thus, our panel of anti-nucleolin HuMAbs bind specifically to cell surface nucleolin expressed on human AML and breast cancer cell lines and can induce substantial tumor cell cytotoxicity that is independent of the immune mechanisms of ADCC and CDCC. but can be potentiated by serum complement.

TABLE 4

Summary of Results Performed on Characterization of Human Anti-Nucleolin Antibodies

| Hu-anti Nuc | ELISA Recombinant[a]/ Endogenous[b] | | Western | FACS | Cytotoxicity MV4-11[c]/ MCF-7[d] | | Heavy Chain | Light Chain | IHC |
|---|---|---|---|---|---|---|---|---|---|
| 2D3 | +++ | ++ | ++ | ++ | ++ | ++++ | IgG1 | Lambda | n.d. |
| 2H3 | +++ | n.d. | n.d. | + | ++ | +++ | IgG1 | Kappa | n.d. |
| 3H11 | ++++ | − | ++ | ++ | ++ | ++++ | IgG1 | Lambda | n.d. |
| 5D1 | +++ | + | ++ | ++++ | +++ | ++++ | IgG1 | Kappa | + |
| 7G7 | +++ | +++ | − | ++ | +++ | +++ | IgG1 | Kappa | n.d. |
| 9F9 | ++++ | n.d. | n.d. | ++ | ++ | ++++ | IgG1 | Kappa | + |
| 8G4 | +++ | n.d. | n.d. | +++ | +++ | ++++ | IgG1 | Lambda | n.d. |
| P1C6 | +++ | n.d. | n.d. | +++ | +++ | ++++ | IgG1 | Kappa | n.d. |

[a]Binding to recombinant 1-283Nuc-$(His)_6$ nucleolin;
[b]binding to nucleolin purified from MV4-11 leukemia cells;
[c]cytotoxicity against MV4-11 cells measured by MTS assay at 96 h;
[d]cytotoxicity against MCF-7 cells measured by MTS assay at 96 h;
n.d.: not done.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the method described herein without departing from the concept, spirit and scope of the invention. More specifically, it will be apparent that certain agents which are both chemically and physiologically related can be substituted for the agents described herein while the same or similar results would be achieved. All such similar substitutes and modifications apparent to those skilled in the art are deemed to be within the spirit, scope and concept of the invention as defined by the appended claims.

VIII. References

The following references, and any others cited throughout the application, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,179,337
U.S. Pat. No. 4,275,149
U.S. Pat. No. 4,277,437
U.S. Pat. No. 4,301,144
U.S. Pat. No. 4,366,241
U.S. Pat. No. 4,472,509
U.S. Pat. No. 4,485,045
U.S. Pat. No. 4,496,689
U.S. Pat. No. 4,544,545.
U.S. Pat. No. 4,640,835
U.S. Pat. No. 4,657,760
U.S. Pat. No. 4,670,417
U.S. Pat. No. 4,791,192
U.S. Pat. No. 4,816,567
U.S. Pat. No. 4,938,948
U.S. Pat. No. 4,975,278
U.S. Pat. No. 5,013,556
U.S. Pat. No. 5,021,236
U.S. Pat. No. 5,047,335
U.S. Pat. No. 5,196,066
U.S. Pat. No. 5,206,344
U.S. Pat. No. 5,225,212

U.S. Pat. No. 5,278,299
U.S. Pat. No. 5,510,261
U.S. Pat. No. 5,534,615
U.S. patent application Ser. No. 12/671,936
U.S. Patent Publn. 2009/0191244
U.S. Patent Publn. 2007/0066554
U.S. Patent Publn. 2007/0066554
Atherton et al., *Biol. Reprod.*, 32(1):155-171, 1985.
Bakhshi et al., *Cell,* 41(3):899-906, 1985.
Bates et al., *Exp. Mol. Path.*, 86:151, 2009.
Bose et al., *J. Virol.*, 78:8146, 2004.
Boyd et al., *Mol. Immunol.*, 32:1311-1318, 1996.
Chen et al., Cell, 107(4):451-64, 2001.
Chen et al., *Genes Dev.*, 14(10):1236-48, 2000.
Chen et al., *Mol. Ther.*, 16(2):333-42, 2008.
Christian et al., *J. Cell Biol.*, 163:871-878, 2003.
Cunningham and Wells, *Science,* 244:1081-1085, 1989.
Destouches et al., *PLoS ONE,* 3 (6):e2518, 2008.
Dholakia et al., *J. Biol. Chem.*, 264(34):20638-20642, 1989.
Epstein et al., *Proc. Natl. Acad. Sci. USA,* 82:3688, 1985.
Evan et al., *Molec. Cell. Biol.* 5:3610-3616, 1985.
Farin et al., *PLoS ONE,* 4(7): 6128, 2009.
Field et al., *Mol. Cell. Biol.*, 8:2159-2165, 1988.
Fogal et al., *Angiogenesis,* 12(1):91-100, 2009.
Gabizon et al., *J. National Cancer Inst.*, 81(19):1484, 1989.
Gattoni-Celli et al., *Am. J. Hematol.*, 84(8):535-8, 2009.
Geahlen et at, *Biochim. Biophys. Acta.*, 804:169-175, 1984.
Ginisty et al., *J. Biol. Chem.*, 276(17):14338-43, 2001.
Hopp et al., *BioTechnology,* 6:1204-1210, 1988.
Hovanessian et al., *Cell Research,* 16:174-181, 2006.
Hovanessian et al., *Exp. Cell Res.*, 261(2):312-28, 2000.
Hse et al., *J. Biol. Chem.*, 272:9062-9070, 1997.
Hwang et al., *Proc. Natl. Acad. Sci. USA,* 77:4030, 1980.
Ishimaru et al., *Mol. Cancer Res.*, 7(8):1354-66, 2009.
Izumi et al., *Viral Research,* 76(1):17-29, 2001.
Jefferis and Lund, Chem. *Immunol.*, 65:111-128, 1997.
Jefferis and Lund, *Current Opin. Biotech.*, 7:409-416, 1996.
Khatoon et al., *Ann. Neurol,* 26(2):210-215, 1989.
Kibbey et al., *J. Neurosci. Res.*, 42(3):314-22, 1995.
Kim and Baldwin, *Ann. Rev. Biochem.*, 51:459-89, 1982.
King et al., *J. Biol. Chem.*, 264(17):10210-10218, 1989.
Klein et al., *Leukemia,* 14(1):40-6, 2000.
Lapeyre et al., *Proc. Natl. Acad. Sci. USA,* 84(6):1472-6, 1987.
Lutz-Freyermuth et al., *Proc. Natl. Acad. Sci. USA,* 87:6393-6397, 1990.
Malhotra et al., *Nature Med.*, 1:237-243, 1995.
Martin et al., *J. Biol. Chem.*, 257:286-288, 1982.
Martin et al., *Science,* 255:192-194, 1992.
Massey, *Nature,* 328:457-458, 1987.
Miller and Lipman, *Proc. Natl. Acad. Sci. USA,* 70:190-194, 1973.
Mukherjee et al., *Embo. J.*, 21 (1-2):165-74, 2002.
Neuberger et al., *Nature,* 312:604-608, 1984.
O'Shannessy et al., *Anal. Biochem.*, 163(1):204-9, 1987.
Otake et al., *Blood,* 109(7):3069-75, 2007.
Owens and Haley, *Biochem. Biophys. Res. Commun.*, 142 (3):964-971, 1987.
Paborsky et al., *Protein Engineering,* 3(6):547-553, 1990.
PCT Appln. PCT/US2008/072124
PCT Appln. WO 81/01145
PCT Appln. WO 88/07378
PCT Appln. WO 93/23572
PCT Appln. WO 94/11026
PCT Appln. WO 96/32478
Pfeifle and Anderer, *Biochim. Biophys. Acta,* 762(1):86-93, 1983.
Potter and Haley, *Methods Enzymol,* 91:613-633, 1983.
*Remington's Pharmaceutical* Sci., Maack Publishing Co, Easton Pa., 1990.
Robertson et al., *Leukemia,* 10(3):456-9, 1996.
Said et al., *J. Biol. Chem.*, 277(40):37492-502, 2002.
Sengupta et al., *J. Biol. Chem.*, 279(12):10855-63, 2004.
Serin et al., *J. Biol. Chem.*, 272(20):13109-16, 1997.
Sinclair and O'Brien, *J. Biol. Chem.*, 277(4):2876-85, 2002.
Skinner et al., *J. Biol. Chem.*, 266:15163-15166, 1991.
Soundararajan et al., *Cancer Res.*, 68(7):2358-65, 2008.
Soundararajan et al., *Mol. Pharmacol.*, 76(5):984-91, 2009.
Speck et al., *Arch. Virol.*, 144(6):1123-37, 1999b.
Speck et al., *J. Gen. Viral.*, 80 (Pt 8):2193-2203, 1999a.
Srivastava and Pollard, *Faseb J.*, β(14):1911-22, 1999.
Srivastava et al., *FEBS Lett.*, 250(1):99-105, 1989.
Steube et al., *Leukemia,* 9(11):1841-6, 1995.
Takekoshi et al., *J. Biochem.*, 130:299-303, 2001.
Umana et al. *Mature Biotech.*, 17:176-180, 1999.
Vitetta et al., *Science,* 238:1098, 1987.
Weltschof et al., *J. Immunol. Methods,* 179:203-214, 1995.
Westmark and Malter, *Brain Res. Mol. Brain Res.*, 90(2):193-201, 2001.
Wittwe and Howard, *Biochem.*, 29:4175-4180, 1990.
Wright and Morrison, *Trends Biotechnol.*, 15:26-32, 1997).
Yang et al., *Nucl Acids Res.*, 30:2251-2260, 2002.

What is claimed is:

1. A method of treating a disease in a subject in need thereof, comprising administering to the subject in need thereof a therapeutically effective amount of an anti-nucleolin agent and a pharmaceutically acceptable carrier, wherein the disease is characterized by a diseased cell that overexpresses cell surface or cytoplasmic nucleolin, wherein the anti-nucleolin agent comprises an anti-nucleolin antibody, and wherein the anti-nucleolin agent binds to amino acid sequence SEQ ID NO:4 and kills the diseased cell that overexpresses cell surface or cytoplasmic nucleolin.

2. The method of claim 1, wherein the disease is a cancer.

3. The method of claim 2, wherein the cancer is breast cancer, prostate cancer, lung cancer, colon cancer, pancreatic cancer, leukemia, or ovarian cancer.

4. The method of claim 1, wherein the anti-nucleolin agent is non-toxic to a normal cell in the subject in need thereof.

5. The method of claim 1, wherein the anti-nucleolin agent further comprises a nanoparticle, a radionuclide, a fluorophore, a chemilluminescent compound, a fluorescent compound, an enzyme, a toxin, an antiviral agent, or a chemotherapeutic agent.

6. The method of claim 5, wherein the anti-nucleolin agent comprises the nanoparticle.

7. The method of claim 6, wherein the nanoparticle comprises nucleic acids.

8. The method of claim 7, wherein the nanoparticle is a DNA nanoparticle.

9. The method of claim 1, wherein the anti-nucleolin antibody is human or humanized.

10. The method of claim 1, wherein the anti-nucleolin antibody is an IgG antibody.

11. The method of claim 1, wherein the anti-nucleolin antibody is an IgG1 antibody.

12. A method of treating a disease in a subject in need thereof, comprising administering to the subject in need thereof a therapeutically effective amount of an antinucleolin agent and a pharmaceutically acceptable carrier, wherein the disease is characterized by a diseased cell that overexpresses cell surface or cytoplasmic nucleolin, wherein the anti-nucleolin agent comprises an antibody, wherein the antinucleolin agent binds to amino acid sequence SEQ ID NO:4 and kills the diseased cell that overexpresses cell surface or cytoplasmic nucleolin, and wherein the antibody is conjugated to a nanoparticle, a radionuclide, a fluorophore, a chemilluminescent compound, a fluorescent compound, an enzyme, a toxin, an antiviral agent, or a chemotherapeutic agent.

* * * * *

SEQUENCE LISTING

```
<160> NUMBER OF SEQ ID NOS: 16

<210> SEQ ID NO 1
<211> LENGTH: 2732
<212> TYPE: DNA
<213> ORGANISM: Homo sapiens

<400> SEQUENCE: 1

ctttcgcctc agtctcgagc tctcgctggc cttcgggtgt acgtgctccg ggatcttcag      60

cacccgcggc cgccatcgcc gtcgcttggc ttcttctgga ctcatctgcg ccacttgtcc     120

gcttcacact ccgccgccat catggtgaag ctcgcgaagg caggtaaaaa tcaaggtgac     180

cccaagaaaa tggctcctcc tccaaaggag gtagaagaag atagtgaaga tgaggaaatg     240

tcagaagatg aagaagatga tagcagtgga gaagaggtcg tcatacctca gaagaaaggc     300

aagaaggctg ctgcaacctc agcaaagaag gtggtcgttt ccccaacaaa aaaggttgca     360
```

-continued

```
gttgccacac cagccaagaa agcagctgtc actccaggca aaaaggcagc agcaacacct    420
gccaagaaga cagttacacc agccaaagca gttaccacac ctggcaagaa gggagccaca    480
ccaggcaaag cattggtagc aactcctggt aagaagggtg ctgccatccc agccaagggg    540
gcaaagaatg gcaagaatgc caagaaggaa gacagtgatg aagaggagga tgatgacagt    600
gaggaggatg aggaggatga cgaggacgag gatgaggatg aagatgaaat tgaaccagca    660
gcgatgaaag cagcagctgc tgcccctgcc tcagaggatg aggacgatga ggatgacgaa    720
gatgatgagg atgacgatga cgatgaggaa gatgactctg aagaagaagc tatggagact    780
acaccagcca aaggaaagaa agctgcaaaa gttgttcctg tgaaagccaa gaacgtggct    840
gaggatgaag atgaagaaga ggatgatgag gacgaggatg acgacgacga cgaagatgat    900
gaagatgatg atgatgaaga tgatgaggag gaggaagaag aggaggagga agagcctgtc    960
aaagaagcac ctggaaaacg aaagaaggaa atggccaaac agaaagcagc tcctgaagcc   1020
aagaaacaga aagtggaagg cacagaaccg actacggctt tcaatctctt tgttggaaac   1080
ctaaacttta acaaatctgc tcctgaatta aaaactggta tcagcgatgt ttttgctaaa   1140
aatgatcttg ctgttgtgga tgtcagaatt ggtatgacta ggaaatttgg ttatgtggat   1200
tttgaatctg ctgaagacct ggagaaagcg ttggaactca ctggtttgaa agtctttggc   1260
aatgaaatta aactagagaa accaaaagga aaagacagta agaaagagcg agatgcgaga   1320
acacttttgg ctaaaaatct cccttacaaa gtcactcagg atgaattgaa agaagtgttt   1380
gaagatgctg cggagatcag attagtcagc aaggatggga aaagtaaagg gattgcttat   1440
attgaattta agacagaagc tgatgcagag aaaacctttg aagaaaagca gggaacagag   1500
atcgatgggc gatctatttc cctgtactat actggagaga aaggtcaaaa tcaagactat   1560
agaggtggaa agaatagcac ttggagtggt gaatcaaaaa ctctggtttt aagcaacctc   1620
tcctacagtg caacagaaga aactcttcag gaagtatttg agaaagcaac ttttatcaaa   1680
gtaccccaga accaaaatgg caaatctaaa gggtatgcat ttatagagtt tgcttcattc   1740
gaagacgcta aagaagcttt aaattcctgt aataaaaggg aaattgaggg cagagcaatc   1800
aggctggagt tgcaaggacc caggggatca cctaatgcca gaagccagcc atccaaaact   1860
ctgtttgtca aaggcctgtc tgaggatacc actgaagaga cattaaagga gtcatttgac   1920
ggctccgttc gggcaaggat agttactgac cgggaaactg ggtcctccaa agggtttggt   1980
tttgtagact tcaacagtga ggaggatgcc aaagctgcca aggaggccat ggaagacggt   2040
gaaattgatg gaaataaagt taccttggac tgggccaaac ctaagggtga aggtggcttc   2100
gggggtcgtg gtggaggcag aggcggcttt ggaggacgag gtggtggtag aggaggccga   2160
ggaggatttg gtggcagagg ccggggaggc tttggagggc gaggaggctt ccgaggaggc   2220
agaggaggag gaggtgacca caagccacaa ggaaagaaga cgaagtttga atagcttctg   2280
tccctctgct ttccctttc catttgaaag aaaggactct ggggttttta ctgttacctg    2340
atcaatgaca gagccttctg aggacattcc aagacagtat acagtcctgt ggtctccttg   2400
gaaatccgtc tagttaacat ttcaagggca ataccgtgtt ggttttgact ggatattcat   2460
ataaactttt taaagagttg agtgatagag ctaaccctta tctgtaagtt ttgaatttat   2520
attgtttcat cccatgtaca aaaccatttt ttcctacaaa tagtttgggt tttgttgttg   2580
tttcttttt ttgttttgtt tttgtttttt ttttttttgc gttcgtgggg ttgtaaaaga    2640
aaagaaagca gaatgtttta tcatggtttt tgcttcagcg gctttaggac aaattaaaag   2700
```

tcaactctgg tgccagaaaa aaaaaaaaaa aa 2732

<210> SEQ ID NO 2
<211> LENGTH: 710
<212> TYPE: PRT
<213> ORGANISM: Homo sapiens

<400> SEQUENCE: 2

Met Val Lys Leu Ala Lys Ala Gly Lys Asn Gln Gly Asp Pro Lys Lys
1 5 10 15

Met Ala Pro Pro Pro Lys Glu Val Glu Glu Asp Ser Glu Asp Glu Glu
20 25 30

Met Ser Glu Asp Glu Glu Asp Asp Ser Ser Gly Glu Glu Val Val Ile
35 40 45

Pro Gln Lys Lys Gly Lys Lys Ala Ala Ala Thr Ser Ala Lys Lys Val
50 55 60

Val Val Ser Pro Thr Lys Lys Val Ala Val Ala Thr Pro Ala Lys Lys
65 70 75 80

Ala Ala Val Thr Pro Gly Lys Lys Ala Ala Ala Thr Pro Ala Lys Lys
85 90 95

Thr Val Thr Pro Ala Lys Ala Val Thr Thr Pro Gly Lys Lys Gly Ala
100 105 110

Thr Pro Gly Lys Ala Leu Val Ala Thr Pro Gly Lys Lys Gly Ala Ala
115 120 125

Ile Pro Ala Lys Gly Ala Lys Asn Gly Lys Asn Ala Lys Lys Glu Asp
130 135 140

Ser Asp Glu Glu Glu Asp Asp Asp Ser Glu Glu Asp Glu Glu Asp Asp
145 150 155 160

Glu Asp Glu Asp Glu Asp Glu Asp Glu Ile Glu Pro Ala Ala Met Lys
165 170 175

Ala Ala Ala Ala Ala Pro Ala Ser Glu Asp Glu Asp Asp Glu Asp Asp
180 185 190

Glu Asp Asp Glu Asp Asp Asp Asp Asp Glu Glu Asp Asp Ser Glu Glu
195 200 205

Glu Ala Met Glu Thr Thr Pro Ala Lys Gly Lys Lys Ala Ala Lys Val
210 215 220

Val Pro Val Lys Ala Lys Asn Val Ala Glu Asp Glu Asp Glu Glu Glu
225 230 235 240

Asp Asp Glu Asp Glu Asp Asp Asp Asp Asp Glu Asp Asp Glu Asp Asp
245 250 255

Asp Asp Glu Asp Asp Glu Glu Glu Glu Glu Glu Glu Glu Glu Glu Pro
260 265 270

Val Lys Glu Ala Pro Gly Lys Arg Lys Lys Glu Met Ala Lys Gln Lys
275 280 285

Ala Ala Pro Glu Ala Lys Lys Gln Lys Val Glu Gly Thr Glu Pro Thr
290 295 300

Thr Ala Phe Asn Leu Phe Val Gly Asn Leu Asn Phe Asn Lys Ser Ala
305 310 315 320

Pro Glu Leu Lys Thr Gly Ile Ser Asp Val Phe Ala Lys Asn Asp Leu
325 330 335

Ala Val Val Asp Val Arg Ile Gly Met Thr Arg Lys Phe Gly Tyr Val
340 345 350

Asp Phe Glu Ser Ala Glu Asp Leu Glu Lys Ala Leu Glu Leu Thr Gly
355 360 365

-continued

```
Leu Lys Val Phe Gly Asn Glu Ile Lys Leu Glu Lys Pro Lys Gly Lys
    370                 375                 380

Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
                405                 410                 415

Ala Glu Ile Arg Leu Val Ser Lys Asp Gly Lys Ser Lys Gly Ile Ala
            420                 425                 430

Tyr Ile Glu Phe Lys Thr Glu Ala Asp Ala Glu Lys Thr Phe Glu Glu
        435                 440                 445

Lys Gln Gly Thr Glu Ile Asp Gly Arg Ser Ile Ser Leu Tyr Tyr Thr
    450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
                485                 490                 495

Ala Thr Glu Glu Thr Leu Gln Glu Val Phe Glu Lys Ala Thr Phe Ile
            500                 505                 510

Lys Val Pro Gln Asn Gln Asn Gly Lys Ser Lys Gly Tyr Ala Phe Ile
        515                 520                 525

Glu Phe Ala Ser Phe Glu Asp Ala Lys Glu Ala Leu Asn Ser Cys Asn
    530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
                565                 570                 575

Lys Gly Leu Ser Glu Asp Thr Thr Glu Glu Thr Leu Lys Glu Ser Phe
            580                 585                 590

Asp Gly Ser Val Arg Ala Arg Ile Val Thr Asp Arg Glu Thr Gly Ser
        595                 600                 605

Ser Lys Gly Phe Gly Phe Val Asp Phe Asn Ser Glu Glu Asp Ala Lys
    610                 615                 620

Ala Ala Lys Glu Ala Met Glu Asp Gly Glu Ile Asp Gly Asn Lys Val
625                 630                 635                 640

Thr Leu Asp Trp Ala Lys Pro Lys Gly Glu Gly Gly Phe Gly Gly Arg
                645                 650                 655

Gly Gly Gly Arg Gly Gly Phe Gly Gly Arg Gly Gly Gly Arg Gly Gly
            660                 665                 670

Arg Gly Gly Phe Gly Gly Arg Gly Arg Gly Gly Phe Gly Gly Arg Gly
        675                 680                 685

Gly Phe Arg Gly Gly Arg Gly Gly Gly Gly Asp His Lys Pro Gln Gly
    690                 695                 700

Lys Lys Thr Lys Phe Glu
705                 710
```

<210> SEQ ID NO 3
<211> LENGTH: 1298
<212> TYPE: DNA
<213> ORGANISM: Homo sapiens

<400> SEQUENCE: 3

```
aagaaggaaa tggccaaaca gaaagcagct cctgaagcca agaaacagaa agtggaaggc      60

acagaaccga ctacggcttt caatctcttt gttggaaacc taaactttaa caaatctgct     120

cctgaattaa aaactggtat cagcgatgtt tttgctaaaa atgatcttgc tgttgtggat     180
```

-continued

```
gtcagaattg gtatgactag gaaatttggt tatgtggatt ttgaatctgc tgaagacctg    240

gagaaagcgt tggaactcac tggtttgaaa gtctttggca atgaaattaa actagagaaa    300

ccaaaaggaa aagacagtaa gaaagagcga gatgcgagaa cacttttggc taaaaatctc    360

ccttacaaag tcactcagga tgaattgaaa gaagtgtttg aagatgctgc ggagatcaga    420

ttagtcagca aggatgggaa aagtaaaggg attgcttata ttgaatttaa gacagaagct    480

gatgcagaga aaacctttga agaaaagcag ggaacagaga tcgatgggcg atctatttcc    540

ctgtactata ctggagagaa aggtcaaaat caagactata gaggtggaaa gaatagcact    600

tggagtggtg aatcaaaaac tctggtttta agcaacctct cctacagtgc aacagaagaa    660

actcttcagg aagtatttga gaaagcaact tttatcaaag taccccagaa ccaaaatggc    720

aaatctaaag ggtatgcatt tatagagttt gcttcattcg aagacgctaa agaagcttta    780

aattcctgta ataaaaggga aattgagggc agagcaatca ggctggagtt gcaaggaccc    840

aggggatcac ctaatgccag aagccagcca tccaaaactc tgtttgtcaa aggcctgtct    900

gaggatacca ctgaagagac attaaaggag tcatttgacg gctccgttcg ggcaaggata    960

gttactgacc gggaaactgg gtcctccaaa gggtttggtt ttgtagactt caacagtgag   1020

gaggatgcca aagctgccaa ggaggccatg gaagacggtg aaattgatgg aaataaagtt   1080

accttggact gggccaaacc taagggtgaa ggtggcttcg gggtcgtgg tggaggcaga   1140

ggcggctttg gaggacgagg tggtggtaga ggaggccgag gaggatttgg tggcagaggc   1200

cggggaggct ttggagggcg aggaggcttc cgaggaggca gaggaggagg aggtgaccac   1260

aagccacaag gaaagaagac gaagtttgaa gtttaaac                           1298
```

<210> SEQ ID NO 4
<211> LENGTH: 427
<212> TYPE: PRT
<213> ORGANISM: Homo sapiens

<400> SEQUENCE: 4

```
Met Ala Lys Gln Lys Ala Ala Pro Glu Ala Lys Lys Gln Lys Val Glu
1               5                   10                  15

Gly Thr Glu Pro Thr Thr Ala Phe Asn Leu Phe Val Gly Asn Leu Asn
            20                  25                  30

Phe Asn Lys Ser Ala Pro Glu Leu Lys Thr Gly Ile Ser Asp Val Phe
        35                  40                  45

Ala Lys Asn Asp Leu Ala Val Val Asp Val Arg Ile Gly Met Thr Arg
    50                  55                  60

Lys Phe Gly Tyr Val Asp Phe Glu Ser Ala Glu Asp Leu Glu Lys Ala
65                  70                  75                  80

Leu Glu Leu Thr Gly Leu Lys Val Phe Gly Asn Glu Ile Lys Leu Glu
                85                  90                  95

Lys Pro Lys Gly Lys Asp Ser Lys Lys Glu Arg Asp Ala Arg Thr Leu
            100                 105                 110

Leu Ala Lys Asn Leu Pro Tyr Lys Val Thr Gln Asp Glu Leu Lys Glu
        115                 120                 125

Val Phe Glu Asp Ala Ala Glu Ile Arg Leu Val Ser Lys Asp Gly Lys
    130                 135                 140

Ser Lys Gly Ile Ala Tyr Ile Glu Phe Lys Thr Glu Ala Asp Ala Glu
145                 150                 155                 160

Lys Thr Phe Glu Glu Lys Gln Gly Thr Glu Ile Asp Gly Arg Ser Ile
                165                 170                 175
```

-continued

```
Ser Leu Tyr Tyr Thr Gly Glu Lys Gly Gln Asn Gln Asp Tyr Arg Gly
            180                 185                 190

Gly Lys Asn Ser Thr Trp Ser Gly Glu Ser Lys Thr Leu Val Leu Ser
        195                 200                 205

Asn Leu Ser Tyr Ser Ala Thr Glu Glu Thr Leu Gln Glu Val Phe Glu
    210                 215                 220

Lys Ala Thr Phe Ile Lys Val Pro Gln Asn Gln Asn Gly Lys Ser Lys
225                 230                 235                 240

Gly Tyr Ala Phe Ile Glu Phe Ala Ser Phe Glu Asp Ala Lys Glu Ala
                245                 250                 255

Leu Asn Ser Cys Asn Lys Arg Glu Ile Glu Gly Arg Ala Ile Arg Leu
            260                 265                 270

Glu Leu Gln Gly Pro Arg Gly Ser Pro Asn Ala Arg Ser Gln Pro Ser
        275                 280                 285

Lys Thr Leu Phe Val Lys Gly Leu Ser Glu Asp Thr Thr Glu Glu Thr
    290                 295                 300

Leu Lys Glu Ser Phe Asp Gly Ser Val Arg Ala Arg Ile Val Thr Asp
305                 310                 315                 320

Arg Glu Thr Gly Ser Ser Lys Gly Phe Gly Phe Val Asp Phe Asn Ser
                325                 330                 335

Glu Glu Asp Ala Lys Ala Ala Lys Glu Ala Met Glu Asp Gly Glu Ile
            340                 345                 350

Asp Gly Asn Lys Val Thr Leu Asp Trp Ala Lys Pro Lys Gly Glu Gly
        355                 360                 365

Gly Phe Gly Gly Arg Gly Gly Gly Arg Gly Gly Phe Gly Gly Arg Gly
    370                 375                 380

Gly Gly Arg Gly Gly Arg Gly Gly Phe Gly Gly Arg Gly Arg Gly Gly
385                 390                 395                 400

Phe Gly Gly Arg Gly Gly Phe Arg Gly Gly Arg Gly Gly Gly Gly Asp
                405                 410                 415

His Lys Pro Gln Gly Lys Lys Thr Lys Phe Glu
            420                 425


<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Arg Arg Arg Arg Arg
1               5


<210> SEQ ID NO 6
<211> LENGTH: 4
<212> TYPE: PRT
<213> ORGANISM: Artificial Sequence
<220> FEATURE:
<223> OTHER INFORMATION: Synthetic peptide

<400> SEQUENCE: 6

Lys Lys Lys Lys
1


<210> SEQ ID NO 7
<211> LENGTH: 6
<212> TYPE: PRT
```

<213> ORGANISM: Artificial Sequence
<220> FEATURE:
<223> OTHER INFORMATION: Synthetic peptide

<400> SEQUENCE: 7

His His His His His His
1 5

<210> SEQ ID NO 8
<211> LENGTH: 8
<212> TYPE: PRT
<213> ORGANISM: Artificial Sequence
<220> FEATURE:
<223> OTHER INFORMATION: Synthetic peptide

<400> SEQUENCE: 8

Asp Tyr Lys Asp Asp Asp Asp Lys
1 5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Trp Ser His Pro Gln Phe Glu Lys
1 5

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Glu Gln Lys Leu Ile Ser Glu Glu Asp Leu
1 5 10

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide

<400> SEQUENCE: 11

Lys Glu Thr Ala Ala Ala Lys Phe Glu Arg Gln His Met Asp Ser
1 5 10 15

<210> SEQ ID NO 12
<211> LENGTH: 19
<212> TYPE: PRT
<213> ORGANISM: Artificial Sequence
<220> FEATURE:
<223> OTHER INFORMATION: Synthetic peptide

<400> SEQUENCE: 12

Lys Asp His Leu Ile His Asn Val His Lys Glu Phe His Ala His Ala
1 5 10 15

His Asn Lys

<210> SEQ ID NO 13
<211> LENGTH: 22

-continued

```
<212> TYPE: PRT
<213> ORGANISM: Artificial Sequence
<220> FEATURE:
<223> OTHER INFORMATION: Synthetic peptide

<400> SEQUENCE: 13

Asp Tyr Lys Asp His Asp Gly Asp Tyr Lys Asp His Asp Ile Asp Tyr
1               5                   10                  15

Lys Asp Asp Asp Asp Lys
            20


<210> SEQ ID NO 14
<211> LENGTH: 26
<212> TYPE: PRT
<213> ORGANISM: Artificial Sequence
<220> FEATURE:
<223> OTHER INFORMATION: Synthetic peptide

<400> SEQUENCE: 14

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25


<210> SEQ ID NO 15
<211> LENGTH: 38
<212> TYPE: PRT
<213> ORGANISM: Artificial Sequence
<220> FEATURE:
<223> OTHER INFORMATION: Synthetic peptide

<400> SEQUENCE: 15

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35


<210> SEQ ID NO 16
<211> LENGTH: 51
<212> TYPE: PRT
<213> ORGANISM: Artificial Sequence
<220> FEATURE:
<223> OTHER INFORMATION: Synthetic peptide

<400> SEQUENCE: 16

Thr Asn Pro Gly Val Ser Ala Trp Gln Val Asn Thr Ala Tyr Thr Ala
1               5                   10                  15

Gly Gln Leu Val Thr Tyr Asn Gly Lys Thr Tyr Lys Cys Leu Gln Pro
            20                  25                  30

His Thr Ser Leu Ala Gly Trp Glu Pro Ser Asn Val Pro Ala Leu Trp
        35                  40                  45

Gln Leu Gln
    50
```